United States Patent
Pellecchia et al.

(10) Patent No.: US 11,739,121 B2
(45) Date of Patent: Aug. 29, 2023

(54) EPHA2 AGONISTS AND USES THEREOF

(71) Applicant: THE REGENTS OF THE UNIVERSITY OF CALIFORNIA, Oakland, CA (US)

(72) Inventors: Maurizio Pellecchia, San Diego, CA (US); Luca Gambini, Riverside, CA (US); Alexander Aronson, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/058,519

(22) PCT Filed: Jun. 7, 2019

(86) PCT No.: PCT/US2019/036167
§ 371 (c)(1),
(2) Date: Nov. 24, 2020

(87) PCT Pub. No.: WO2019/237075
PCT Pub. Date: Dec. 12, 2019

(65) Prior Publication Data
US 2021/0221843 A1   Jul. 22, 2021

Related U.S. Application Data

(60) Provisional application No. 62/682,079, filed on Jun. 7, 2018, provisional application No. 62/718,267, filed on Aug. 13, 2018.

(51) Int. Cl.
*C07K 7/08* (2006.01)
*C07K 7/06* (2006.01)
*A61P 35/00* (2006.01)

(52) U.S. Cl.
CPC ............... *C07K 7/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,222,253 | B2 | 7/2012 | Wang et al. |
| 8,591,887 | B2 | 11/2013 | Kinch et al. |
| 2005/0059592 | A1 | 3/2005 | Kiener et al. |

OTHER PUBLICATIONS

Barile, E. et al. (Jul. 2014, e-published Mar. 26, 2014). "Design, synthesis and bioevaluation of an EphA2 receptor-based targeted delivery system," *ChemMedChem* 9(7):1403-1412.
Castelli, R. et al. (Oct. 20, 2015, e-published Aug. 29, 2015). "$\Delta^5$Cholenoyl-amino acids as selective and orally available antagonists of the Eph-ephrin system," *Eur J Med Chem* 103:312-324.
Duggineni, S. et al. (Feb. 5, 2013). "Design and Synthesis of Potent Bivalent Peptide Agonists Targeting the EphA2 Receptor," *ACS Med Chem Lett* 4(3):344-348.
Gambini, L. et al. (Sep. 21, 2018, e-published Aug. 29, 2018). "Structure-Based Design of Novel EphA2 Agonistic Agents with Nanomolar Affinity in Vitro and in Cell," *ACS Chem Biol* 13(9):2633-2644.
Gomez-Soler, M. et al. (May 31, 2019, e-published Apr. 23, 2019). "Engineering nanomolar peptide ligands that differentially modulate EphA2 receptor signaling," *J Biol Chem* 294(22):8791-8805.
Hasegawa, J. et al. (Nov. 2016, e-published Sep. 21, 2016). "Novel anti-EPHA2 antibody, DS-8895a for cancer treatment," *Cancer Biol Ther* 17(11):1158-1167.
Hassan-Mohamed, I. et al. (Dec. 2014, e-published Aug. 28, 2014). "UniPR129 is a competitive small molecule Eph-ephrin antagonist blocking in vitro angiogenesis at low micromolar concentrations," *Br J Pharmacol* 171(23):5195-5208.
Incerti, M. et al. (Apr. 11, 2013, e-published Mar. 14, 2013). "Amino acid conjugates of lithocholic acid as antagonists of the EphA2 receptor," *J Med Chem* 56(7):2936-2947.
International Search Report dated Oct. 10, 2019 for PCT Application No. PCT/US2019/036167, filed Jun. 7, 2019, 4 pages.
Koolpe, M. et al. (Dec. 6, 2002, e-published Sep. 25, 2002). "An ephrin mimetic peptide that selectively targets the EphA2 receptor," *J Biol Chem* 277(49):46974-46979.
Liu, Y. et al. (Jul. 2014, e-published Mar. 29, 2014). "$^{99m}$Tc-labeled SWL specific peptide for targeting EphA2 receptor," *Nucl Med Biol* 41 (6):450-456.
Mitra, S. et al. (Aug. 10, 2010). "Structure-activity relationship analysis of peptides targeting the EphA2 receptor," *Biochemistry* 49(31):6687-6695.
Patel, A.R. et al. (Oct. 2014, e-published May 29, 2014). "EphA2 targeting pegylated nanocarrier drug delivery system for treatment of lung cancer," *Pharm Res* 31(10):2796-2809.
Quinn, B.A. et al. (Mar. 29, 2016, e-published Mar. 5, 2016). "Therapy of pancreatic cancer via an EphA2 receptor-targeted delivery of gemcitabine," *Oncotarget* 7(13):17103-17110.
Salem, A.F. et al. (Mar. 8, 2018, e-published Feb. 22, 2018). "Reduction of Circulating Cancer Cells and Metastases in Breast-Cancer Models by a Potent EphA2-Agonistic Peptide-Drug Conjugate," *J Med Chem* 61(5):2052-2061.
Salem, A.F. et al. (May 10, 2020). "Therapeutic Targeting of Pancreatic Cancer via EphA2 Dimeric Agonistic Agents," *Pharmaceuticals* 13(5):90.

(Continued)

*Primary Examiner* — Ronald T Niebauer
(74) *Attorney, Agent, or Firm* — Viksnins Harris Padys Malen LLP

(57) ABSTRACT

The methods and compositions of the disclosure provide for novel therapeutic compounds to treat obesity and aspects related thereto. Embodiments of the disclosure relate to oligonucleotide therapeutic (ONT) agents targeting miR-22 miRNA for the treatment of human obesity and related cardiometabolic disorders. Accordingly, aspects of the disclosure relate to modified nucleic acids, including locked nucleic acids, ethylene-bridged nucleotides, peptide nucleic acids, phosphorodiamidate morpholino oligonucleotides, and or a 5'(E)-vinyl-phosphonate modification.

5 Claims, 22 Drawing Sheets

Specification includes a Sequence Listing.

(56) References Cited

OTHER PUBLICATIONS

Salem, A.F. et al. (Oct. 2, 2020). "Prostate Cancer Metastases Are Strongly Inhibited by Agonistic Epha2 Ligands in an Orthotopic Mouse Model," *Cancers* 12(10):2854.

Wang, S. et al. (Mar. 8, 2012, e-published Feb. 13, 2012). "Novel targeted system to deliver chemotherapeutic drugs to EphA2-expressing cancer cells," *J Med Chem* 55(5):2427-2436.

Wang, S. et al. (Jan. 1, 2013, e-published Nov. 15, 2012). "Targeted delivery of paclitaxel to EphA2-expressing cancer cells," *Clin Cancer Res* 19(1):128-137.

Written Opinion dated Oct. 10, 2019 for PCT Application No. PCT/US2019/036167, filed Jun. 7, 2019, 3 pages.

Wu, B. et al. (Jul. 23, 2015, e-published Jul. 9, 2015). "Design and Characterization of Novel EphA2 Agonists for Targeted Delivery of Chemotherapy to Cancer Cells," *Chem Biol* 22(7):876-887.

EPHA2 AGONISTS AND USES THEREOF

CROSS-REFERENCES TO RELATED APPLICATIONS

This application is the national stage filing under 35 U.S.C. § 371 of International Application No. PCT/US2019/036167 filed Jun. 7, 2019, which claims the benefit of U.S. Provisional Application No. 62/682,079, filed Jun. 7, 2018, and U.S. Provisional Application No. 62/718,267, filed Aug. 13, 2018, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. CA168517 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 054156-503N01US_Sequence_Listing_ST25.txt, created Dec. 6, 2021, 37,462 bytes, machine format IBM-PC, MS Windows operating system, is hereby incorporated by reference.

BACKGROUND

EphA2 belongs to a class of receptor tyrosine kinases that have been implicated in tumorigenesis, drug resistance, and metastatic behaviors of several solid tumors including prostate cancer, melanoma, urinary bladder, breast, ovarian, pancreatic, brain, esophagus, lung, and stomach cancers, and leukemia. In cancer cells, the unbalanced overexpression of the receptor compared to its ligands (ephrin-A) primes the EphA2 pro-oncogenic activity. Hence, deriving novel and more potent EphA2 binding agents that displayed a nanomolar affinity for the receptoris needed. Described herein, inter alia, are solutions to these and other problems in the art.

BRIEF SUMMARY OF THE INVENTION

In an aspect is provided a compound having the formula:

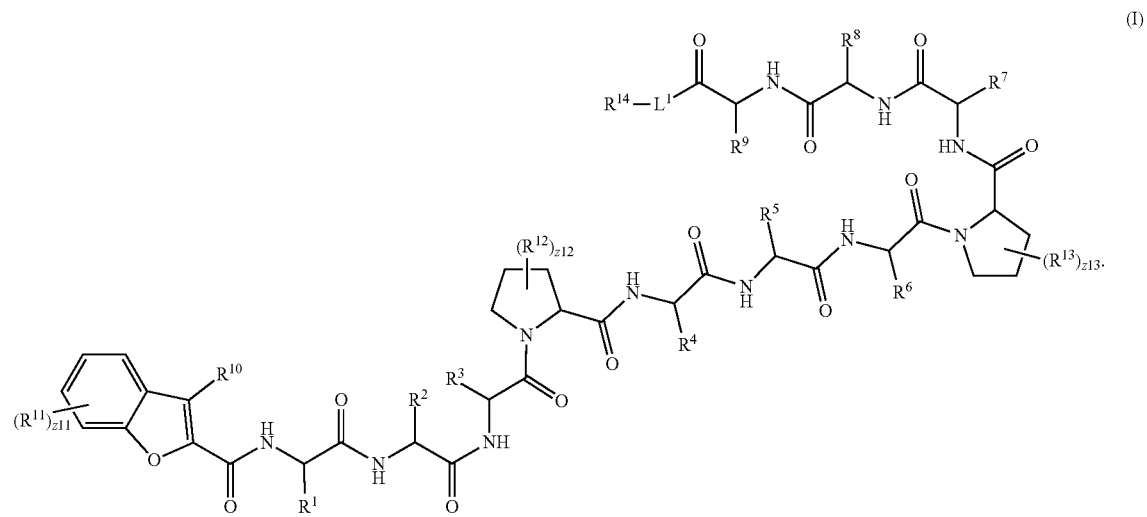

(I)

$R^1$, $R^2$, $R^3$, $R^4$, $R^5$, $R^6$, $R^7$, and $R^8$ are each independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, an amino acid side chain, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^5$ may optionally be joined to form $L^2$; $R^9$ and the nitrogen atom adjacent to the carbon to which $R^9$ is attached may optionally be joined to form a substituted or unsubstituted heterocycloalkyl. $L^2$ is a covalent linker. $R^9$ is an amino acid side chain, bioconjugate reactive moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is halogen, —$CCl_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ and $R^{13}$ are each independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. z11 is an integer from 0 to 4. z12 is an integer from 0 to 7. z13 is an integer from 0 to 5. $L^1$ is a covalent linker. $R^{14}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

In an aspect is provided a pharmaceutical composition including a pharmaceutically acceptable excipient and a compound described herein (including in an aspect, embodiment, table, example, or claim), or a pharmaceutically acceptable salt thereof.

In an aspect is provided a method of treating cancer, the method including administering to a subject in need thereof a therapeutically effective amount of a compound described herein (including in an aspect, embodiment, table, example, or claim), or a pharmaceutically acceptable salt thereof.

In an aspect is provided a method of increasing EphA2 activity, the method including contacting a EphA2 protein with a compound described herein (including in an aspect, embodiment, table, example, or claim), or a pharmaceutically acceptable salt thereof.

In an aspect is provided a method of suppressing the pro-oncogenic EphA2 activity, the method including contacting a EphA2 protein with a compound described herein (including in an aspect, embodiment, table, example, or claim), or a pharmaceutically acceptable salt thereof. In embodiments, suppressing is relative to a control.

In an aspect is provided a method of reducing levels of EphA2, the method including contacting a EphA2 protein with a compound described herein (including in an aspect, embodiment, table, example, or claim), or a pharmaceutically acceptable salt thereof. In embodiments, reducing is relative to a control.

In an aspect is provided a method of inhibiting cancer cell migration and invasion, the method including contacting a EphA2 protein with a compound described herein (including in an aspect, embodiment, table, example, or claim), or a pharmaceutically acceptable salt thereof.

In an aspect is provided a method of selectively delivering a chemotherapeutic agent to EphA2 expressing cancer cells, the method including contacting a EphA2 protein with a compound described herein (including in an aspect, embodiment, table, example, or claim), or a pharmaceutically acceptable salt thereof, wherein the compound includes a drug moiety (e.g., $R^{14}$ includes a drug moiety).

BRIEF DESCRIPTION OF THE DRAWINGS

(FIG. 1A) Schematic representation of the DELFIA assay. (FIG. 1B) DELFIA displacement curves relative to YSA (IC$_{50}$=16.5 µM), 123B9 (IC$_{50}$=6.5 µM) and 135G3 (IC$_{50}$=0.6 µM) against the EphA2-LBD. (FIG. 1C) Close-up view of the structure of EphA2-LBD (ribbons, PDB ID 3MX0) in complex with various ephrin ligands or the 1C1 antibody (short rods). Only the loop regions of the ligands are shown as short rods: ephrinA1 (3CZU), ephrinA2 (2WO3), ephrinA4 (3MX0), ephrinB2 (1KGY) and the anti-EphA2 antibody 1C1 (3SKJ). (FIG. 1D) Isothermal Titration calorimetry (ITC) curves for the binding between 135G3 and EphA2-LBD (ΔH=−21.9 kcal/mol, −TΔS=13.5 kcal/mol) and EphA4-LBD (no appreciable binding). (FIG. 1E) EphA2 receptor phosphorylation assay in HEK293 cells by various doses of YSA, 123B9 and 135G3.

(FIG. 2A) 135E2 is depicted as a stick model, while the EphA2 is depicted as a ribbon model and with several side chains that interact with the peptide displayed. (FIG. 2B) Superposition of the structures of 135H2 (stick model) in complex with EphA2-LBD (ribbon) and the complex between EphA2-LBD (ribbon model) and ephrinA5 (only the interacting loop region is shown as a rod). (FIG. 2C) Detailed interactions between 135E2 (stick model) and EphA2-LBD (surface representation). The surface was generated with MOLCAD and colored according to a lipophilic potential (darker, more lipophilic; lighter, more polar).

(FIG. 3A) DELFIA displacement dose response curves comparing 123B9, 135G3, and 135H11 (Table 2). (FIG. 3B) Model of the complex between 135H11 and EphA2-LBD. The model was obtained using Sybyl (Cetara) and our derived X-ray structure of the complex between 135H2 and EphA2-LBD (PDB ID 6B9L). Intermolecular hydrogen binding involving side chains are highlighted in green. (FIG. 3C) ITC curves for 135H11 against EphA2-LBD (Kd=150 nM) and (FIG. 3D) EphA4-LBD (inactive).

(FIG. 4A) Comparison studies between the two dimeric EphA2 agonists, 135H12 and 135G4, in a cell-based assay. BxPC3 cell line was treated with the indicated doses for 3 hours, then cells were lysed and Western blot studies were performed. Both dimers degraded total EphA2 receptor and phosphorylated pEphA2 5897 at nanomolar concentrations, but 135H12 was more potent at lower doses compared to 135G4 (evident comparing the 50 nM and 100 nM treated lanes). (FIG. 4B) 135H12 was an effective agonist compared to EphA2 agonistic monomers. BxPC3 or PANC-1 cells were treated and lysed similar to the previous Western blot. 135H12 degraded total EphA2 receptor and dephosphorylated pEphA2 S897 at 1 µM in both cell lines. Moreover, the monomer 135H11 was more effective than the monomer 123B9. EphrinA1-Fc is a clustered natural ligand and used as a positive control. (FIG. 4C) Kinetics of EphA2 degradation after treatment with 135H12 (1 µM). BxPC3 cells were treated with 1 µM 135H12, and cell lysates collected at the indicated time points and blotted with phospho-EphA2 S897 or EphA2. EphA2 receptor was dephosphorylated and degraded after 10 min of adding 135H12. Moreover, the receptor band disappeared after 1 hour of treatment. (FIG. 4D) 135H12 altered EphA2 cellular localization. BxPC3 cells were plated in chamber slides and the following day they were treated with clustered Fc, clustered EphrinA1, 1 µM of 135H11, or 1 µM 135H12 for 30 min. Cells were immunostained with EphA2 antibody (light) and nuclei were counterstained with DAPI(dark). Punctuated EphA2 fluorescence (lighter dots) can be observed in the clustered EphrinA1 and in 135H12 treated cells. Images were acquired using confocal Inverted Zeiss 880. EphA2 receptor was located at the cell membrane when treated with Fc or 135H11. On the contrary, punctuated fluorescence was observed in the cytoplasm of ephrinA1-Fc and 135H12 treated cells, suggesting receptor clustering and internalization.

(FIG. 5A) 135H12 and 135H11 inhibit cell invasion. $7 \times 10^5$ BxPC3 cells were plated in each well of a 96-well plate and treated the following day. Plates were treated once and imaged every 6 h for 6 days. (FIG. 5B) 135H12 and 135H11 inhibit cell migration. BxPC3 cells were plated and treated similarly to the invasion assay. Plates were imaged every 6 h for 36 hours. (5C) Time dependent inhibition of invasion and migration of pancreatic cancer cells when treated with 135H11 (monomer) and 135H12 (dimer). Both agonists inhibited cell invasion, while 135H12 showed more significant inhibition of cell migration than its monomer counterpart, 135H11. Invasion assay n=5, migration assay n=10. Error bars are SEM. **, P=0.0001; *, P=0.0002; **, P=0.003.

FIG. 1; 135G10, ΔH=−19.4 kcal/mol, −TΔS=10.6 kcal/mol). The introduction of a disulfide bond between Cys in position 2 and hCys in position 5, while reducing the entropic loss upon binding even further (135I3 ΔH=−18.1 kcal/mol, −TΔS=10.4 kcal/mol), was also paired with a major loss of enthalpy. This is accentuated when the two stabilizing methods are used in the side chain optimized sequence (135H11 ΔH=−19.1 kcal/mol, −TΔS=10.0 kcal/mol; ΔH=−13.8 kcal/mol, −TΔS=5.2 kcal/mol; Table 2). These data suggest that 135H11 was favored to the cyclic agents, although further optimizations of the cyclic compounds could be performed.

(FIG. 8A) Representative images of each treatment at time 0, 12, 24 h. (FIG. 8B) Summary of the time-dependent migration of BxPC3 cells when treated with 135H11 (monomer) and 135H12 (dimer). Error bars are SEM. ****, P=0.0001; *, P=0.01, n=4.

FIG. 9A: The interaction diagram of 135E2 with EphA2-LBD. The diagram was generated using Maestro 11.1. Peptide sequences shown left to right, top to bottom: C188-V189-A190---L192; L163-V161-R159---F156; R103---T101; P109-F108-S107; M73---C70-V69-S68---M66-Y65-I64; M59-I58-N57-Q56-M55-L54-D53 (DLMQNIM (SEQ ID NO:80)); G38-G39-E40. FIG. 9B: the interaction diagram of 135H11 with EphA2-LBD. Peptide sequences shown left to right, top to bottom: S107-F108-P109; L192---A190-V189-C188; E40-G39-G38; R103---T101; F156---A158-R159---V161; M73-V72---C70-V69-S68---M66-Y65-I64; M59-I58-N57-Q56-M55-L54-D53 (DLMQNIM (SEQ ID NO:80)). The diagram was generated using Maestro 11.1.

DETAILED DESCRIPTION

I. Definitions

Figure 1A:
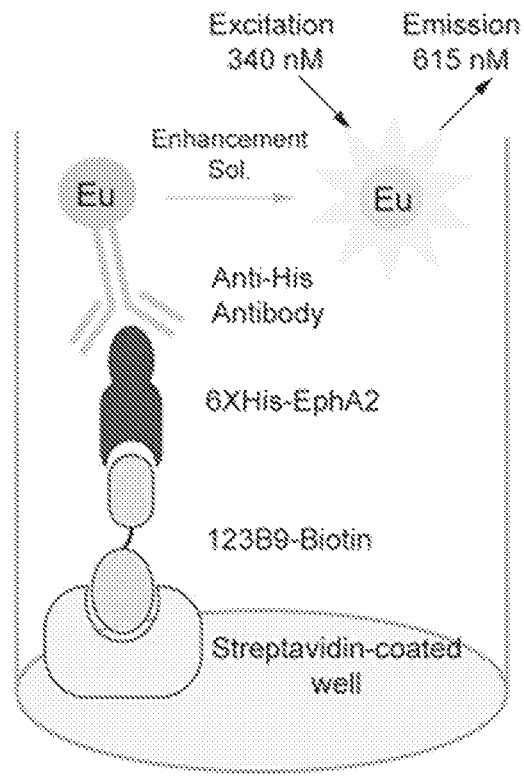
FIG. 1A-E. Design of 135G3.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

The term "alkylarylene" as an arylene moiety covalently bonded to an alkylene moiety (also referred to herein as an alkylene linker). In embodiments, the alkylarylene group has the formula:

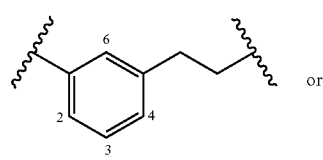 or

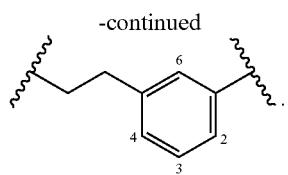

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —$N_3$, —CH (Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The term "bioconjugate group" or "bioconjugate reactive moiety" or "bioconjugate reactive group" refers to a chemical moiety which participates in a reaction to form bioconjugate linker (e.g., covalent linker) or the resulting association between atoms or molecules of bioconjugate reactive moieties. The association can be direct or indirect. For example, a conjugate between a first bioconjugate reactive moiety (e.g., —NH$_2$, —COOH, —N-hydroxysuccinimide, or -maleimide) and a second bioconjugate reactive moiety (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive moieties) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive moiety (e.g., maleimide moiety) is covalently attached to the second bioconjugate reactive moiety (e.g. a sulfhydryl). In embodiments, the first bioconjugate reactive moiety (e.g., haloacetyl moiety) is covalently attached to the second bioconjugate reactive moiety (e.g. a sulfhydryl). In embodiments, the first bioconjugate reactive moiety (e.g., pyridyl moiety) is covalently attached to the second bioconjugate reactive moiety (e.g. a sulfhydryl). In embodiments, the first bioconjugate reactive moiety (e.g., —N-hydroxysuccinimide moiety) is covalently attached to the second bioconjugate reactive moiety (e.g. an amine). In embodiments, the first bioconjugate reactive moiety (e.g., maleimide moiety) is covalently attached to the second bioconjugate reactive moiety (e.g. a sulfhydryl). In embodiments, the first bioconjugate reactive moiety (e.g., -sulfo-N-hydroxysuccinimide moiety) is covalently attached to the second bioconjugate reactive moiety (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds;

(n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive moieties can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently. When a substituent or linker (e.g., an R group or an L linker) appears multiple times, each appearance of that substituent or linker can be different, i.e., each occurrence of the substituent or the linker may be independently a member of the Markush group for that variable, wherein each occurrence may be optionally different.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu. Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "lipid moiety" is used in accordance with its ordinary meaning in chemistry and refers to a hydrophobic molecule which is typically characterized by an aliphatic hydrocarbon chain. In embodiments, the lipid moiety includes a carbon chain of 3 to 100 carbons. In embodiments, the lipid moiety includes a carbon chain of 5 to 50 carbons. In embodiments, the lipid moiety includes a carbon chain of 5 to 25 carbons. In embodiments, the lipid moiety includes a carbon chain of 8 to 25 carbons. Lipid moieties may include saturated or unsaturated carbon chains, and may be optionally substituted. In embodiments, the lipid moiety is optionally substituted with a charged moiety at the terminal end. In embodiments, the lipid moiety is an alkyl or heteroalkyl optionally substituted with a carboxylic acid moiety at the terminal end.

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anti-cancer agent" or "anticancer agent" as used herein refers to a molecule (e.g. compound, peptide, protein, or nucleic acid) used to treat cancer through destruction or inhibition of cancer cells or tissues. Anticancer agents may be selective for certain cancers or certain tissues.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin, ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e., E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g., Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e., LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-(Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39·HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-(Tularik, i.e., T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e., T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-(Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™) cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

An "epigenetic inhibitor" as used herein, refers to an inhibitor of an epigenetic process, such as DNA methylation (a DNA methylation Inhibitor) or modification of histones (a Histone Modification Inhibitor). An epigenetic inhibitor may be a histone-deacetylase (HDAC) inhibitor, a DNA methyltransferase (DNMT) inhibitor, a histone methyltransferase (HMT) inhibitor, a histone demethylase (HDM) inhibitor, or a histone acetyltransferase (HAT). Examples of HDAC inhibitors include Vorinostat, romidepsin, CI-994, Belinostat, Panobinostat, Givinostat, Entinostat, Mocetinostat, SRT501, CUDC-101, JNJ-26481585, or PCI24781. Examples of DNMT inhibitors include azacitidine and decitabine. Examples of HMT inhibitors include EPZ-5676. Examples of HDM inhibitors include pargyline and tranylcypromine. Examples of HAT inhibitors include CCT077791 and garcinol.

A "multi-kinase inhibitor" is a small molecule inhibitor of at least one protein kinase, including tyrosine protein kinases and serine/threonine kinases. A multi-kinase inhibitor may include a single kinase inhibitor. Multi-kinase inhibitors may block phosphorylation. Multi-kinases inhibitors may act as covalent modifiers of protein kinases. Multi-kinase inhibitors may bind to the kinase active site or to a secondary or tertiary site inhibiting protein kinase activity. A multi-kinase inhibitor may be an anti-cancer multi-kinase inhibitor. Exemplary anti-cancer multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

"Selective" or "selectivity" or the like of a compound refers to the compound's ability to discriminate between molecular targets.

"Specific", "specifically", "specificity", or the like of a compound refers to the compound's ability to cause a particular action, such as inhibition, to a particular molecular target with minimal or no action to other proteins in the cell.

An amino acid residue in a protein "corresponds" to a given residue when it occupies the same essential structural position within the protein as the given residue.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is hydrogen,

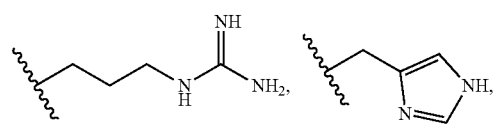

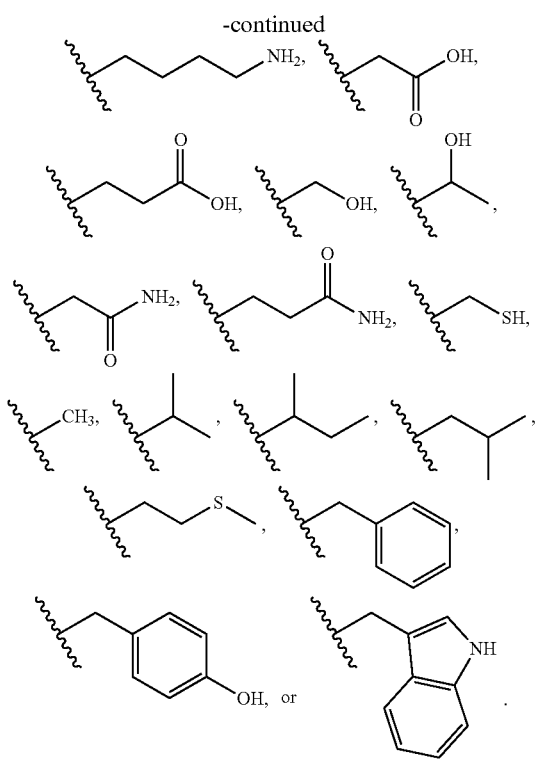

The term "non-natural amino acid side chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride,cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe (4-NH2)-OH, Boc-Phe(3-NO2)OH, Boc-Phe(3,5-F2)OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N-Boc-1,2,3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobulyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)OH, Fmoc-β-(4-thiazolyl)-Ala-OH, Fmoc-β-(2-thienyl)-Ala-OH, 4-(Hydroxymethyl)-D-phenylalanine.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTI- SENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, *Scientific American,* 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, *Anal. Biochem.,* 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or precursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "synergistic amount" as used herein refers to the sum of a first amount (e.g., an amount of a NSC including a chimeric poxvirus provided herein) and a second amount (e.g., a therapeutic agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the NSC including a chimeric poxvirus administered in combination where the measured effect is greater than the sum of the individual effects of each of the NSC including a chimeric poxvirus provided herein administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the NSC including a chimeric poxvirus provided herein when used separately from the therapeutic agent. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the therapeutic agent when used separately from the NSC including a chimeric poxvirus provided herein.

An "EphA2 inhibitor" refers to a compound (e.g. compounds described herein) that reduces the activity of EphA2 when compared to a control, such as absence of the compound or a compound with known inactivity.

An "EphA2 agonist" refers to a compound (e.g. compounds described herein) that increases the activity of EphA2 when compared to a control, such as absence of the compound or a compound with known inactivity. In embodiments, an EphA2 agonist is a monovalent compound of Formula (I), having the formula:

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^1$, z11, z12, and z13 are independent and as described herein. In embodiments, an EphA2 agonist is a monovalent compound of Formula (I), having the formula:

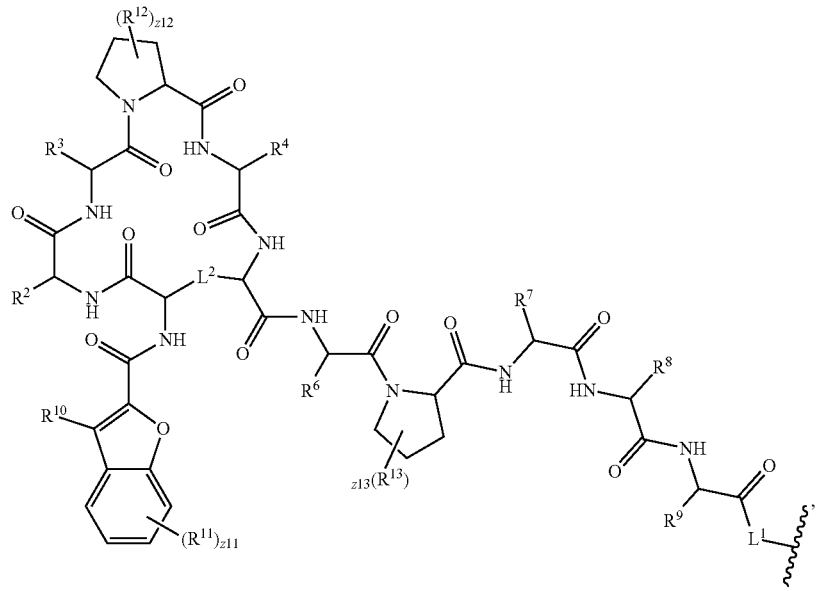

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^2$, $L^1$, z11, z12, and z13 are independent and as described herein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "EphA2 inhibitor" is a compound that negatively affects (e.g. decreases) the activity or function of EphA2 relative to the activity or function of EphA2 in the absence of the inhibitor.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "EphA2 protein" or "EphA2" or "Ephrin type-A receptor 2" refer to a protein (including homologs, isoforms, and functional fragments thereof) with EphA2 activity. The term includes any recombinant or naturally-occurring form of EphA2 variants thereof that maintain EphA2 activity (e.g. within at least 30%, 40%, 50%, 60%, 70%, 80%, 90%, 95%, or 100% activity compared to wildtype EphA2). In embodiments, the EphA2 protein encoded by the GENE gene has the amino acid sequence set forth in or corresponding to Entrez 1969, UniProt P29317, or RefSeq (protein) NP_001316019, or RefSeq (protein) NP_004422. In embodiments, the amino acid sequence or nucleic acid sequence is the sequence known at the time of filing of the present application. In embodiments, the EphA2 is a human EphA2, such as a human cancer causing EphA2. In embodiments, EphA2 has the sequence:

```
                                                      (SEQ ID NO: 1)
MELQAARACFALLWGCALAAAAAAQGKEVVLLDFAAAGGELGWLTHPYGKGWDLMQNIMN

DMPIYMYSVCNVMSGDQDNWLRTNWVYRGEAERIFIELKFTVRDCNSFPGGASSCKETFN

LYYAESDLDYGTNFQKRLFTKIDTIAPDEITVSSDFEARHVKLNVEERSVGPLTRKGFYL

AFQDIGACVALLSVRVYYKKCPELLQGLAHFPETIAGSDAPSLATVAGTCVDHAVVPPGG

EEPRMHCAVDGEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTPPQDSGGREDI

VYSVTCEQCWPESGECGPCEASVRYSEPPHGLTRTSVTVSDLEPHMNYTFTVEARNGVSG

LVTSRSFRTASVSINQTEPPKVRLEGRSTTSLSVSWSIPPPQQSRVWKYEVTYRKKGDSN

SYNVRRTEGFSVTLDDLAPDTTYLVQVQALTQEGQGAGSKVHEFQTLSPEGSGNLAVIGG

VAVGVVLLLVLAGVGFFIHRRRKNQRARQSPEDVYFSKSEQLKPLKTYVDPHTYEDPNQA

VLKFTTEIHPSCVTRQKVIGAGEFGEVYKGMLKTSSGKKEVPVAIKTLKAGYTEKQRVDF

LGEAGIMGQFSHHNIIRLEGVISKYKPMMIITEYMENGALDKFLREKDGEFSVLQLVGML

RGIAAGMKYLANMNYVHRDLAARNILVNSNLVCKVSDFGLSRVLEDDPEATYTTSGGKIP

IRWTAPEAISYRKFTSASDVWSFGIVMWEVMTYGERPYWELSNHEVMKAINDGFRLPTPM

DCPSAIYQLMMQCWQQERARRPKFADIVSILDKLIRAPDSLKTLADFDPRVSIRLPSTSG

SEGVPFRTVSEWLESIKMQQYTEHFMAAGYTAIEKVVQMTNDDIKRIGVRLPGHQKRIAY

SLLGLKDQVNTVGIPI.
```

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. In some embodiments, an EphA2 associated disease modulator is a compound that reduces the severity of one or more symptoms of a disease associated with EphA2 (e.g. cancer, inflammatory disease, autoimmune disease, or infectious disease). A EphA2 modulator is a compound that increases or decreases the activity or function or level of activity or level of function of EphA2.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with EPHA2 activity, EPHA2 associated cancer, EPHA2 associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. For example, a cancer associated with EPHA2 activity or function may be a cancer that results (entirely or partially) from aberrant EPHA2 function (e.g. enzyme activity, protein-protein interaction, signaling pathway) or a cancer wherein a particular symptom of the disease is caused (entirely or partially) by aberrant EPHA2 activity or function. As used herein, what is described as being associated with a disease, if a causative agent, could be a target for treatment of the disease. For example, a cancer associated with EPHA2 activity or function or a EPHA2 associated disease (e.g., cancer, inflammatory disease, autoimmune disease, or infectious disease), may be treated with a EPHA2 modulator or EPHA2 inhibitor, in the instance where increased EPHA2 activity or function (e.g. signaling pathway activity) causes the disease (e.g., cancer, inflammatory disease, autoimmune disease, or infectious disease). For example, an inflammatory disease associated with EPHA2 activity or function or an EPHA2 associated inflammatory disease, may be treated with an EPHA2 modulator or EPHA2 inhibitor, in the instance where increased EPHA2 activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

The term "electrophilic" as used herein refers to the ability to accept electron density. An "electrophilic substituent", "electrophilic chemical moiety", or "electrophic moiety" refers to an electron-poor chemical group, substituent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue (e.g., EphA2 cysteine residue) and may be referred to as a "covalent cysteine modifier moiety" or "covalent cysteine modifier substituent". The covalent bond formed between the electrophilic substituent and the sulfhydryl group of the cysteine may be a reversible or irreversible bond. In some embodiments, the electrophilic substituent is capable of forming a covalent bond with a lysine residue (e.g., EphA2 lysine residue) and may be referred to as a "covalent lysine modifier moiety" or "covalent lysine modifier substituent". In some embodiments, the electrophilic substituent is capable of forming a covalent bond with a tyrosine residue (e.g., EphA2 tyrosine residue) and may be referred to as a "covalent tyrosine modifier moiety" or "covalent tyrosine modifier substituent". In some embodiments, the electrophilic substituent is capable of forming a covalent bond with a histidine residue (e.g., EphA2 histidine residue) and may be referred to as a "covalent histidine modifier moiety" or "covalent histidine modifier substituent".

"Nucleophilic" as used herein refers to a chemical group that is capable of donating electron density.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a EphA2 protein with a compound as described herein may reduce the level of a product of the EphA2 catalyzed reaction or the level of a downstream derivative of the product or binding may reduce the interactions between the EphA2 protein or an EphA2 reaction product and downstream effectors or signaling pathway components, resulting in changes in cell growth, proliferation, or survival.

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "drug moiety" as used herein refers to a monovalent agent (e.g., compound or composition) that when administered to a subject will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms or the intended therapeutic effect, e.g., treatment or amelioration of an injury, disease, pathology or condition, or their symptoms including any objective or subjective parameter of treatment such as abatement; remission; diminishing of symptoms or making the injury, pathology or condition more tolerable to the patient; slowing in the rate of degeneration or decline; making the final point of degeneration less debilitating; or improving a patient's physical or mental well-being. Non-limiting examples of a drug moiety include paclitaxel, docetaxel, amphotericin B, artemisinin, atovaquone, camptothecin, rapamycin, aprepitant, thymectacin, fenofibrate, budesonide, or insulin.

The term "targeting moiety" refers to an agent for targeting the compound to a specific location in a cell or organism.

The term "cell migration" is used in accordance with its ordinary meaning and refers to the locomotion of a cell. For example, cell migration may refer to the movement from a cell from its place of origin to another site (e.g., a different tissue). In embodiments, cell migration may alternatively be referred to as cell motility. Cell motility refers to the ability of a cell to move independently using metabolic energy. In embodiments, the cell migration is flagellar motility, (i.e. a swimming-like motion), amoeboid movement (i.e. a crawling-like movement), gliding motility, swarming motility, twitching motility, (i.e. a form of motility used by bacteria to crawl over surfaces), filopodia, (i.e. enabling movement of the axonal growth cones. Typically, cells may migrate in response to specific external signals (e.g., chemical signals or mechanical signals), and disrupting external signals may reduce cell migration. Cell migration may be quantified using known techniques in the arts, for example utilizing the methods described herein. Additional information regarding cell migration may be found in Trepat, X., et al; Comprehensive Physiology, 2(4), 2369-2392, which is incorporated herein by reference in its entirety.

The term "cell invasion" is used in accordance with its ordinary meaning and refers the ability of a cell migrate from its place of origin to a different site (e.g., a different tissue). Cell invasion may be qualified using known techniques in the arts, for example utilizing the methods described herein. In embodiments, cell invasion refers to the ability to navigate through the extracellular matrix within a tissue or to infiltrate neighbouring tissues.

A "nanoparticle," as used herein, is a particle wherein the longest diameter is less than or equal to 1000 nanometers. The longest dimension of the nanoparticle may be referred to herein as the length of the nanoparticle. The shortest dimension of the nanoparticle may be referred to herein refer as the width of the nanoparticle. Nanoparticles may be composed of any appropriate material. For example, nanoparticle cores may include appropriate metals and metal oxides thereof (e.g., a metal nanoparticle core), carbon (e.g., an organic nanoparticle core) silicon and oxides thereof (e.g., a silicon nanoparticle core) or boron and oxides thereof (e.g., a boron nanoparticle core), or mixtures thereof. In embodiments, the nanoparticle has the shape of a sphere, rod, cube, triangular, hexagonal, cylinder, spherocylinder, or ellipsoid.

II. Compounds

In an aspect is provided a compound having the formula:

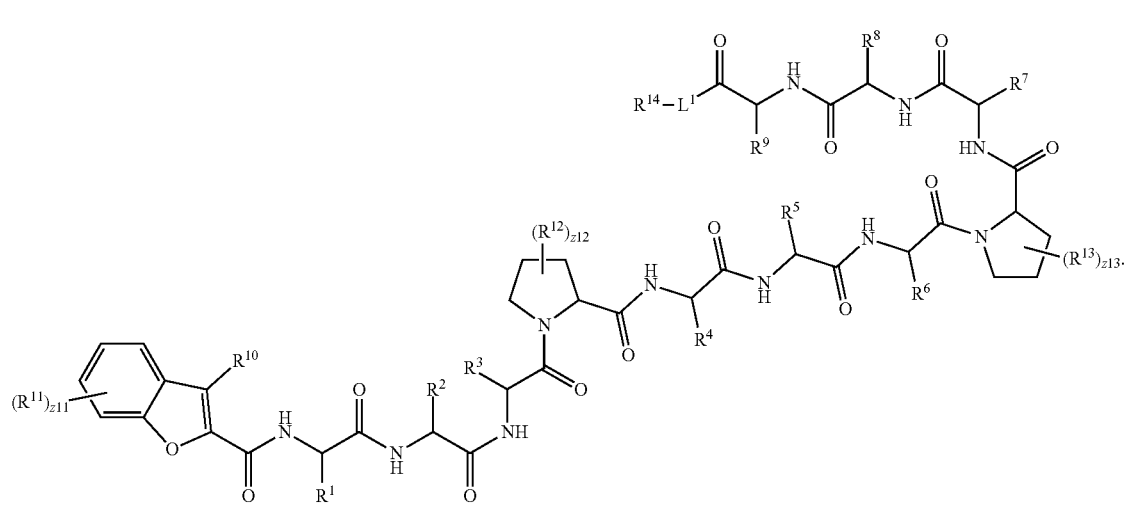

(I)

$R^1$, $R^2$, $R^3$, $R^4$, $R^5$, $R^6$, $R^7$, and $R^8$ are each independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, an amino acid side chain, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^5$ may optionally be joined to form $L^2$; $R^9$ and the nitrogen atom adjacent to the carbon to which $R^9$ is attached may optionally be joined to form a substituted or unsubstituted heterocycloalkyl. $L^2$ is a covalent linker. $R^9$ is an amino acid side chain, bioconjugate reactive moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ are $R^{13}$ each independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. z11 is an integer from 0 to 4. z12 is an integer from 0 to 7. z13 is an integer from 0 to 5. L1 is a covalent linker. $R^{14}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

It will be understood that "nanoparticle", "peptide", and "EphA2 agonist" as used herein in Formula (I) (e.g., in $R^{14}$ and $R^{15}$) refer to monovalent forms of such groups (i.e., "nanoparticle" and "monovalent nanoparticle" and "nanoparticle moiety" are used interchangeably, "peptide" and "monovalent peptide" and "peptide moiety" are used interchangeably, and "EphA2 agonist" and "monovalent EphA2 agonist" "EphA2 agonist moiety" are used interchangeably).

In embodiments, $R^{14}$ is a bioconjugate reactive moiety, a nanoparticle (nanoparticle moiety), a peptide (peptide moiety), an EphA2 agonist (EphA2 agonist moiety), a drug moiety, a targeting moiety, or a detectable moiety.

In embodiments, the compound has the formula:

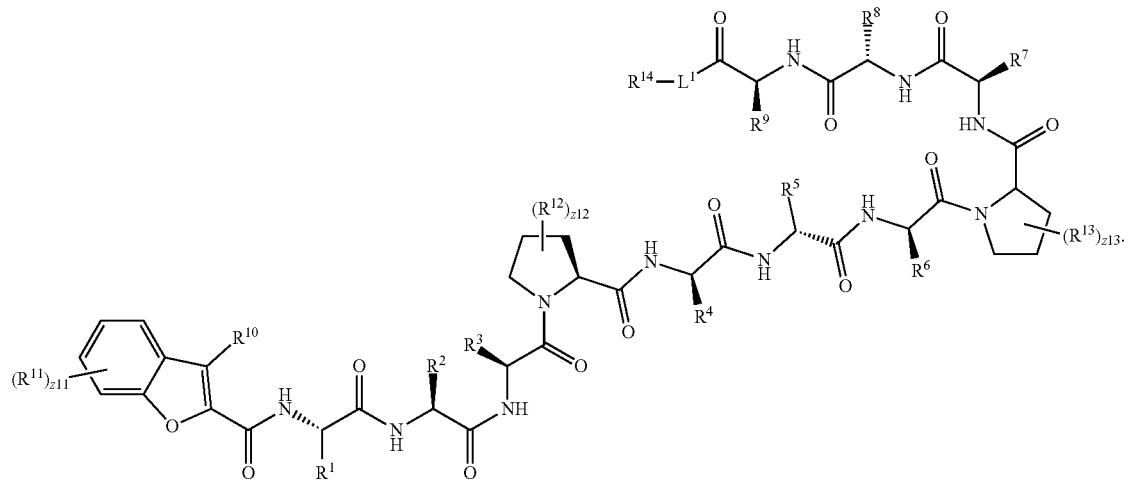

$R^1$, $R^2$, $R^3$, $R^4$, $R^5$, $R^6$, $R^7$, $R^8$, $R^9$, $R^{10}$, $R^{11}$, z11, $R^{12}$, z12, $R^{13}$, z13, $R^{14}$, and $L^1$ are as described herein, including in embodiments.

In embodiments, the compound has the formula:

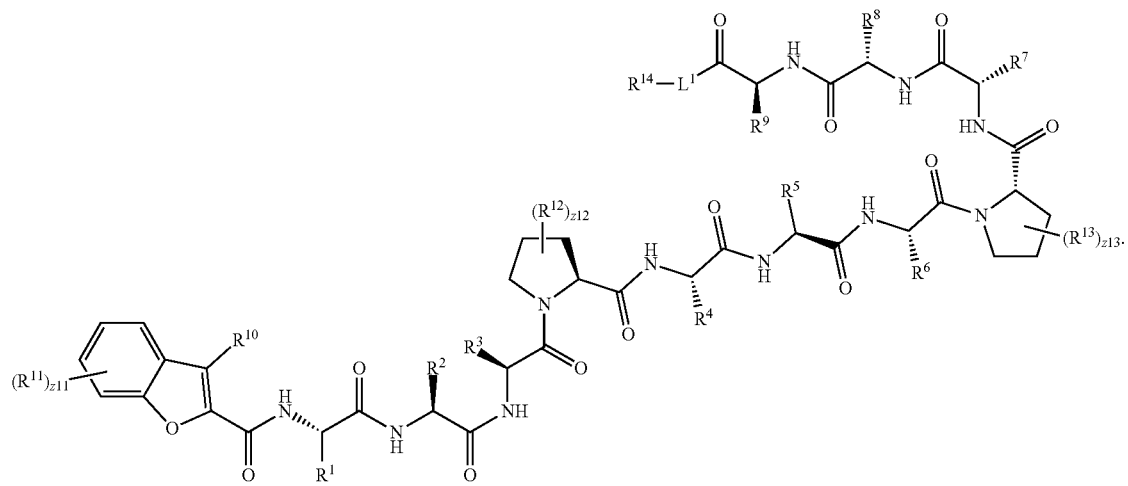

$R^1$, $R^2$, $R^3$, $R^4$, $R^5$, $R^6$, $R^7$, $R^8$, $R^9$, $R^{10}$, $R^{11}$, z11, $R^{12}$, z12, $R^{13}$, z13, and $L^1$ are as described herein, including in embodiments.

In embodiments, the compound has the formula:

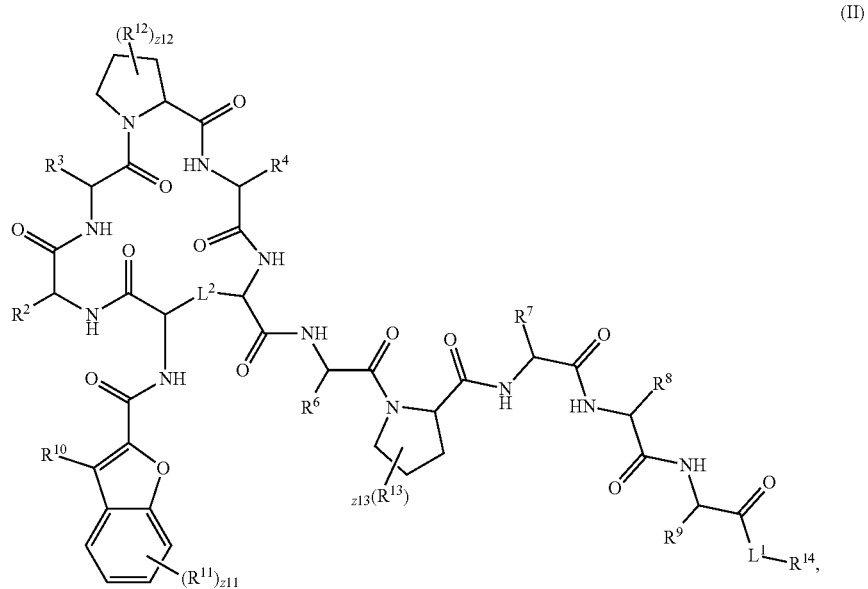

(II)

wherein $R^2$, $R^3$, $R^4$, $R^6$, $R^7$, $R^8$, $R^9$, $R^{10}$, $R^{11}$, $R^{12}$, $R^{13}$, z11, z12, z13, L1, and $R^{14}$ are as described herein. $L^2$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the compound has the formula:

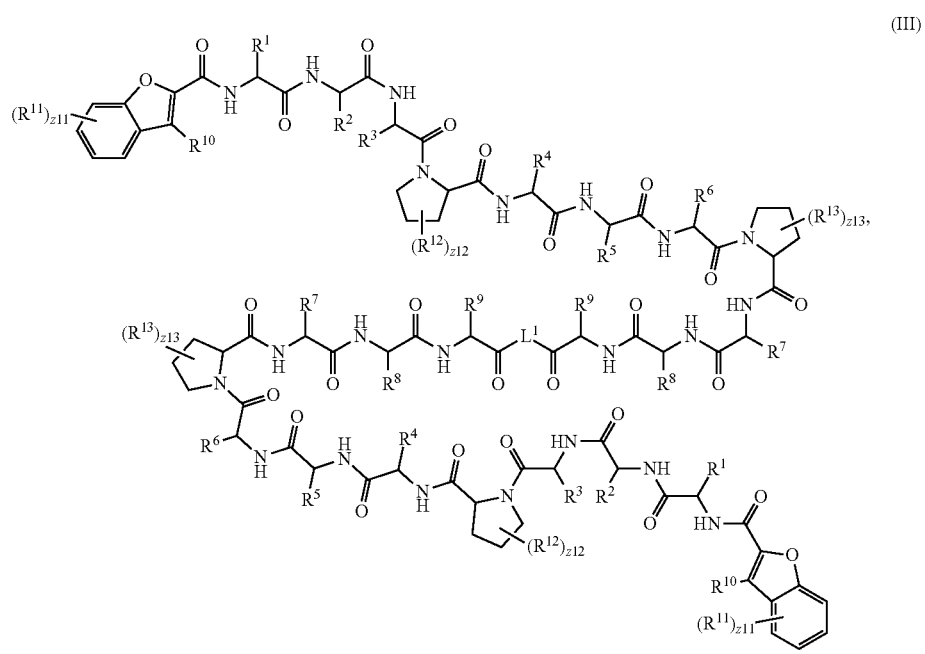

(III)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^1$, z11, z12, and z13 are independent and as described herein.

In embodiments, $R^1$ is a halogen, —CCl$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCHCl$_2$, —OCHBr$_2$, —OCHF$_2$, —OCHI$_2$, an amino acid side chain, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl).

$R^{20}$ is independently oxo, halogen, —CCl$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{21}$-substituted or unsubstituted alkyl (e.g., $C_1$-$C_8$ alkyl, $C_1$-$C_6$ alkyl, or $C_1$-$C_4$ alkyl), $R^{21}$-substituted or unsubstituted heteroalkyl (e.g., 2 to 8 membered heteroalkyl, 2 to 6 membered heteroalkyl, or 2 to 4 membered heteroalkyl), $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{21}$-substituted or unsubstituted heterocycloalkyl (e.g., 3 to 8 membered heterocycloalkyl, 3 to 6 membered heterocycloalkyl, or 5 to 6 membered heterocycloalkyl), $R^{21}$-substituted or unsubstituted aryl (e.g., $C_6$-$C_{10}$ aryl, $C_{10}$ aryl, or phenyl), or $R^{21}$-substituted or unsubstituted heteroaryl (e.g., 5 to 10 membered heteroaryl, 5 to 9 membered heteroaryl, or 5 to 6 membered heteroaryl).

In embodiments, $R^1$ and $R^5$ are each independently the side chain of glycine, alanine, valine, leucine, isoleucine, proline, phenylalanine, methionine, or tryptophan.

In embodiments, $R^1$ is a side chain of a hydrophobic amino acid (e.g., the side chain of glycine (Gly), alanine (Ala), valine (Val), leucine (Leu), isoleucine (Ile), proline (Pro), phenylalanine (Phe), methionine (Met), or tryptophan (Trp)). In embodiments, $R^1$ is a side chain of glycine. In embodiments, $R^1$ is a side chain of alanine. In embodiments, $R^1$ is a side chain of valine. In embodiments, $R^1$ is a side chain of leucine. In embodiments, $R^1$ is a side chain of isoleucine. In embodiments, $R^1$ is a side chain of proline. In embodiments, $R^1$ is a side chain of phenylalanine. In embodiments, $R^1$ is a side chain methionine. In embodiments, $R^1$ is a side chain of tryptophan.

In embodiments, $R^1$ is $R^{20}$-substituted or unsubstituted alkyl (e.g., $C_1$-$C_8$ alkyl, $C_1$-$C_6$ alkyl, or $C_1$-$C_4$ alkyl). In embodiments, $R^1$ is $R^{20}$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl).

In embodiments, $R^1$ is $R^{20}$-substituted or unsubstituted methyl. In embodiments, $R^1$ is $R^{20}$-substituted or unsubstituted $C_2$ alkyl. In embodiments, $R^1$ is $R^{20}$-substituted or unsubstituted $C_3$ alkyl. In embodiments, $R^1$ is $R^{20}$-substituted or unsubstituted $C_4$ alkyl. In embodiments, $R^1$ is $R^{20}$-substituted or unsubstituted $C_5$ alkyl. In embodiments, $R^1$ is $R^{20}$-substituted or unsubstituted $C_6$ alkyl. In embodiments, $R^1$ is $R^{20}$-substituted or unsubstituted $C_7$ alkyl. In embodiments, $R^1$ is $R^{20}$-substituted or unsubstituted $C_8$ alkyl. In embodiments, $R^1$ is $R^{20}$-substituted methyl. In embodiments, $R^1$ is $R^{20}$-substituted $C_2$ alkyl. In embodiments, $R^1$ is $R^{20}$-substituted $C_3$ alkyl. In embodiments, $R^1$ is $R^{20}$-substituted $C_4$ alkyl. In embodiments, $R^1$ is —CH$_2$CH(CH$_3$)$_2$. In embodiments, $R^1$ is $R^{20}$-substituted $C_5$ alkyl. In embodiments, $R^1$ is $R^{20}$-substituted $C_6$ alkyl. In embodiments, $R^1$ is $R^{20}$-substituted $C_7$ alkyl. In embodiments, $R^1$ is $R^{20}$-substituted $C_8$ alkyl. In embodiments, $R^1$ is an unsubstituted methyl. In embodiments, $R^1$ is an unsubstituted $C_2$ alkyl. In embodiments, $R^1$ is an unsubstituted $C_3$ alkyl. In embodiments, $R^1$ is an unsubstituted $C_4$ alkyl. In embodiments, $R^1$ is an unsubstituted $C_5$ alkyl. In embodiments, $R^1$ is an unsubstituted $C_6$ alkyl. In embodiments, $R^1$ is an unsubstituted $C_7$ alkyl. In embodiments, $R^1$ is an unsubstituted $C_8$ alkyl.

In embodiments, $R^1$ is $R^{20}$-substituted or unsubstituted heteroalkyl (e.g., 2 to 8 membered heteroalkyl, 2 to 6 membered heteroalkyl, or 2 to 4 membered heteroalkyl). In embodiments, $R^1$ is $R^{20}$-substituted heteroalkyl (e.g., 2 to 8 membered heteroalkyl, 2 to 6 membered heteroalkyl, or 2 to 4 membered heteroalkyl). In embodiments, $R^1$ is an unsubstituted heteroalkyl (e.g., 2 to 8 membered heteroalkyl, 2 to 6 membered heteroalkyl, or 2 to 4 membered heteroalkyl).

In embodiments, $R^1$ is $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is $R^{20}$-substituted cycloalkyl (e.g., $C_3$-$C_8$ cycloalkyl, $C_3$-$C_6$ cycloalkyl, or $C_5$-$C_6$ cycloalkyl). In embodiments, $R^1$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^1$ is $R^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^{20}$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^1$ is $R^{20}$-substituted or unsubstituted aryl (e.g., $C_6$-$C_{10}$ aryl, $C_{10}$ aryl, or phenyl). In embodiments, $R^1$ is $R^{20}$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl).

In embodiments, $R^1$ is $R^{20}$-substituted or unsubstituted heteroaryl (e.g., 5 to 10 membered heteroaryl, 5 to 9 membered heteroaryl, or 5 to 6 membered heteroaryl). In embodiments, $R^1$ is $R^{20}$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl).

In embodiments, $R^1$ and $R^5$ may optionally be joined to form $L^2$. In embodiments, $L^2$ is a bond, —S(O)$_2$—, —NH—, —O—, —S—, —S—S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is a bond. In embodiments, $L^2$ is —S(O)$_2$—. In embodiments, $L^2$ is —NH—. In embodiments, $L^2$ is —O—. In embodiments, $L^2$ is —S—. In embodiments, $L^2$ is —C(O)—. In embodiments, $L^2$ is —C(O)NH—. In embodiments, $L^2$ is —NHC(O)—. In embodiments, $L^2$ is —NHC(O)NH—. In embodiments, $L^2$ is —C(O)O—. In embodiments, $L^2$ is —OC(O)—. In embodiments, $L^2$ is substituted or unsubstituted alkylene. In embodiments, $L^2$ is substituted or unsubstituted heteroalkylene. In embodiments, $L^2$ is substituted or unsubstituted cycloalkylene. In embodiments, $L^2$ is substituted or unsubstituted heterocycloalkylene. In embodiments, $L^2$ is substituted or unsubstituted arylene. In embodiments, $L^2$ is substituted or unsubstituted heteroarylene. In embodiments, $L^2$ is a 5 membered substituted or unsubstituted heteroalkylene. In embodiments, $L^2$ is a 6 membered substituted or unsubstituted heteroalkylene. In embodiments, $L^2$ is

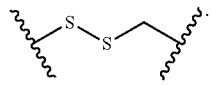 [SMILES: *CSS*]

In embodiments, $L^2$ is

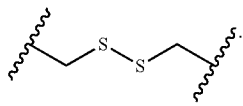 [SMILES: *CSSC*]

In embodiments, $L^2$ is

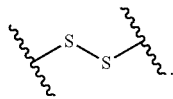

In embodiments, $L^2$ is a bond, —S(O)$_2$—, —NH—, —O—, —S—, —C(O)—, —C(O)NH—, —NHC(O)—, —NHC(O)NH—, —C(O)O—, —OC(O)—, $R^{20}$-substituted or unsubstituted alkylene (e.g., $C_1$-$C_8$ alkylene, $C_1$-$C_6$ alkylene, or $C_1$-$C_4$ alkylene), $R^{20}$-substituted or unsubstituted heteroalkylene (e.g., 2 to 8 membered heteroalkylene, 2 to 6 membered heteroalkylene, or 2 to 4 membered heteroalkylene), $R^{20}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{20}$-substituted or unsubstituted heterocycloalkylene (e.g., 3 to 8 membered heterocycloalkylene, 3 to 6 membered heterocycloalkylene, or 5 to 6 membered heterocycloalkylene), $R^{20}$-substituted or unsubstituted arylene (e.g., $C_6$-$C_{10}$ arylene, $C_{10}$ arylene, or phenylene), or $R^{20}$-substituted or unsubstituted heteroarylene (e.g., 5 to 10 membered heteroarylene, 5 to 9 membered heteroarylene, or 5 to 6 membered heteroarylene).

In embodiments, $L^2$ is $R^{20}$-substituted or unsubstituted alkylene (e.g., $C_1$-$C_8$ alkylene, $C_1$-$C_6$ alkylene, or $C_1$-$C_4$ alkylene). In embodiments, $L^2$ is $R^{20}$-substituted alkylene (e.g., $C_1$-$C_8$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene).

In embodiments, $L^2$ is $R^{20}$-substituted or unsubstituted heteroalkylene (e.g., 2 to 8 membered heteroalkylene, 2 to 6 membered heteroalkylene, or 2 to 4 membered heteroalkylene). In embodiments, $L^2$ is $R^{20}$-substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene).

In embodiments, $L^2$ is $R^{20}$-substituted or unsubstituted cycloalkylene (e.g., $C_3$-$C^8$ cycloalkylene, $C_3$-$C_6$ cycloalkylene, or $C_5$-$C_6$ cycloalkylene). In embodiments, $L^2$ is $R^{20}$-substituted cycloalkylene (e.g., $C_3$-$C_8$ cycloalkylene, $C_3$-$C_6$ cycloalkylene, or $C_5$-$C_6$ cycloalkylene). In embodiments, $L^2$ is an unsubstituted cycloalkylene (e.g., $C_3$-$C^8$ cycloalkylene, $C_3$-$C_6$ cycloalkylene, or $C_5$-$C_6$ cycloalkylene).

In embodiments, $L^2$ is $R^{20}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is $R^{20}$-substituted heterocycloalkylene (e.g., 3 to 8 membered heterocycloalkylene, 3 to 6 membered heterocycloalkylene, or 5 to 6 membered heterocycloalkylene). In embodiments, $L^2$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^2$ is $R^{20}$-substituted or unsubstituted arylene (e.g., $C_6$-$C_{10}$ arylene, $C_{10}$ arylene, or phenylene). In embodiments, $L^2$ is $R^{20}$-substituted arylene (e.g., $C_6$-$C_{10}$ arylene, $C_{10}$ arylene, or phenylene). In embodiments, $L^2$ is an unsubstituted arylene (e.g., $C_6$-$C_{10}$ arylene, $C_{10}$ arylene, or phenylene).

In embodiments, $L^2$ is $R^{20}$-substituted or unsubstituted heteroarylene (e.g., 5 to 10 membered heteroarylene, 5 to 9 membered heteroarylene, or 5 to 6 membered heteroarylene). In embodiments, $L^2$ is $R^{20}$-substituted heteroarylene (e.g., 5 to 10 membered heteroarylene, 5 to 9 membered heteroarylene, or 5 to 6 membered heteroarylene). In embodiments, $L^2$ is an unsubstituted heteroarylene (e.g., 5 to 10 membered heteroarylene, 5 to 9 membered heteroarylene, or 5 to 6 membered heteroarylene).

In embodiments, $R^2$ is a halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, an amino acid side chain, $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl).

$R^{22}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{23}$-substituted or unsubstituted alkyl (e.g., C$_1$-C$_8$ alkyl, C$_1$-C$_6$ alkyl, or C$_1$-C$_4$ alkyl), R$^{23}$-substituted or unsubstituted heteroalkyl (e.g., 2 to 8 membered heteroalkyl, 2 to 6 membered heteroalkyl, or 2 to 4 membered heteroalkyl), R$^{23}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{23}$-substituted or unsubstituted heterocycloalkyl (e.g., 3 to 8 membered heterocycloalkyl, 3 to 6 membered heterocycloalkyl, or 5 to 6 membered heterocycloalkyl), R$^{23}$-substituted or unsubstituted aryl (e.g., C$_6$-C$_{10}$ aryl, C$_{10}$ aryl, or phenyl), or R$^{23}$-substituted or unsubstituted heteroaryl (e.g., 5 to 10 membered heteroaryl, 5 to 9 membered heteroaryl, or 5 to 6 membered heteroaryl).

In embodiments, R$^2$ is —CH$_3$. In embodiments, R$^2$ is —CH$_2$CH$_3$. In embodiments, R$^2$ is —CH$_2$CH$_2$CH$_3$. In embodiments, R$^2$ is —C$_2$H$_5$. In embodiments, R$^2$ is —CF$_3$.

In embodiments, R$^2$ is R$^{22}$-substituted or unsubstituted alkyl (e.g., C$_1$-C$_8$ alkyl, C$_1$-C$_6$ alkyl, or C$_1$-C$_4$ alkyl). In embodiments, R$^2$ is R$^{22}$-substituted alkyl (e.g., C$_1$-C$_8$ alkyl, C$_1$-C$_6$ alkyl, or C$_1$-C$_4$ alkyl). In embodiments, R$^2$ is an unsubstituted alkyl (e.g., C$_1$-C$_8$ alkyl, C$_1$-C$_6$ alkyl, or C$_1$-C$_4$ alkyl).

In embodiments, R$^2$ is R$^{22}$-substituted or unsubstituted methyl. In embodiments, R$^2$ is R$^{22}$-substituted or unsubstituted C$_2$ alkyl. In embodiments, R$^2$ is R$^{22}$-substituted or unsubstituted C$_3$ alkyl. In embodiments, R$^2$ is R$^{22}$-substituted or unsubstituted C$_4$ alkyl. In embodiments, R$^2$ is R$^{22}$-substituted or unsubstituted C$_5$ alkyl. In embodiments, R$^2$ is R$^{22}$-substituted or unsubstituted C$_6$ alkyl. In embodiments, R$^2$ is R$^{22}$-substituted or unsubstituted C$_7$ alkyl. In embodiments, R$^2$ is R$^{22}$-substituted or unsubstituted C$_8$ alkyl. In embodiments, R$^2$ is R$^{22}$-substituted methyl. In embodiments, R$^2$ is R$^{22}$-substituted C$_2$ alkyl. In embodiments, R$^2$ is R$^{22}$-substituted C$_3$ alkyl. In embodiments, R$^2$ is R$^{22}$-substituted C$_4$ alkyl. In embodiments, R$^2$ is R$^{22}$-substituted C$_5$ alkyl. In embodiments, R$^2$ is R$^{22}$-substituted C$_6$ alkyl. In embodiments, R$^2$ is R$^{22}$-substituted C$_7$ alkyl. In embodiments, R$^2$ is R$^{22}$-substituted C$_8$ alkyl. In embodiments, R$^2$ is an unsubstituted methyl. In embodiments, R$^2$ is an unsubstituted C$_2$ alkyl. In embodiments, R$^2$ is an unsubstituted C$_3$ alkyl. In embodiments, R$^2$ is an unsubstituted C$_4$ alkyl. In embodiments, R$^2$ is an unsubstituted C$_5$ alkyl. In embodiments, R$^2$ is an unsubstituted C$_6$ alkyl. In embodiments, R$^2$ is an unsubstituted C$_7$ alkyl. In embodiments, R$^2$ is an unsubstituted C$_8$ alkyl.

In embodiments, R$^2$ is R$^{22}$-substituted or unsubstituted heteroalkyl (e.g., 2 to 8 membered heteroalkyl, 2 to 6 membered heteroalkyl, or 2 to 4 membered heteroalkyl). In embodiments, R$^2$ is R$^{22}$-substituted heteroalkyl (e.g., 2 to 8 membered heteroalkyl, 2 to 6 membered heteroalkyl, or 2 to 4 membered heteroalkyl). In embodiments, R$^2$ is an unsubstituted heteroalkyl (e.g., 2 to 8 membered heteroalkyl, 2 to 6 membered heteroalkyl, or 2 to 4 membered heteroalkyl).

In embodiments, R$^2$ is R$^{22}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^2$ is R$^{22}$-substituted cycloalkyl (e.g., C$_3$-C$_8$ cycloalkyl, C$_3$-C$_6$ cycloalkyl, or C$_5$-C$_6$ cycloalkyl). In embodiments, R$^2$ is an unsubstituted cycloalkyl (e.g., C$_3$-C$_8$ cycloalkyl, C$_3$-C$_6$ cycloalkyl, or C$_5$-C$_6$ cycloalkyl). In embodiments, R$^2$ is an unsubstituted C$_3$ cycloalkyl. In embodiments, R$^2$ is an unsubstituted C$_4$ cycloalkyl. In embodiments, R$^2$ is an unsubstituted C$_5$ cycloalkyl. In embodiments, R$^2$ is an unsubstituted C$_6$ cycloalkyl.

In embodiments, R$^2$ is R$^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^2$ is R$^{22}$-substituted heterocycloalkyl (e.g., 3 to 8 membered heterocycloalkyl, 3 to 6 membered heterocycloalkyl, or 5 to 6 membered heterocycloalkyl). In embodiments, R$^2$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^2$ is R$^{22}$-substituted or unsubstituted aryl (e.g., C$_6$-C$_{10}$ aryl, C$_{10}$ aryl, or phenyl). In embodiments, R$^2$ is R$^{22}$-substituted aryl (e.g., C$_6$-C$_{10}$ aryl, C$_{10}$ aryl, or phenyl). In embodiments, R$^2$ is an unsubstituted aryl (e.g., C$_6$-C$_{10}$ aryl, C$_{10}$ aryl, or phenyl).

In embodiments, R$^2$ is R$^{22}$-substituted or unsubstituted heteroaryl (e.g., 5 to 10 membered heteroaryl, 5 to 9 membered heteroaryl, or 5 to 6 membered heteroaryl). In embodiments, R$^2$ is R$^{22}$-substituted heteroaryl (e.g., 5 to 10 membered heteroaryl, 5 to 9 membered heteroaryl, or 5 to 6 membered heteroaryl). In embodiments, R$^2$ is an unsubstituted heteroaryl (e.g., 5 to 10 membered heteroaryl, 5 to 9 membered heteroaryl, or 5 to 6 membered heteroaryl).

In embodiments, R$^2$ is —CCl$_3$, —CBr$_3$, —CF$_3$, —CI$_3$, substituted or unsubstituted alkyl, substituted or unsubstituted heteroalkyl, substituted or unsubstituted cycloalkyl. In embodiments, R$^2$ is —CCl$_3$. In embodiments, R$^2$ is —CBr$_3$. In embodiments, R$^2$ is —CF$_3$. In embodiments, R$^2$ is —CI$_3$. In embodiments, R$^2$ is substituted or unsubstituted alkyl. In embodiments, R$^2$ is substituted or unsubstituted heteroalkyl. In embodiments, R$^2$ is substituted or unsubstituted cycloalkyl.

In embodiments, R$^3$ is a halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, an amino acid side chain, R$^{24}$-substituted or unsubstituted alkyl (e.g., C$_1$-C$_8$ alkyl, C$_1$-C$_6$ alkyl, or C$_1$-C$_4$ alkyl), R$^{24}$-substituted or unsubstituted heteroalkyl (e.g., 2 to 8 membered heteroalkyl, 2 to 6 membered heteroalkyl, or 2 to 4 membered heteroalkyl), R$^{24}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{24}$-substituted or unsubstituted heterocycloalkyl (e.g., 3 to 8 membered heterocycloalkyl, 3 to 6 membered heterocycloalkyl, or 5 to 6 membered heterocycloalkyl), R$^{24}$-substituted or unsubstituted aryl (e.g., C$_6$-C$_{10}$ aryl, C$_{10}$ aryl, or phenyl), or R$^{24}$-substituted or unsubstituted heteroaryl (e.g., 5 to 10 membered heteroaryl, 5 to 9 membered heteroaryl, or 5 to 6 membered heteroaryl).

R$^{24}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{25}$-substituted or unsubstituted alkyl (e.g., C$_1$-C$_8$ alkyl, C$_1$-C$_6$ alkyl, or C$_1$-C$_4$ alkyl), R$^{25}$-substituted or unsubstituted heteroalkyl (e.g., 2 to 8 membered heteroalkyl, 2 to 6 membered heteroalkyl, or 2 to 4 membered heteroalkyl), R$^{25}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{25}$-substituted or unsubstituted heterocycloalkyl (e.g., 3 to 8 membered heterocycloalkyl, 3 to 6 membered heterocycloalkyl, or 5 to 6 membered heterocycloalkyl), R$^{25}$-substituted or unsubstituted aryl (e.g., C$_6$-C$_{10}$ aryl, C$_{10}$ aryl, or phenyl), or R$^{25}$-substituted or unsubstituted heteroaryl (e.g., 5 to 10 membered heteroaryl, 5 to 9 membered heteroaryl, or 5 to 6 membered heteroaryl).

In embodiments, R$^3$ is R$^{24}$-substituted or unsubstituted alkyl (e.g., C$_1$-C$_8$ alkyl, C$_1$-C$_6$ alkyl, or C$_1$-C$_4$ alkyl). In embodiments, R$^3$ is R$^{24}$-substituted alkyl (e.g., C$_1$-C$_8$ alkyl, C$_1$-C$_6$ alkyl, or C$_1$-C$_4$ alkyl). In embodiments, R$^3$ is an unsubstituted alkyl (e.g., C$_1$-C$_8$ alkyl, C$_1$-C$_6$ alkyl, or C$_1$-C$_4$ alkyl).

In embodiments, R$^3$ is R$^{24}$-substituted or unsubstituted heteroalkyl (e.g., 2 to 8 membered heteroalkyl, 2 to 6 membered heteroalkyl, or 2 to 4 membered heteroalkyl). In embodiments, R$^3$ is R$^{24}$-substituted heteroalkyl (e.g., 2 to 8 membered heteroalkyl, 2 to 6 membered heteroalkyl, or 2 to 4 membered heteroalkyl). In embodiments, R$^3$ is an unsubstituted heteroalkyl (e.g., 2 to 8 membered heteroalkyl, 2 to 6 membered heteroalkyl, or 2 to 4 membered heteroalkyl).

In embodiments, R$^3$ is R$^{24}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^3$ is R$^{24}$-substituted cycloalkyl (e.g., C$_3$-C$_8$ cycloalkyl, C$_3$-C$_6$ cycloalkyl, or C$_5$-C$_6$ cycloalkyl). In embodiments, R$^3$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^3$ is R$^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^3$ is R$^{24}$-substituted heterocycloalkyl (e.g., 3 to 8 membered heterocycloalkyl, 3 to 6 membered heterocycloalkyl, or 5 to 6 membered heterocycloalkyl). In embodiments, R$^3$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^3$ is R$^{24}$-substituted or unsubstituted aryl (e.g., C$_6$-C$_{10}$ aryl, C$_{10}$ aryl, or phenyl). In embodiments, R$^3$ is R$^{24}$-substituted aryl (e.g., C$_6$-C$_{10}$ aryl, C$_{10}$ aryl, or phenyl). In embodiments, R$^3$ is an unsubstituted aryl (e.g., C$_6$-C$_{10}$ aryl, C$_{10}$ aryl, or phenyl).

In embodiments, R$^3$ is R$^{24}$-substituted or unsubstituted heteroaryl (e.g., 5 to 10 membered heteroaryl, 5 to 9 membered heteroaryl, or 5 to 6 membered heteroaryl). In embodiments, R$^3$ is R$^{24}$-substituted heteroaryl (e.g., 5 to 10 membered heteroaryl, 5 to 9 membered heteroaryl, or 5 to 6 membered heteroaryl). In embodiments, R$^3$ is an unsubstituted heteroaryl (e.g., 5 to 10 membered heteroaryl, 5 to 9 membered heteroaryl, or 5 to 6 membered heteroaryl).

In embodiments, R$^3$ is the side chain of phenylalanine, tryptophan, tyrosine, thyroxine, 5-hydroxytryptophan, dihydroxyphenylalanine, or histidine. In embodiments, R$^3$ is the side chain of phenylalanine. In embodiments, R$^3$ is the side chain of tryptophan. In embodiments, R$^3$ is the side chain of tyrosine. In embodiments, R$^3$ is the side chain of thyroxine. In embodiments, R$^3$ is the side chain of 5-hydroxytryptophan. In embodiments, R$^3$ is the side chain of dihydroxyphenylalanine. In embodiments, R$^3$ is the side chain of histidine.

In embodiments, R$^3$ is a substituted or unsubstituted phenyl. In embodiments, R$^3$ is a substituted phenyl. In embodiments, R$^3$ is an unsubstituted phenyl. In embodiments, R$^3$ is a substituted or unsubstituted imidazolyl, substituted or unsubstituted pyrrolyl, substituted or unsubstituted pyrazolyl, substituted or unsubstituted triazolyl, substituted or unsubstituted tetrazolyl, substituted or unsubstituted furanyl, substituted or unsubstituted oxazolyl, substituted or unsubstituted isooxazolyl, substituted or unsubstituted oxadiazolyl, substituted or unsubstituted oxatriazolyl, substituted or unsubstituted thienyl, substituted or unsubstituted thiazolyl, substituted or unsubstituted isothiazolyl, substituted or unsubstituted pyridinyl, substituted or unsubstituted pyrazinyl, substituted or unsubstituted pyrimidinyl, substituted or unsubstituted pyridazinyl, or substituted or unsubstituted triazinyl (e.g., 1,3,5-triazinyl, 1,2,3-triazinyl, or 1,2,4-triazinyl).

In embodiments, R$^3$ is substituted or unsubstituted heterocycloalkyl. In embodiments, R$^3$ is substituted or unsubstituted aryl. In embodiments, R$^3$ is substituted or unsubstituted heteroaryl.

In embodiments, R$^3$ is

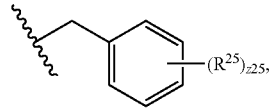

wherein R$^{25}$ is as described herein. The symbol z25 is an integer from 0 to 5. In embodiments, z25 is 1. In embodiments, z25 is 2. In embodiments, z25 is 0. In embodiments, R$^{25}$ is —OCH$_3$. In embodiments, R$^3$ is —CH$_2$(4-methoxybenzene).

In embodiments, R$^4$ is a halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, an amino acid side chain, R$^{26}$-substituted or unsubstituted alkyl (e.g., C$_1$-C$_8$ alkyl, C$_1$-C$_6$ alkyl, or C$_1$-C$_4$ alkyl), R$^{26}$-substituted or unsubstituted heteroalkyl (e.g., 2 to 8 membered heteroalkyl, 2 to 6 membered heteroalkyl, or 2 to 4 membered heteroalkyl), R$^{26}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{26}$-substituted or unsubstituted heterocycloalkyl (e.g., 3 to 8 membered heterocycloalkyl, 3 to 6 membered heterocycloalkyl, or 5 to 6 membered heterocycloalkyl), R$^{26}$-substituted or unsubstituted aryl (e.g., C$_6$-C$_{10}$ aryl, C$_{10}$ aryl, or phenyl), or R$^{26}$-substituted or unsubstituted heteroaryl (e.g., 5 to 10 membered heteroaryl, 5 to 9 membered heteroaryl, or 5 to 6 membered heteroaryl).

R$^{26}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{27}$-substituted or unsubstituted alkyl (e.g., C$_1$-C$_8$ alkyl, C$_1$-C$_6$ alkyl, or C$_1$-C$_4$ alkyl), R$^{27}$-substituted or unsubstituted heteroalkyl (e.g., 2 to 8 membered heteroalkyl, 2 to 6 membered heteroalkyl, or 2 to 4 membered heteroalkyl), R$^{27}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{27}$-substituted or unsubstituted heterocycloalkyl (e.g., 3 to 8 membered heterocycloalkyl, 3 to 6 membered heterocycloalkyl, or 5 to 6 membered heterocycloalkyl), R$^{27}$-substituted or unsubstituted aryl (e.g., C$_6$-C$_{10}$ aryl, C$_{10}$ aryl, or phenyl), or R$^{27}$-substituted or unsubstituted heteroaryl (e.g., 5 to 10 membered heteroaryl, 5 to 9 membered heteroaryl, or 5 to 6 membered heteroaryl).

In embodiments, R$^4$ is R$^{26}$-substituted or unsubstituted alkyl (e.g., C$_1$-C$_8$ alkyl, C$_1$-C$_6$ alkyl, or C$_1$-C$_4$ alkyl). In embodiments, R$^4$ is R$^{26}$-substituted alkyl (e.g., C$_1$-C$_8$ alkyl, C$_1$-C$_6$ alkyl, or C$_1$-C$_4$ alkyl). In embodiments, R$^4$ is an unsubstituted alkyl (e.g., C$_1$-C$_8$ alkyl, C$_1$-C$_6$ alkyl, or C$_1$-C$_4$ alkyl).

In embodiments, R$^4$ is R$^{26}$-substituted or unsubstituted heteroalkyl (e.g., 2 to 8 membered heteroalkyl, 2 to 6 membered heteroalkyl, or 2 to 4 membered heteroalkyl). In embodiments, R$^4$ is R$^{26}$-substituted heteroalkyl (e.g., 2 to 8 membered heteroalkyl, 2 to 6 membered heteroalkyl, or 2 to 4 membered heteroalkyl). In embodiments, R$^4$ is an unsubstituted heteroalkyl (e.g., 2 to 8 membered heteroalkyl, 2 to 6 membered heteroalkyl, or 2 to 4 membered heteroalkyl).

In embodiments, R$^4$ is R$^{26}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^4$ is R$^{26}$-substituted cycloalkyl (e.g., C$_3$-C$_8$ cycloalkyl, C$_3$-C$_6$ cycloalkyl, or C$_5$-C$_6$ cycloalkyl). In embodiments, R$^4$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^4$ is R$^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^4$ is R$^{26}$-substituted heterocycloalkyl (e.g., 3 to 8 membered heterocycloalkyl, 3 to 6 membered heterocycloalkyl, or 5 to 6 membered heterocycloalkyl). In embodiments, R$^4$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^4$ is R$^{26}$-substituted or unsubstituted aryl (e.g., C$_6$-C$_{10}$ aryl, C$_{10}$ aryl, or phenyl). In embodiments, R$^4$ is R$^{26}$-substituted aryl (e.g., C$_6$-C$_{10}$ aryl, C$_{10}$ aryl, or phenyl). In embodiments, R$^4$ is an unsubstituted aryl (e.g., C$_6$-C$_{10}$ aryl, C$_{10}$ aryl, or phenyl).

In embodiments, R$^4$ is R$^{26}$-substituted or unsubstituted heteroaryl (e.g., 5 to 10 membered heteroaryl, 5 to 9 membered heteroaryl, or 5 to 6 membered heteroaryl). In embodiments, R$^4$ is R$^{26}$-substituted heteroaryl (e.g., 5 to 10 membered heteroaryl, 5 to 9 membered heteroaryl, or 5 to 6 membered heteroaryl). In embodiments, R$^4$ is an unsubstituted heteroaryl (e.g., 5 to 10 membered heteroaryl, 5 to 9 membered heteroaryl, or 5 to 6 membered heteroaryl).

In embodiments, R$^4$ is the side chain of aspartic acid, glutamic acid, 2-amino-3-(2H-1,2,3,4-tetrazol-5-yl)propanoic acid (AspTtz), or 2-amino-3-(2H-1,2,3,4-tetrazol-5-yl)butanoic acid (GluTtz). In embodiments, R$^4$ is the side chain of aspartic acid. In embodiments, R$^4$ is the side chain of glutamic acid. In embodiments, R$^4$ is the side chain of 2-amino-3-(2H-1,2,3,4-tetrazol-5-yl)propanoic acid (AspTtz). In embodiments, R$^4$ is the side chain of 2-amino-3-(2H-1,2,3,4-tetrazol-5-yl)butanoic acid (GluTtz).

In embodiments, R$^4$ is CH$_2$COOH.

In embodiments, R$^4$ is —OH, —NH$_2$, —COOH, —CONH$_2$, —SH, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted aryl, or substituted or unsubstituted heteroaryl. In embodiments, R$^4$ is —OH. In embodiments, R$^4$ is —NH$_2$. In embodiments, R$^4$ is —COOH. In embodiments, R$^4$ is —CONH$_2$. In embodiments, R$^4$ is —SH. In embodiments, R$^4$ is —NHC(O)NH$_2$. In embodiments, R$^4$ is —NHSO$_2$H. In embodiments, R$^4$ is —NHC(O)H. In embodiments, R$^4$ is —NHC(O)OH. In embodiments, R$^4$ is —NHOH. In embodiments, R$^4$ is substituted or unsubstituted alkyl. In embodiments, R$^4$ is substituted or unsubstituted heteroalkyl. In embodiments, R$^4$ is substituted or unsubstituted aryl. In embodiments, R$^4$ is or substituted or unsubstituted heteroaryl.

In embodiments, R$^5$ is a halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, an amino acid side chain, R$^{28}$-substituted or unsubstituted alkyl (e.g., C$_1$-C$_8$ alkyl, C$_1$-C$_6$ alkyl, or C$_1$-C$_4$ alkyl), R$^{28}$-substituted or unsubstituted heteroalkyl (e.g., 2 to 8 membered heteroalkyl, 2 to 6 membered heteroalkyl, or 2 to 4 membered heteroalkyl), R$^{28}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{28}$-substituted or unsubstituted heterocycloalkyl (e.g., 3 to 8 membered heterocycloalkyl, 3 to 6 membered heterocycloalkyl, or 5 to 6 membered heterocycloalkyl), R$^{28}$-substituted or unsubstituted aryl (e.g., C$_6$-C$_{10}$ aryl, C$_{10}$ aryl, or phenyl), or R$^{28}$-substituted or unsubstituted heteroaryl (e.g., 5 to 10 membered heteroaryl, 5 to 9 membered heteroaryl, or 5 to 6 membered heteroaryl).

R$^{28}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{29}$-substituted or unsubstituted alkyl (e.g., C$_1$-C$_8$ alkyl, C$_1$-C$_6$ alkyl, or C$_1$-C$_4$ alkyl), R$^{29}$-substituted or unsubstituted heteroalkyl (e.g., 2 to 8 membered heteroalkyl, 2 to 6 membered heteroalkyl, or 2 to 4 membered heteroalkyl), R$^{29}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{29}$-substituted or unsubstituted heterocycloalkyl (e.g., 3 to 8 membered heterocycloalkyl, 3 to 6 membered heterocycloalkyl, or 5 to 6 membered heterocycloalkyl), R$^{29}$-substituted or unsubstituted aryl (e.g., C$_6$-C$_{10}$ aryl, C$_{10}$ aryl, or phenyl), or R$^{29}$-substituted or unsubstituted heteroaryl (e.g., 5 to 10 membered heteroaryl, 5 to 9 membered heteroaryl, or 5 to 6 membered heteroaryl).

In embodiments, R$^5$ is R$^{28}$-substituted or unsubstituted alkyl (e.g., C$_1$-C$_8$ alkyl, C$_1$-C$_6$ alkyl, or C$_1$-C$_4$ alkyl). In embodiments, R$^5$ is R$^{28}$-substituted alkyl (e.g., C$_1$-C$_8$ alkyl, $C_1$-$C_6$ alkyl, or $C_1$-$C_4$ alkyl). In embodiments, $R^5$ is an unsubstituted alkyl (e.g., $C_1$-$C_8$ alkyl, $C_1$-$C_6$ alkyl, or $C_1$-$C_4$ alkyl).

In embodiments, $R^5$ is $R^{28}$-substituted or unsubstituted methyl. In embodiments, $R^5$ is $R^{28}$-substituted or unsubstituted $C_2$ alkyl. In embodiments, $R^5$ is $R^{28}$-substituted or unsubstituted $C_3$ alkyl. In embodiments, $R^5$ is $R^{28}$-substituted or unsubstituted $C_4$ alkyl. In embodiments, $R^5$ is $R^{28}$-substituted or unsubstituted $C_5$ alkyl. In embodiments, $R^5$ is $R^{28}$-substituted or unsubstituted $C_6$ alkyl. In embodiments, $R^5$ is $R^{28}$-substituted or unsubstituted $C_7$ alkyl. In embodiments, $R^5$ is $R^{28}$-substituted or unsubstituted $C_8$ alkyl. In embodiments, $R^5$ is $R^{28}$-substituted methyl. In embodiments, $R^5$ is $R^{28}$-substituted $C_2$ alkyl. In embodiments, $R^5$ is $R^{28}$-substituted $C_3$ alkyl. In embodiments, $R^5$ is $R^{28}$-substituted $C_4$ alkyl. In embodiments, $R^5$ is $R^{28}$-substituted $C_5$ alkyl. In embodiments, $R^5$ is $R^{28}$-substituted $C_6$ alkyl. In embodiments, $R^5$ is $R^{28}$-substituted $C_7$ alkyl. In embodiments, $R^5$ is $R^{28}$-substituted $C_8$ alkyl. In embodiments, $R^5$ is an unsubstituted methyl. In embodiments, $R^5$ is an unsubstituted $C_2$ alkyl. In embodiments, $R^5$ is an unsubstituted $C_3$ alkyl. In embodiments, $R^5$ is an unsubstituted $C_4$ alkyl. In embodiments, $R^5$ is an unsubstituted $C_5$ alkyl. In embodiments, $R^5$ is an unsubstituted $C_6$ alkyl. In embodiments, $R^5$ is an unsubstituted $C_7$ alkyl. In embodiments, $R^5$ is an unsubstituted $C_8$ alkyl.

In embodiments, $R^5$ is $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^5$ is $R^{28}$-substituted heteroalkyl (e.g., 2 to 8 membered heteroalkyl, 2 to 6 membered heteroalkyl, or 2 to 4 membered heteroalkyl). In embodiments, $R^5$ is an unsubstituted heteroalkyl (e.g., 2 to 8 membered heteroalkyl, 2 to 6 membered heteroalkyl, or 2 to 4 membered heteroalkyl).

In embodiments, $R^5$ is $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is $R^{28}$-substituted cycloalkyl (e.g., $C_3$-$C_8$ cycloalkyl, $C_3$-$C_6$ cycloalkyl, or $C_5$-$C_6$ cycloalkyl). In embodiments, $R^5$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^5$ is $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is $R^{28}$-substituted heterocycloalkyl (e.g., 3 to 8 membered heterocycloalkyl, 3 to 6 membered heterocycloalkyl, or 5 to 6 membered heterocycloalkyl). In embodiments, $R^5$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^5$ is $R^{28}$-substituted or unsubstituted aryl (e.g., $C_6$-$C_{10}$ aryl, $C_{10}$ aryl, or phenyl). In embodiments, $R^5$ is $R^{28}$-substituted aryl (e.g., $C_6$-$C_{10}$ aryl, $C_{10}$ aryl, or phenyl). In embodiments, $R^5$ is an unsubstituted aryl (e.g., $C_6$-$C_{10}$ aryl, $C_{10}$ aryl, or phenyl).

In embodiments, $R^5$ is $R^{28}$-substituted or unsubstituted heteroaryl (e.g., 5 to 10 membered heteroaryl, 5 to 9 membered heteroaryl, or 5 to 6 membered heteroaryl). In embodiments, $R^5$ is $R^{28}$-substituted heteroaryl (e.g., 5 to 10 membered heteroaryl, 5 to 9 membered heteroaryl, or 5 to 6 membered heteroaryl). In embodiments, $R^5$ is an unsubstituted heteroaryl (e.g., 5 to 10 membered heteroaryl, 5 to 9 membered heteroaryl, or 5 to 6 membered heteroaryl).

In embodiments, $R^5$ is a side chain of a hydrophobic amino acid (e.g., the side chain of glycine (Gly), alanine (Ala), valine (Val), leucine (Leu), isoleucine (Ile), proline (Pro), phenylalanine (Phe), methionine (Met), or tryptophan (Trp)). In embodiments, $R^5$ is a side chain of glycine. In embodiments, $R^5$ is a side chain of alanine. In embodiments, $R^5$ is a side chain of valine. In embodiments, $R^5$ is a side chain of leucine. In embodiments, $R^5$ is a side chain of isoleucine. In embodiments, $R^5$ is a side chain of proline. In embodiments, $R^5$ is a side chain of phenylalanine. In embodiments, $R^5$ is a side chain methionine. In embodiments, $R^5$ is a side chain of tryptophan.

In embodiments, $R^6$ is a halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, an amino acid side chain, $R^{30}$-substituted or unsubstituted alkyl (e.g., $C_1$-$C_8$ alkyl, $C_1$-$C_6$ alkyl, or $C_1$-$C_4$ alkyl), $R^{30}$-substituted or unsubstituted heteroalkyl (e.g., 2 to 8 membered heteroalkyl, 2 to 6 membered heteroalkyl, or 2 to 4 membered heteroalkyl), $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{30}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30}$-substituted or unsubstituted aryl (e.g., $C_6$-$C_{10}$ aryl, $C_{10}$ aryl, or phenyl), or $R^{30}$-substituted or unsubstituted heteroaryl (e.g., 5 to 10 membered heteroaryl, 5 to 9 membered heteroaryl, or 5 to 6 membered heteroaryl).

$R^{30}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{31}$-substituted or unsubstituted alkyl (e.g., $C_1$-$C_8$ alkyl, $C_1$-$C_6$ alkyl, or $C_1$-$C_4$ alkyl), $R^{31}$-substituted or unsubstituted heteroalkyl (e.g., 2 to 8 membered heteroalkyl, 2 to 6 membered heteroalkyl, or 2 to 4 membered heteroalkyl), $R^{31}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31}$-substituted or unsubstituted aryl (e.g., $C_6$-$C_{10}$ aryl, $C_{10}$ aryl, or phenyl), or $R^{31}$-substituted or unsubstituted heteroaryl (e.g., 5 to 10 membered heteroaryl, 5 to 9 membered heteroaryl, or 5 to 6 membered heteroaryl).

In embodiments, $R^6$ is $R^{30}$-substituted or unsubstituted alkyl (e.g., $C_1$-$C_5$ alkyl, $C_1$-$C_6$ alkyl, or $C_1$-$C_4$ alkyl). In embodiments, $R^6$ is $R^{30}$-substituted alkyl (e.g., $C_1$-$C_5$ alkyl, $C_1$-$C_6$ alkyl, or $C_1$-$C_4$ alkyl). In embodiments, $R^6$ is an unsubstituted alkyl (e.g., $C_1$-$C_8$ alkyl, $C_1$-$C_6$ alkyl, or $C_1$-$C_4$ alkyl).

In embodiments, $R^6$ is $R^{30}$-substituted or unsubstituted methyl. In embodiments, $R^6$ is $R^{30}$-substituted or unsubstituted $C_2$ alkyl. In embodiments, $R^6$ is $R^{30}$-substituted or unsubstituted $C_3$ alkyl. In embodiments, $R^6$ is $R^{30}$-substituted or unsubstituted $C_4$ alkyl. In embodiments, $R^6$ is $R^{30}$-substituted or unsubstituted $C_5$ alkyl. In embodiments, $R^6$ is $R^{30}$-substituted or unsubstituted $C_6$ alkyl. In embodiments, $R^6$ is $R^{30}$-substituted or unsubstituted $C_7$ alkyl. In embodiments, $R^6$ is $R^{30}$-substituted or unsubstituted $C_8$ alkyl. In embodiments, $R^6$ is $R^{30}$-substituted methyl. In embodiments, $R^6$ is $R^{30}$-substituted $C_2$ alkyl. In embodiments, $R^6$ is $R^{30}$-substituted $C_3$ alkyl. In embodiments, $R^6$ is $R^{30}$-substituted $C_4$ alkyl. In embodiments, $R^6$ is $R^{30}$-substituted $C_5$ alkyl. In embodiments, $R^6$ is $R^{30}$-substituted $C_6$ alkyl. In embodiments, $R^6$ is $R^{30}$-substituted $C_7$ alkyl. In embodiments, $R^6$ is $R^{30}$-substituted $C_5$ alkyl. In embodiments, $R^6$ is an unsubstituted methyl. In embodiments, $R^6$ is an unsubstituted $C_2$ alkyl. In embodiments, $R^6$ is an unsubstituted $C_3$ alkyl. In embodiments, $R^6$ is an unsubstituted $C_4$ alkyl. In embodiments, $R^6$ is an unsubstituted $C_5$ alkyl. In embodiments, $R^6$ is an unsubstituted $C_6$ alkyl. In embodiments, $R^6$ is an unsubstituted $C_7$ alkyl. In embodiments, $R^6$ is an unsubstituted $C_5$ alkyl.

In embodiments, $R^6$ is $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^6$ is $R^{30}$-substituted heteroalkyl (e.g., 2 to 8 membered heteroalkyl, 2 to 6 membered heteroalkyl, or 2 to 4 membered heteroalkyl). In embodiments, $R^6$ is an unsubstituted heteroalkyl (e.g., 2 to 8 membered heteroalkyl, 2 to 6 membered heteroalkyl, or 2 to 4 membered heteroalkyl).

In embodiments, $R^6$ is $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^6$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^6$ is $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^6$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^6$ is $R^{30}$-substituted or unsubstituted aryl (e.g., $C_6$-$C_{10}$ aryl, $C_{10}$ aryl, or phenyl). In embodiments, $R^6$ is $R^{30}$-substituted aryl (e.g., $C_6$-$C_{10}$ aryl, $C_{10}$ aryl, or phenyl). In embodiments, $R^6$ is an unsubstituted aryl (e.g., $C_6$-$C_{10}$ aryl, $C_{10}$ aryl, or phenyl).

In embodiments, $R^6$ is $R^{30}$-substituted or unsubstituted heteroaryl (e.g., 5 to 10 membered heteroaryl, 5 to 9 membered heteroaryl, or 5 to 6 membered heteroaryl). In embodiments, $R^6$ is $R^{30}$-substituted heteroaryl (e.g., 5 to 10 membered heteroaryl, 5 to 9 membered heteroaryl, or 5 to 6 membered heteroaryl). In embodiments, $R^6$ is an unsubstituted heteroaryl (e.g., 5 to 10 membered heteroaryl, 5 to 9 membered heteroaryl, or 5 to 6 membered heteroaryl).

In embodiments, $R^6$ is the side chain of an amino acid. In embodiments, $R^6$ is hydrogen,

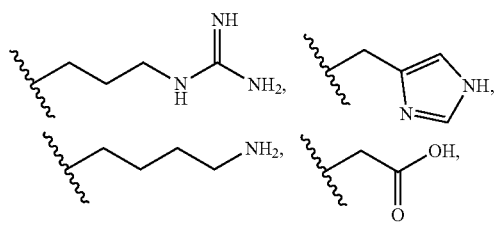

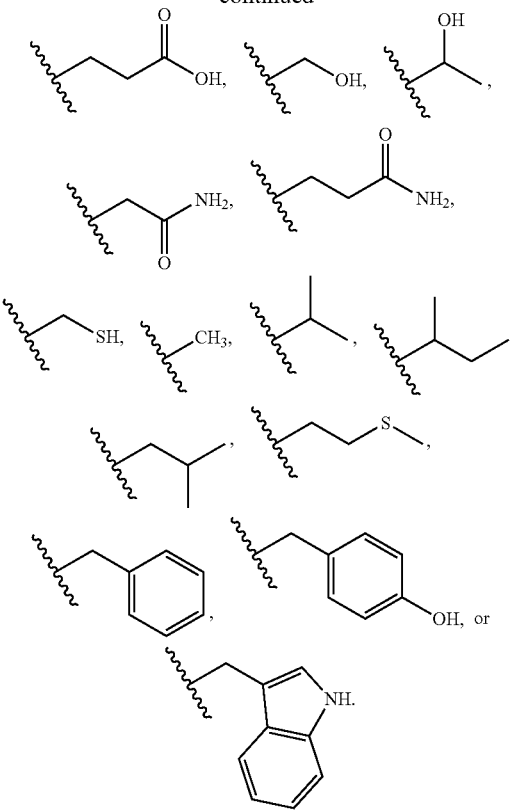

In embodiments, $R^7$ is a halogen, —$CCl_3$, —$CF_3$, —$CI_3$, —$CH_2Cl$, —$CH_2Br$, —$CH_2F$, —$CHCl_2$, —$CHBr_2$, —$CHF_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCBr_3$, —$OCF_3$, —$OCI_3$, —$OCH_2Cl$, —$OCH_2Br$, —$OCH_2F$, —$OCHCl_2$, —$OCHBr_2$, —$OCHF_2$, —$OCHI_2$, an amino acid side chain, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl).

$R^{32}$ is independently oxo, halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, —$SO_2F$, —$OSO_2F$, E, $R^{33}$-substituted or unsubstituted alkyl (e.g., $C_1$-$C_8$ alkyl, $C_1$-$C_6$ alkyl, or $C_1$-$C_4$ alkyl), $R^{33}$-substituted or unsubstituted heteroalkyl (e.g., 2 to 8 membered heteroalkyl, 2 to 6 membered heteroalkyl, or 2 to 4 membered heteroalkyl), $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33}$-substituted or unsubstituted aryl (e.g., $C_6$-$C_{10}$ aryl, $C_{10}$ aryl, or phenyl), or $R^{33}$-substituted or unsubstituted heteroaryl (e.g., 5 to 10 membered heteroaryl, 5 to 9 membered heteroaryl, or 5 to 6 membered heteroaryl).

In embodiments, $R^{32}$ is independently oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $R^{33}$-substituted or unsubstituted alkyl (e.g., $C_1$-$C_8$ alkyl, $C_1$-$C_6$ alkyl, or $C_1$-$C_4$ alkyl), $R^{33}$-substituted or unsubstituted heteroalkyl (e.g., 2 to 8 membered heteroalkyl, 2 to 6 membered heteroalkyl, or 2 to 4 membered heteroalkyl), $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33}$-substituted or unsubstituted aryl (e.g., $C_6$-$C_{10}$ aryl, $C_{10}$ aryl, or phenyl), or $R^{33}$-substituted or unsubstituted heteroaryl (e.g., 5 to 10 membered heteroaryl, 5 to 9 membered heteroaryl, or 5 to 6 membered heteroaryl).

In embodiments, $R^{32}$ is independently $-SO_2F$, $-OSO_2F$, or E. In embodiments, $R^{32}$ is independently $-SO_2F$. In embodiments, $R^{32}$ is independently $-OSO_2F$. In embodiments, $R^{32}$ is independently E.

In embodiments, $R^7$ is $R^{32}$-substituted or unsubstituted alkyl (e.g., $C_1$-$C_8$ alkyl, $C_1$-$C_6$ alkyl, or $C_1$-$C_4$ alkyl). In embodiments, $R^7$ is $R^{32}$-substituted alkyl (e.g., $C_1$-$C_8$ alkyl, $C_1$-$C_6$ alkyl, or $C_1$-$C_4$ alkyl). In embodiments, $R^7$ is an unsubstituted alkyl (e.g., $C_1$-$C_8$ alkyl, $C_1$-$C_6$ alkyl, or $C_1$-$C_4$ alkyl).

In embodiments, $R^7$ is $R^{32}$-substituted or unsubstituted heteroalkyl (e.g., 2 to 8 membered heteroalkyl, 2 to 6 membered heteroalkyl, or 2 to 4 membered heteroalkyl). In embodiments, $R^7$ is $R^{32}$-substituted heteroalkyl (e.g., 2 to 8 membered heteroalkyl, 2 to 6 membered heteroalkyl, or 2 to 4 membered heteroalkyl). In embodiments, $R^7$ is an unsubstituted heteroalkyl (e.g., 2 to 8 membered heteroalkyl, 2 to 6 membered heteroalkyl, or 2 to 4 membered heteroalkyl).

In embodiments, $R^7$ is $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^7$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^7$ is $R^{32}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{32}$-substituted heterocycloalkyl (e.g., 3 to 8 membered heterocycloalkyl, 3 to 6 membered heterocycloalkyl, or 5 to 6 membered heterocycloalkyl). In embodiments, $R^7$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^7$ is $R^{32}$-substituted or unsubstituted aryl (e.g., $C_6$-$C_{10}$ aryl, $C_{10}$ aryl, or phenyl). In embodiments, $R^7$ is $R^{32}$-substituted aryl (e.g., $C_6$-$C_{10}$ aryl, $C_{10}$ aryl, or phenyl). In embodiments, $R^7$ is an unsubstituted aryl (e.g., $C_6$-$C_{10}$ aryl, $C_{10}$ aryl, or phenyl).

In embodiments, $R^7$ is $R^{32}$-substituted or unsubstituted heteroaryl (e.g., 5 to 10 membered heteroaryl, 5 to 9 membered heteroaryl, or 5 to 6 membered heteroaryl). In embodiments, $R^7$ is $R^{32}$-substituted heteroaryl (e.g., 5 to 10 membered heteroaryl, 5 to 9 membered heteroaryl, or 5 to 6 membered heteroaryl). In embodiments, $R^7$ is an unsubstituted heteroaryl (e.g., 5 to 10 membered heteroaryl, 5 to 9 membered heteroaryl, or 5 to 6 membered heteroaryl).

In embodiments, $R^7$ is the side chain of an amino acid. In embodiments, $R^7$ is hydrogen,

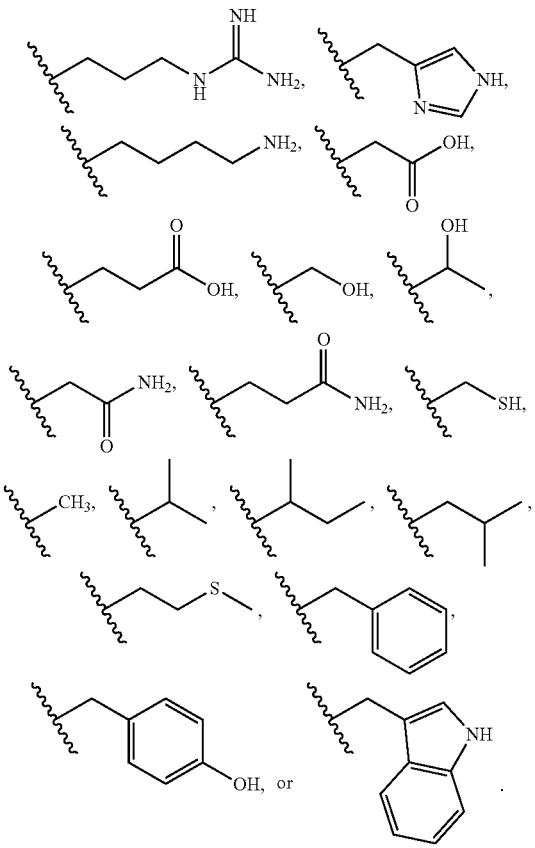

In embodiments, $R^7$ is the side chain of an amino acid, substituted or unsubstituted aryl, or substituted or unsubstituted heteroaryl. In embodiments, $R^7$ is substituted or unsubstituted aryl, or substituted or unsubstituted heteroaryl. In embodiments, $R^7$ is substituted or unsubstituted aryl. In embodiments, $R^7$ is substituted or unsubstituted heteroaryl.

In embodiments, $R^7$ is

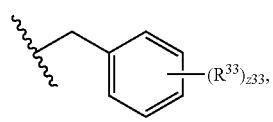

wherein $R^{33}$ is as described herein. The symbol z33 is an integer from 0 to 5. In embodiments, z33 is 1. In embodiments, z33 is 2. In embodiments, z33 is 0. In embodiments, $R^7$ is

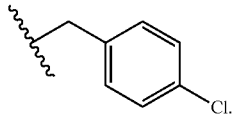 [SMILES: *Cc1ccc(Cl)cc1]

In embodiments, $R^7$ is

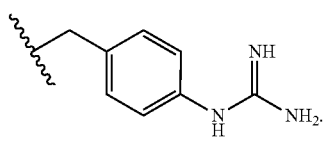 [SMILES: *Cc1ccc(NC(=N)N)cc1]

In embodiments, $R^7$ is

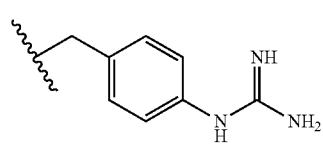 [SMILES: *Cc1ccc(NC(=N)N)cc1]

and $R^8$ is hydrogen. In embodiments, $R^7$ is

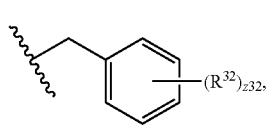

wherein z32 and $R^{32}$ are as described herein; and $R^8$ is

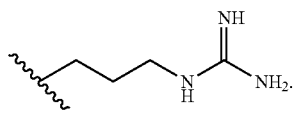

In embodiments, $R^7$ is

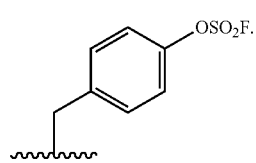

In embodiments, $R^7$ is

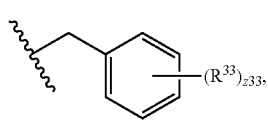

wherein $R^{33}$ is as described herein. The symbol z33 is an integer from 0 to 5. In embodiments, z33 is 1. In embodiments, z33 is 2. In embodiments, z33 is 0. In embodiments, $R^7$ is

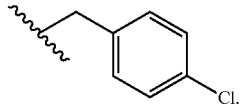 [SMILES: *Cc1ccc(Cl)cc1]

In embodiments, $R^7$ is

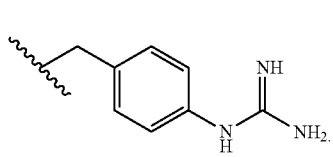 [SMILES: *Cc1ccc(NC(=N)N)cc1]

In embodiments, $R^7$ is

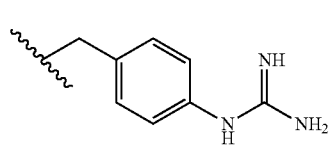 [SMILES: *Cc1ccc(NC(=N)N)cc1]

and $R^8$ is hydrogen. In embodiments, $R^7$ is

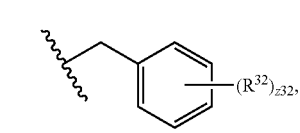

wherein z32 and $R^{32}$ are as described herein; and $R^8$ is

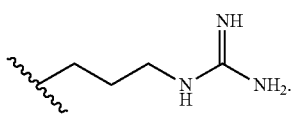 [SMILES: *CCCNC(=N)N]

In embodiments, $R^7$ includes an electrophilic moiety. In embodiments, $R^7$ includes an electrophilic moiety capable of forming a covalent bond with a cysteine residue (e.g., EphA2 cysteine residue). In embodiments, $R^7$ includes an electrophilic moiety capable of forming a covalent bond with a lysine residue (e.g., EphA2 lysine residue). In embodiments, $R^7$ includes an electrophilic moiety capable of forming a covalent bond with a tyrosine residue (e.g., EphA2 tyrosine residue). In embodiments, $R^7$ includes an electrophilic moiety capable of forming a covalent bond with a histidine residue (e.g., EphA2 histidine residue). In embodiments, $R^7$ is independently

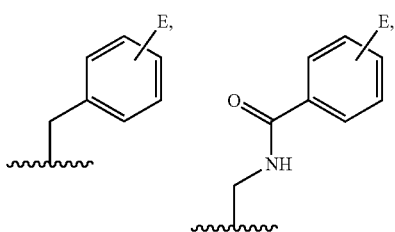

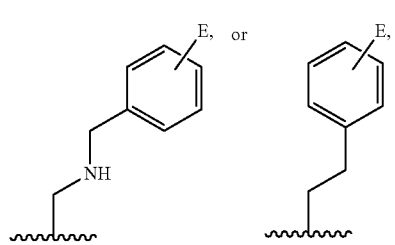

wherein E is an electrophilic moiety. In embodiments, $R^7$ is independently

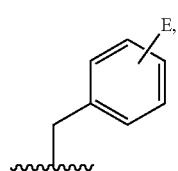

wherein E is an electrophilic moiety. In embodiments, $R^7$ is independently

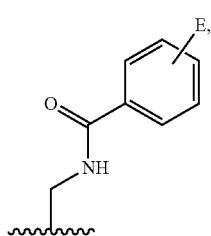

wherein E is an electrophilic moiety. In embodiments, $R^7$ is independently

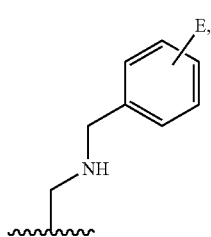

wherein E is an electrophilic moiety. In embodiments, $R^7$ is independently

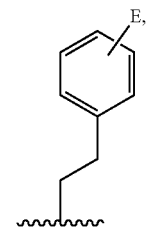

wherein E is an electrophilic moiety. In embodiments, $R^7$ is independently

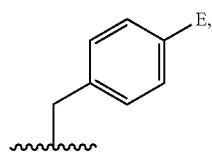

wherein E is an electrophilic moiety. In embodiments, $R^7$ is independently

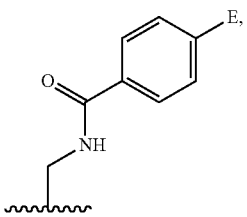 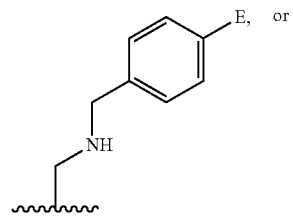

wherein E is an electrophilic moiety. In embodiments, $R^7$ is independently

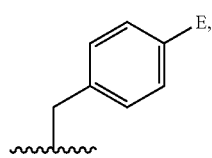

wherein E is an electrophilic moiety. In embodiments, $R^7$ is independently

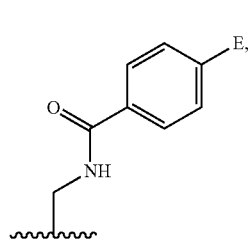

wherein E is an electrophilic moiety. In embodiments, $R^7$ is independently

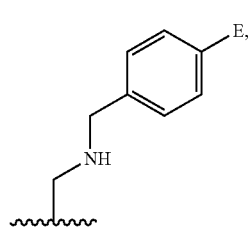

wherein E is an electrophilic moiety. In embodiments, $R^7$ is independently

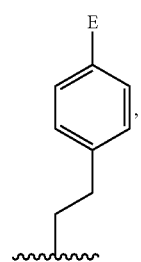

wherein E is an electrophilic moiety. In embodiments, $R^7$ is independently

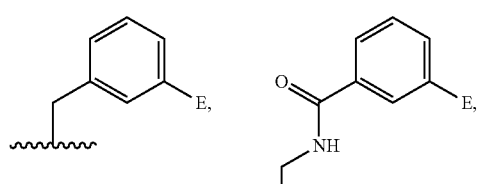

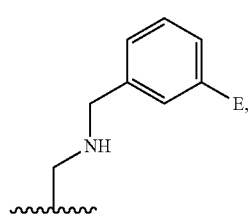

or

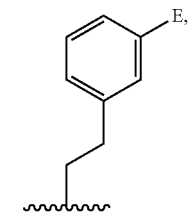

wherein E is an electrophilic moiety. In embodiments, $R^7$ is independently

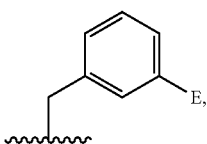

wherein E is an electrophilic moiety. In embodiments, $R^7$ is independently

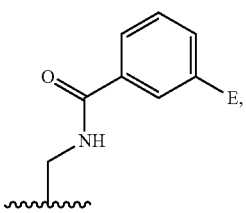

wherein E is an electrophilic moiety. In embodiments, $R^7$ is independently

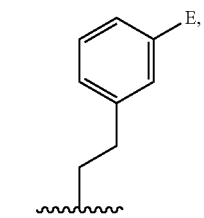

wherein E is an electrophilic moiety. In embodiments, $R^7$ is independently

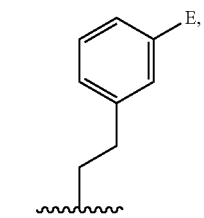

wherein E is an electrophilic moiety. In embodiments, E is —$OSO^2F$ or —$SO_2F$. In embodiments, E is —$OSO_2F$. In embodiments, E is —$SO_2F$.

In embodiments, $R^7$ is independently
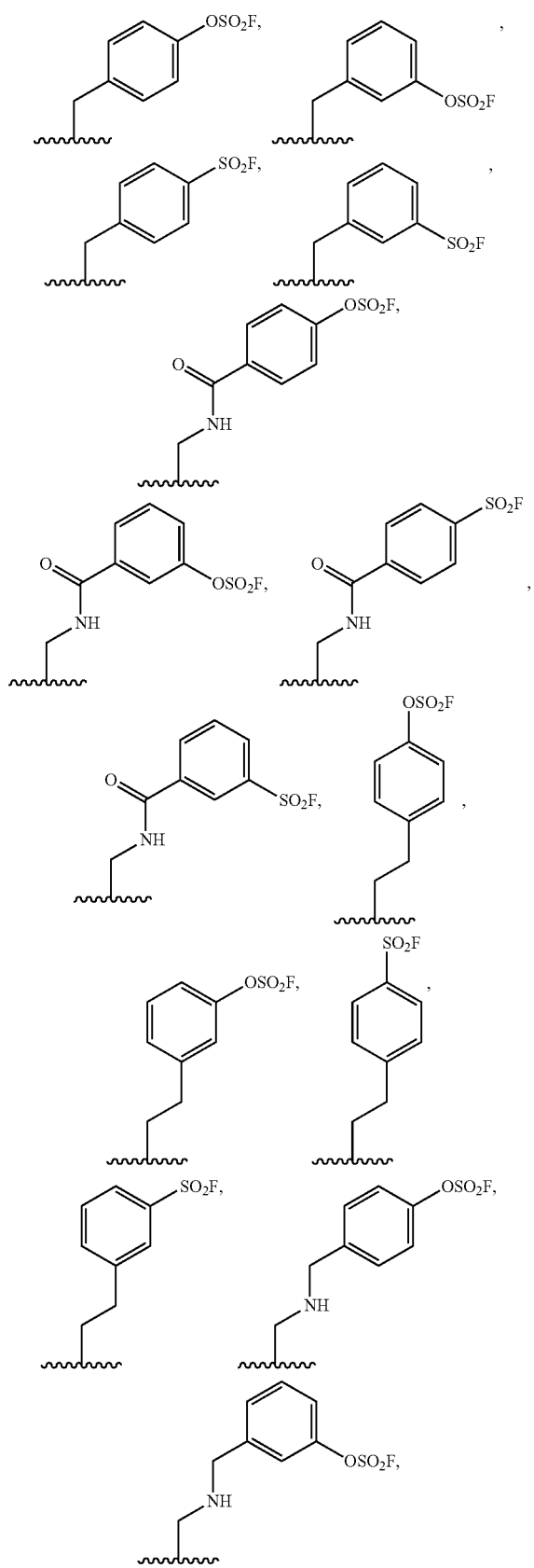
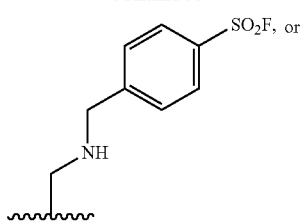
In embodiments, $R^7$ is independently
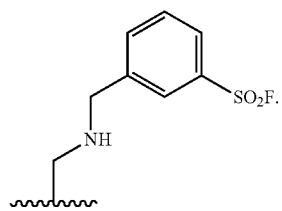
In embodiments, $R^7$ is independently
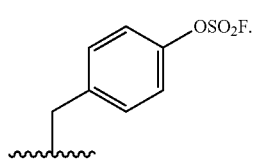
In embodiments, $R^7$ is independently
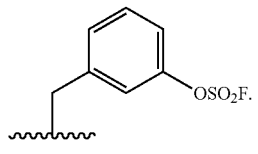
In embodiments, $R^7$ is independently
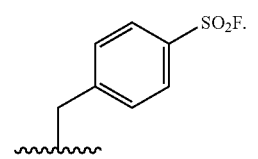 [SMILES: *Cc1ccc(S(=O)(=O)F)cc1]
In embodiments, $R^7$ is independently
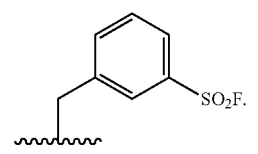 [SMILES: *Cc1cccc(S(=O)(=O)F)c1]

In embodiments, $R^7$ is independently

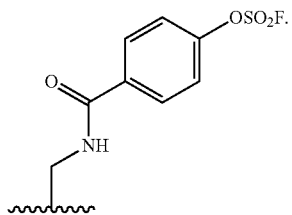

In embodiments, $R^7$ is independently

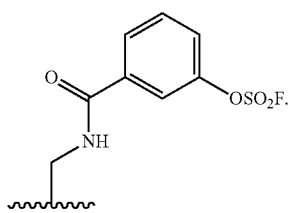

In embodiments, $R^7$ is independently

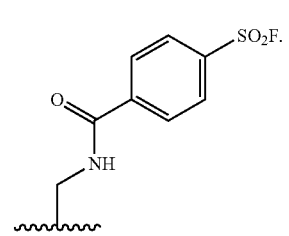 [SMILES: *CNC(=O)c1ccc(S(=O)(=O)F)cc1]

In embodiments, $R^7$ is independently

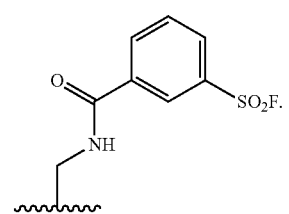 [SMILES: *CNC(=O)c1cccc(S(=O)(=O)F)c1]

In embodiments, $R^7$ is independently

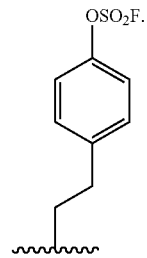

In embodiments, $R^7$ is independently

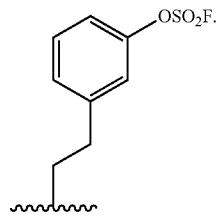

In embodiments, $R^7$ is independently

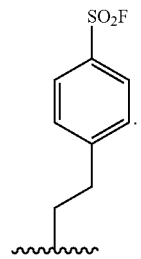 [SMILES: *CCc1ccc(S(=O)(=O)F)cc1]

In embodiments, $R^7$ is independently

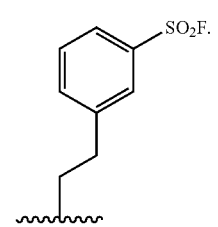 [SMILES: *CCc1cccc(S(=O)(=O)F)c1]

In embodiments, $R^7$ is independently

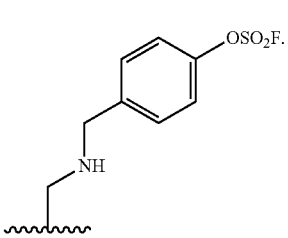

In embodiments, $R^7$ is independently

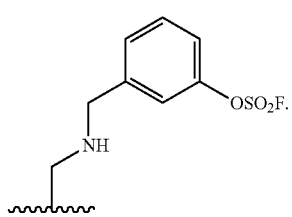

In embodiments, R⁷ is independently

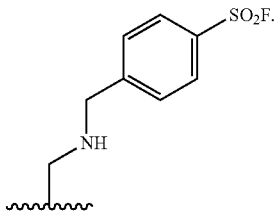

In embodiments, R⁷ is independently

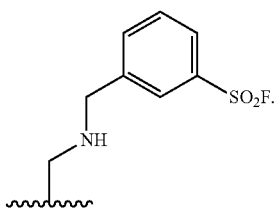 [SMILES: *CNCc1cccc(S(=O)(=O)F)c1]

In embodiments, R⁷ is independently

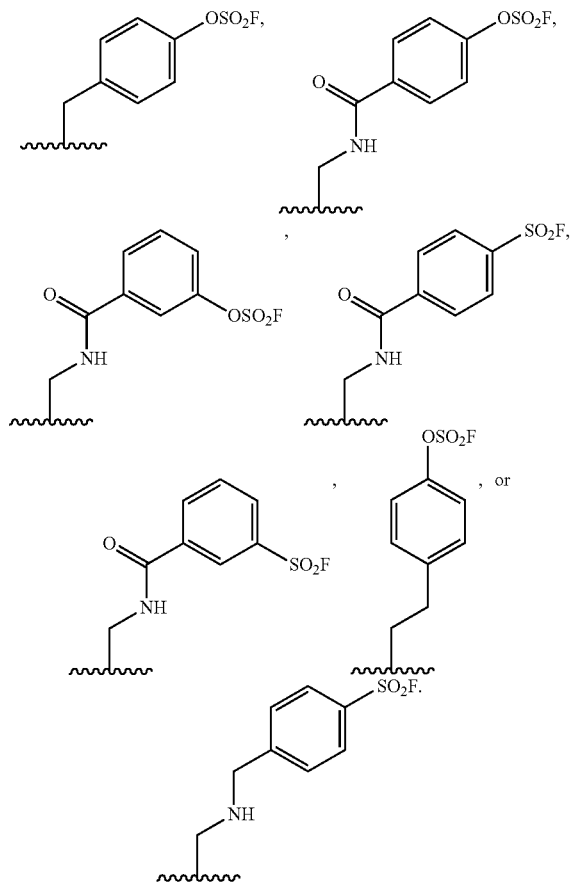

In embodiments, R⁸ is a halogen, —CCl₃, —CF₃, —CI₃, —CH₂Cl, —CH₂Br, —CH₂F, —CH₂I, —CHCl₂, —CHBr₂, —CHF₂, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCBr₃, —OCF₃, —OCI₃, —OCH₂Cl, —OCH₂Br, —OCH₂F, —OCHCl₂, —OCHBr₂, —OCHF₂, —OCHI₂, an amino acid side chain, R³⁴-substituted or unsubstituted alkyl (e.g., C₁-C₈ alkyl, C₁-C₆ alkyl, or C₁-C₄ alkyl), R³⁴-substituted or unsubstituted heteroalkyl (e.g., 2 to 8 membered heteroalkyl, 2 to 6 membered heteroalkyl, or 2 to 4 membered heteroalkyl), R³⁴-substituted or unsubstituted cycloalkyl (e.g., C₃-C₈ cycloalkyl, C₃-C₆ cycloalkyl, or C₅-C₆ cycloalkyl), R³⁴-substituted or unsubstituted heterocycloalkyl (e.g., 3 to 8 membered heterocycloalkyl, 3 to 6 membered heterocycloalkyl, or 5 to 6 membered heterocycloalkyl), R³⁴-substituted or unsubstituted aryl (e.g., C₆-C₁₀ aryl, C₁₀ aryl, or phenyl), or R³⁴-substituted or unsubstituted heteroaryl (e.g., 5 to 10 membered heteroaryl, 5 to 9 membered heteroaryl, or 5 to 6 membered heteroaryl).

R³⁴ is independently oxo, halogen, —CCl₃, —CF₃, —CI₃, —CHCl₂, —CHBr₂, —CHF₂, —CH₂Cl, —CH₂Br, —CH₂F, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHF₂, —OCH₂Cl, —OCH₂Br, —OCH₂F, —N₃, R³⁵-substituted or unsubstituted alkyl (e.g., C₁-C₈ alkyl, C₁-C₆ alkyl, or C₁-C₄ alkyl), R³⁵-substituted or unsubstituted heteroalkyl (e.g., 2 to 8 membered heteroalkyl, 2 to 6 membered heteroalkyl, or 2 to 4 membered heteroalkyl), R³⁵-substituted or unsubstituted cycloalkyl (e.g., C₃-C₈ cycloalkyl, C₃-C₆ cycloalkyl, or C₅-C₆ cycloalkyl), R³⁵-substituted or unsubstituted heterocycloalkyl (e.g., 3 to 8 membered heterocycloalkyl, 3 to 6 membered heterocycloalkyl, or 5 to 6 membered heterocycloalkyl), R³⁵-substituted or unsubstituted aryl (e.g., C₆-C₁₀ aryl, C₁₀ aryl, or phenyl), or R³⁵-substituted or unsubstituted heteroaryl (e.g., 5 to 10 membered heteroaryl, 5 to 9 membered heteroaryl, or 5 to 6 membered heteroaryl).

In embodiments, R⁸ is R³⁴-substituted or unsubstituted alkyl (e.g., C₁-C₈ alkyl, C₁-C₆ alkyl, or C₁-C₄ alkyl). In embodiments, R⁸ is R³⁴-substituted alkyl (e.g., C₁-C₈ alkyl, C₁-C₆ alkyl, or C₁-C₄ alkyl). In embodiments, R⁸ is an unsubstituted alkyl (e.g., C₁-C₈ alkyl, C₁-C₆ alkyl, or C₁-C₄ alkyl).

In embodiments, R⁸ is R³⁴-substituted or unsubstituted heteroalkyl (e.g., 2 to 8 membered heteroalkyl, 2 to 6 membered heteroalkyl, or 2 to 4 membered heteroalkyl). In embodiments, R⁸ is R³⁴-substituted heteroalkyl (e.g., 2 to 8 membered heteroalkyl, 2 to 6 membered heteroalkyl, or 2 to 4 membered heteroalkyl). In embodiments, R⁸ is an unsubstituted heteroalkyl (e.g., 2 to 8 membered heteroalkyl, 2 to 6 membered heteroalkyl, or 2 to 4 membered heteroalkyl).

In embodiments, R⁸ is R³⁴-substituted or unsubstituted cycloalkyl (e.g., C₃-C₈ cycloalkyl, C₃-C₆ cycloalkyl, or C₅-C₆ cycloalkyl). In embodiments, R⁸ is R³⁴-substituted cycloalkyl (e.g., C₃-C₈ cycloalkyl, C₃-C₆ cycloalkyl, or C₅-C₆ cycloalkyl). In embodiments, R⁸ is an unsubstituted cycloalkyl (e.g., C₃-C₈ cycloalkyl, C₃-C₆ cycloalkyl, or C₅-C₆ cycloalkyl).

In embodiments, R⁸ is R³⁴-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R⁸ is R³⁴-substituted heterocycloalkyl (e.g., 3 to 8 membered heterocycloalkyl, 3 to 6 membered heterocycloalkyl, or 5 to 6 membered heterocycloalkyl). In embodiments, R⁸ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^8$ is $R^{34}$-substituted or unsubstituted aryl (e.g., $C_6$-$C_{10}$ aryl, $C_{10}$ aryl, or phenyl). In embodiments, $R^8$ is $R^{34}$-substituted aryl (e.g., $C_6$-$C_{10}$ aryl, $C_{10}$ aryl, or phenyl). In embodiments, $R^8$ is an unsubstituted aryl (e.g., $C_6$-$C_{10}$ aryl, $C_{10}$ aryl, or phenyl).

In embodiments, $R^8$ is $R^{34}$-substituted or unsubstituted heteroaryl (e.g., 5 to 10 membered heteroaryl, 5 to 9 membered heteroaryl, or 5 to 6 membered heteroaryl). In embodiments, $R^8$ is $R^{34}$-substituted heteroaryl (e.g., 5 to 10 membered heteroaryl, 5 to 9 membered heteroaryl, or 5 to 6 membered heteroaryl). In embodiments, $R^8$ is an unsubstituted heteroaryl (e.g., 5 to 10 membered heteroaryl, 5 to 9 membered heteroaryl, or 5 to 6 membered heteroaryl).

In embodiments, $R^8$ is the side chain of an amino acid. In embodiments, $R^8$ is hydrogen,

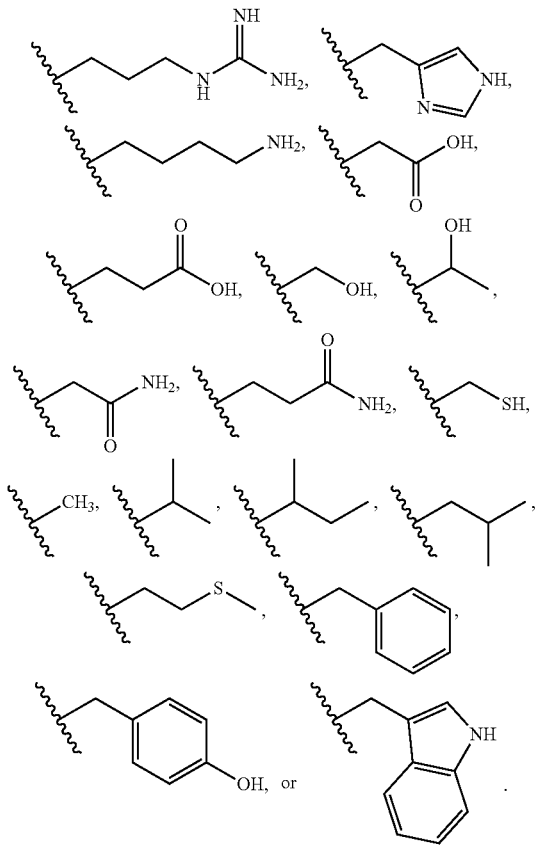

In embodiments, $R^8$ is the side chain of an amino acid, substituted or unsubstituted aryl, or substituted or unsubstituted heteroaryl. In embodiments, $R^8$ is substituted or unsubstituted aryl, or substituted or unsubstituted heteroaryl. In embodiments, $R^8$ is substituted or unsubstituted aryl. In embodiments, $R^8$ is substituted or unsubstituted heteroaryl. In embodiments, $R^8$ is

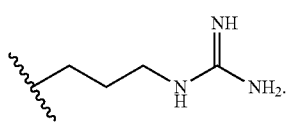 [SMILES: *CCCNC(=N)N]

In embodiments, $R^9$ and the nitrogen atom adjacent to the carbon to which $R^9$ is attached may optionally be joined to form a substituted or unsubstituted heterocycloalkyl, referred to as Ring B, for example having the formula:

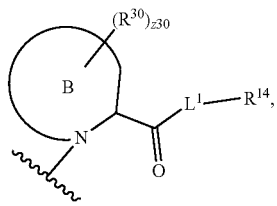

wherein $R^{30}$, $L^1$, and $R^{14}$ are as described herein. The symbol z30 is an integer from 0 to 10. In embodiments, z30 is 0. In embodiments, z30 is 1. In embodiments, z30 is 2. In embodiments, Ring B has the formula:

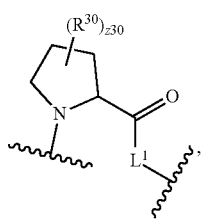

wherein $L^1$ is as described herein. In embodiments, Ring B has the formula:

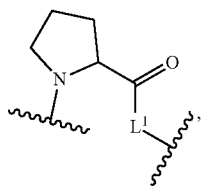

wherein $L^1$ is as described herein. In embodiments, Ring B has the formula:

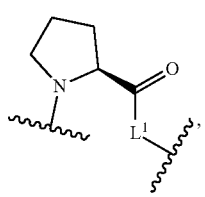

wherein $L^1$ is as described herein. In embodiments, Ring B has the formula:

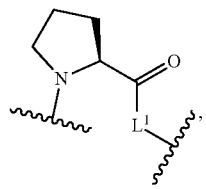

wherein $L^1$ is as described herein.

In embodiments, $R^9$ is an amino acid side chain, bioconjugate reactive moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is an amino acid side chain. In embodiments, $R^9$ is bioconjugate reactive moiety. In embodiments, $R^9$ is substituted or unsubstituted alkyl. In embodiments, $R^9$ is substituted or unsubstituted heteroalkyl. In embodiments, $R^9$ is substituted or unsubstituted cycloalkyl. In embodiments, $R^9$ is substituted or unsubstituted heterocycloalkyl. In embodiments, $R^9$ is substituted or unsubstituted aryl. In embodiments, $R^9$ is substituted or unsubstituted heteroaryl.

In embodiments, $R^9$ is bioconjugate reactive moiety, $R^{50}$-substituted or unsubstituted alkyl (e.g., $C_1$-$C_8$ alkyl, $C_1$-$C_6$ alkyl, or $C_1$-$C_4$ alkyl), $R^{50}$-substituted or unsubstituted heteroalkyl (e.g., 2 to 8 membered heteroalkyl, 2 to 6 membered heteroalkyl, or to 4 membered heteroalkyl), $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50}$-substituted or unsubstituted aryl (e.g., $C_6$-$C_{10}$ aryl, $C_{10}$ aryl, or phenyl), or $R^{50}$-substituted or unsubstituted heteroaryl (e.g., 5 to 10 membered heteroaryl, 5 to 9 membered heteroaryl, or 5 to 6 membered heteroaryl).

$R^{50}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{51}$-substituted or unsubstituted alkyl (e.g., $C_1$-$C_8$ alkyl, $C_1$-$C_6$ alkyl, or $C_1$-$C_4$ alkyl), $R^{51}$-substituted or unsubstituted heteroalkyl (e.g., 2 to 8 membered heteroalkyl, 2 to 6 membered heteroalkyl, or 2 to 4 membered heteroalkyl), $R^{51}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{51}$-substituted or unsubstituted heterocycloalkyl (e.g., 3 to 8 membered heterocycloalkyl, 3 to 6 membered heterocycloalkyl, or 5 to 6 membered heterocycloalkyl), $R^{51}$-substituted or unsubstituted aryl (e.g., $C_6$-$C_{10}$ aryl, $C_{10}$ aryl, or phenyl), or $R^{51}$-substituted or unsubstituted heteroaryl (e.g., 5 to 10 membered heteroaryl, 5 to 9 membered heteroaryl, or 5 to 6 membered heteroaryl).

In embodiments, $R^9$ is $R^{50}$-substituted or unsubstituted alkyl (e.g., $C_1$-$C_8$ alkyl, $C_1$-$C_6$ alkyl, or $C_1$-$C_4$ alkyl). In embodiments, $R^9$ is $R^{50}$-substituted alkyl (e.g., $C_1$-$C_8$ alkyl, $C_1$-$C_6$ alkyl, or $C_1$-$C_4$ alkyl). In embodiments, $R^9$ is an unsubstituted alkyl (e.g., $C_1$-$C_8$ alkyl, $C_1$-$C_6$ alkyl, or $C_1$-$C_4$ alkyl).

In embodiments, $R^9$ is $R^{50}$-substituted or unsubstituted heteroalkyl (e.g., 2 to 8 membered heteroalkyl, 2 to 6 membered heteroalkyl, or 2 to 4 membered heteroalkyl). In embodiments, $R^9$ is $R^{50}$-substituted heteroalkyl (e.g., 2 to 8 membered heteroalkyl, 2 to 6 membered heteroalkyl, or 2 to 4 membered heteroalkyl). In embodiments, $R^9$ is an unsubstituted heteroalkyl (e.g., 2 to 8 membered heteroalkyl, 2 to 6 membered heteroalkyl, or 2 to 4 membered heteroalkyl).

In embodiments, $R^9$ is $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is $R^{50}$-substituted cycloalkyl (e.g., $C_3$-$C_8$ cycloalkyl, $C_3$-$C_6$ cycloalkyl, or $C_5$-$C_6$ cycloalkyl). In embodiments, $R^9$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^9$ is $R^{50}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is $R^{50}$-substituted heterocycloalkyl (e.g., 3 to 8 membered heterocycloalkyl, 3 to 6 membered heterocycloalkyl, or 5 to 6 membered heterocycloalkyl). In embodiments, $R^9$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^9$ is $R^{50}$-substituted or unsubstituted aryl (e.g., $C_6$-$C_{10}$ aryl, $C_{10}$ aryl, or phenyl). In embodiments, $R^9$ is $R^{50}$-substituted aryl (e.g., $C_6$-$C_{10}$ aryl, $C_{10}$ aryl, or phenyl). In embodiments, $R^9$ is an unsubstituted aryl (e.g., $C_6$-$C_{10}$ aryl, $C_{10}$ aryl, or phenyl).

In embodiments, $R^9$ is $R^{50}$-substituted or unsubstituted heteroaryl (e.g., 5 to 10 membered heteroaryl, 5 to 9 membered heteroaryl, or 5 to 6 membered heteroaryl). In embodiments, $R^9$ is $R^{50}$-substituted heteroaryl (e.g., 5 to 10 membered heteroaryl, 5 to 9 membered heteroaryl, or 5 to 6 membered heteroaryl). In embodiments, $R^9$ is an unsubstituted heteroaryl (e.g., 5 to 10 membered heteroaryl, 5 to 9 membered heteroaryl, or 5 to 6 membered heteroaryl).

In embodiments, $R^9$ is a bioconjugate reactive moiety.

In embodiments, $R^{10}$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{10}$ is hydrogen. In embodiments, $R^{10}$ is —$CH_3$.

In embodiments, $R^{10}$ is a hydrogen, halogen, —$CCl_3$, —$CF_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, $R^{36}$-substituted or unsubstituted alkyl (e.g., $C_1$-$C_8$ alkyl, $C_1$-$C_6$ alkyl, or $C_1$-$C_4$ alkyl), $R^{36}$-substituted or unsubstituted heteroalkyl (e.g., 2 to 8 membered heteroalkyl, 2 to 6 membered heteroalkyl, or 2 to 4 membered heteroalkyl), $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted or unsubstituted aryl (e.g., $C_6$-$C_{10}$ aryl, $C_{10}$ aryl, or phenyl), or $R^{36}$-substituted or unsubstituted heteroaryl (e.g., 5 to 10 membered heteroaryl, 5 to 9 membered heteroaryl, or 5 to 6 membered heteroaryl).

$R^{36}$ is independently oxo, halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, $R^{37}$-substituted or unsubstituted alkyl (e.g., $C_1$-$C_8$ alkyl, $C_1$-$C_6$ alkyl, or $C_1$-$C_4$ alkyl), $R^{37}$-substituted or unsubstituted heteroalkyl (e.g., 2 to 8 membered heteroalkyl, 2 to 6 membered heteroalkyl, or 2 to 4 membered heteroalkyl), $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted or unsubstituted aryl (e.g., $C_6$-$C_{10}$ aryl, $C_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl).

In embodiments, $R^{10}$ is $R^{36}$-substituted or unsubstituted alkyl (e.g., $C_1$-$C_8$ alkyl, $C_1$-$C_6$ alkyl, or $C_1$-$C_4$ alkyl). In embodiments, $R^{10}$ is $R^{36}$-substituted alkyl (e.g., $C_1$-$C_8$ alkyl, $C_1$-$C_6$ alkyl, or $C_1$-$C_4$ alkyl). In embodiments, $R^{10}$ is an unsubstituted alkyl (e.g., $C_1$-$C_8$ alkyl, $C_1$-$C_6$ alkyl, or $C_1$-$C_4$ alkyl).

In embodiments, $R^{10}$ is $R^{36}$-substituted or unsubstituted heteroalkyl (e.g., 2 to 8 membered heteroalkyl, 2 to 6 membered heteroalkyl, or 2 to 4 membered heteroalkyl). In embodiments, $R^{10}$ is $R^{36}$-substituted heteroalkyl (e.g., 2 to 8 membered heteroalkyl, 2 to 6 membered heteroalkyl, or 2 to 4 membered heteroalkyl). In embodiments, $R^{10}$ is an unsubstituted heteroalkyl (e.g., 2 to 8 membered heteroalkyl, 2 to 6 membered heteroalkyl, or 2 to 4 membered heteroalkyl).

In embodiments, $R^{10}$ is $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{36}$-substituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{10}$ is $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{36}$-substituted heterocycloalkyl (e.g., 3 to 8 membered heterocycloalkyl, 3 to 6 membered heterocycloalkyl, or 5 to 6 membered heterocycloalkyl). In embodiments, $R^{10}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{10}$ is $R^{36}$-substituted or unsubstituted aryl (e.g., $C_6$-$C_{10}$ aryl, $C_{10}$ aryl, or phenyl). In embodiments, $R^{10}$ is $R^{36}$-substituted aryl (e.g., $C_6$-$C_{10}$ aryl, $C_{10}$ aryl, or phenyl). In embodiments, $R^{10}$ is an unsubstituted aryl (e.g., $C_6$-$C_{10}$ aryl, $C_{10}$ aryl, or phenyl).

In embodiments, $R^{10}$ is $R^{36}$-substituted or unsubstituted heteroaryl (e.g., 5 to 10 membered heteroaryl, 5 to 9 membered heteroaryl, or 5 to 6 membered heteroaryl). In embodiments, $R^{10}$ is $R^{36}$-substituted heteroaryl (e.g., 5 to 10 membered heteroaryl, 5 to 9 membered heteroaryl, or 5 to 6 membered heteroaryl). In embodiments, $R^{10}$ is an unsubstituted heteroaryl (e.g., 5 to 10 membered heteroaryl, 5 to 9 membered heteroaryl, or 5 to 6 membered heteroaryl).

In embodiments, $R^{10}$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{10}$ is hydrogen. In embodiments, $R^{10}$ is —$CH_3$. In embodiments, $R^{10}$ is —$OCH_3$.

In embodiments, $R^{11}$ is halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{11}$ is —$CH_3$. In embodiments, $R^{11}$ is —$OCH_3$.

In embodiments, $R^{11}$ is halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, $R^{38}$-substituted or unsubstituted alkyl (e.g., $C_1$-$C_8$ alkyl, $C_1$-$C_6$ alkyl, or $C_1$-$C_4$ alkyl), $R^{38}$-substituted or unsubstituted heteroalkyl (e.g., 2 to 8 membered heteroalkyl, 2 to 6 membered heteroalkyl, or 2 to 4 membered heteroalkyl), $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted or unsubstituted aryl (e.g., $C_6$-$C_{10}$ aryl, $C_{10}$ aryl, or phenyl), or $R^{38}$-substituted or unsubstituted heteroaryl (e.g., 5 to 10 membered heteroaryl, 5 to 9 membered heteroaryl, or 5 to 6 membered heteroaryl).

$R^{38}$ is independently oxo, halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —OCHBr$_2$, —OCHF$_2$, —OCH$_2$Cl, —OCH$_2$Br, —OCH$_2$F, —N$_3$, R$^{39}$-substituted or unsubstituted alkyl (e.g., C$_1$-C$_8$ alkyl, C$_1$-C$_6$ alkyl, or C$_1$-C$_4$ alkyl), R$^{39}$-substituted or unsubstituted heteroalkyl (e.g., 2 to 8 membered heteroalkyl, 2 to 6 membered heteroalkyl, or 2 to 4 membered heteroalkyl), R$^{39}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{39}$-substituted or unsubstituted heterocycloalkyl (e.g., 3 to 8 membered heterocycloalkyl, 3 to 6 membered heterocycloalkyl, or 5 to 6 membered heterocycloalkyl), R$^{39}$-substituted or unsubstituted aryl (e.g., C$_6$-C$_{10}$ aryl, C$_{10}$ aryl, or phenyl), or R$^{39}$-substituted or unsubstituted heteroaryl (e.g., 5 to 10 membered heteroaryl, 5 to 9 membered heteroaryl, or 5 to 6 membered heteroaryl).

In embodiments, R$^{11}$ is R$^{38}$-substituted or unsubstituted alkyl (e.g., C$_1$-C$_8$ alkyl, C$_1$-C$_6$ alkyl, or C$_1$-C$_4$ alkyl). In embodiments, R$^{11}$ is R$^{38}$-substituted alkyl (e.g., C$_1$-C$_8$ alkyl, C$_1$-C$_6$ alkyl, or C$_1$-C$_4$ alkyl). In embodiments, R$^{11}$ is an unsubstituted alkyl (e.g., C$_1$-C$_8$ alkyl, C$_1$-C$_6$ alkyl, or C$_1$-C$_4$ alkyl).

In embodiments, R$^{11}$ is R$^{38}$-substituted or unsubstituted heteroalkyl (e.g., 2 to 8 membered heteroalkyl, 2 to 6 membered heteroalkyl, or 2 to 4 membered heteroalkyl). In embodiments, R$^{11}$ is R$^{38}$-substituted heteroalkyl (e.g., 2 to 8 membered heteroalkyl, 2 to 6 membered heteroalkyl, or 2 to 4 membered heteroalkyl). In embodiments, R$^{11}$ is an unsubstituted heteroalkyl (e.g., 2 to 8 membered heteroalkyl, 2 to 6 membered heteroalkyl, or 2 to 4 membered heteroalkyl).

In embodiments, R$^{11}$ is R$^{38}$-substituted or unsubstituted cycloalkyl (e.g., C$_3$-C$_5$ cycloalkyl, C$_3$-C$_6$ cycloalkyl, or C$_5$-C$_6$ cycloalkyl). In embodiments, R$^{11}$ is R$^{38}$-substituted cycloalkyl (e.g., C$_3$-C$_8$ cycloalkyl, C$_3$-C$_6$ cycloalkyl, or C$_5$-C$_6$ cycloalkyl). In embodiments, R$^{11}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{11}$ is R$^{38}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{11}$ is R$^{38}$-substituted heterocycloalkyl (e.g., 3 to 8 membered heterocycloalkyl, 3 to 6 membered heterocycloalkyl, or 5 to 6 membered heterocycloalkyl). In embodiments, R$^{11}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{11}$ is R$^{38}$-substituted or unsubstituted aryl (e.g., C$_6$-C$_{10}$ aryl, C$_{10}$ aryl, or phenyl). In embodiments, R$^{11}$ is R$^{38}$-substituted aryl (e.g., C$_6$-C$_{10}$ aryl, C$_{10}$ aryl, or phenyl). In embodiments, R$^{11}$ is an unsubstituted aryl (e.g., C$_6$-C$_{10}$ aryl, C$_{10}$ aryl, or phenyl).

In embodiments, R$^{11}$ is R$^{38}$-substituted or unsubstituted heteroaryl (e.g., 5 to 10 membered heteroaryl, 5 to 9 membered heteroaryl, or 5 to 6 membered heteroaryl). In embodiments, R$^{11}$ is R$^{38}$-substituted heteroaryl (e.g., 5 to 10 membered heteroaryl, 5 to 9 membered heteroaryl, or 5 to 6 membered heteroaryl). In embodiments, R$^{11}$ is an unsubstituted heteroaryl (e.g., 5 to 10 membered heteroaryl, 5 to 9 membered heteroaryl, or 5 to 6 membered heteroaryl).

In embodiments, R$^{11}$ is —CH$_3$. In embodiments, R$^{11}$ is —OCH$_3$. In embodiments, RH is —OCH$_2$CH$_3$. In embodiments, R$^{11}$ is —Cl. In embodiments, R$^{11}$ is halogen. In embodiments, R$^{11}$ is —F.

In embodiments,

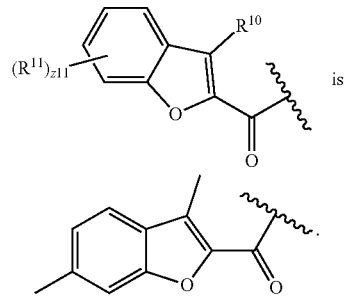

is

In embodiments,

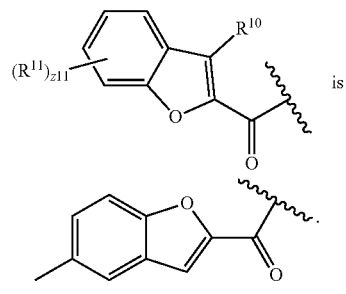

In embodiments,

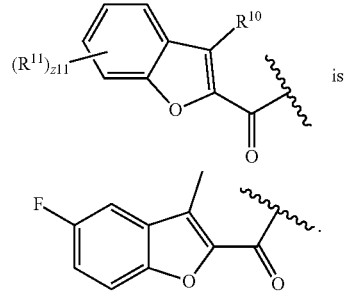

In embodiments,

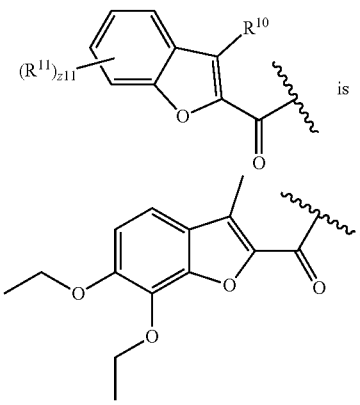

In embodiments,

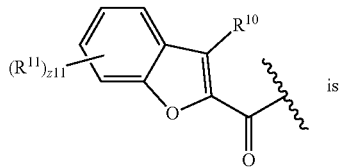 is

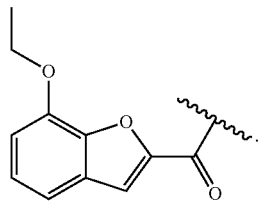.

In embodiments,

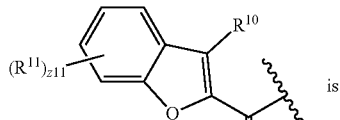 is

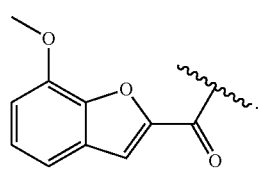.

In embodiments,

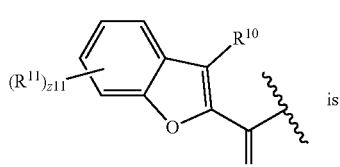 is

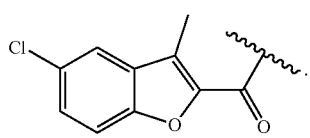.

In embodiments,

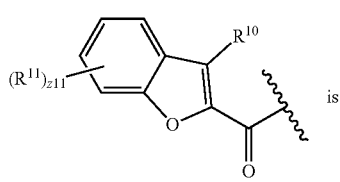 is

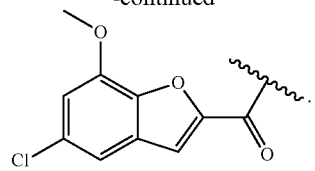.

In embodiments,

 is

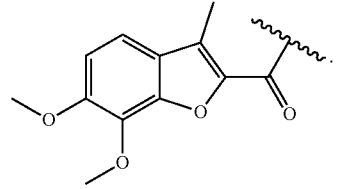.

In embodiments, $R^{12}$ is oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{12}$ is oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, Wm-substituted or unsubstituted heteroalkyl (e.g., 2 to 8 membered heteroalkyl, 2 to 6 membered heteroalkyl, or 2 to 4 membered heteroalkyl), $R^{40}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{40}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted or unsubstituted aryl (e.g., C$_6$-C$_{10}$ aryl, C$_{10}$ aryl, or phenyl), or $R^{40}$-substituted or unsubstituted heteroaryl (e.g., 5 to 10 membered heteroaryl, 5 to 9 membered heteroaryl, or 5 to 6 membered heteroaryl).

$R^{40}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{41}$-substituted or unsubstituted alkyl (e.g., C$_1$-C$_8$ alkyl, C$_1$-C$_6$ alkyl, or C$_1$-C$_4$ alkyl), R$^{41}$-substituted or unsubstituted heteroalkyl (e.g., 2 to 8 membered heteroalkyl, 2 to 6 membered heteroalkyl, or 2 to 4 membered heteroalkyl), R$^{41}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{41}$-substituted or unsubstituted heterocycloalkyl (e.g., 3 to 8 membered heterocycloalkyl, 3 to 6 membered heterocycloalkyl, or 5 to 6 membered heterocycloalkyl), R$^{41}$-substituted or unsubstituted aryl (e.g., C$_6$-C$_{10}$ aryl, C$_{10}$ aryl, or phenyl), or R$^{41}$-substituted or unsubstituted heteroaryl (e.g., 5 to 10 membered heteroaryl, 5 to 9 membered heteroaryl, or 5 to 6 membered heteroaryl).

In embodiments, R$^{12}$ is R$^{40}$-substituted or unsubstituted alkyl (e.g., C$_1$-C$_8$ alkyl, C$_1$-C$_6$ alkyl, or C$_1$-C$_4$ alkyl). In embodiments, R$^{12}$ is R$^{40}$-substituted alkyl (e.g., C$_1$-C$_8$ alkyl, C$_1$-C$_6$ alkyl, or C$_1$-C$_4$ alkyl). In embodiments, R$^{12}$ is an unsubstituted alkyl (e.g., C$_1$-C$_8$ alkyl, C$_1$-C$_6$ alkyl, or C$_1$-C$_4$ alkyl). In embodiments, R$^{12}$ is unsubstituted methyl. In embodiments, R$^{12}$ is unsubstituted ethyl. In embodiments, R$^{12}$ is unsubstituted propyl (e.g., n-proypl or isopropyl).

In embodiments, R$^{12}$ is R$^{40}$-substituted or unsubstituted heteroalkyl (e.g., 2 to 8 membered heteroalkyl, 2 to 6 membered heteroalkyl, or 2 to 4 membered heteroalkyl). In embodiments, R$^{12}$ is R$^{40}$-substituted heteroalkyl (e.g., 2 to 8 membered heteroalkyl, 2 to 6 membered heteroalkyl, or 2 to 4 membered heteroalkyl). In embodiments, R$^{12}$ is an unsubstituted heteroalkyl (e.g., 2 to 8 membered heteroalkyl, 2 to 6 membered heteroalkyl, or 2 to 4 membered heteroalkyl).

In embodiments, R$^{12}$ is R$^{40}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{12}$ is R$^{40}$-substituted cycloalkyl (e.g., C$_3$-C$_8$ cycloalkyl, C$_3$-C$_6$ cycloalkyl, or C$_5$-C$_6$ cycloalkyl). In embodiments, R$^{12}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{12}$ is Wm-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{12}$ is R$^{40}$-substituted heterocycloalkyl (e.g., 3 to 8 membered heterocycloalkyl, 3 to 6 membered heterocycloalkyl, or 5 to 6 membered heterocycloalkyl). In embodiments, R$^{12}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{12}$ is R$^{40}$-substituted or unsubstituted aryl (e.g., C$_6$-C$_{10}$ aryl, C$_{10}$ aryl, or phenyl). In embodiments, R$^{12}$ is R$^{40}$-substituted aryl (e.g., C$_6$-C$_{10}$ aryl, C$_{10}$ aryl, or phenyl). In embodiments, R$^{12}$ is an unsubstituted aryl (e.g., C$_6$-C$_{10}$ aryl, C$_{10}$ aryl, or phenyl).

In embodiments, R$^{12}$ is R$^{40}$-substituted or unsubstituted heteroaryl (e.g., 5 to 10 membered heteroaryl, 5 to 9 membered heteroaryl, or 5 to 6 membered heteroaryl). In embodiments, R$^{12}$ is Wm-substituted heteroaryl (e.g., 5 to 10 membered heteroaryl, 5 to 9 membered heteroaryl, or 5 to 6 membered heteroaryl). In embodiments, R$^{12}$ is an unsubstituted heteroaryl (e.g., 5 to 10 membered heteroaryl, 5 to 9 membered heteroaryl, or 5 to 6 membered heteroaryl).

In embodiments, R$^{12}$ is independently substituted or unsubstituted alkyl, substituted or unsubstituted heteroalkyl, or substituted or unsubstituted cycloalkyl. In embodiments, R$^{12}$ is independently substituted or unsubstituted alkyl. In embodiments, R$^{11}$ is substituted or unsubstituted heteroalkyl. In embodiments, R$^{12}$ is substituted or unsubstituted cycloalkyl.

In embodiments, R$^{13}$ is oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{13}$ is oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCHCl$_2$, —OCHBr$_2$, —OCHF$_2$, —OCH$_2$Cl, —OCH$_2$Br, —OCH$_2$F, —N$_3$, R$^{42}$-substituted or unsubstituted heteroalkyl (e.g., 2 to 8 membered heteroalkyl, 2 to 6 membered heteroalkyl, or 2 to 4 membered heteroalkyl), R$^{42}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{42}$-substituted or unsubstituted heterocycloalkyl (e.g., 3 to 8 membered heterocycloalkyl, 3 to 6 membered heterocycloalkyl, or 5 to 6 membered heterocycloalkyl), R$^{42}$-substituted or unsubstituted aryl (e.g., C$_6$-C$_{10}$ aryl, C$_{10}$ aryl, or phenyl), or R$^{42}$-substituted or unsubstituted heteroaryl (e.g., 5 to 10 membered heteroaryl, 5 to 9 membered heteroaryl, or 5 to 6 membered heteroaryl).

R$^{42}$ is independently oxo, halogen, —CCl$_3$, —CF$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —N$_3$, R$^{43}$-substituted or unsubstituted alkyl (e.g., C$_1$-C$_8$ alkyl, C$_1$-C$_6$ alkyl, or C$_1$-C$_4$ alkyl), R$^{43}$-substituted or unsubstituted heteroalkyl (e.g., 2 to 8 membered heteroalkyl, 2 to 6 membered heteroalkyl, or 2 to 4 membered heteroalkyl), R$^{43}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{43}$-substituted or unsubstituted heterocycloalkyl (e.g., 3 to 8 membered heterocycloalkyl, 3 to 6 membered heterocycloalkyl, or 5 to 6 membered heterocycloalkyl), R$^{43}$-substituted or unsubstituted aryl (e.g., C$_6$-C$_{10}$ aryl, C$_{10}$ aryl, or phenyl), or R$^{43}$-substituted or unsubstituted heteroaryl (e.g., 5 to 10 membered heteroaryl, 5 to 9 membered heteroaryl, or 5 to 6 membered heteroaryl).

In embodiments, R$^{13}$ is R$^{42}$-substituted or unsubstituted alkyl (e.g., C$_1$-C$_8$ alkyl, C$_1$-C$_6$ alkyl, or C$_1$-C$_4$ alkyl). In embodiments, R$^{13}$ is R$^{42}$-substituted alkyl (e.g., C$_1$-C$_8$ alkyl, C$_1$-C$_6$ alkyl, or C$_1$-C$_4$ alkyl). In embodiments, R$^{13}$ is an unsubstituted alkyl (e.g., C$_1$-C$_8$ alkyl, C$_1$-C$_6$ alkyl, or C$_1$-C$_4$ alkyl).

In embodiments, R$^{13}$ is R$^{42}$-substituted or unsubstituted heteroalkyl (e.g., 2 to 8 membered heteroalkyl, 2 to 6 membered heteroalkyl, or 2 to 4 membered heteroalkyl). In embodiments, R$^{13}$ is R$^{42}$-substituted heteroalkyl (e.g., 2 to 8 membered heteroalkyl, 2 to 6 membered heteroalkyl, or 2 to 4 membered heteroalkyl). In embodiments, $R^{13}$ is an unsubstituted heteroalkyl (e.g., 2 to 8 membered heteroalkyl, 2 to 6 membered heteroalkyl, or 2 to 4 membered heteroalkyl).

In embodiments, $R^{13}$ is $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{13}$ is $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{13}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{13}$ is $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{13}$ is $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{13}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{13}$ is $R^{42}$-substituted or unsubstituted aryl (e.g., $C_6$-$C_{10}$ aryl, $C_{10}$ aryl, or phenyl). In embodiments, $R^{13}$ is $R^{42}$-substituted aryl (e.g., $C_6$-$C_{10}$ aryl, $C_{10}$ aryl, or phenyl). In embodiments, $R^{13}$ is an unsubstituted aryl (e.g., $C_6$-$C_{10}$ aryl, $C_{10}$ aryl, or phenyl).

In embodiments, $R^{13}$ is $R^{42}$-substituted or unsubstituted heteroaryl (e.g., 5 to 10 membered heteroaryl, 5 to 9 membered heteroaryl, or 5 to 6 membered heteroaryl). In embodiments, $R^{13}$ is $R^{42}$-substituted heteroaryl (e.g., 5 to 10 membered heteroaryl, 5 to 9 membered heteroaryl, or 5 to 6 membered heteroaryl). In embodiments, $R^{13}$ is an unsubstituted heteroaryl (e.g., 5 to 10 membered heteroaryl, 5 to 9 membered heteroaryl, or 5 to 6 membered heteroaryl).

In embodiments, $R^{13}$ independently is —OH, —NH$_2$, —COOH, —CONH$_2$, —SH, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted aryl, or substituted or unsubstituted heteroaryl. In embodiments, $R^{13}$ independently is —OH. In embodiments, $R^{13}$ independently is —NH$_2$. In embodiments, $R^{13}$ independently is —COOH. In embodiments, $R^{13}$ independently is —CONH$_2$. In embodiments, $R^{13}$ independently is —SH. In embodiments, $R^{13}$ independently is —NHC(O)NH$_2$. In embodiments, $R^{13}$ independently is —NHSO$_2$H. In embodiments, $R^{13}$ independently is —NHC(O)H. In embodiments, $R^{13}$ independently is —NHC(O)OH. In embodiments, $R^{13}$ independently is —NHOH. In embodiments, $R^{13}$ independently is substituted or unsubstituted alkyl. In embodiments, $R^{13}$ independently is substituted or unsubstituted heteroalkyl. In embodiments, $R^{13}$ independently is substituted or unsubstituted aryl. In embodiments, $R^{13}$ independently is substituted or unsubstituted heteroaryl.

In embodiments, $R^{14}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^{14}$ is independently hydrogen. In embodiments, $R^{14}$ is independently a bioconjugate reactive moiety, a nanoparticle, a peptide, an EphA2 agonist, a drug moiety, a targeting moiety, or a detectable moiety. In embodiments, $R^{14}$ is independently a bioconjugate reactive moiety. In embodiments, $R^{14}$ is independently a nanoparticle. In embodiments, $R^{14}$ is independently a peptide. In embodiments, $R^{14}$ is independently an EphA2 agonist, (e.g., a monovalent compound of Formula (I)), having the formula:

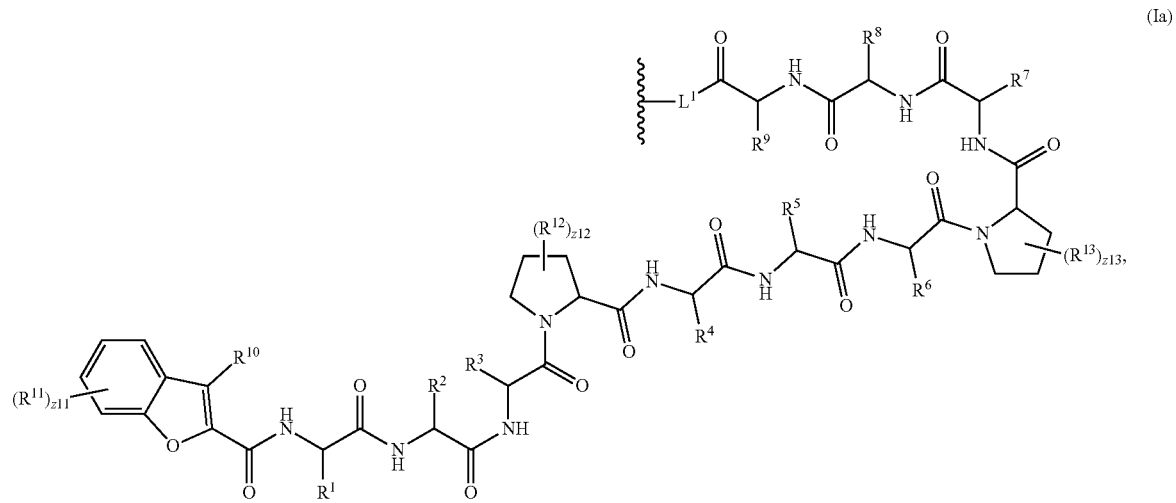

(Ia)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^1$, z11, z12, and z13 are independent and as described herein. In embodiments, $R^{14}$ is independently a drug moiety. In embodiments, $R^{14}$ is independently a targeting moiety (e.g. a molecule for targeting the compound to a specific location in a cell or organism). In embodiments, $R^{14}$ is independently a detectable moiety.

When $R^{14}$ has formula (Ia) and the compound of Formula (I) includes multiple $L^1$ linkers, each $L^1$ linker may optionally be different (e.g., the $L^1$ of Formula (Ia) is a bond and the $L^1$ not of Formula (Ia) is not a bond).

In embodiments, $R^{14}$ is independently an EphA2 agonist, (e.g., a monovalent compound of Formula (I)), having the formula:

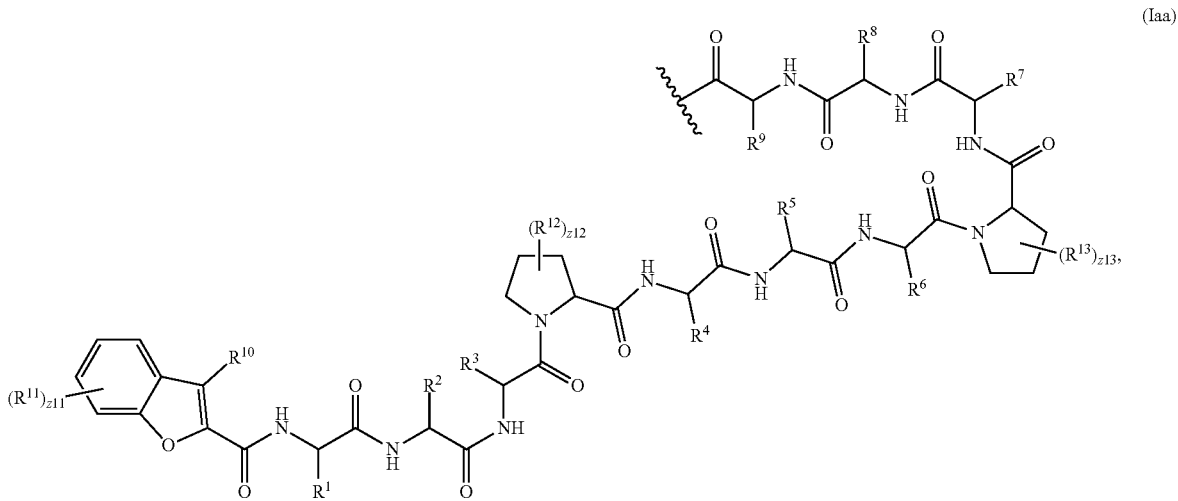

(Iaa)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, Z11, z12, and z13 are independent and as described herein.

In embodiments, $R^{14}$ is independently an EphA2 agonist, (e.g., a monovalent compound of Formula (I)), having the formula:

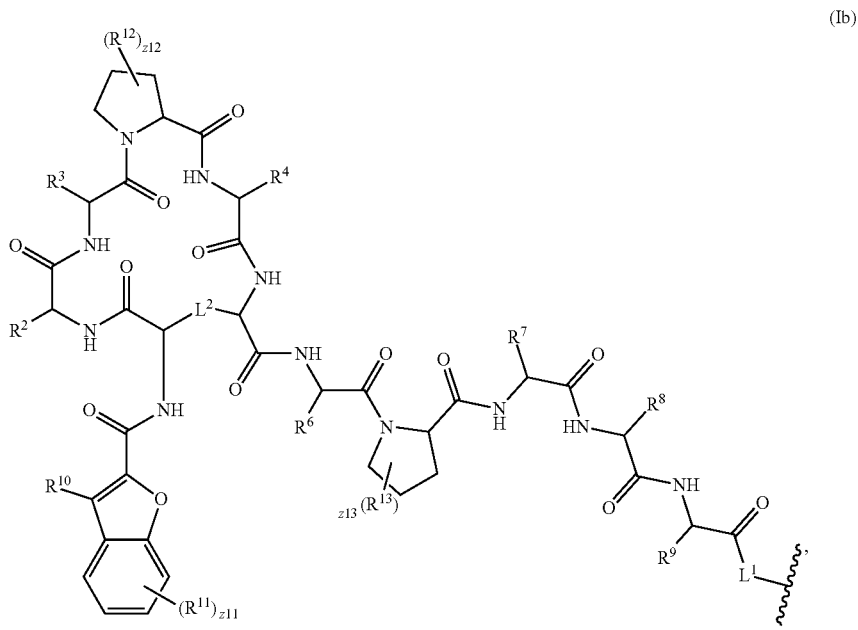

(Ib)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^1$, $L^2$, z11, z12, and z13 are independent and as described herein.

When $R^{14}$ has formula (Ia) and the compound of Formula (I) includes multiple $L^1$ linkers, each $L^1$ linker may optionally be different (e.g., the $L^1$ of Formula (Ia) is a bond and the $L^1$ not of Formula (Ia) is not a bond).

In embodiments, $R^{14}$ is independently an EphA2 agonist, (e.g., a monovalent compound of Formula (I)), having the formula:

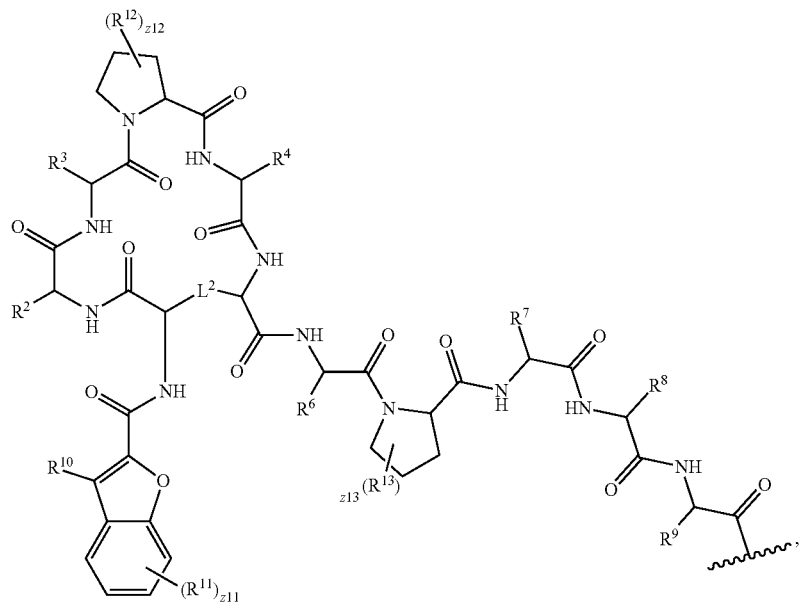

(Iba)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^2$, z11, z12, and z13 are independent and as described herein.

In embodiments, $R^{14}$ is oxo, halogen, —CCl$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{14}$ is oxo, halogen, —CCl$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —N$_3$, $R^{44}$-substituted or unsubstituted heteroalkyl (e.g., 2 to 8 membered heteroalkyl, 2 to 6 membered heteroalkyl, or to 4 membered heteroalkyl), $R^{44}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44}$-substituted or unsubstituted hetero cycloalkyl (e.g., 3 to 8 membered heterocycloalkyl, 3 to 6 membered heterocycloalkyl, or 5 to 6 membered heterocycloalkyl), $R^{44}$-substituted or unsubstituted aryl (e.g., $C_6$-$C_{10}$ aryl, $C_{10}$ aryl, or phenyl), or $R^{44}$-substituted or unsubstituted heteroaryl (e.g., 5 to 10 membered heteroaryl, 5 to 9 membered heteroaryl, or 5 to 6 membered heteroaryl).

$R^{44}$ is independently oxo, halogen, —CCl$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —N$_3$, $R^{45}$-substituted or unsubstituted alkyl (e.g., $C_1$-$C_8$ alkyl, $C_1$-$C_6$ alkyl, or $C_1$-$C_4$ alkyl), $R^{45}$-substituted or unsubstituted heteroalkyl (e.g., 2 to 8 membered heteroalkyl, 2 to 6 membered heteroalkyl, or 2 to 4 membered heteroalkyl), $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45}$-substituted or unsubstituted aryl (e.g., $C_6$-$C_{10}$ aryl, $C_{10}$ aryl, or phenyl), or $R^{45}$-substituted or unsubstituted heteroaryl (e.g., 5 to 10 membered heteroaryl, 5 to 9 membered heteroaryl, or 5 to 6 membered heteroaryl).

In embodiments, $R^{14}$ is $R^{44}$-substituted or unsubstituted alkyl (e.g., $C_1$-$C_8$ alkyl, $C_1$-$C_6$ alkyl, or $C_1$-$C_4$ alkyl). In embodiments, $R^{14}$ is $R^{44}$-substituted alkyl (e.g., $C_1$-$C_8$ alkyl, $C_1$-$C_6$ alkyl, or $C_1$-$C_4$ alkyl). In embodiments, $R^{14}$ is an unsubstituted alkyl (e.g., $C_1$-$C_8$ alkyl, $C_1$-$C_6$ alkyl, or $C_1$-$C_4$ alkyl).

In embodiments, $R^{14}$ is $R^{44}$-substituted or unsubstituted heteroalkyl (e.g., 2 to 8 membered heteroalkyl, 2 to 6 membered heteroalkyl, or 2 to 4 membered heteroalkyl). In embodiments, $R^{14}$ is $R^{44}$-substituted heteroalkyl (e.g., 2 to 8 membered heteroalkyl, 2 to 6 membered heteroalkyl, or 2 to 4 membered heteroalkyl). In embodiments, $R^{14}$ is an unsubstituted heteroalkyl (e.g., 2 to 8 membered heteroalkyl, 2 to 6 membered heteroalkyl, or 2 to 4 membered heteroalkyl).

In embodiments, $R^{14}$ is $R^{44}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is $R^{44}$-substituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{14}$ is $R^{44}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{14}$ is $R^{44}$-substituted heterocycloalkyl (e.g., 3 to 8 membered heterocycloalkyl, 3 to 6 membered heterocycloalkyl, or 5 to 6 membered heterocycloalkyl). In embodiments, $R^{14}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{14}$ is $R^{44}$-substituted or unsubstituted aryl (e.g., $C_6$-$C_{10}$ aryl, $C_{10}$ aryl, or phenyl). In embodiments, $R^{14}$ is $R^{44}$-substituted aryl (e.g., $C_6$-$C_{10}$ aryl, $C_{10}$ aryl, or phenyl). In embodiments, $R^{14}$ is an unsubstituted aryl (e.g., $C_6$-$C_{10}$ aryl, $C_{10}$ aryl, or phenyl).

In embodiments, $R^{14}$ is $R^{44}$-substituted or unsubstituted heteroaryl (e.g., 5 to 10 membered heteroaryl, 5 to 9 membered heteroaryl, or 5 to 6 membered heteroaryl). In embodiments, $R^{14}$ is $R^{44}$-substituted heteroaryl (e.g., 5 to 10 membered heteroaryl, 5 to 9 membered heteroaryl, or 5 to 6 membered heteroaryl). In embodiments, $R^{14}$ is an unsubstituted heteroaryl (e.g., 5 to 10 membered heteroaryl, 5 to 9 membered heteroaryl, or 5 to 6 membered heteroaryl).

In embodiments, $L^1$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, -$L^1$-$R^{14}$ has the formula:

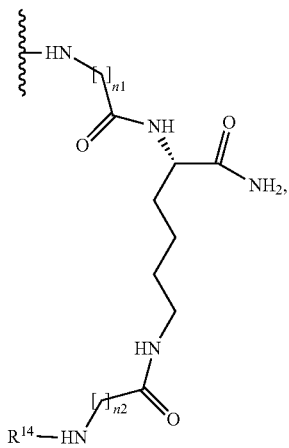

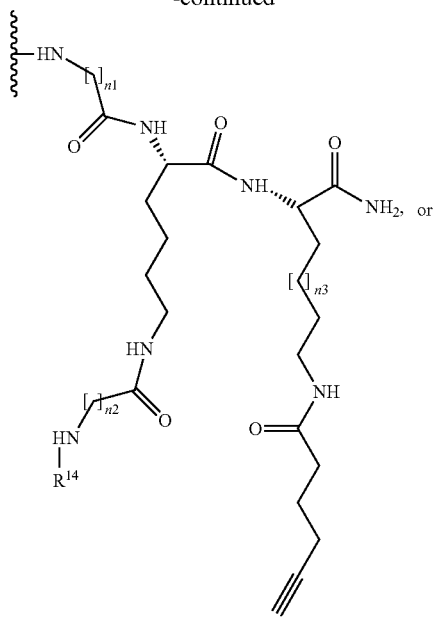

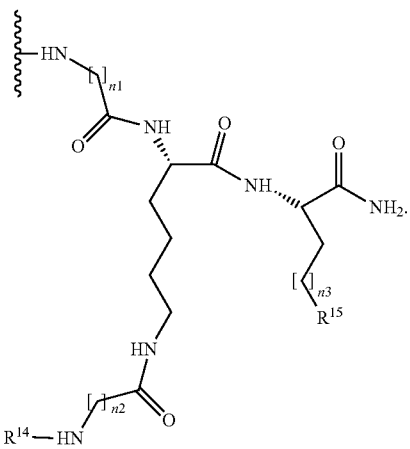

The symbols n1, n2, and n3 are each independently integers from 1 to 20. $R^{15}$ is independently halogen, —CCl$_3$, —CBr$_3$, —CF$_3$, —CI$_3$, —CHCl$_2$, —CHBr$_2$, —CHF$_2$, —CHI$_2$, —CH$_2$C$_1$, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

In embodiments, $R^{15}$ is a bioconjugate reactive moiety, a nanoparticle (nanoparticle moiety), a peptide (peptide moiety), an EphA2 agonist (EphA2 agonist moiety), a drug moiety, a targeting moiety, or a detectable moiety.

In embodiments, $R^{15}$ is independently halogen, —CCl$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCHCl$_2$, —OCHBr$_2$, —OCHF$_2$, —OCH$_2$Cl, —OCH$_2$Br, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In embodiments, $R^{15}$ is independently halogen, —CCl$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —N$_3$, $R^{46}$-substituted or unsubstituted heteroalkyl (e.g., 2 to 8 membered heteroalkyl, 2 to 6 membered heteroalkyl, or 2 to 4 membered heteroalkyl), $R^{46}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{46}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46}$-substituted or unsubstituted aryl (e.g., C$_6$-C$_{10}$ aryl, C$_{10}$ aryl, or phenyl), or $R^{46}$-substituted or unsubstituted heteroaryl (e.g., 5 to 10 membered heteroaryl, 5 to 9 membered heteroaryl, or 5 to 6 membered heteroaryl).

$R^{46}$ is independently oxo, halogen, —CCl$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —N$_3$, $R^{47}$-substituted or unsubstituted alkyl (e.g., C$_1$-C$_8$ alkyl, C$_1$-C$_6$ alkyl, or C$_1$-C$_4$ alkyl), $R^{47}$-substituted or unsubstituted heteroalkyl (e.g., 2 to 8 membered heteroalkyl, 2 to 6 membered heteroalkyl, or 2 to 4 membered heteroalkyl), $R^{47}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{47}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47}$-substituted or unsubstituted aryl (e.g., C$_6$-C$_{10}$ aryl, C$_{10}$ aryl, or phenyl), or $R^{47}$-substituted or unsubstituted heteroaryl (e.g., 5 to 10 membered heteroaryl, 5 to 9 membered heteroaryl, or 5 to 6 membered heteroaryl).

In embodiments, $R^{15}$ is $R^{46}$-substituted or unsubstituted alkyl (e.g., C$_1$-C$_8$ alkyl, C$_1$-C$_6$ alkyl, or C$_1$-C$_4$ alkyl). In embodiments, $R^{15}$ is $R^{46}$-substituted alkyl (e.g., C$_1$-C$_8$ alkyl, C$_1$-C$_6$ alkyl, or C$_1$-C$_4$ alkyl). In embodiments, $R^{15}$ is an unsubstituted alkyl (e.g., C$_1$-C$_8$ alkyl, C$_1$-C$_6$ alkyl, or C$_1$-C$_4$ alkyl).

In embodiments, $R^{15}$ is $R^{46}$-substituted or unsubstituted heteroalkyl (e.g., 2 to 8 membered heteroalkyl, 2 to 6 membered heteroalkyl, or 2 to 4 membered heteroalkyl). In embodiments, $R^{15}$ is $R^{46}$-substituted heteroalkyl (e.g., 2 to 8 membered heteroalkyl, 2 to 6 membered heteroalkyl, or 2 to 4 membered heteroalkyl). In embodiments, $R^{15}$ is an unsubstituted heteroalkyl (e.g., 2 to 8 membered heteroalkyl, 2 to 6 membered heteroalkyl, or 2 to 4 membered heteroalkyl).

In embodiments, $R^{15}$ is $R^{46}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{15}$ is $R^{46}$-substituted cycloalkyl (e.g., C$_3$-C$_8$ cycloalkyl, C$_3$-C$_6$ cycloalkyl, or C$_5$-C$_6$ cycloalkyl). In embodiments, $R^{15}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{15}$ is $R^{46}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is $R^{46}$-substituted heterocycloalkyl (e.g., 3 to 8 membered heterocycloalkyl, 3 to 6 membered heterocycloalkyl, or 5 to 6 membered heterocycloalkyl). In embodiments, $R^{15}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{15}$ is $R^{46}$-substituted or unsubstituted aryl (e.g., C$_6$-C$_{10}$ aryl, C$_{10}$ aryl, or phenyl). In embodiments, $R^{15}$ is $R^{46}$-substituted aryl (e.g., C$_6$-C$_{10}$ aryl, C$_{10}$ aryl, or phenyl). In embodiments, $R^{15}$ is an unsubstituted aryl (e.g., C$_6$-C$_{10}$ aryl, C$_{10}$ aryl, or phenyl).

In embodiments, $R^{15}$ is $R^{46}$-substituted or unsubstituted heteroaryl (e.g., 5 to 10 membered heteroaryl, 5 to 9 membered heteroaryl, or 5 to 6 membered heteroaryl). In embodiments, $R^{15}$ is $R^{46}$-substituted heteroaryl (e.g., 5 to 10 membered heteroaryl, 5 to 9 membered heteroaryl, or 5 to 6 membered heteroaryl). In embodiments, IV is an unsubstituted heteroaryl (e.g., 5 to 10 membered heteroaryl, 5 to 9 membered heteroaryl, or 5 to 6 membered heteroaryl).

In embodiments, $R^{15}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^{15}$ is independently hydrogen. In embodiments, $R^{15}$ is independently a bioconjugate reactive moiety, a nanoparticle, a peptide, an EphA2 agonist, a drug moiety, a targeting moiety, or a detectable moiety. In embodiments, $R^{15}$ is independently a bioconjugate reactive moiety. In embodiments, $R^{15}$ is independently a nanoparticle. In embodiments, $R^{15}$ is independently a peptide. In embodiments, $R^{15}$ is independently an EphA2 agonist, (e.g., a monovalent compound of Formula (I)), having the formula:

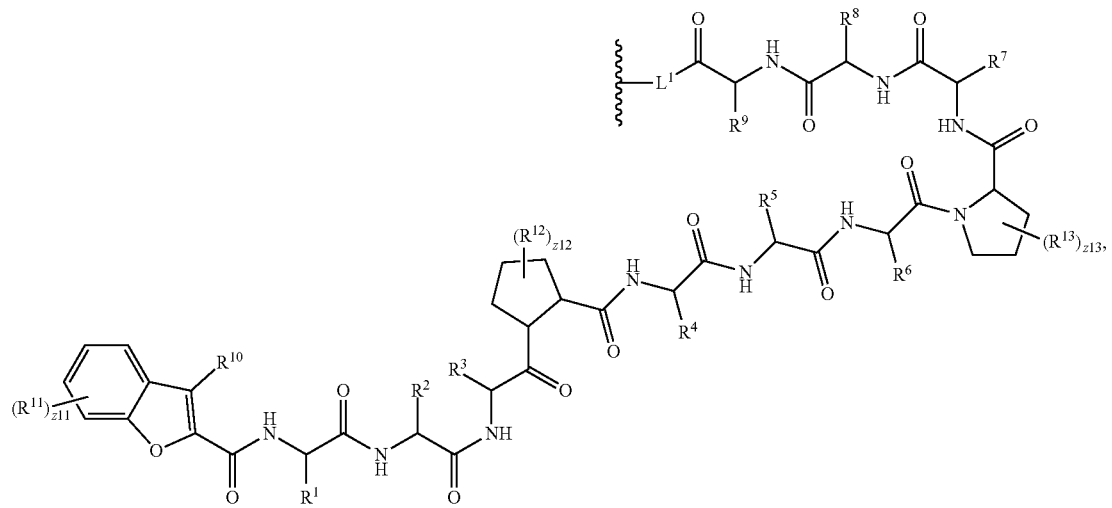

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^1$, z11, z12, and z13 are independent and as described herein.

When one or more $R^{15}$ groups have the formula above and the compound of Formula (I) includes multiple $L^1$ linkers, each $L^1$ linker may optionally be different (e.g., one $L^1$ of the formula above is a bond, additional $L^1$ linkers of the formula above may optionally be a bond, the $L^1$ linker not of the formula above is not a bond).

In embodiments, $R^{15}$ is independently an EphA2 agonist, (e.g., a monovalent compound of Formula (I)), having the formula:

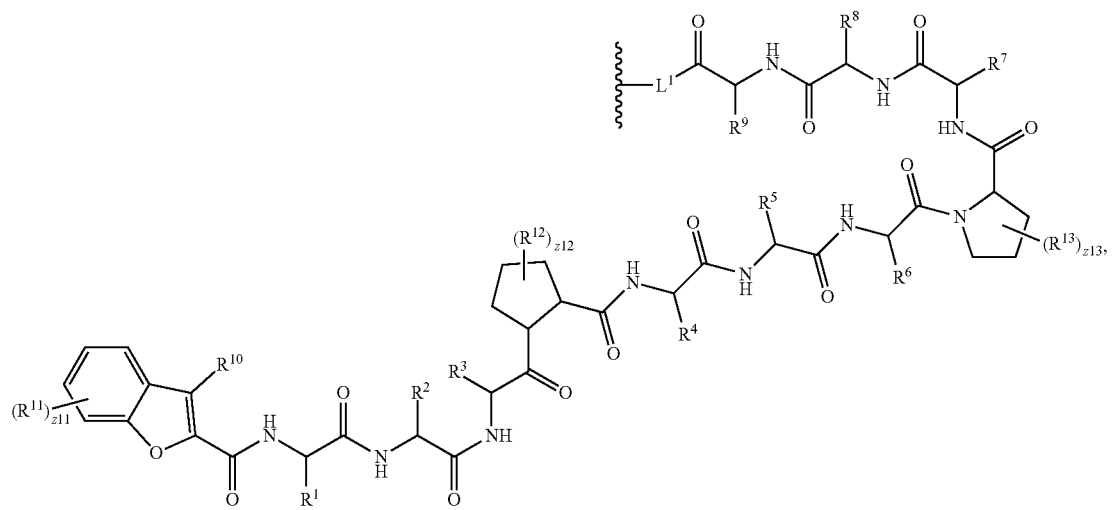

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, z11, z12, and z13 are independent and as described herein.

In embodiments, $R^{15}$ is independently an EphA2 agonist, (e.g., a monovalent compound of Formula (I)), having the formula:

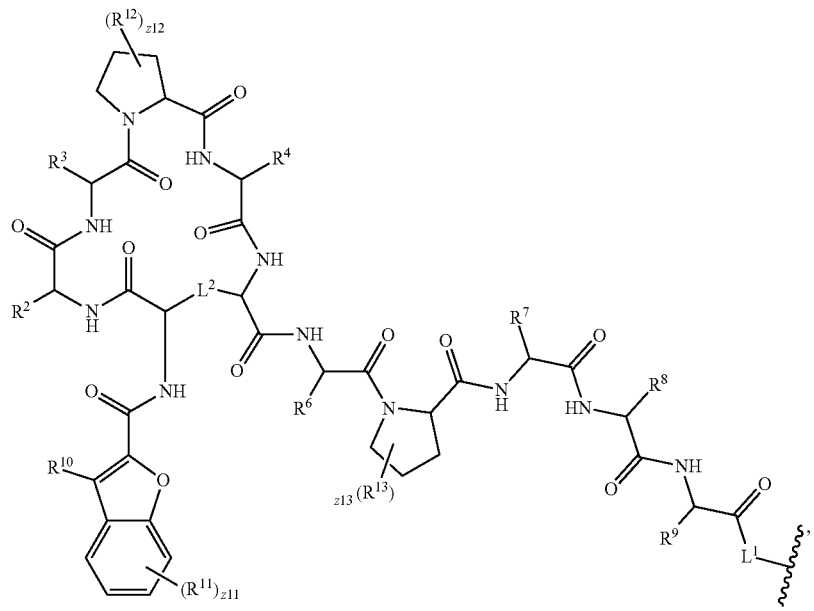

wherein $R^1$, $R^2$, $R^3$, $R^4$, $R^5$, $R^6$, $R^7$, $R^8$, $R^9$, $R^{11}$, $R^{12}$, $R^{13}$, $L^1$, $L^2$, z11, z12, and z13 are independent and as described herein. In embodiments, $R^{15}$ is independently a drug moiety. In embodiments, $R^{15}$ is independently a targeting moiety. In embodiments, $R^{15}$ is independently a detectable moiety.

When one or more $R^{15}$ groups have the formula above and the compound of Formula (I) includes multiple $L^1$ linkers, each $L^1$ linker may optionally be different (e.g., one $L^1$ of the formula above is a bond, additional Clinkers of the formula above may optionally be a bond, the $L^1$ linker not of the formula above is not a bond).

In embodiments, $R^{15}$ is independently an EphA2 agonist, (e.g., a monovalent compound of Formula (I)), having the formula:

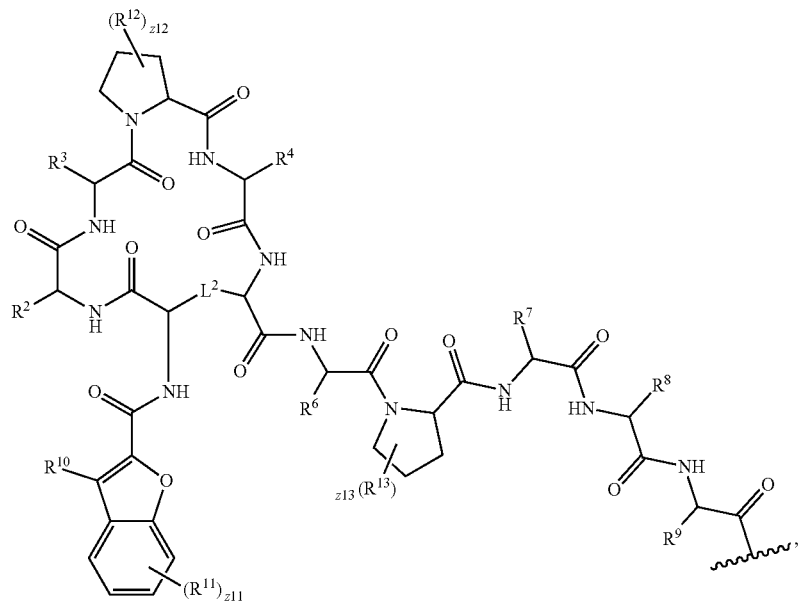

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^2$, z11, z12, and z13 are independent and as described herein.

In embodiments, $L^1$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is a bond. In embodiments, $L^1$ is —S(O)$_2$—. In embodiments, $L^1$ is —NH—. In embodiments, $L^1$ is —O—. In embodiments, $L^1$ is —S—. In embodiments, $L^1$ is —C(O)—. In embodiments, $L^1$ is —C(O)NH—. In embodiments, $L^1$ is —NHC(O)—. In embodiments, $L^1$ is —NHC(O)NH—. In embodiments, $L^1$ is —C(O)O—. In embodiments, $L^1$ is —OC(O)—. In embodiments, $L^1$ is substituted or unsubstituted alkylene. In embodiments, $L^1$ is substituted or unsubstituted heteroalkylene. In embodiments, $L^1$ is substituted or unsubstituted cycloalkylene. In embodiments, $L^1$ is substituted or unsubstituted heterocycloalkylene. In embodiments, $L^1$ is substituted or unsubstituted arylene. In embodiments, $L^1$ is substituted or unsubstituted heteroarylene.

In embodiments, $L^1$ is a bond, —S(O)$_2$—, —NH—, —O—, —S—, —C(O)—, —C(O)NH—, —NHC(O)—, —NHC(O)NH—, —C(O)O—, —OC(O)—, $R^{15}$-substituted or unsubstituted alkylene (e.g., $C_1$-$C_8$ alkylene, $C_1$-$C_6$ alkylene, or $C_1$-$C_4$ alkylene), $R^{15}$-substituted or unsubstituted heteroalkylene (e.g., 2 to 8 membered heteroalkylene, 2 to 6 membered heteroalkylene, or 2 to 4 membered heteroalkylene), $R^{15}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{15}$-substituted or unsubstituted heterocycloalkylene (e.g., 3 to 8 membered heterocycloalkylene, 3 to 6 membered heterocycloalkylene, or 5 to 6 membered heterocycloalkylene), $R^{15}$-substituted or unsubstituted arylene (e.g., $C_6$-$C_{10}$ arylene, $C_{10}$ arylene, or phenylene), or $R^{15}$-substituted or unsubstituted heteroarylene (e.g., 5 to 10 membered heteroarylene, 5 to 9 membered heteroarylene, or 5 to 6 membered heteroarylene).

In embodiments, $L^1$ is $R^{15}$-substituted or unsubstituted alkylene (e.g., $C_1$-$C_8$ alkylene, $C_1$-$C_6$ alkylene, or $C_1$-$C_4$ alkylene). In embodiments, $L^1$ is $R^{15}$-substituted alkylene (e.g., $C_1$-$C_8$ alkylene, $C_1$-$C_6$ alkylene, or $C_1$-$C_4$ alkylene). In embodiments, $L^1$ is an unsubstituted alkylene (e.g., $C_1$-$C_8$ alkylene, $C_1$-$C_6$ alkylene, or $C_1$-$C_4$ alkylene).

In embodiments, $L^1$ is $R^{15}$-substituted or unsubstituted heteroalkylene (e.g., 2 to 8 membered heteroalkylene, 2 to 6 membered heteroalkylene, or 2 to 4 membered heteroalkylene). In embodiments, $L^1$ is $R^{15}$-substituted heteroalkylene (e.g., 2 to 8 membered heteroalkylene, 2 to 6 membered heteroalkylene, or 2 to 4 membered heteroalkylene). In embodiments, $L^1$ is an unsubstituted heteroalkylene (e.g., 2 to 8 membered heteroalkylene, 2 to 6 membered heteroalkylene, or 2 to 4 membered heteroalkylene).

In embodiments, $L^1$ is $R^{15}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^1$ is $R^{15}$-substituted cycloalkylene (e.g., $C_3$-$C_8$ cycloalkylene, $C_3$-$C_6$ cycloalkylene, or $C_5$-$C_6$ cycloalkylene). In embodiments, $L^1$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^1$ is $R^{15}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^1$ is $R^{15}$-substituted heterocycloalkylene (e.g., 3 to 8 membered heterocycloalkylene, 3 to 6 membered heterocycloalkylene, or 5 to 6 membered heterocycloalkylene). In embodiments, $L^1$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^1$ is $R^{15}$-substituted or unsubstituted arylene (e.g., $C_6$-$C_{10}$ arylene, $C_{10}$ arylene, or phenylene). In embodiments, $L^1$ is $R^{15}$-substituted arylene (e.g., $C_6$-$C_{10}$ arylene, $C_{10}$ arylene, or phenylene). In embodiments, $L^1$ is an unsubstituted arylene (e.g., $C_6$-$C_{10}$ arylene, $C_{10}$ arylene, or phenylene).

In embodiments, $L^1$ is $R^{15}$-substituted or unsubstituted heteroarylene (e.g., 5 to 10 membered heteroarylene, 5 to 9 membered heteroarylene, or 5 to 6 membered heteroarylene). In embodiments, $L^1$ is $R^{15}$-substituted heteroarylene (e.g., 5 to 10 membered heteroarylene, 5 to 9 membered heteroarylene, or 5 to 6 membered heteroarylene). In embodiments, $L^1$ is an unsubstituted heteroarylene (e.g., 5 to 10 membered heteroarylene, 5 to 9 membered heteroarylene, or 5 to 6 membered heteroarylene).

In embodiments, -$L^1$-$R^{14}$ has the formula:

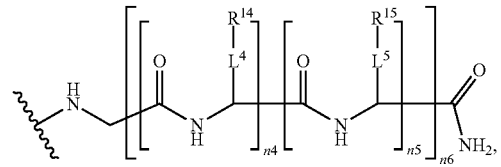

wherein $R^{14}$ and $R^{15}$ are as described herein. $L^4$ and $L^5$ are each independently a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). The symbol n4 is an integer from 1 to 5. The symbol n5 is an integer from 0 to 5. The symbol n5 is an integer from 1 to 5. In embodiments, n4 is 1. In embodiments, n5 is 1. In embodiments, n6 is 1.

In embodiments, -$L^1$-$R^{14}$ has the formula:

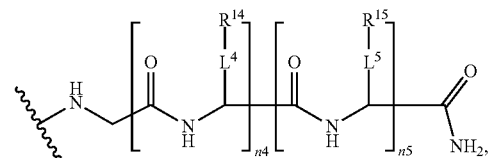

wherein $L^4$, $L^5$, n4, n5, $R^{14}$, and $R^{15}$ are as described herein.

In embodiments, -$L^1$-$R^{14}$ has the formula:

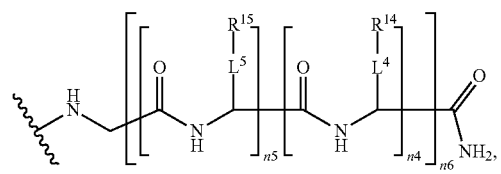

wherein $L^4$, $L^5$, n4, n5, $R^{14}$, and $R^{15}$ are as described herein. In embodiments, n4 is 1. In embodiments, n5 is 1. In embodiments, n6 is 1.

In embodiments, -L$^1$-R$^{14}$ has the formula:

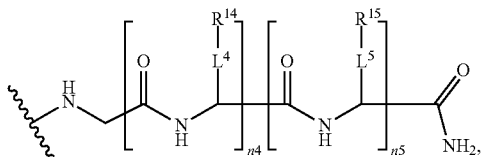

wherein L$^4$, L$^5$, n4, n5, R$^{14}$, and R$^{15}$ are as described herein.

In embodiments, L$^4$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L$^4$ is a bond. In embodiments, L$^4$ is —S(O)$_2$—. In embodiments, L$^4$ is —NH—. In embodiments, L$^4$ is —O—. In embodiments, L$^4$ is —S—. In embodiments, L$^4$ is —C(O)—. In embodiments, L$^4$ is —C(O)NH—. In embodiments, L$^4$ is —NHC(O)—. In embodiments, L$^4$ is —NHC(O)NH—. In embodiments, L$^4$ is —C(O)O—. In embodiments, L$^4$ is —OC(O)—. In embodiments, L$^4$ is substituted or unsubstituted alkylene. In embodiments, L$^4$ is substituted or unsubstituted heteroalkylene. In embodiments, L$^4$ is substituted or unsubstituted cycloalkylene. In embodiments, L$^4$ is substituted or unsubstituted heterocycloalkylene. In embodiments, L$^4$ is substituted or unsubstituted arylene. In embodiments, L$^4$ is substituted or unsubstituted heteroarylene.

In embodiments, L$^4$ is a bond, —S(O)$_2$—, —NH—, —O—, —S—, —C(O)—, —C(O)NH—, —NHC(O)—, —NHC(O)NH—, —C(O)O—, —OC(O)—, R$^{52}$-substituted or unsubstituted alkylene (e.g., C$_1$-C$_8$ alkylene, C$_1$-C$_6$ alkylene, or C$_1$-C$_4$ alkylene), R$^{52}$-substituted or unsubstituted heteroalkylene (e.g., 2 to 8 membered heteroalkylene, 2 to 6 membered heteroalkylene, or 2 to 4 membered heteroalkylene), R$^{52}$-substituted or unsubstituted cycloalkylene (e.g., C$_3$-C$_8$ cycloalkylene, C$_3$-C$_6$ cycloalkylene, or C$_5$-C$_6$ cycloalkylene), R$^{52}$-substituted or unsubstituted heterocycloalkylene (e.g., 3 to 8 membered heterocycloalkylene, 3 to 6 membered heterocycloalkylene, or 5 to 6 membered heterocycloalkylene), R$^{52}$-substituted or unsubstituted arylene (e.g., C$_6$-C$_{10}$ arylene, C$_{10}$ arylene, or phenylene), or R$^{52}$-substituted or unsubstituted heteroarylene (e.g., 5 to 10 membered heteroarylene, 5 to 9 membered heteroarylene, or 5 to 6 membered heteroarylene).

In embodiments, L$^4$ is R$^{52}$-substituted or unsubstituted alkylene (e.g., C$_1$-C$_8$ alkylene, C$_1$-C$_6$ alkylene, or C$_1$-C$_4$ alkylene). In embodiments, L$^4$ is R$^{52}$-substituted alkylene (e.g., C$_1$-C$_8$ alkylene, C$_1$-C$_6$ alkylene, or C$_1$-C$_4$ alkylene). In embodiments, L$^4$ is an unsubstituted alkylene (e.g., C$_1$-C$_8$ alkylene, C$_1$-C$_6$ alkylene, or C$_1$-C$_4$ alkylene).

In embodiments, L$^4$ is R$^{52}$-substituted or unsubstituted heteroalkylene (e.g., 2 to 8 membered heteroalkylene, 2 to 6 membered heteroalkylene, or 2 to 4 membered heteroalkylene). In embodiments, L$^4$ is R$^{52}$-substituted heteroalkylene (e.g., 2 to 8 membered heteroalkylene, 2 to 6 membered heteroalkylene, or 2 to 4 membered heteroalkylene). In embodiments, L$^4$ is an unsubstituted heteroalkylene (e.g., 2 to 8 membered heteroalkylene, 2 to 6 membered heteroalkylene, or 2 to 4 membered heteroalkylene).

In embodiments, L$^4$ is R$^{52}$-substituted or unsubstituted cycloalkylene (e.g., C$_3$-C$_8$ cycloalkylene, C$_3$-C$_6$ cycloalkylene, or C$_5$-C$_6$ cycloalkylene). In embodiments, L$^4$ is R$^{52}$-substituted cycloalkylene (e.g., C$_3$-C$_8$ cycloalkylene, C$_3$-C$_6$ cycloalkylene, or C$_5$-C$_6$ cycloalkylene). In embodiments, L$^4$ is an unsubstituted cycloalkylene (e.g., C$_3$-C$_8$ cycloalkylene, C$_3$-C$_6$ cycloalkylene, or C$_5$-C$_6$ cycloalkylene).

In embodiments, L$^4$ is R$^{52}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, L$^4$ is R$^{52}$-substituted heterocycloalkylene (e.g., 3 to 8 membered heterocycloalkylene, 3 to 6 membered heterocycloalkylene, or 5 to 6 membered heterocycloalkylene). In embodiments, L$^4$ is an unsubstituted heterocycloalkylene (e.g., 3 to 8 membered heterocycloalkylene, 3 to 6 membered heterocycloalkylene, or 5 to 6 membered heterocycloalkylene).

In embodiments, L$^4$ is R$^{52}$-substituted or unsubstituted arylene (e.g., C$_6$-C$_{10}$ arylene, C$_{10}$ arylene, or phenylene). In embodiments, L$^4$ is R$^{52}$-substituted arylene (e.g., C$_6$-C$_{10}$ arylene, C$_{10}$ arylene, or phenylene). In embodiments, L$^4$ is an unsubstituted arylene (e.g., C$_6$-C$_{10}$ arylene, C$_{10}$ arylene, or phenylene).

In embodiments, L$^4$ is R$^{52}$-substituted or unsubstituted heteroarylene (e.g., 5 to 10 membered heteroarylene, 5 to 9 membered heteroarylene, or 5 to 6 membered heteroarylene). In embodiments, L$^4$ is R$^{52}$-substituted heteroarylene (e.g., 5 to 10 membered heteroarylene, 5 to 9 membered heteroarylene, or 5 to 6 membered heteroarylene). In embodiments, L$^4$ is an unsubstituted heteroarylene (e.g., 5 to 10 membered heteroarylene, 5 to 9 membered heteroarylene, or 5 to 6 membered heteroarylene).

In embodiments, L$^5$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L$^5$ is a bond. In embodiments, L$^5$ is —S(O)$_2$—. In embodiments, L$^5$ is —NH—. In embodiments, L$^5$ is —O—. In embodiments, L$^5$ is —S—. In embodiments, L$^5$ is —C(O)—. In embodiments, L$^5$ is —C(O)NH—. In embodiments, L$^5$ is —NHC(O)—. In embodiments, L$^5$ is —NHC(O)NH—. In embodiments, L$^5$ is —C(O)O—. In embodiments, L$^5$ is —OC(O)—. In embodiments, L$^5$ is substituted or unsubstituted alkylene. In embodiments, L$^5$ is substituted or unsubstituted heteroalkylene. In embodiments, L$^5$ is substituted or unsubstituted cycloalkylene. In embodiments, L$^5$ is substituted or unsubstituted heterocycloalkylene. In embodiments, L$^5$ is substituted or unsubstituted arylene. In embodiments, L$^5$ is substituted or unsubstituted heteroarylene.

In embodiments, L$^5$ is a bond, —S(O)$_2$—, —NH—, —O—, —S—, —C(O)—, —C(O)NH—, —NHC(O)—, —NHC(O)NH—, —C(O)O—, —OC(O)—, R$^{53}$-substituted or unsubstituted alkylene (e.g., $C_1$-$C_8$ alkylene, $C_1$-$C_6$ alkylene, or $C_1$-$C_4$ alkylene), $R^{53}$-substituted or unsubstituted heteroalkylene (e.g., 2 to 8 membered heteroalkylene, 2 to 6 membered heteroalkylene, or 2 to 4 membered heteroalkylene), $R^{53}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{53}$-substituted or unsubstituted heterocycloalkylene (e.g., 3 to 8 membered heterocycloalkylene, 3 to 6 membered heterocycloalkylene, or 5 to 6 membered heterocycloalkylene), $R^{53}$-substituted or unsubstituted arylene (e.g., $C_6$-$C_{10}$ arylene, $C_{10}$ arylene, or phenylene), or $R^{53}$-substituted or unsubstituted heteroarylene (e.g., 5 to 10 membered heteroarylene, 5 to 9 membered heteroarylene, or 5 to 6 membered heteroarylene).

In embodiments, $L^5$ is $R^{53}$-substituted or unsubstituted alkylene (e.g., $C_1$-$C_8$ alkylene, $C_1$-$C_6$ alkylene, or $C_1$-$C_4$ alkylene). In embodiments, $L^5$ is $R^{53}$-substituted alkylene (e.g., $C_1$-$C_8$ alkylene, $C_1$-$C_6$ alkylene, or $C_1$-$C_4$ alkylene). In embodiments, $L^5$ is an unsubstituted alkylene (e.g., $C_1$-$C_8$ alkylene, $C_1$-$C_6$ alkylene, or $C_1$-$C_4$ alkylene).

In embodiments, $L^5$ is $R^{53}$-substituted or unsubstituted heteroalkylene (e.g., 2 to 8 membered heteroalkylene, 2 to 6 membered heteroalkylene, or 2 to 4 membered heteroalkylene). In embodiments, $L^5$ is $R^{53}$-substituted heteroalkylene (e.g., 2 to 8 membered heteroalkylene, 2 to 6 membered heteroalkylene, or 2 to 4 membered heteroalkylene). In embodiments, $L^5$ is an unsubstituted heteroalkylene (e.g., 2 to 8 membered heteroalkylene, 2 to 6 membered heteroalkylene, or 2 to 4 membered heteroalkylene).

In embodiments, $L^5$ is $R^{53}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^5$ is $R^{53}$-substituted cycloalkylene (e.g., $C_3$-$C_8$ cycloalkylene, $C_3$-$C_6$ cycloalkylene, or $C_5$-$C_6$ cycloalkylene). In embodiments, $L^5$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^5$ is $R^{53}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^5$ is $R^{53}$-substituted heterocycloalkylene (e.g., 3 to 8 membered heterocycloalkylene, 3 to 6 membered heterocycloalkylene, or 5 to 6 membered heterocycloalkylene). In embodiments, $L^5$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^5$ is $R^{53}$-substituted or unsubstituted arylene (e.g., $C_6$-$C_{10}$ arylene, $C_{10}$ arylene, or phenylene). In embodiments, $L^5$ is $R^{53}$-substituted arylene (e.g., $C_6$-$C_{10}$ arylene, $C_{10}$ arylene, or phenylene). In embodiments, $L^5$ is an unsubstituted arylene (e.g., $C_6$-$C_{10}$ arylene, $C_{10}$ arylene, or phenylene).

In embodiments, $L^5$ is $R^{53}$-substituted or unsubstituted heteroarylene (e.g., 5 to 10 membered heteroarylene, 5 to 9 membered heteroarylene, or 5 to 6 membered heteroarylene). In embodiments, $L^5$ is $R^{53}$-substituted heteroarylene (e.g., 5 to 10 membered heteroarylene, 5 to 9 membered heteroarylene, or 5 to 6 membered heteroarylene). In embodiments, $L^5$ is an unsubstituted heteroarylene (e.g., 5 to 10 membered heteroarylene, 5 to 9 membered heteroarylene, or 5 to 6 membered heteroarylene).

In embodiments, -$L^1$-$R^{14}$ has the formula:

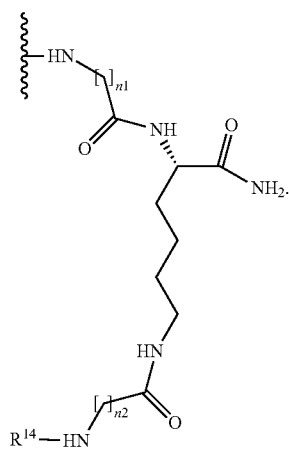

In embodiments, -$L^1$-$R^{14}$ has the formula:

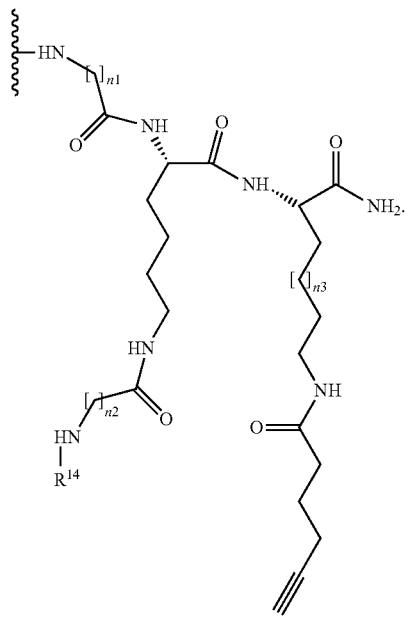

In embodiments, -L$^1$-R$^{14}$ has the formula:
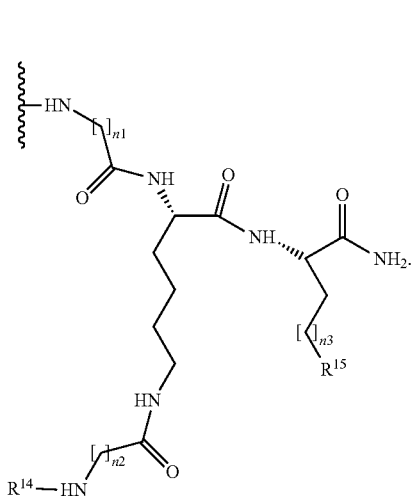
In embodiments, L$^1$ has the formula:
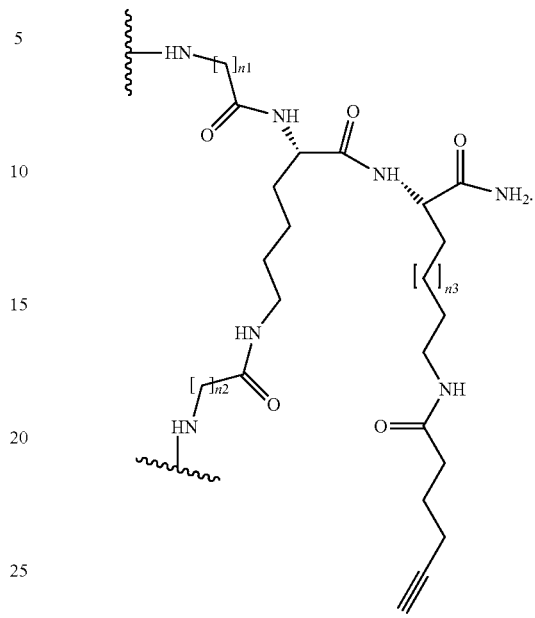
In embodiments, L$^1$ has the formula:
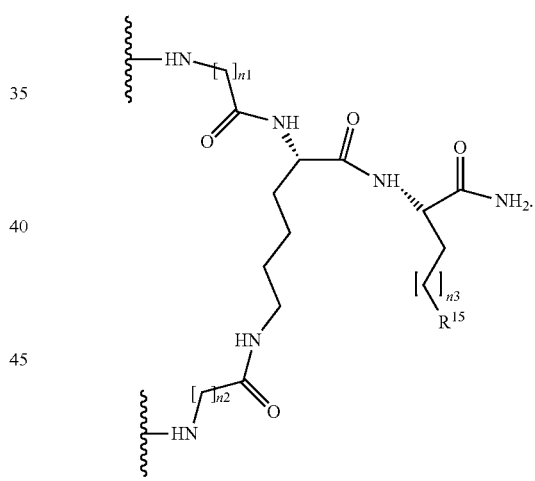
In embodiments, L$^1$ has the formula:
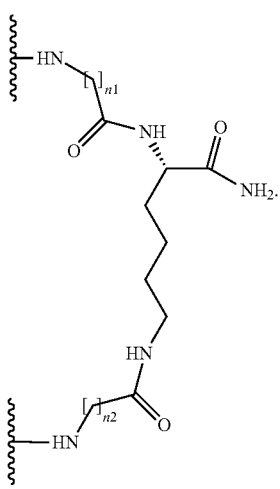 [SMILES: *NCC(=O)NCCCC[C@H](NC(=O)CN*)C(N)=O]
In embodiments, L$_1$ has the formula:
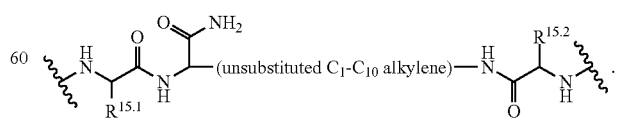
R$^{15.1}$ and R$^{15.2}$ may be any value of R$^{15}$ described herein, including in any aspect, embodiment, example, figure, table, or claim.

In embodiments, -$L^1$-$R^{14}$ has the formula:
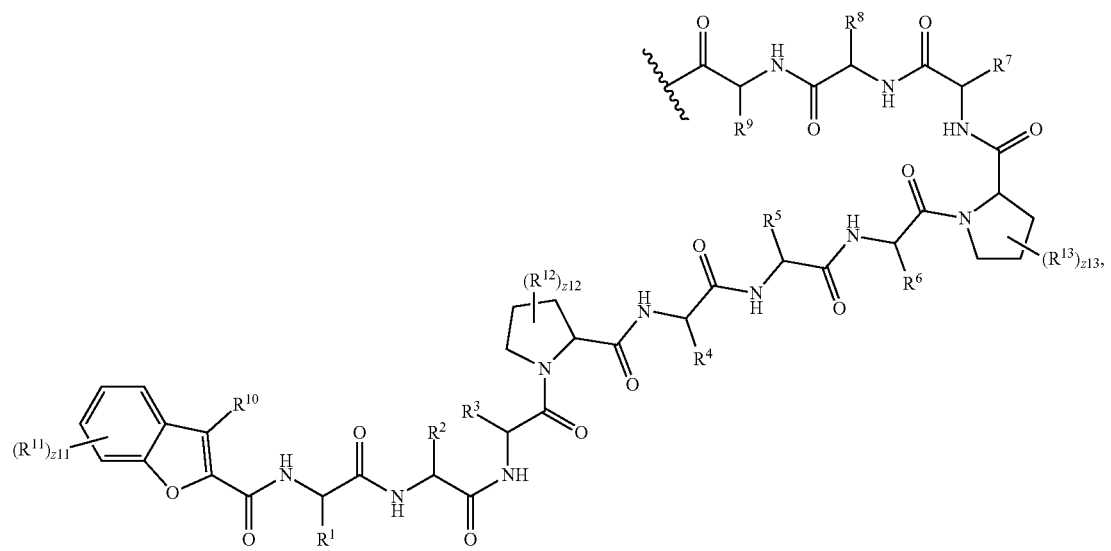
wherein $R^1$, $R^2$, $R^3$, $R^4$, $R^5$, $R^6$, $R^7$, $R^8$, $R^9$, $R^{10}$, $R^{11}$, $R^{12}$, $R^{13}$, z13, z12, and z11 are as described herein.
In embodiments, -$L^1$-$R^{14}$ has the formula:
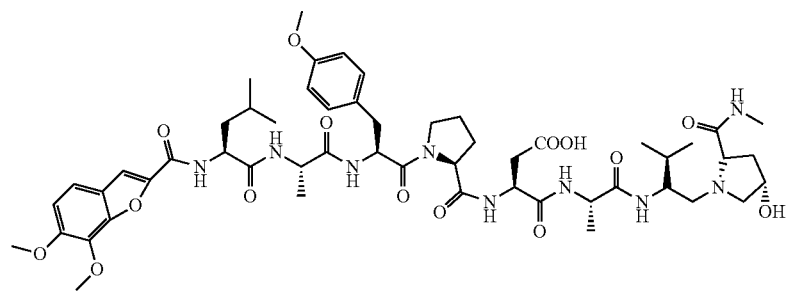

-continued
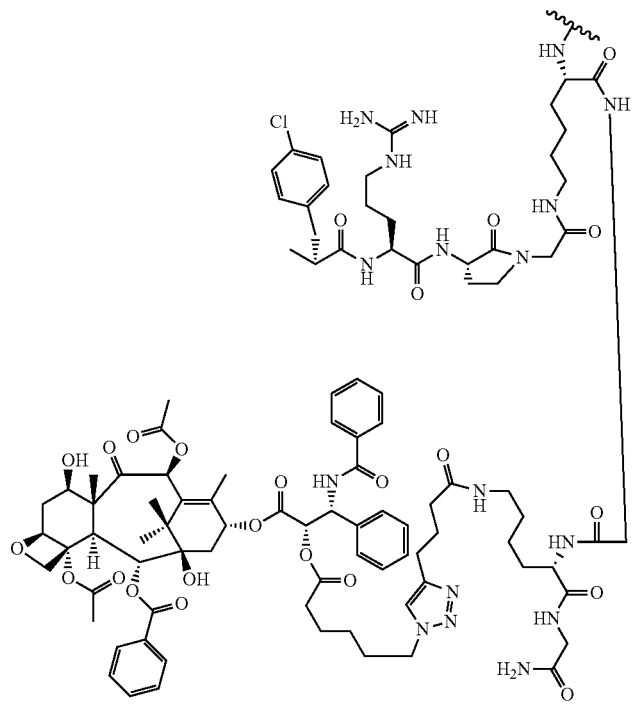

In embodiments, -L$^1$-R$^{14}$ has the formula:
(SEQ ID NO:81)
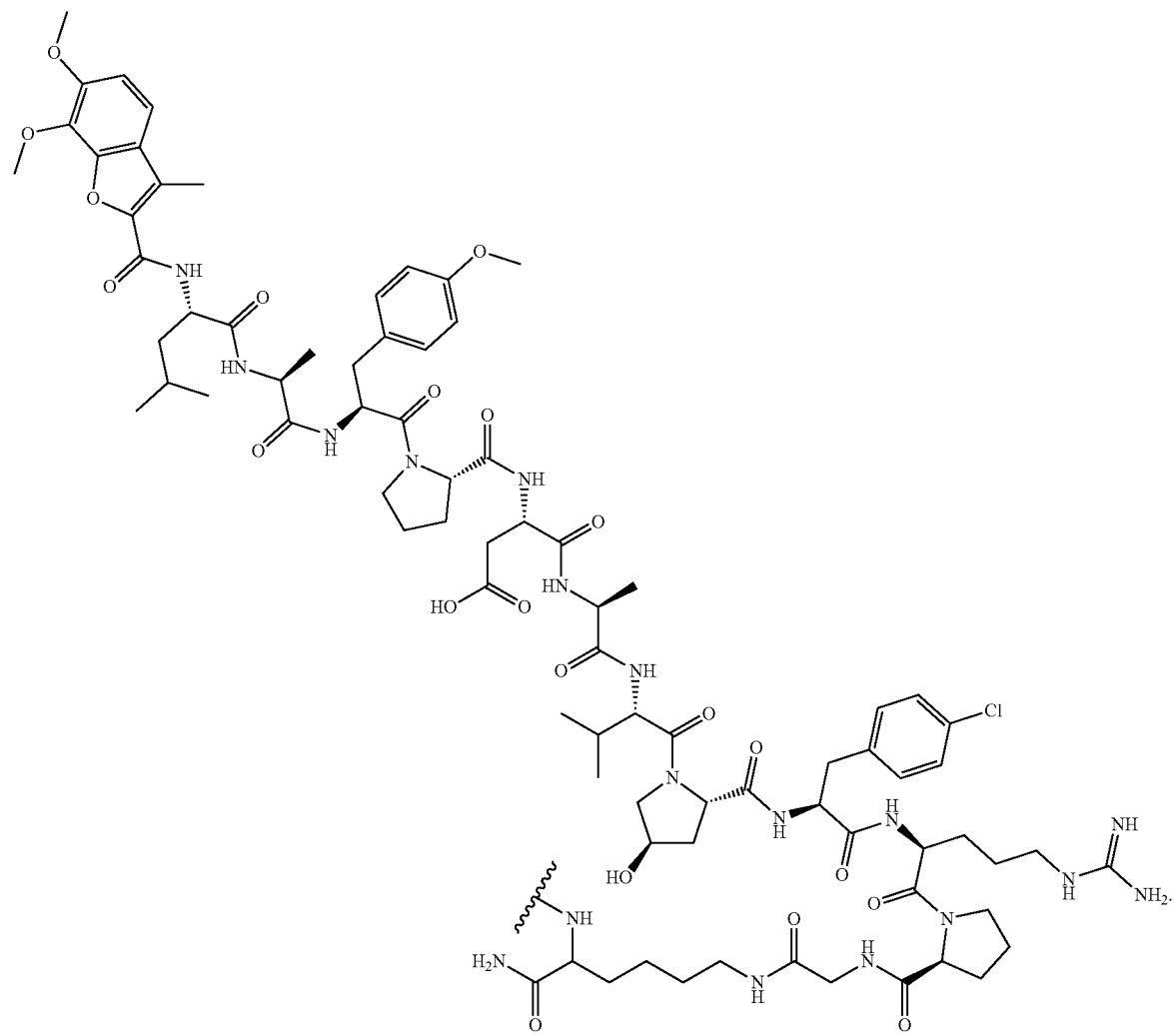

In embodiments, -$L^1$-$R^{14}$ has the formula:
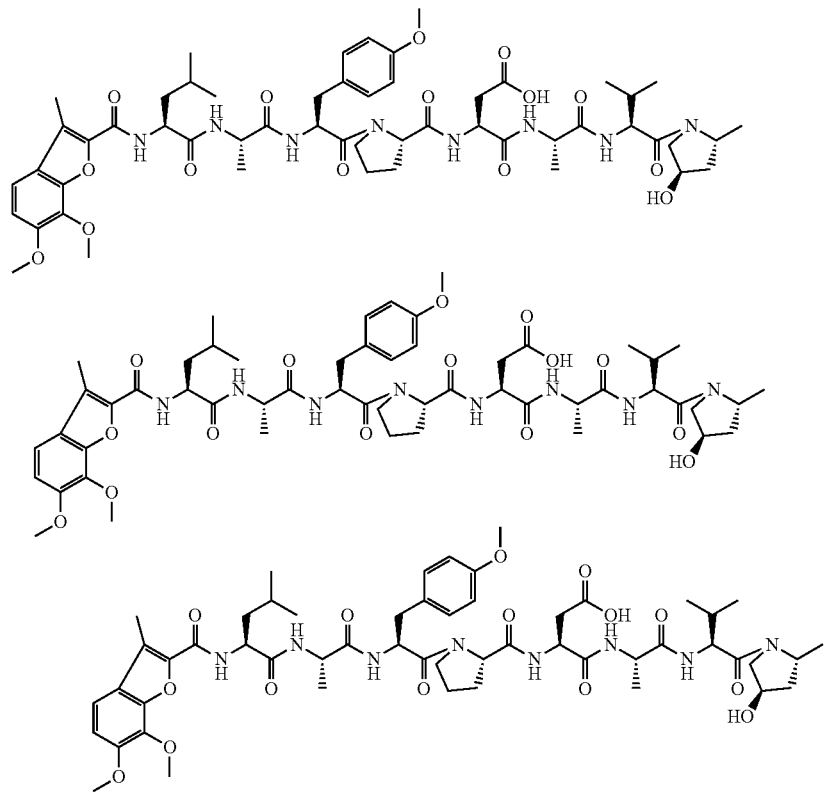

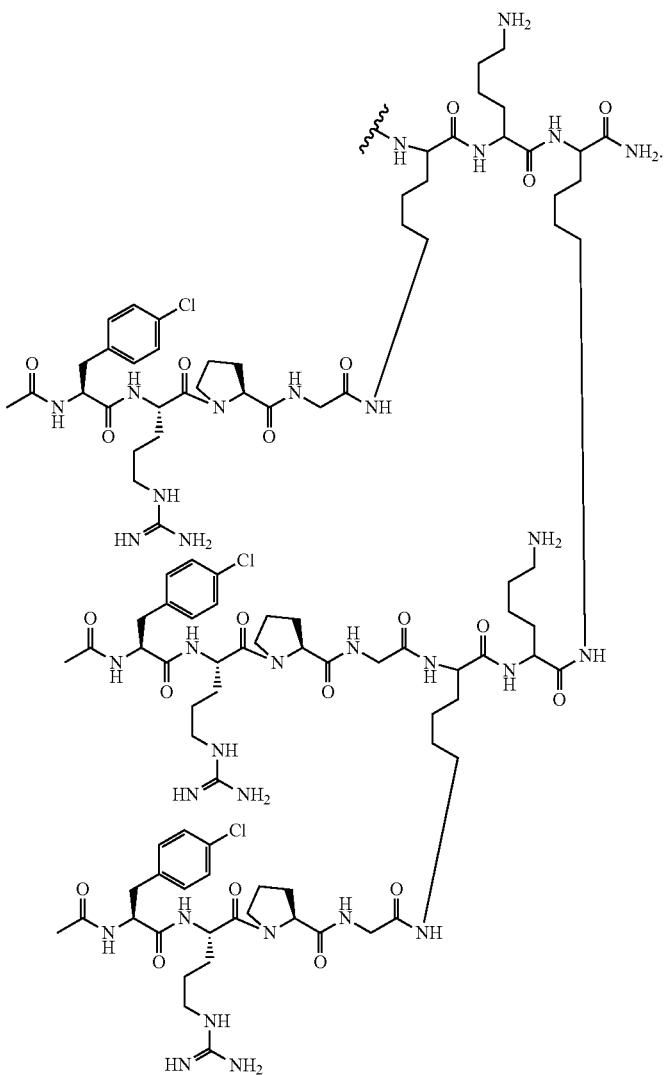 [SMILES: *NC(CCCCNC(=O)CNC(=O)[C@@H]1CCCN1C(=O)[C@H](CCCNC(=N)N)NC(=O)[C@H](Cc1ccc(Cl)cc1)NC(C)=O)C(=O)NC(CCCCN)C(=O)NC(CCCCNC(=O)C(CCCCN)NC(=O)C(CCCCNC(=O)CNC(=O)[C@@H]1CCCN1C(=O)[C@H](CCCNC(=N)N)NC(=O)[C@H](Cc1ccc(Cl)cc1)NC(C)=O)NC(=O)CNC(=O)[C@@H]1CCCN1C(=O)[C@H](CCCNC(=N)N)NC(=O)[C@H](Cc1ccc(Cl)cc1)NC(C)=O)C(N)=O]

In embodiments, -L$^1$-R$^{14}$ has the formula:

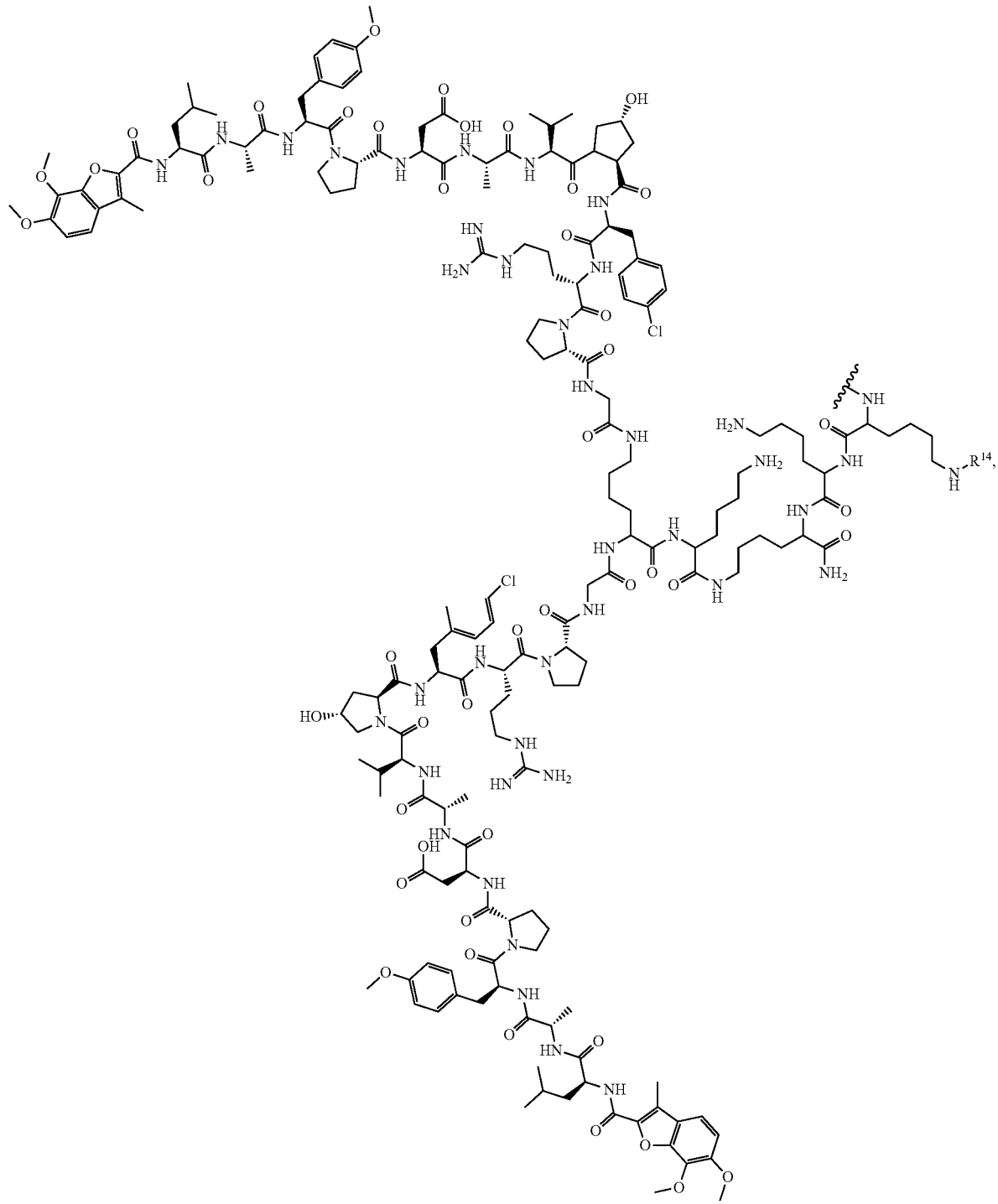

wherein R$^{14}$ is as described herein, including embodiments.

In embodiments, n1 is independently 0. In embodiments, n1 is independently 1. In embodiments, n1 is independently 2. In embodiments, n1 is independently 3. In embodiments, n1 is independently 4. In embodiments, n1 is independently 5. In embodiments, n1 is independently 6. In embodiments, n1 is independently 7. In embodiments, n1 is independently 8. In embodiments, n1 is independently 9. In embodiments, n1 is independently 10. In embodiments, n1 is independently 11. In embodiments, n1 is independently 12. In embodiments, n1 is independently 13. In embodiments, n1 is independently 14. In embodiments, n1 is independently 15. In embodiments, n1 is independently 16. In embodiments, n1 is independently 17. In embodiments, n1 is independently 18. In embodiments, n1 is independently 19. In embodiments, n1 is independently 20.

In embodiments, n2 is independently 0. In embodiments, n2 is independently 1. In embodiments, n2 is independently 2. In embodiments, n2 is independently 3. In embodiments, n2 is independently 4. In embodiments, n2 is independently 5. In embodiments, n2 is independently 6. In embodiments, n2 is independently 7. In embodiments, n2 is independently 8. In embodiments, n2 is independently 9. In embodiments, n2 is independently 10. In embodiments, n2 is independently 11. In embodiments, n2 is independently 12. In embodiments, n2 is independently 13. In embodiments, n2 is independently 14. In embodiments, n2 is independently 15. In embodiments, n2 is independently 16. In embodiments, n2 is independently 17. In embodiments, n2 is independently 18. In embodiments, n2 is independently 19. In embodiments, n2 is independently 20.

In embodiments, n3 is independently 0. In embodiments, n3 is independently 1. In embodiments, n3 is independently 2. In embodiments, n3 is independently 3. In embodiments, n3 is independently 4. In embodiments, n3 is independently 5. In embodiments, n3 is independently 6. In embodiments, n3 is independently 7. In embodiments, n3 is independently 8. In embodiments, n3 is independently 9. In embodiments, n3 is independently 10. In embodiments, n3 is independently 11. In embodiments, n3 is independently 12. In embodiments, n3 is independently 13. In embodiments, n3 is independently 14. In embodiments, n3 is independently 15. In embodiments, n3 is independently 16. In embodiments, n3 is independently 17. In embodiments, n3 is independently 18. In embodiments, n3 is independently 19. In embodiments, n3 is independently 20.

In embodiments, z11 is 0. In embodiments, z11 is 2. In embodiments, z11 is 3. In embodiments, z11 is 4. In embodiments, z12 is 0. In embodiments, z12 is 2. In embodiments, z12 is 3. In embodiments, z12 is 4. In embodiments, z12 is 5. In embodiments, z12 is 6. In embodiments, z12 is 7. In embodiments, z13 is 0. In embodiments, z13 is 2. In embodiments, z13 is 3. In embodiments, z13 is 4. In embodiments, z13 is 4. In embodiments, z13 is 5.

$R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —NHC(NH)NH$_2$, —SO$_2$F, —OSO$_2$F, E, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —NHC(NH)NH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently oxo, halogen, —CCl$_3$, —CF$_3$, —CI$_3$, —CH$_2$Cl, —CH$_2$Br, —CH$_2$F, —CHCl$_2$, —CHBr$_2$, —CHF$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCHCl$_2$, —OCHBr$_2$, —OCHF$_2$, —NHC(NH)NH$_2$, —SO$_2$F, —OSO$_2$F, E, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^1$, $R^2$, $R^3$, $R^4$, $R^5$, $R^6$, $R^7$, and $R^8$ are each independently an amino acid side chain. In embodiments, $R^1$, $R^2$, $R^3$, $R^4$, $R^5$, $R^6$, $R^7$, and $R^8$ are each independently a non-natural amino acid side chain. Where a group of multiple substituents are defined as "independently" being a particular chemical moiety, it is meant that one or more members of the group of multiple substituents may be that particular chemical moiety. For example, as set forth in the first sentence of this paragraph, one or more of $R^1$, $R^2$, $R^3$, $R^4$, $R^5$, $R^6$, $R^7$, and $R^8$ may be an amino acid side chain. The same meaning of "independently" is applied for the the following paragraphs, In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently oxo. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently halogen. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CCl$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CBr$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CF$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CI$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CH$_2$C$_1$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CH$_2$Br. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CH$_2$F. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CH$_2$I. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CHCl$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CHBr$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CHF$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CHI$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CN. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —COOH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CONH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NO$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —SH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —SO$_3$H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —SO$_4$H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —SO$_2$NH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHNH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —ONH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHC(O)NHNH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHC(O)NH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHSO$_2$H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHC(O)H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHC(O)OH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHOH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCCl$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCBr$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCF$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCI$_3$.

In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCH$_2$Cl. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCH$_2$Br. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCH$_2$F. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCH$_2$I. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCHCl$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCHBr$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCHF$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCHI$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —CH$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —OCH$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently —NHC(NH)NH$_2$.

In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently oxo. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently halogen. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CCl$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CBr$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CF$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CI$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CH$_2$Cl. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CH$_2$Br. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CH$_2$F. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CH$_2$I. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CHCl$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CHBr$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CHF$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CHI$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CN. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —COOH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CONH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NO$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —SH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —SO$_3$H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —SO$_4$H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —SO$_2$NH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHNH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —ONH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHC(O)NHNH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHC(O)NH$_2$. In embodiments, Rei $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHSO$_2$H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHC(O)H. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHC(O)OH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHOH. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCCl$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCBr$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCF$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCl$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCH$_2$Cl. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCH$_2$Br. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCH$_2$F. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCH$_2$I. In embodiments, $R^{21}$, $R^{23}$, $R^{25}$, $R_{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCHCl$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCHBr$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCHF$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCHI$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —CH$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OCH$_3$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —NHC(NH)NH$_2$. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —SO$_2$F. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently —OSO$_2$F. In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently E.

In embodiments, $R^{33}$ is independently —SO$_2$F, —OSO$_2$F, or E. In embodiments, $R^{33}$ is independently —SO$_2$F. In embodiments, $R^{33}$ is independently —OSO$_2$F. In embodiments, $R^{33}$ is independently E.

In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently unsubstituted alkyl (e.g., C$_1$-C$_8$ alkyl, C$_1$-C$_6$ alkyl, or C$_1$-C$_4$ alkyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently unsubstituted heteroalkyl (e.g., 2 to 8 membered heteroalkyl, 2 to 6 membered heteroalkyl, or 2 to 4 membered heteroalkyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently unsubstituted cycloalkyl (e.g., C$_3$-C$_8$ cycloalkyl, C$_3$-C$_6$ cycloalkyl, or C$_5$-C$_6$ cycloalkyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently unsubstituted heterocycloalkyl (e.g., 3 to 8 membered heterocycloalkyl, 3 to 6 membered heterocycloalkyl, or 5 to 6 membered heterocycloalkyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently unsubstituted aryl (e.g., C$_6$-C$_{10}$ aryl, C$_{10}$ aryl, or phenyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{49}$, $R^{51}$, $R^{52}$, and $R^{53}$ are independently unsubstituted heteroaryl (e.g., 5 to 10 membered heteroaryl, 5 to 9 membered heteroaryl, or 5 to 6 membered heteroaryl).

In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently unsubstituted alkyl (e.g., C$_1$-C$_8$ alkyl, C$_1$-C$_6$ alkyl, or C$_1$-C$_4$ alkyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently unsubstituted heteroalkyl (e.g., 2 to 8 membered heteroalkyl, 2 to 6 membered heteroalkyl, or 2 to 4 membered heteroalkyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently unsubstituted cycloalkyl (e.g., C$_3$-C$_8$ cycloalkyl, C$_3$-C$_6$ cycloalkyl, or C$_5$-C$_6$ cycloalkyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently unsubstituted heterocycloalkyl (e.g., 3 to 8 membered heterocycloalkyl, 3 to 6 membered heterocycloalkyl, or 5 to 6 membered heterocycloalkyl).

In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently unsubstituted aryl (e.g., C$_6$-C$_{10}$ aryl, C$_{10}$ aryl, or phenyl). In embodiments, $R^{21}$, $R^{23}$, $R^{25}$, $R^{27}$, $R^{29}$, $R^{31}$, $R^{33}$, $R^{35}$, $R^{37}$, $R^{39}$, $R^{41}$, $R^{43}$, $R^{45}$, $R^{47}$, $R^{51}$, $R^{52}$, and $R^{53}$ are independently unsubstituted heteroaryl (e.g., 5 to 10 membered heteroaryl, 5 to 9 membered heteroaryl, or 5 to 6 membered heteroaryl).

In embodiments, the drug moiety is an anti-cancer moiety (e.g., a monovalent anti-cancer agent). In embodiments, the drug moiety is a taxol moiety (e.g., a monovalent taxol). In embodiments, the drug moiety is monovalent paclitaxel. In embodiments, the drug moiety is a DM1 moiety (e.g., a monovalent DM1). In embodiments, the drug moiety is a mertansine moiety (e.g., a monovalent mertansine).

In embodiments, the drug moiety is an anti-cancer moiety (e.g., a monovalent anti-cancer agent). In embodiments, the drug moiety is a taxol moiety (e.g., a monovalent taxol). In embodiments, the drug moiety is monovalent paclitaxel.

In embodiments, the compound has the formula:
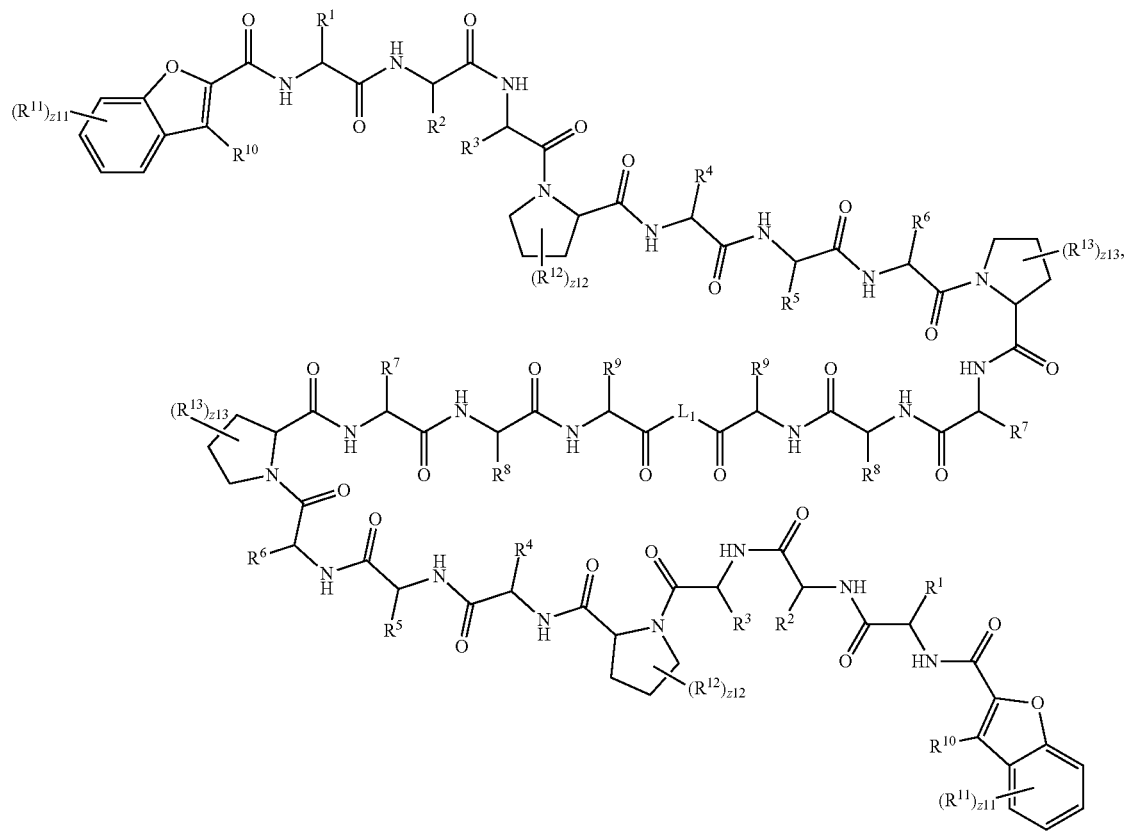
wherein wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $L^1$, z11, z12, and z13 are independent and as described herein.

In embodiments, the compound has the formula:
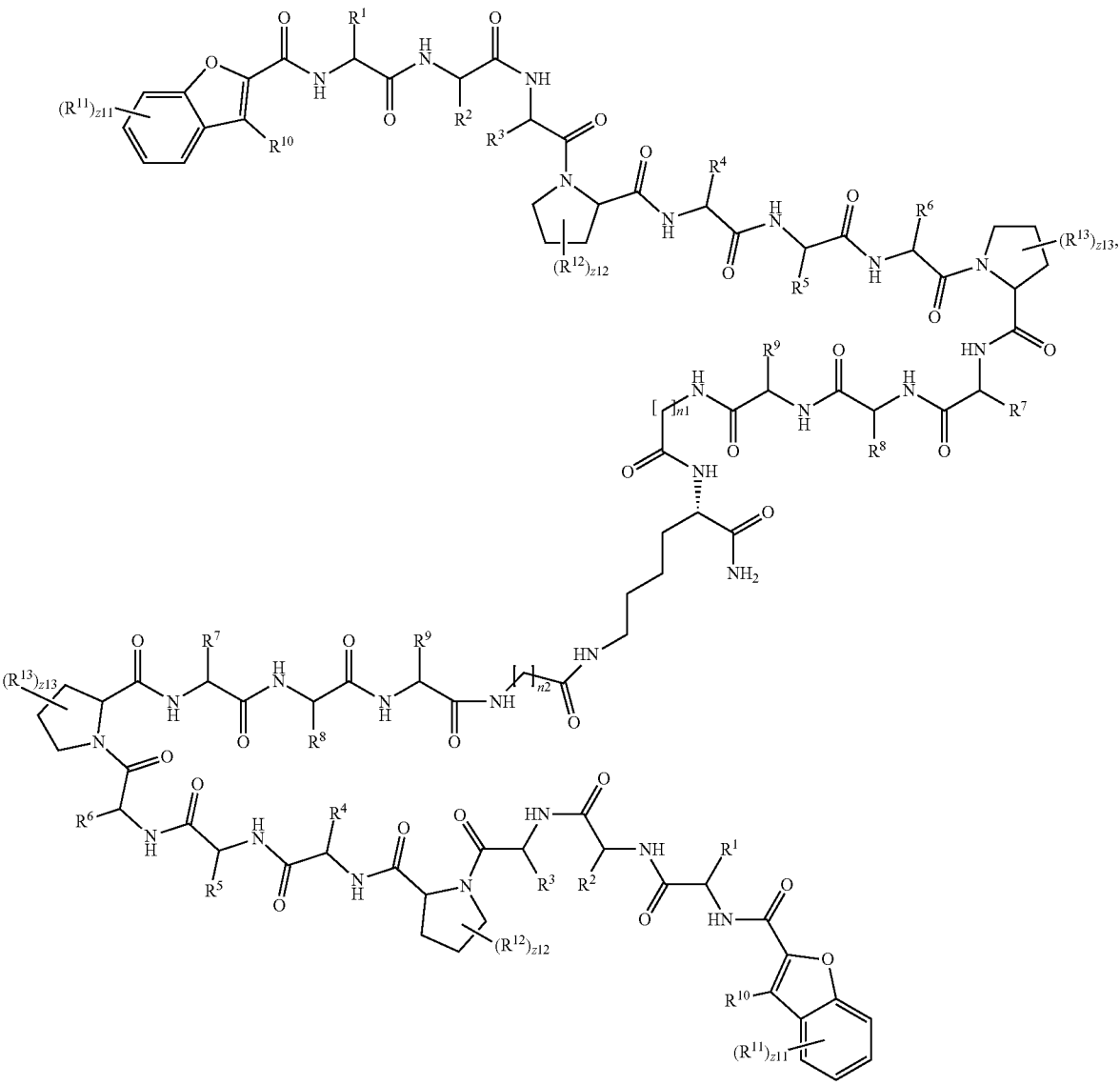
wherein $R^1$, $R^2$, $R^3$, $R^4$, $R^5$, $R^6$, $R^7$, $R^8$, $R^9$, $R^{10}$, $R^{12}$, $R^{13}$, n1, n2, z11, z12, and z13 are independent and as described herein.

In embodiments, the compound has the formula:
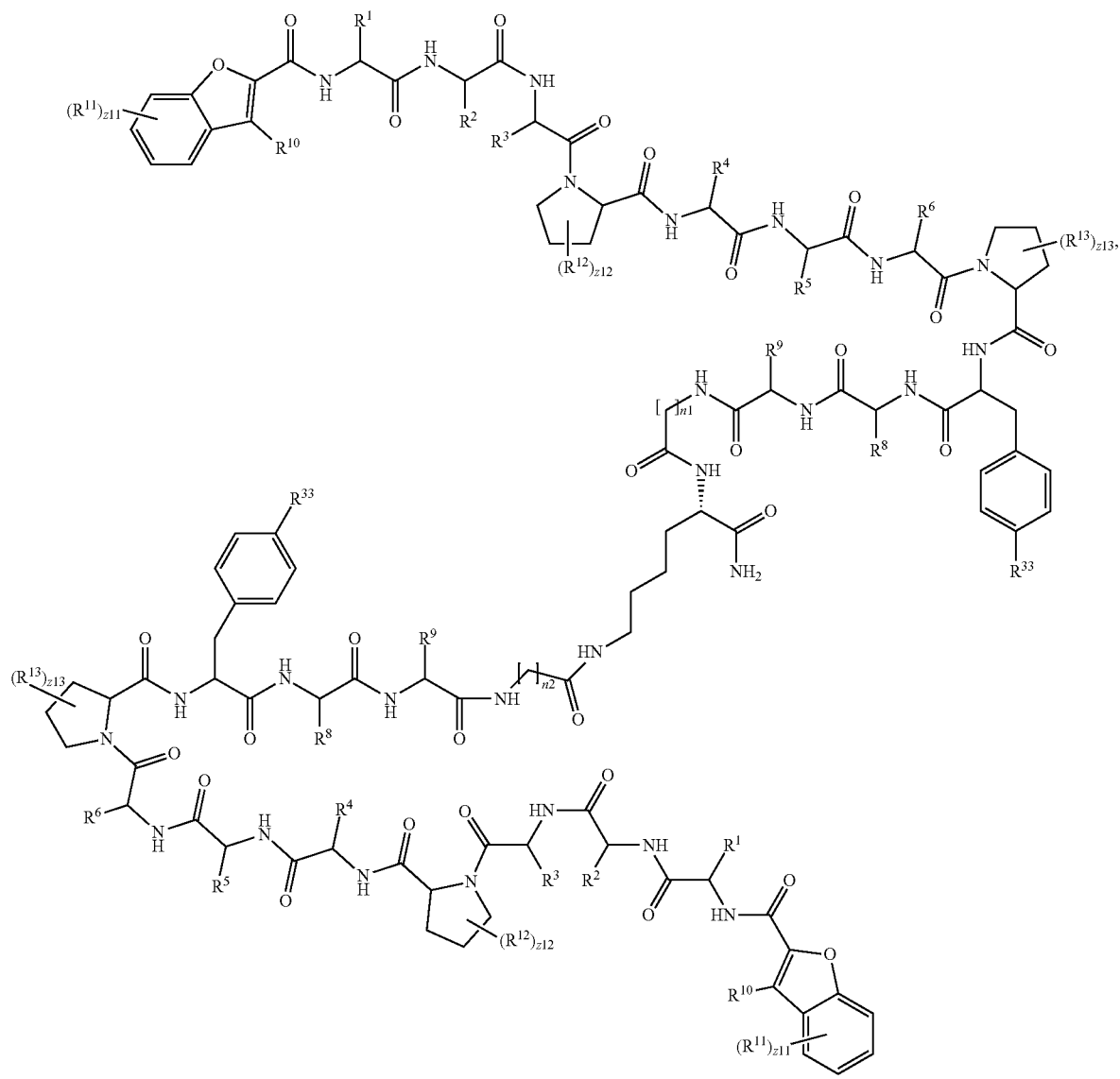
wherein $R^1$, $R^2$, $R^3$, $R^4$, $R^5$, $R^6$, $R^8$, $R^9$, $R^{10}$, $R^{12}$, $R^{13}$, $R^{33}$, n1, n2, z11, z12, and z13 are independent and as described herein.

In embodiments, the compound has the formula:
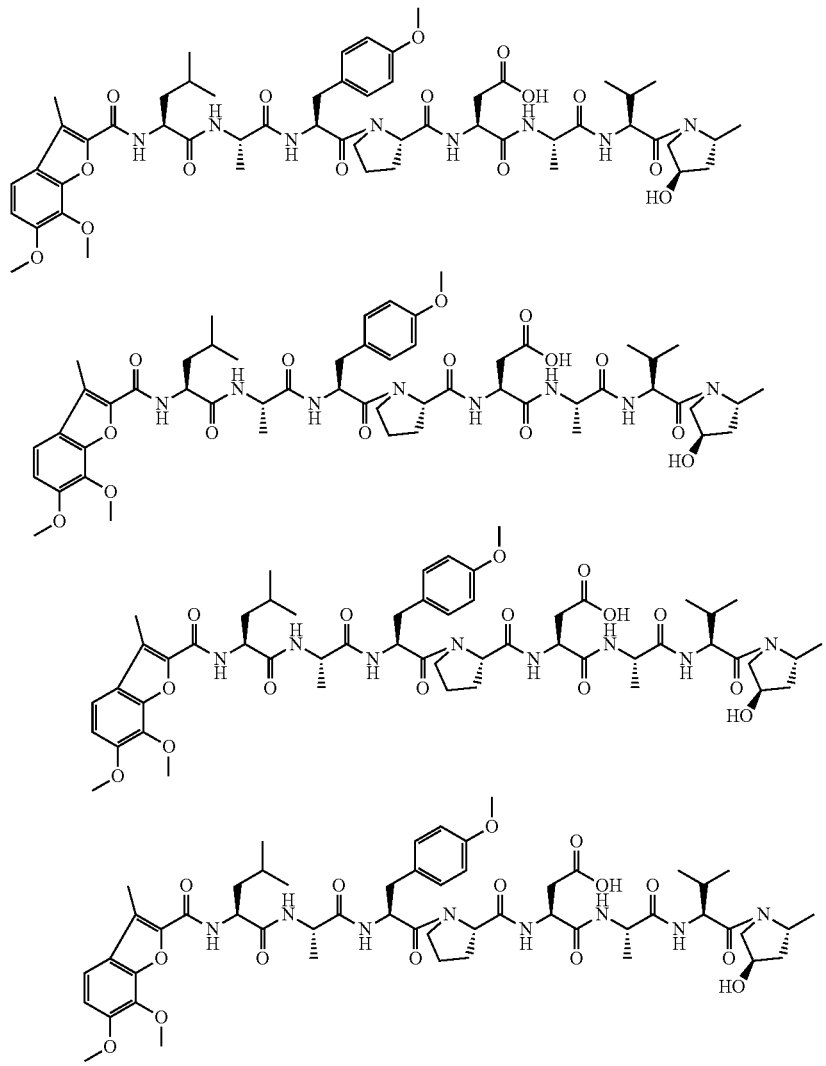

-continued
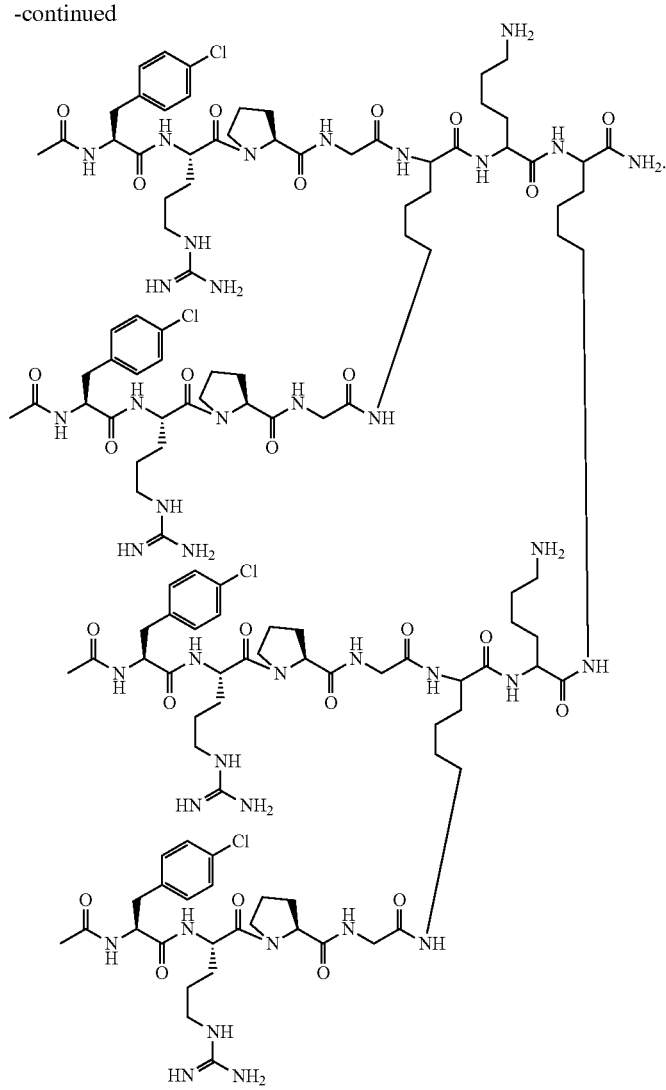
In embodiments, the compound has the formula:
(SEQ ID NO:67)
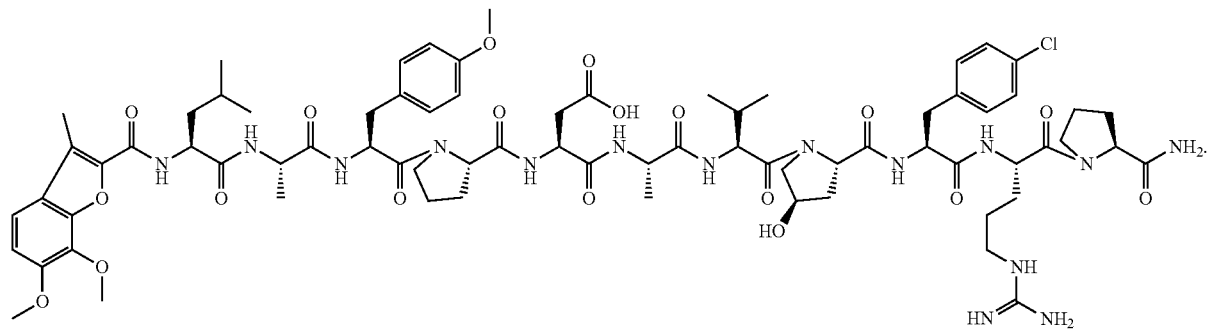

In embodiments, the compound has the formula:
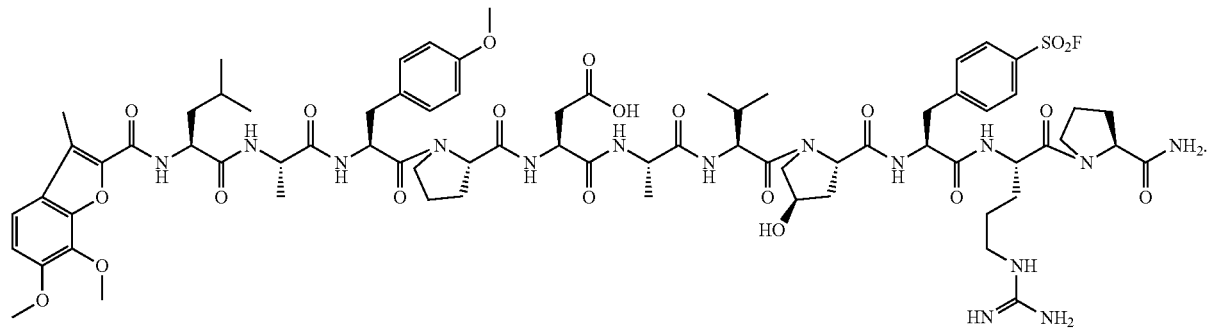
(SEQ ID NO:82)
In embodiments, the compound has the formula:
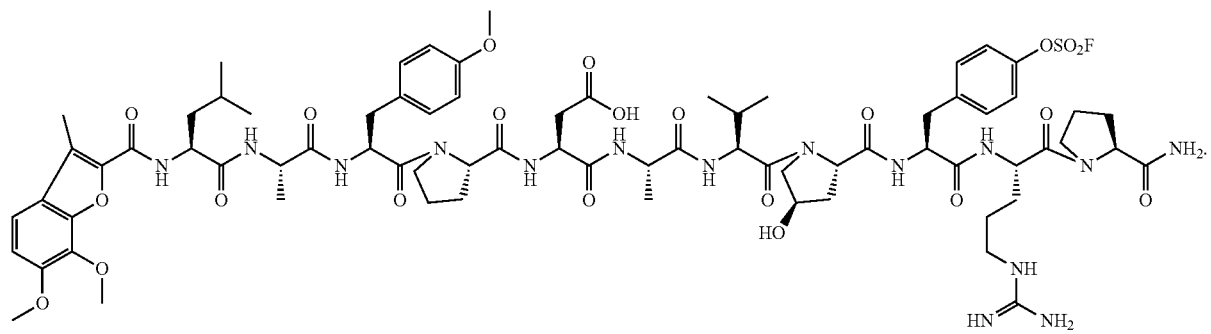
(SEQ ID NO:82)
In embodiments, the compound has the formula:
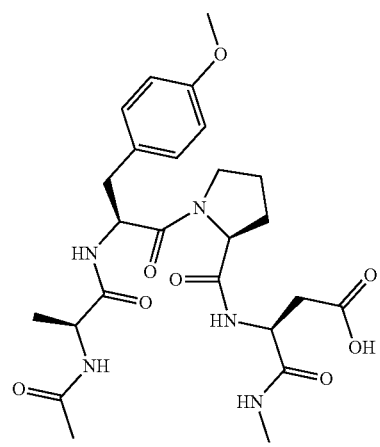

-continued
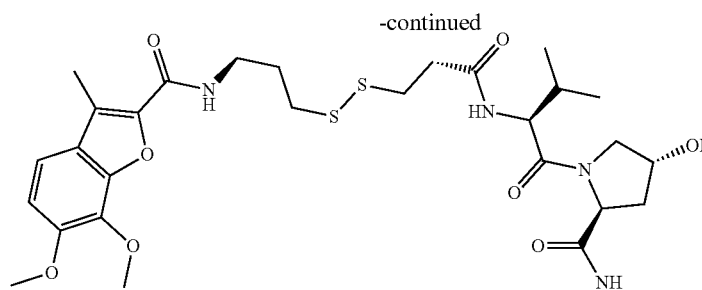
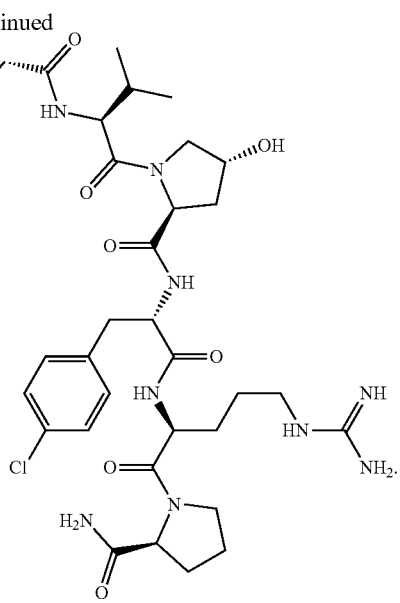
In embodiments, the compound has the formula:
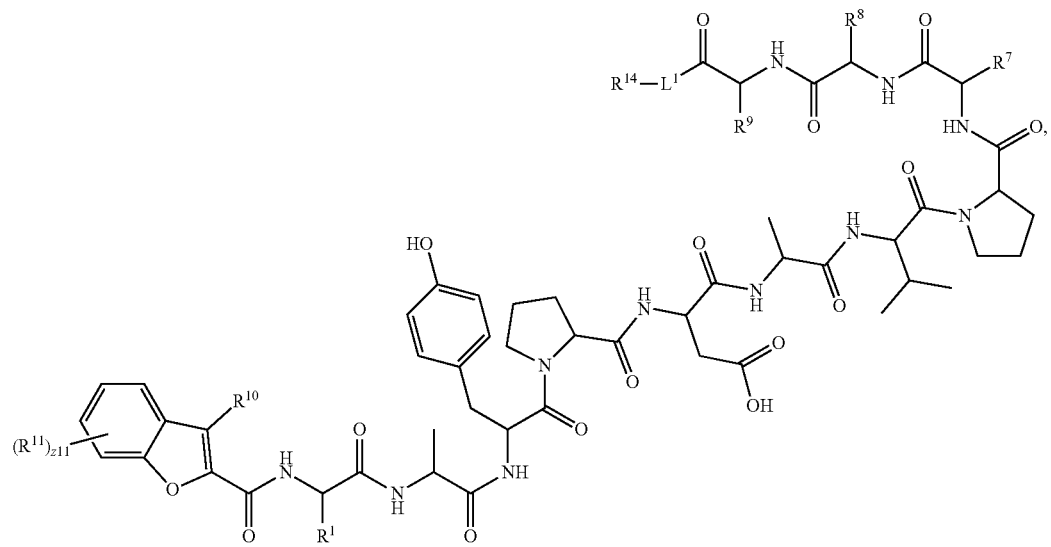
wherein $R^1$, $R^7$, $R^8$, $R^9$, $R^{10}$, $R^{11}$, z11, $R^{14}$, and $L^1$ are as described herein, including in embodiments.

In embodiments, the compound has the formula:
(SEQ ID NO:84)
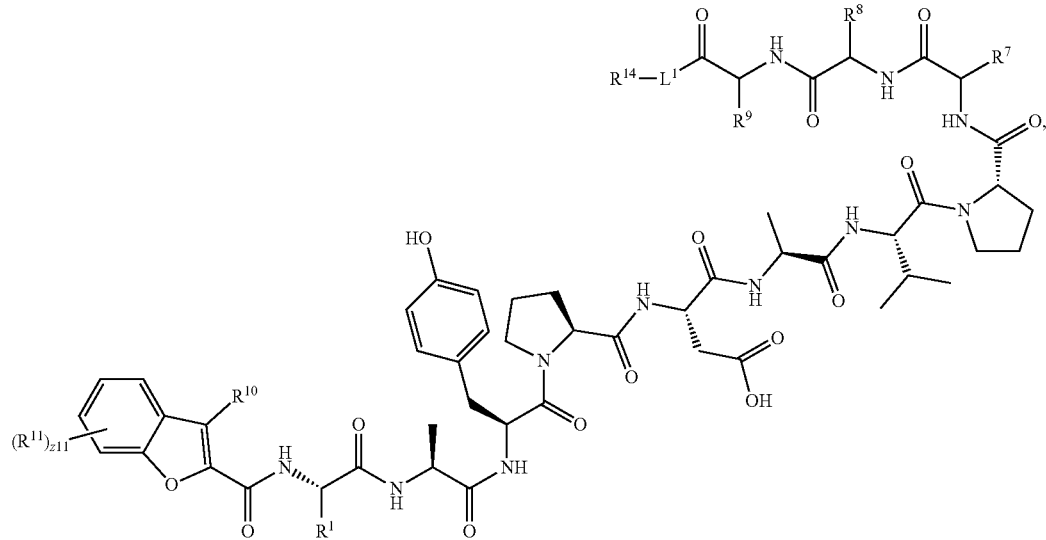
wherein $R^1$, $R^7$, $R^5$, $R^9$, $R^{10}$, $R^{11}$, z11, $R^{14}$, and $L^1$ are as described herein, including in embodiments.
In embodiments, the compound has the formula:
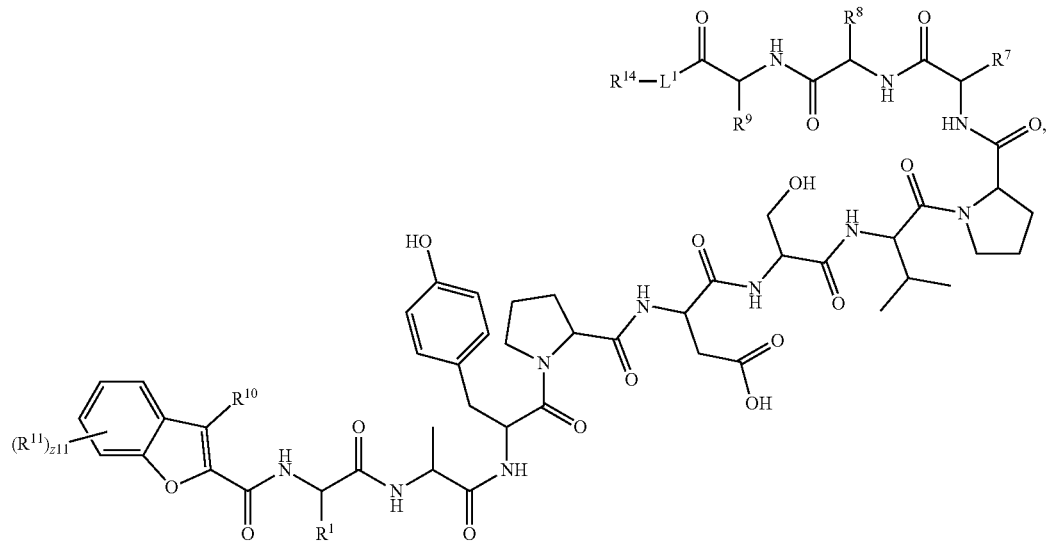
wherein $R^1$, $R^7$, $R^8$, $R^9$, $R^{10}$, $R^{11}$, z11, $R^{14}$, and $L^1$ are as described herein, including in embodiments.

In embodiments, the compound has the formula:

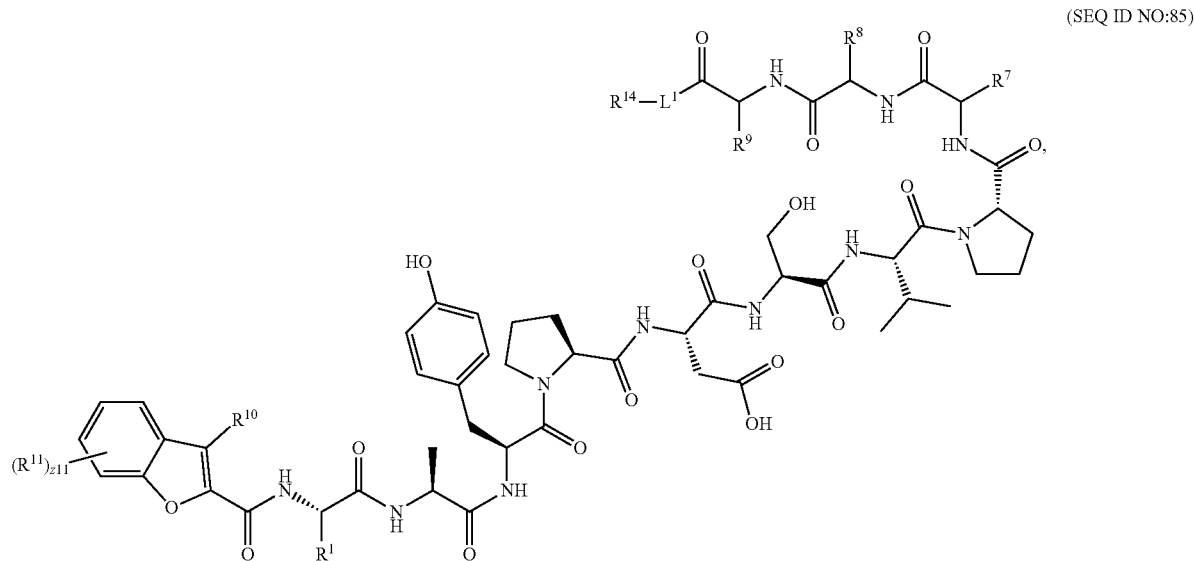

(SEQ ID NO:85)

wherein $R^1$, $R^7$, $R^8$, $R^9$, $R^{10}$, z11, $R^{14}$, and $L^1$ are as described herein, including in embodiments.

In embodiments, the compound has the formula:

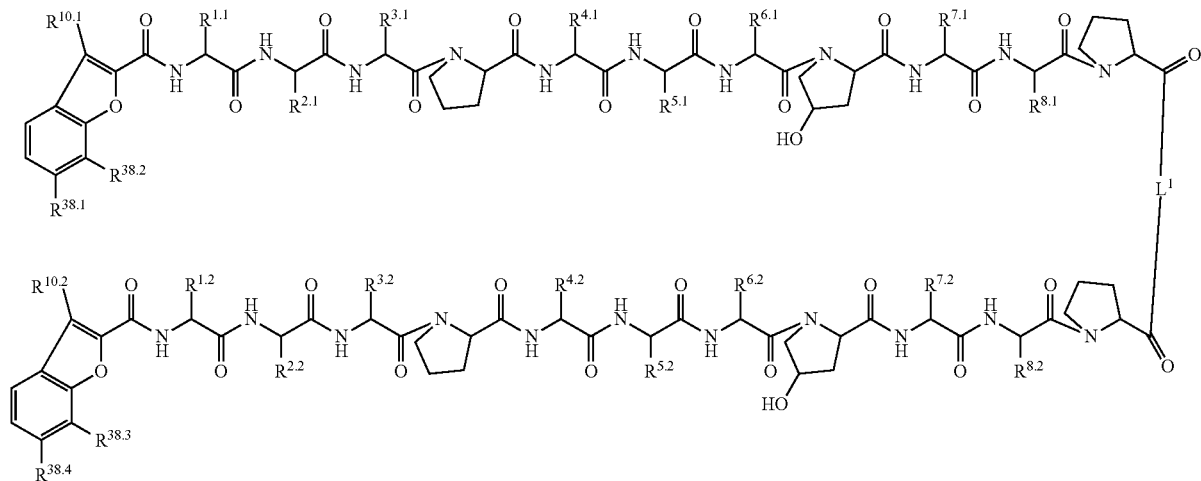

(IV). $L^1$ is as described herein, including in embodiments. $R^{1.1}$ and $R^{1.2}$ may be any value of $R^1$ described herein, including in any aspect, embodiment, example, figure, table, or claim. $R^{2.1}$ and $R^{2.2}$ may be any value of $R^2$ described herein, including in any aspect, embodiment, example, figure, table, or claim. $R^{3.1}$ and $R^{3.2}$ may be any value of $R^3$ described herein, including in any aspect, embodiment, example, figure, table, or claim. $R^{4.1}$ and $R^{4.2}$ may be any value of $R^4$ described herein, including in any aspect, embodiment, example, figure, table, or claim. $R^{5.1}$ and $R^{5.2}$ may be any value of $R^5$ described herein, including in any aspect, embodiment, example, figure, table, or claim. $R^{6.1}$ and $R^{6.2}$ may be any value of $R^6$ described herein, including in any aspect, embodiment, example, figure, table, or claim. $R^{7.1}$ and $R^{7.2}$ may be any value of $R^7$ described herein, including in any aspect, embodiment, example, figure, table, or claim. $R^{8.1}$ and $R^{8.2}$ may be any value of $R^8$ described herein, including in any aspect, embodiment, example, figure, table, or claim. $R^{10.1}$ and $R^{10.2}$ may be any value of $R^{10}$ described herein, including in any aspect, embodiment, example, figure, table, or claim. $R^{38.1}$, $R^{38.2}$, $R^{38.4}$, and $R^{38.4}$ may be any value of $R^{38}$ described herein, including in any aspect, embodiment, example, figure, table, or claim.

In embodiments of formula (IV), $R^{1.1}$ and $R^{1.2}$ are each independently hydrogen or unsubstituted $C_1$-$C_{10}$ alkyl. In embodiments of formula (IV), $R^{2.1}$ and $R^{2.2}$ are each independently hydrogen or unsubstituted $C_1$-$C_{10}$ alkyl. In embodiments of formula (IV), $R^{4.1}$ and $R^{4.2}$ are each independently hydrogen or -(unsubstituted $C_1$-$C_{10}$ alkylene)-$CO_2H$. In embodiments of formula (IV), $R^{5.1}$ and $R^{5.2}$ are each independently hydrogen or unsubstituted $C_1$-$C_{10}$ alkyl. In embodiments of formula (IV), $R^{6.1}$ and $R^{6.2}$ are each independently hydrogen or unsubstituted $C_1$-$C_{10}$ alkyl. In embodiments of formula (IV), $R^{8.1}$ and $R^{8.2}$ are each independently hydrogen or -(unsubstituted $C_1$-$C_{10}$ alkylene)-NHC=(NH)NH$_2$.

In embodiments of formula (IV), $R^{3.1}$ and $R^{3.2}$ each independently have the formula: -(unsubstituted $C_1$-$C_{10}$ alkylene)-(unsubstituted phenylene)-O-(unsubstituted $C_1$-$C_{10}$ alkyl). In embodiments of formula (IV), $R^{1.1}$ and $R^{1.2}$ are each independently hydrogen or

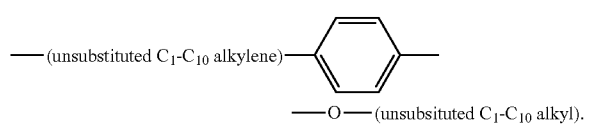

In embodiments of formula (IV), $R^{7.1}$ and $R^{7.2}$ each independently have the formula: -(unsubstituted $C_1$-$C_{10}$ alkylene)-(unsubstituted phenylene)-Cl. In embodiments of formula (IV), $R^{7.1}$ and $R^{7.2}$ are each independently hydrogen or

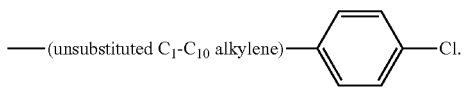

In embodiments of formula (IV), C has the formula:

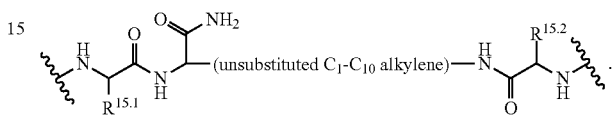

$R^{15.1}$ and $R^{15.2}$ may be any value of $R^{15}$ described herein, including in any aspect, embodiment, example, figure, table, or claim. In embodiments of formula (IV), $R^{15.1}$ and $R^{15.2}$ are each independently hydrogen or unsubstituted $C_1$-$C_{10}$ alkyl.

In embodiments, the compound has the formula:

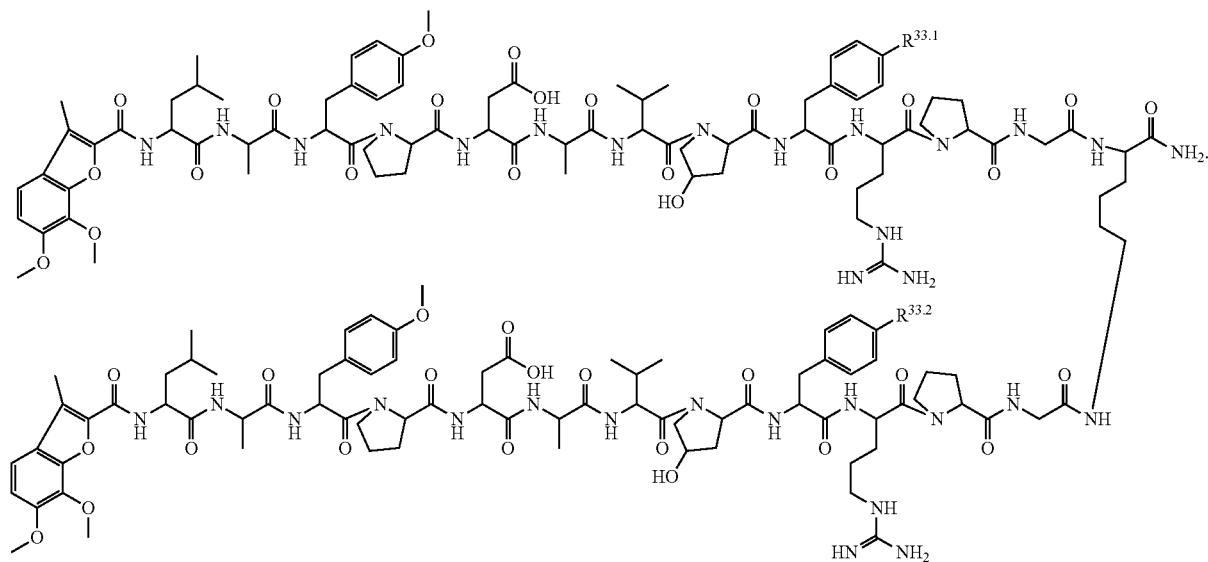

(V)

$R^{33.1}$ and $R^{33.2}$ may be any value of $R^{33}$ described herein, including in any aspect, embodiment, example, figure, table, or claim. In embodiments of Formula (V), $R^{33.1}$ and $R^{33.2}$ are each independently —SO$_2$F, —OSO$_2$F, or E. In embodiments of Formula (V), $R^{33.1}$ is independently —SO$_2$F, —OSO$_2$F, or E. In embodiments of Formula (V), $R^{33.2}$ is independently —SO$_2$F, —OSO$_2$F, or E.

In embodiments, the compound has the formula:

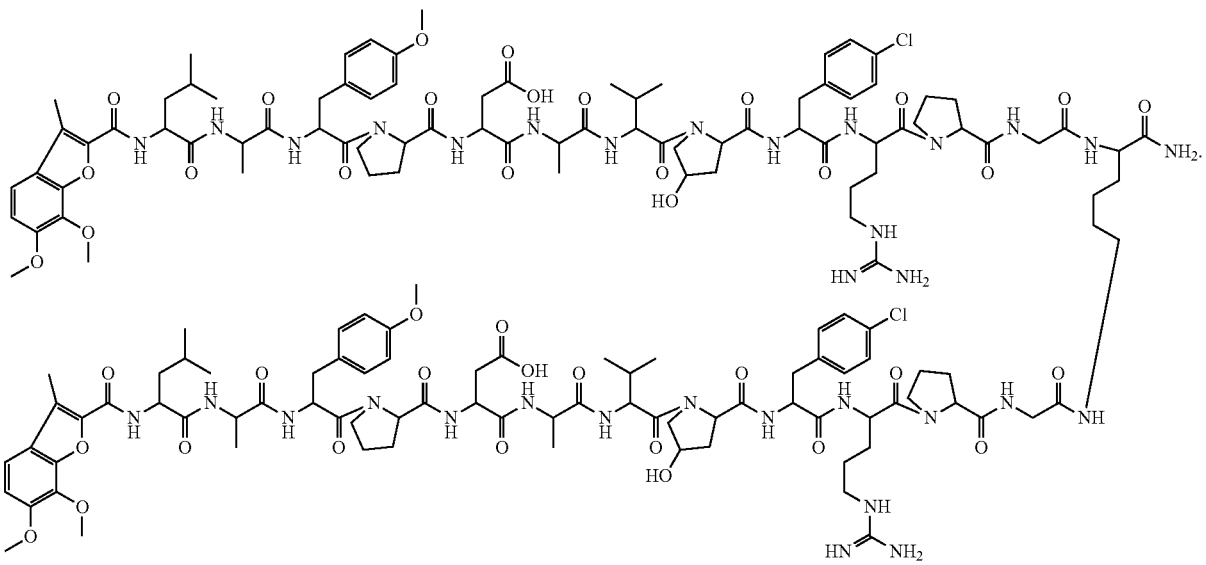 [SMILES: COc1ccc(CC(NC(=O)C(C)NC(=O)C(CC(C)C)NC(=O)c2oc3c(OC)c(OC)ccc3c2C)C(=O)N2CCCC2C(=O)NC(CC(=O)O)C(=O)NC(C)C(=O)NC(C(=O)N2CC(O)CC2C(=O)NC(Cc2ccc(Cl)cc2)C(=O)NC(CCCNC(=N)N)C(=O)N2CCCC2C(=O)NCC(=O)NCCCCC(NC(=O)CNC(=O)C2CCCN2C(=O)C(CCCNC(=N)N)NC(=O)C(Cc2ccc(Cl)cc2)NC(=O)C2CC(O)CN2C(=O)C(NC(=O)C(C)NC(=O)C(CC(=O)O)NC(=O)C2CCCN2C(=O)C(Cc2ccc(OC)cc2)NC(=O)C(C)NC(=O)C(CC(C)C)NC(=O)c2oc3c(OC)c(OC)ccc3c2C)C(C)C)C(N)=O)C(C)C)cc1]

In embodiments, the compound has the formula:

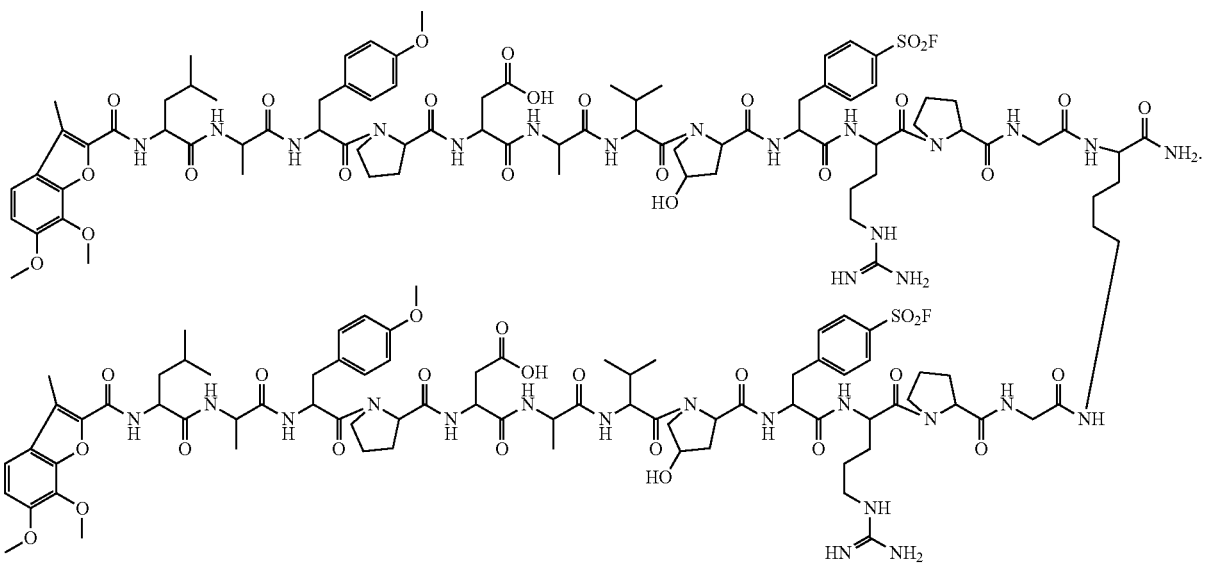 [SMILES: COc1ccc(CC(NC(=O)C(C)NC(=O)C(CC(C)C)NC(=O)c2oc3c(OC)c(OC)ccc3c2C)C(=O)N2CCCC2C(=O)NC(CC(=O)O)C(=O)NC(C)C(=O)NC(C(=O)N2CC(O)CC2C(=O)NC(Cc2ccc(S(=O)(=O)F)cc2)C(=O)NC(CCCNC(=N)N)C(=O)N2CCCC2C(=O)NCC(=O)NCCCCC(NC(=O)CNC(=O)C2CCCN2C(=O)C(CCCNC(=N)N)NC(=O)C(Cc2ccc(S(=O)(=O)F)cc2)NC(=O)C2CC(O)CN2C(=O)C(NC(=O)C(C)NC(=O)C(CC(=O)O)NC(=O)C2CCCN2C(=O)C(Cc2ccc(OC)cc2)NC(=O)C(C)NC(=O)C(CC(C)C)NC(=O)c2oc3c(OC)c(OC)ccc3c2C)C(C)C)C(N)=O)C(C)C)cc1]

In embodiments, the compound has the formula:
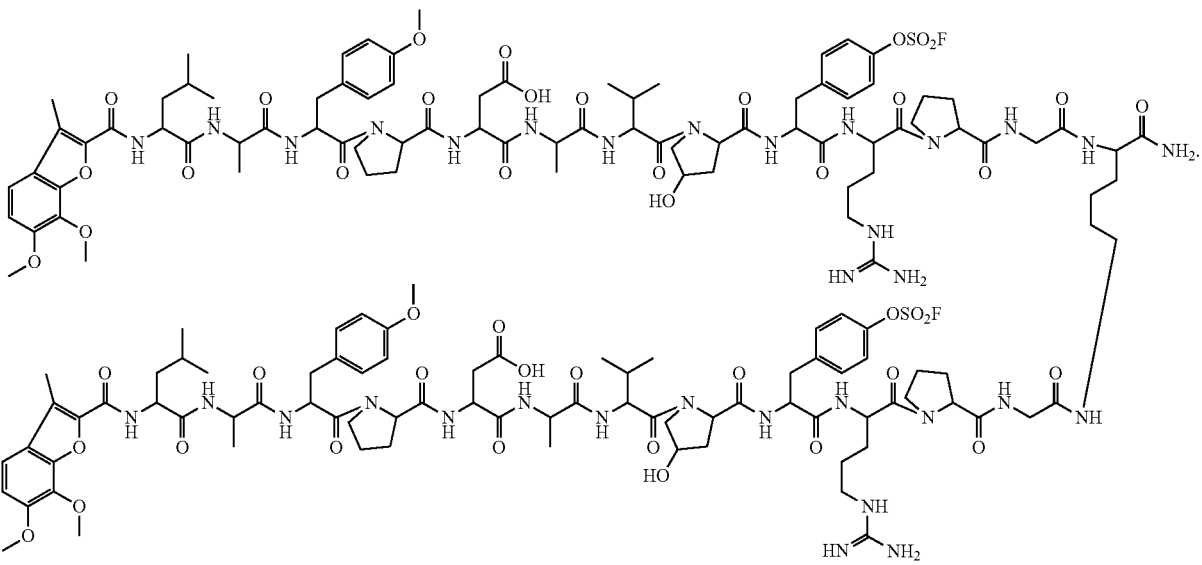
In embodiments, the compound has the formula:
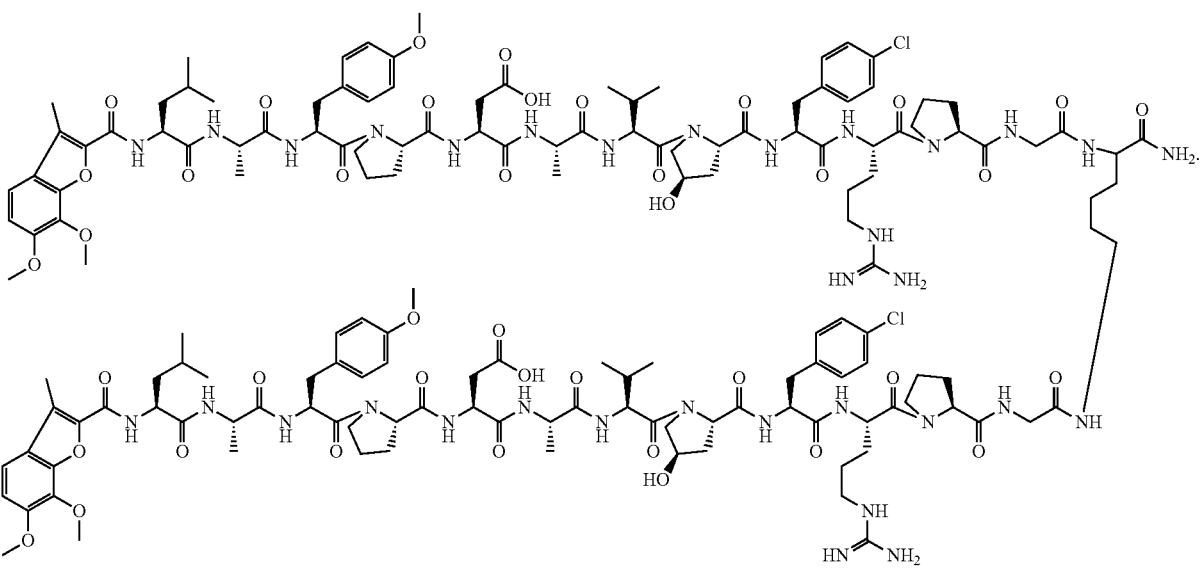

In embodiments, the compound has the formula:
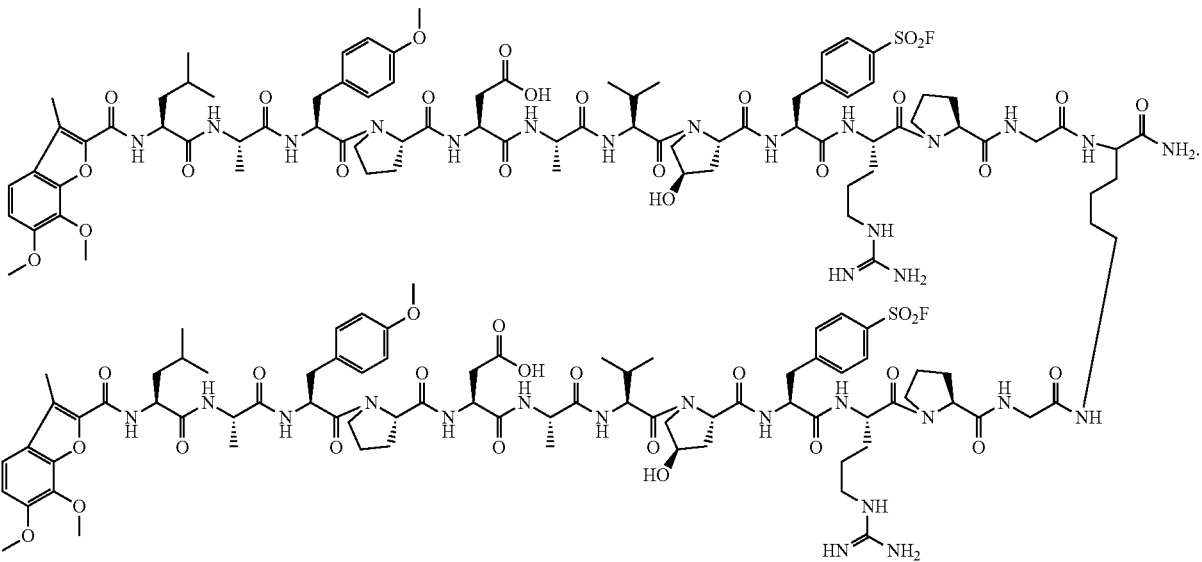
In embodiments, the compound has the formula:
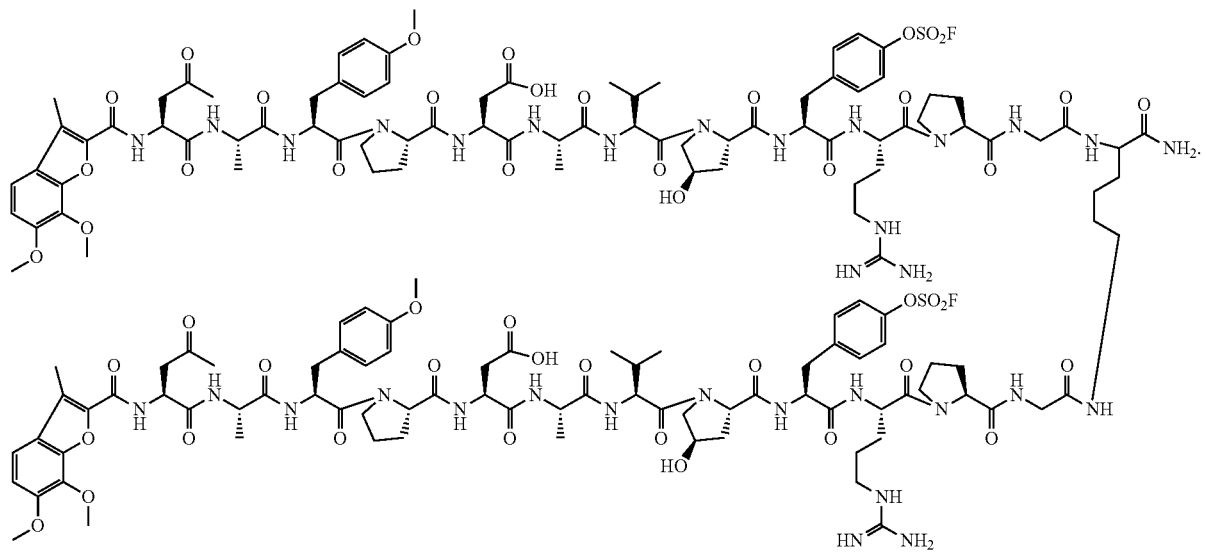

In embodiments, the compound has the formula:
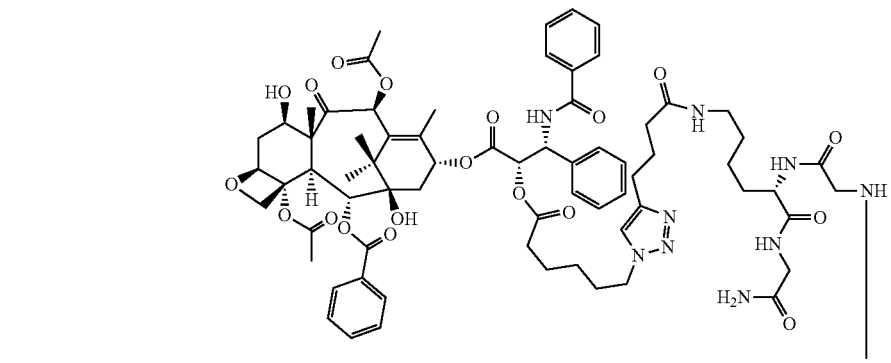
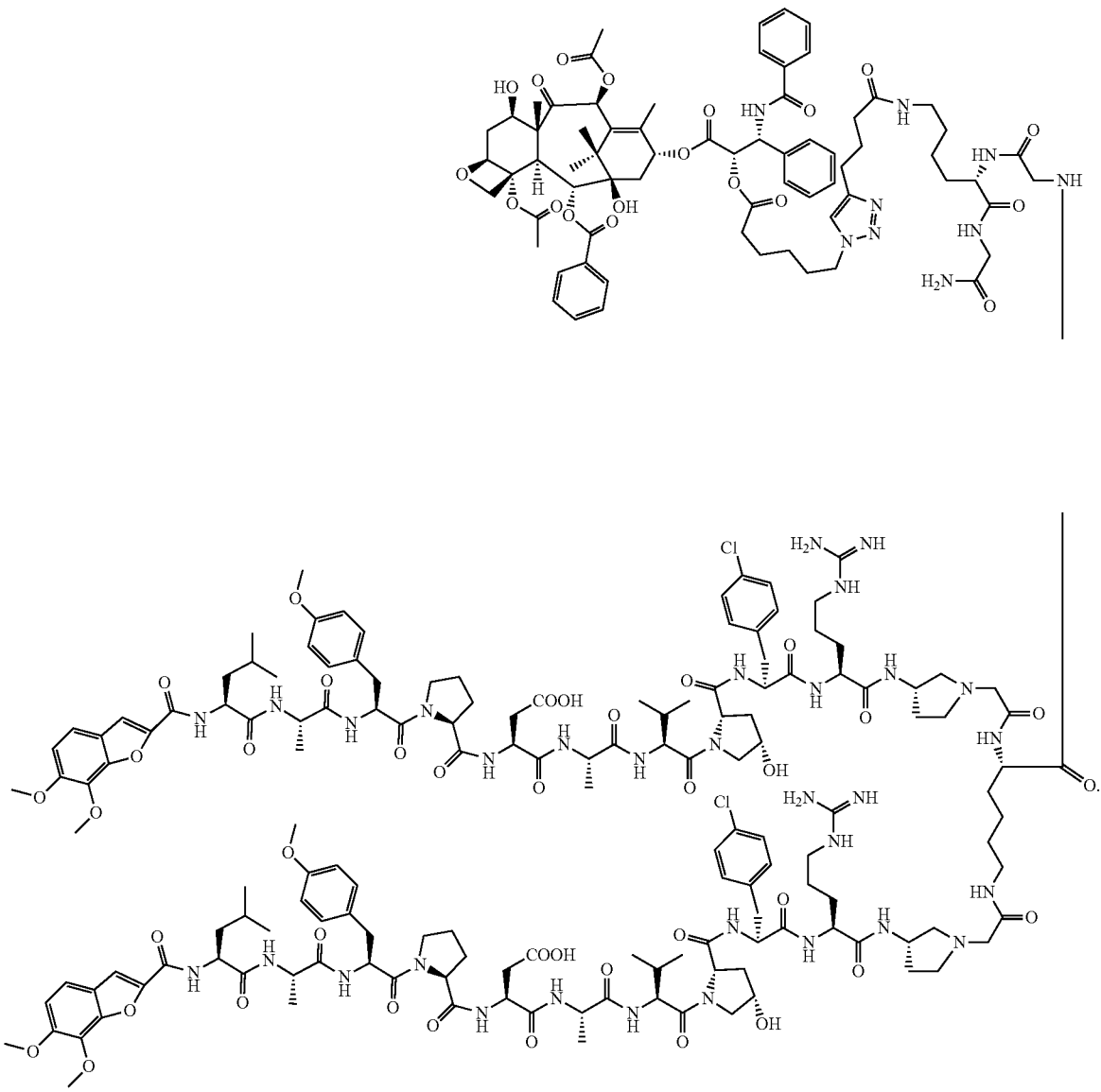
In embodiments, the compound has the formula:
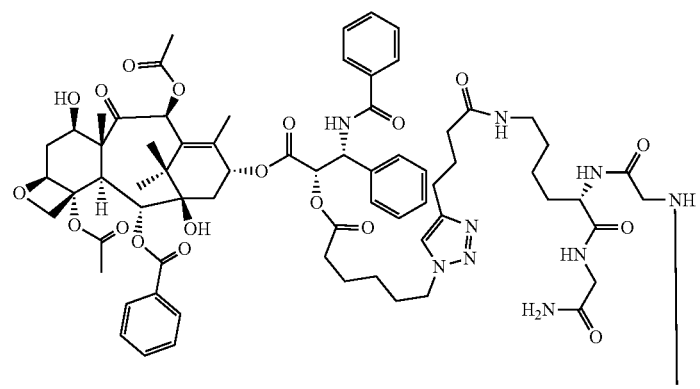

-continued

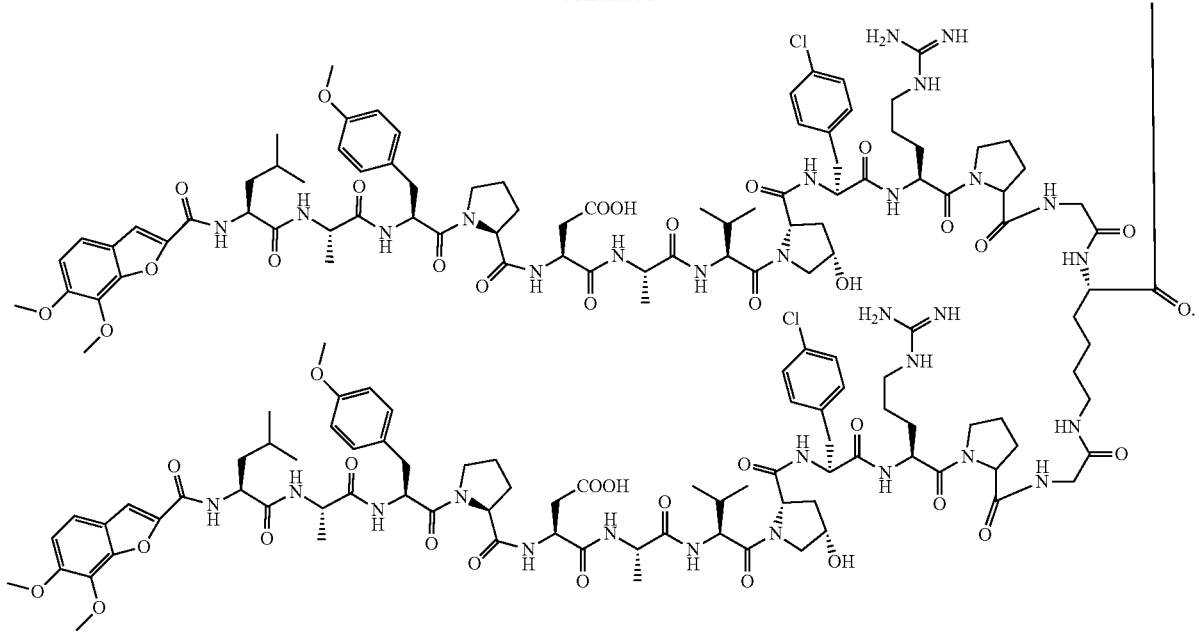

In embodiments, the compound is a compound described herein. In embodiments, the compound is 135A7, 135A8, 135B1, 135B12, 135B2, 135B8, 135B9, 135C1, 135C2, 135C3, 135C4, 135C7, 135C8, 135C9, 135C10, 135D6, 135D7, 135D8, 135D9, 135E2, 135E4, 135E5, 135E6, 135E7, 135E10, 135E11, 135E12, 135F1, 135F2, 135F3, 135F4, 135F5, 135F6, 135F8, 135F10, 135F12, 135G3, or 135C11 as described in Table 1. In embodiments, the compound is a compound described herein. In embodiments, the compound is 135A7 as described in Table 1. In embodiments, the compound is 135A8 as described in Table 1. In embodiments, the compound is 135B1 as described in Table 1. In embodiments, the compound is 135B12 as described in Table 1. In embodiments, the compound is 135B2 as described in Table 1. In embodiments, the compound is 135B8 as described in Table 1. In embodiments, the compound is 135B9 as described in Table 1. In embodiments, the compound is 135C1 as described in Table 1. In embodiments, the compound is 135C2 as described in Table 1. In embodiments, the compound is 135C3 as described in Table 1. In embodiments, the compound is 135C4 as described in Table 1. In embodiments, the compound is 135C7 as described in Table 1. In embodiments, the compound is 135C8 as described in Table 1. In embodiments, the compound is 135C9 as described in Table 1. In embodiments, the compound is 135C10 as described in Table 1. In embodiments, the compound is 135D6 as described in Table 1. In embodiments, the compound is 135D7 as described in Table 1. In embodiments, the compound is 135D8 as described in Table 1. In embodiments, the compound is 135D9 as described in Table 1. In embodiments, the compound is 135E2 as described in Table 1. In embodiments, the compound is 135E4 as described in Table 1. In embodiments, the compound is 135E5 as described in Table 1. In embodiments, the compound is 135E6 as described in Table 1. In embodiments, the compound is 135E7 as described in Table 1. In embodiments, the compound is 135E10 as described in Table 1. In embodiments, the compound is 135E11 as described in Table 1. In embodiments, the compound is 135E12 as described in Table 1. In embodiments, the compound is 135F1 as described in Table 1. In embodiments, the compound is 135F2 as described in Table 1. In embodiments, the compound is 135F3 as described in Table 1. In embodiments, the compound is 135F4 as described in Table 1. In embodiments, the compound is 135F5 as described in Table 1. In embodiments, the compound is 135F6 as described in Table 1. In embodiments, the compound is 135F8 as described in Table 1. In embodiments, the compound is 135F10 as described in Table 1. In embodiments, the compound is 135F12 as described in Table 1. In embodiments, the compound is 135G3 as described in Table 1. In embodiments, the compound is 135C11 as described in Table 1.

In embodiments, the compound is a compound described herein. In embodiments, the compound is 135G8, 135G9, 135I2, 135I3, 135F11, 135G10, 135G11, 135G12, 135H2, 135H3, 135H4, 135G6, 135G5, 135H5, 135G7, 135H1, 135H6, 135H7, 135H8, 135H9, 135H10, 135H11, 135I4, 135G4, or 135H12 as described in Table 2. In embodiments, the compound is 135G8 as described in Table 2. In embodiments, the compound is 135G9 as described in Table 2. In embodiments, the compound is 135I2 as described in Table 2. In embodiments, the compound is 135I3 as described in Table 2. In embodiments, the compound is 135F11 as described in Table 2. In embodiments, the compound is 135G10 as described in Table 2. In embodiments, the compound is 135G11 as described in Table 2. In embodiments, the compound is 135G12 as described in Table 2. In embodiments, the compound is 135H2 as described in Table 2. In embodiments, the compound is 135H3 as described in Table 2. In embodiments, the compound is 135H4 as described in Table 2. In embodiments, the compound is 135G6 as described in Table 2. In embodiments, the compound is 135G5 as described in Table 2. In embodiments, the compound is 135H5 as described in Table 2. In embodiments, the compound is 135G7 as described in Table 2. In embodiments, the compound is 135H1 as described in Table 2. In embodiments, the compound is 135H6 as described in Table 2. In embodiments, the compound is 135H7 as described in Table 2. In embodiments, the compound is 135H8 as described in Table 2. In embodiments, the compound is 135H9 as described in Table 2. In embodiments, the compound is 135H10 as described in Table 2. In embodiments, the compound is 135H11 as described in Table 2. In embodiments, the compound is 135I4 as described in Table 2. In embodiments, the compound is 135G4 as described in Table 2. In embodiments, the compound is or 135H12 as described in Table 2.

In embodiments, the compound is a compound described herein. In embodiments, the compound is 147A1, 147A2, 147A3, 147A4, 147A5, 147A6, 147A7, 147A8, 147A9, 147A10, or 147A11 as described in Table 3. In embodiments, the compound is 147A1 as described in Table 3. In embodiments, the compound is 147A2 as described in Table 3. In embodiments, the compound is 147A3 as described in Table 3. In embodiments, the compound is 147A4 as described in Table 3. In embodiments, the compound is 147A5 as described in Table 3. In embodiments, the compound is 147A6 as described in Table 3. In embodiments, the compound is 147A7 as described in Table 3. In embodiments, the compound is 147A8 as described in Table 3. In embodiments, the compound is 147A9 as described in Table 3. In embodiments, the compound is 147A10 as described in Table 3. In embodiments, the compound is 147A11 as described in Table 3.

In embodiments, $R^{11}$ is —$OCH_3$; $R^{10}$ is —$CH_3$; $R^1$ is —$CH_2CH_2(CH_3)_2$; $R^2$ is —$CH_3$; $R^3$ is —$CH_2$(4-methoxybenzene); z12 is 0; $R^4$ is $CH_2COOH$; $R^5$ is —$CH_3$; $R^6$ is —$CH(CH_3)_2$; $R^{13}$ is —OH; $R^7$ is —$CH_2$(pCl-benzene).

III. Pharmaceutical Compositions

In an aspect is provided a pharmaceutical composition including a pharmaceutically acceptable excipient and a compound described herein (including in an aspect, embodiment, table, example, or claim), or a pharmaceutically acceptable salt thereof.

In embodiments of the pharmaceutical compositions, the pharmaceutical composition includes a compound, or pharmaceutically acceptable salt thereof, as described herein (e.g. compound of formula I, or any embodiment thereof) in a therapeutically effective amount. In embodiments of the pharmaceutical compositions, the pharmaceutical composition includes a compound, or pharmaceutically acceptable salt thereof, as described herein (e.g. compound of formula I, or any embodiment thereof) in a detectable amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent.

IV. Methods of Use

In an aspect is provided a method of treating cancer, the method including administering to a subject in need thereof a therapeutically effective amount of a compound described herein (including in an aspect, embodiment, table, example, or claim), or a pharmaceutically acceptable salt thereof. In embodiments, the cancer is prostate cancer, melanoma, urinary bladder cancer, breast cancer, ovarian cancer, pancreatic cancer, brain cancer, esophagus cancer, lung cancer, or stomach cancers, or leukemia. In embodiments, the compound is a compound described in Table 1 or Table 2.

In an aspect is provided a method of increasing EphA2 activity, the method including contacting a EphA2 protein with a compound described herein (including in an aspect, embodiment, table, example, or claim), or a pharmaceutically acceptable salt thereof. In embodiments, increasing is relative to a control. In embodiments, the compound is a compound described in Table 1 or Table 2. In embodiments, the compound is a compound described herein.

In an aspect is provided a method of suppressing the pro-oncogenic EphA2 activity, the method including contacting a EphA2 protein with a compound described herein (including in an aspect, embodiment, table, example, or claim), or a pharmaceutically acceptable salt thereof. In embodiments, suppressing is relative to a control. In embodiments, the compound is a compound described in Table 1 or Table 2. In embodiments, the compound is a compound described in Table 1, Table 2, or Table 3. In embodiments, the compound is a compound described herein.

In an aspect is provided a method of reducing levels of EphA2, the method including contacting a EphA2 protein with a compound described herein (including in an aspect, embodiment, table, example, or claim), or a pharmaceutically acceptable salt thereof. In embodiments, reducing is relative to a control. In embodiments, the compound is a compound described in Table 1 or Table 2. In embodiments, the compound is a compound described in Table 1, Table 2, or Table 3. In embodiments, the compound is a compound described herein. In embodiments, upon contacting the EphA2 protein with a compound described herein, the EphA2 dimerizes and initiates phosphorylation of the kinase domain.

In an aspect is provided a method of inhibiting cancer cell migration and invasion, the method including contacting a EphA2 protein with a compound described herein (including in an aspect, embodiment, table, example, or claim), or a pharmaceutically acceptable salt thereof. In embodiments, the compound is a compound described in Table 1 or Table 2. In embodiments, the compound is a compound described in Table 1, Table 2, or Table 3. In embodiments, the compound is a compound described herein.

In an aspect is provided a method of selectively delivering a chemotherapeutic agent to EphA2 expressing cancer cells, the method including contacting a EphA2 protein with a compound described herein (including in an aspect, embodiment, table, example, or claim), or a pharmaceutically acceptable salt thereof, wherein the compound includes a drug moiety (e.g., $R^{14}$ includes a drug moiety). In embodiments, the compound is a compound described in Table 1 or Table 2. In embodiments, the compound is a compound described in Table 1, Table 2, or Table 3.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A compound having the formula:

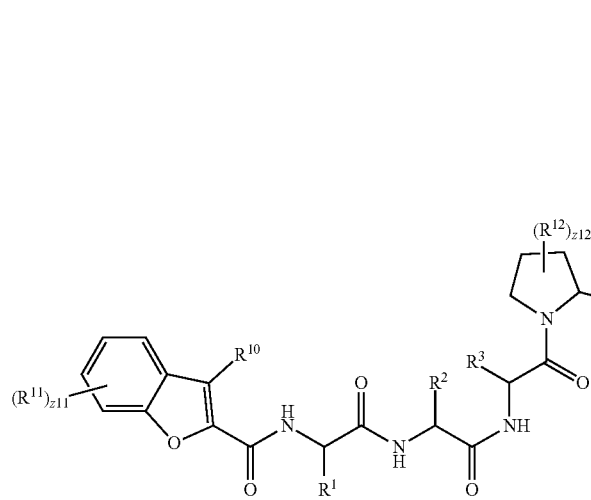
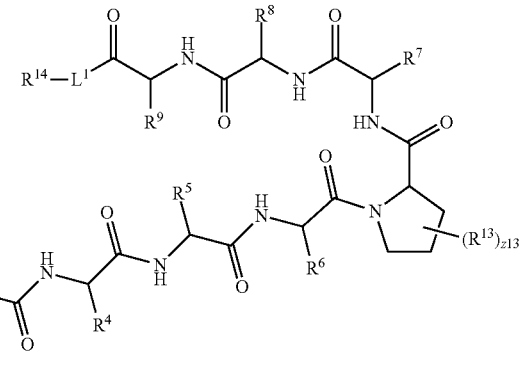

wherein, $R^1$, $R^2$, $R^3$, $R^4$, $R^5$, $R^6$, $R^7$, and $R^8$ are each independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, an amino acid side chain, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^5$ may optionally be joined to form $L^2$; $R^9$ and the nitrogen atom adjacent to the carbon to which $R^9$ is attached may optionally be joined to form a substituted or unsubstituted heterocycloalkyl;

$L^2$ is a covalent linker;

$R^9$ is an amino acid side chain, bioconjugate reactive moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ and $R^{13}$ are each independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z11 is an integer from 0 to 4;
z12 is an integer from 0 to 7;
z13 is an integer from 0 to 5;
$L^1$ is a covalent linker; and
$R^{14}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

Embodiment P2. The compound of embodiment P1, having the formula:
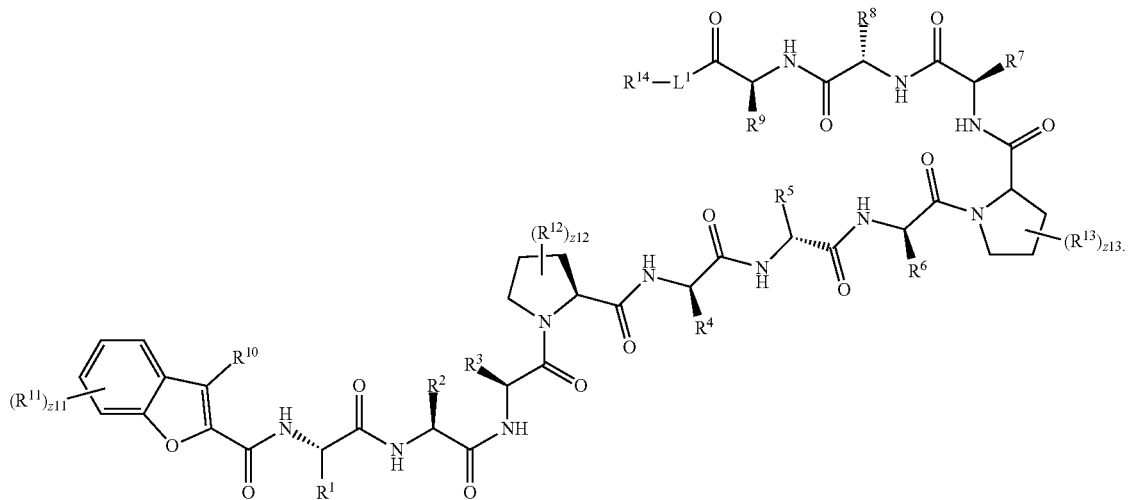
Embodiment P3. The compound of embodiment P1 or embodiment P2, wherein $R^1$ and $R^5$ are each independently the side chain of glycine, alanine, valine, leucine, isoleucine, proline, phenylalanine, methionine, or tryptophan.
Embodiment P4. The compound of embodiment P1, wherein the compound has the formula:
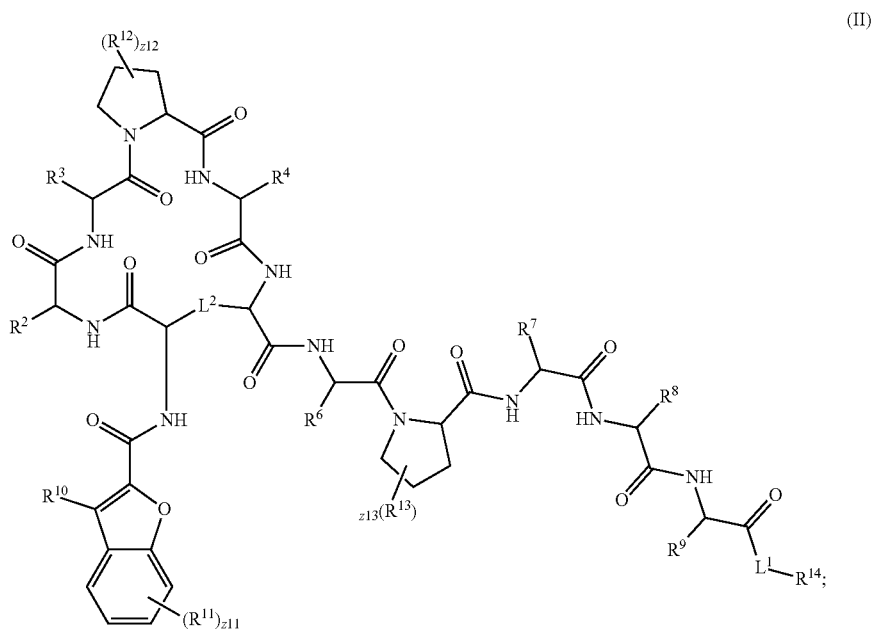
(II)

wherein,

L² is a bond, —S(O)₂—, —NH—, —O—, —S—, —S—S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P5. The compound of any one of embodiments P1 to P4, wherein R² is —CCl₃, —CBr₃, —CF₃, —CI₃, substituted or unsubstituted alkyl, substituted or unsubstituted heteroalkyl, substituted or unsubstituted cycloalkyl.

Embodiment P6. The compound of any one of embodiments P1 to P5, wherein R³ is the side chain of phenylalanine, tryptophan, tyrosine, thyroxine, 5-hydroxytryptophan, dihydroxyphenylalanine, or histidine.

Embodiment P7. The compound of any one of embodiments P1 to P5, wherein R³ is substituted or unsubstituted heterocycloalkyl, substituted or unsubstituted aryl, or substituted or unsubstituted heteroaryl.

Embodiment P8. The compound of any one of embodiments P1 to P7, wherein R⁴ is the side chain of aspartic acid, glutamic acid, 2-amino-3-(2H-1,2,3,4-tetrazol-5-yl)propanoic acid (AspTtz), or 2-amino-3-(2H-1,2,3,4-tetrazol-5-yl)butanoic acid (GluTtz).

Embodiment P9. The compound of any one of embodiments P1 to P7, wherein R⁴ is —OH, —NH₂, —COOH, —CONH₂, —SH, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted aryl, or substituted or unsubstituted heteroaryl.

Embodiment P10. The compound of any one of embodiments P1 to P9, wherein R⁶ is the side chain of an amino acid.

Embodiment P11. The compound of any one of embodiments P1 to P10, wherein R⁷ and R⁸ are each independently the side chain of an amino acid, substituted or unsubstituted aryl, or substituted or unsubstituted heteroaryl.

Embodiment P12. The compound of any one of embodiments P1 to P11, wherein $R^{12}$ is independently substituted or unsubstituted alkyl, substituted or unsubstituted heteroalkyl, or substituted or unsubstituted cycloalkyl.

Embodiment P13. The compound of any one of embodiments P1 to P11, wherein $R^{13}$ independently is —OH, —NH₂, —COOH, —CONH₂, —SH, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted aryl, or substituted or unsubstituted heteroaryl.

Embodiment P14. The compound of any one of embodiments P1 to P13, wherein R⁹ is a bioconjugate reactive moiety.

Embodiment P15. The compound of embodiment P1, having the formula:

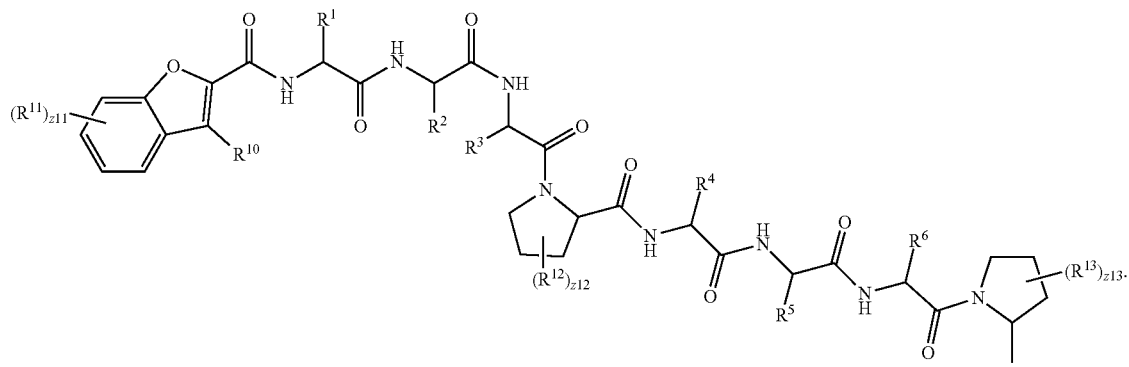

(III)

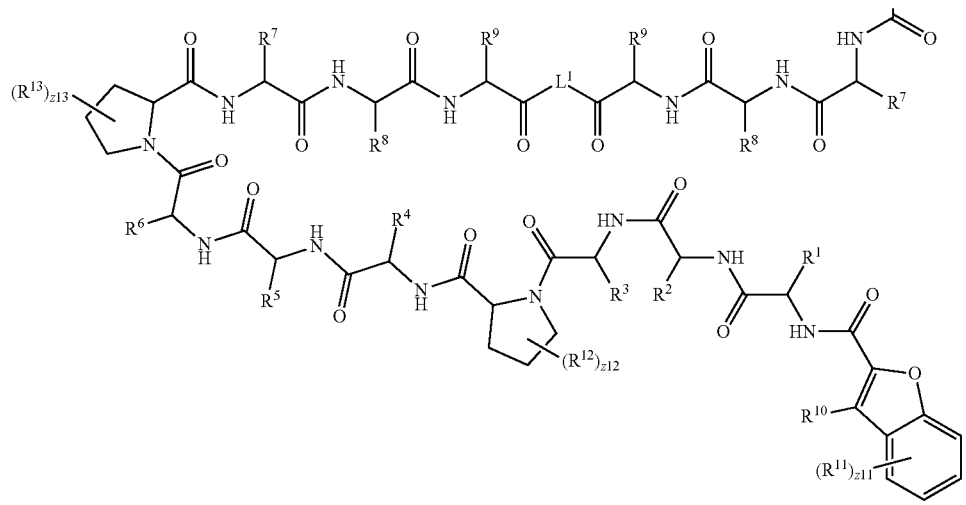

Embodiment P16. The compound of any one of embodiments P1 to P15, wherein $L^1$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P17. The compound of any one of embodiments P1 to P15, wherein -$L^1$-$R^{14}$ has the formula:

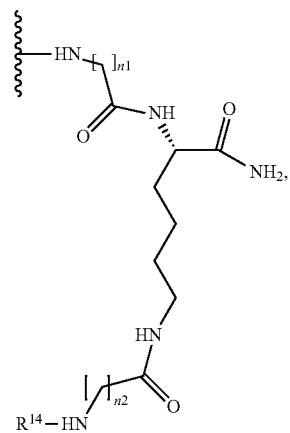

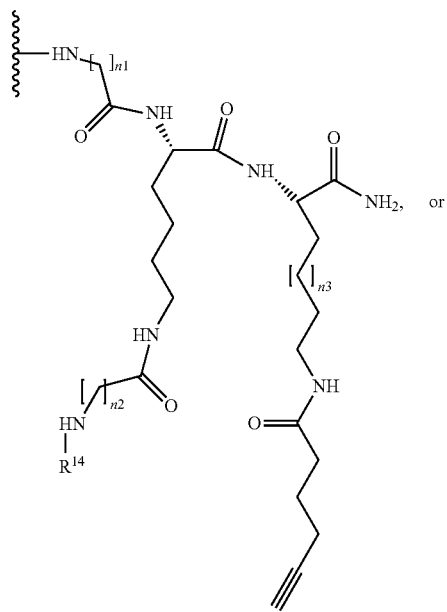

or

-continued

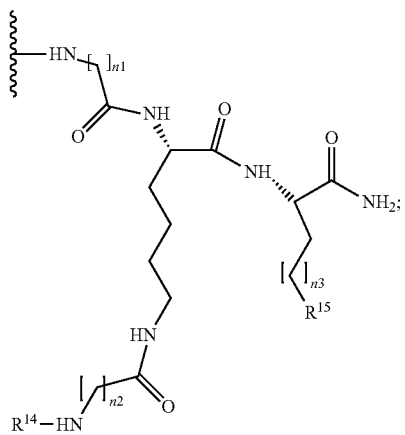

wherein, n1, n2, and n3 are each independently integers from 1 to 20;

$R^{15}$ is independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

Embodiment P18. The compound of any one of embodiments P1 to P15, wherein $L^1$ has the formula:

-continued

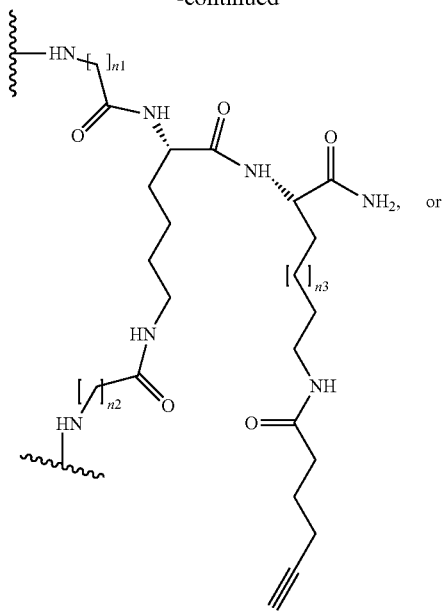

wherein, n1, n2, and n3 are each independently integers from 1 to 20;

$R^{15}$ is independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

Embodiment P19. The compound of any one of embodiments P1 to P18, wherein the drug moiety is a taxol moiety.

Embodiment P20. The compound of any one of embodiments P1 to P18, wherein the drug moiety is monovalent paclitaxel.

Embodiment P21. The compound of embodiment P1, having the formula:

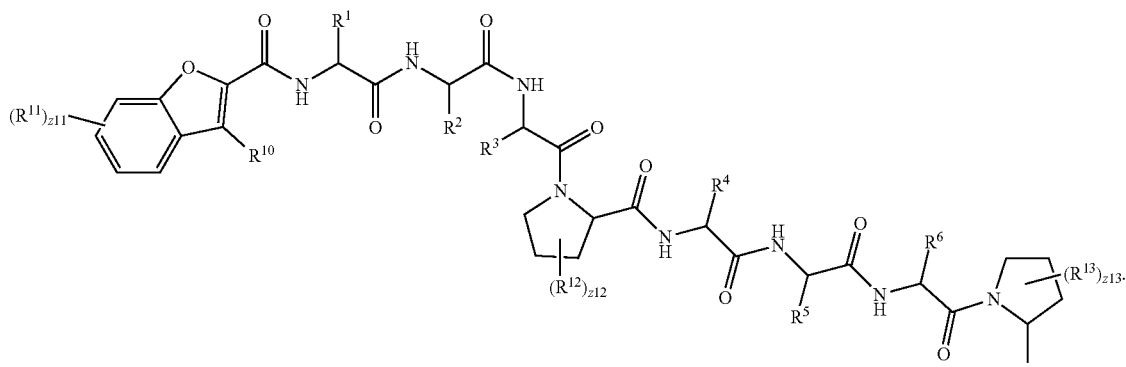

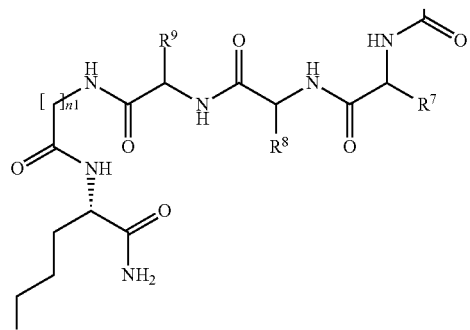
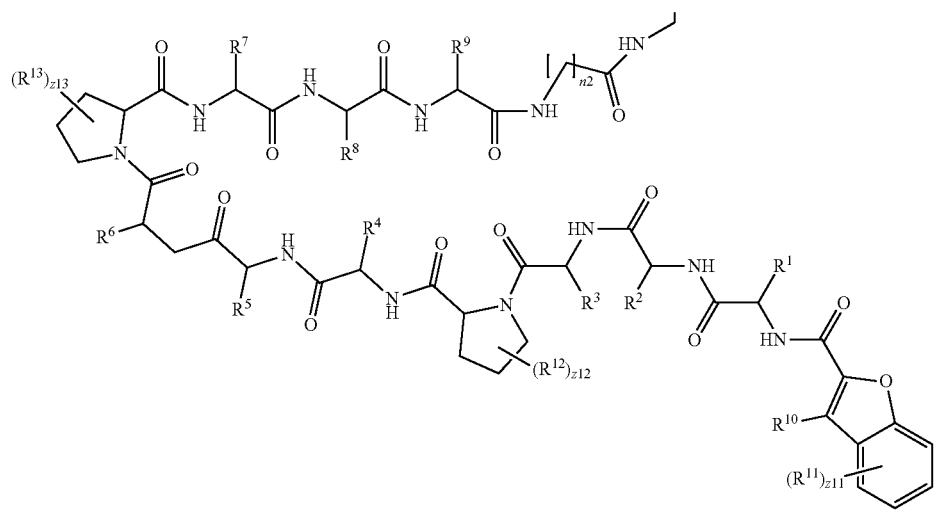
Embodiment P22. The compound of embodiment P1, wherein the compound has the formula:
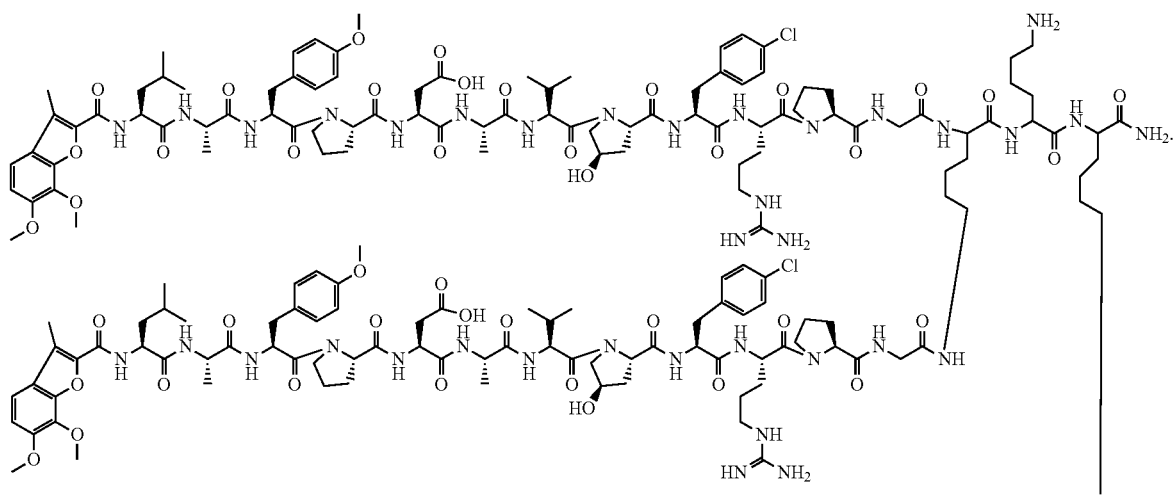

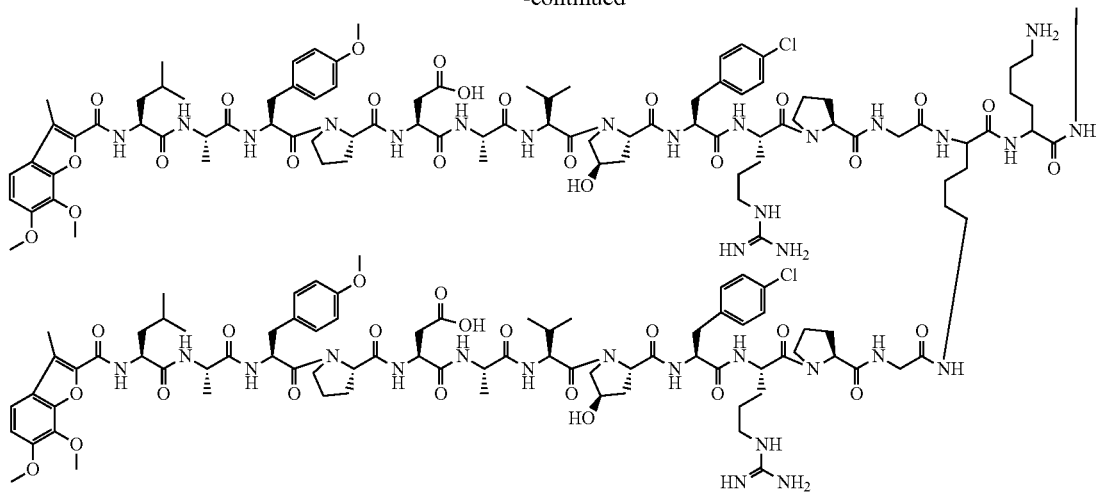

Embodiment P23. The compound of embodiment P1, wherein $R^1$, $R^2$, $R^3$, $R^4$, $R^5$, $R^6$, $R^7$, and $R^8$ are each independently an amino acid side chain.

Embodiment P24. The compound of embodiment P1, wherein $R^1$, $R^2$, $R^3$, $R^4$, $R^5$, $R^6$, $R^7$, and $R^8$ are each independently a non-natural amino acid side chain.

Embodiment P25. The compound of embodiment P1, having the formula:

(SEQ ID NO:67)

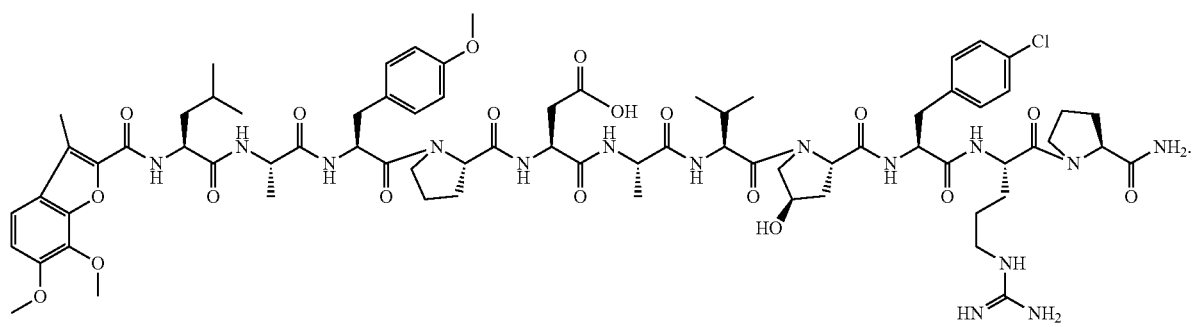

Embodiment P26. The compound of embodiment P1, having the formula:

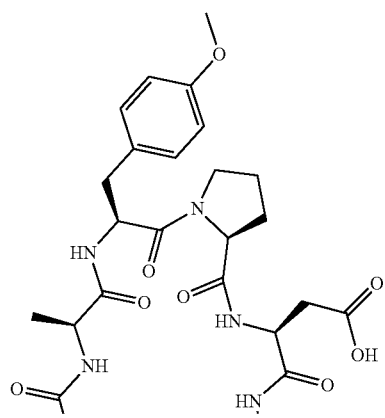

-continued
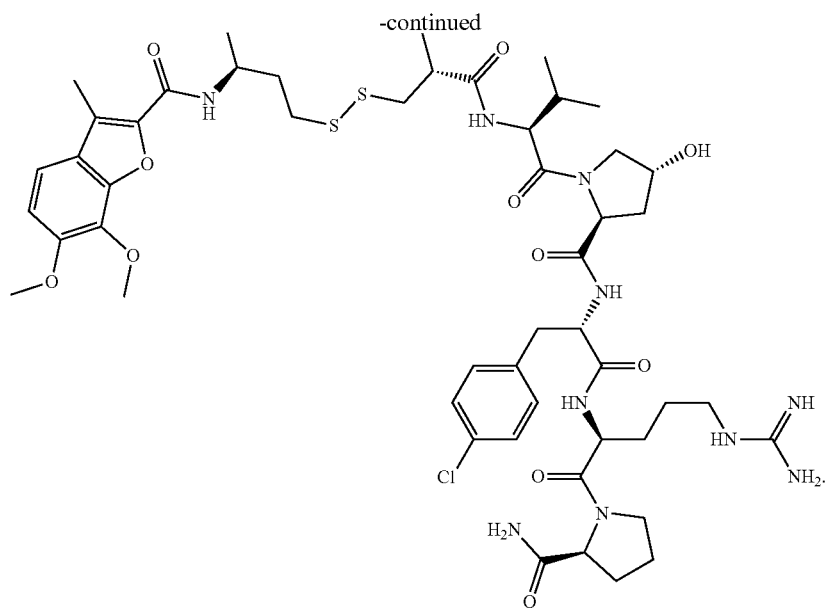
Embodiment P27. The compound of embodiment P1, having the formula:
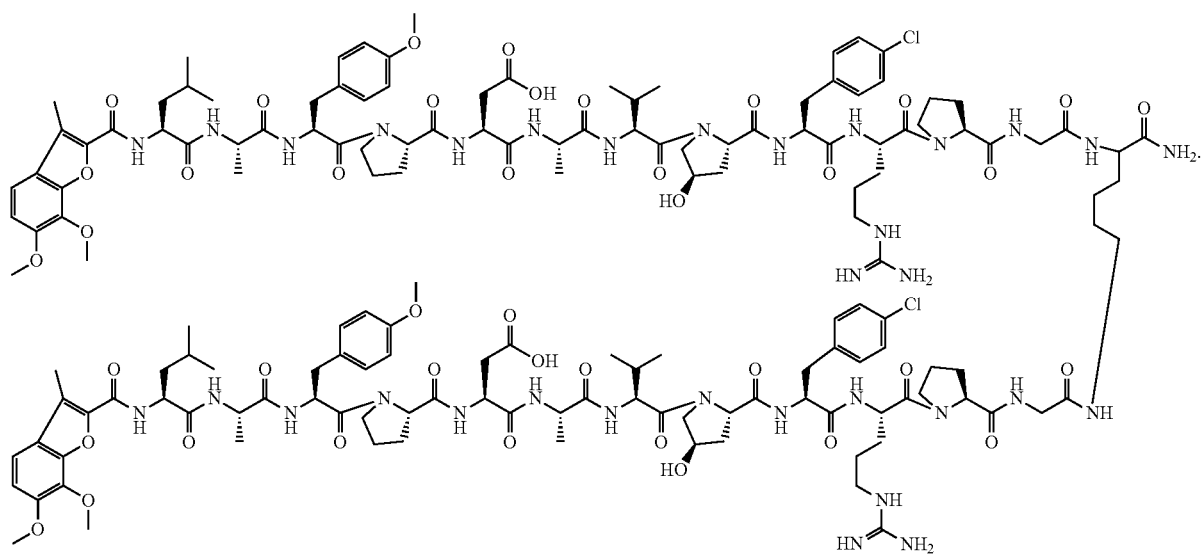

Embodiment P28. The compound of embodiment P1, having the formula:

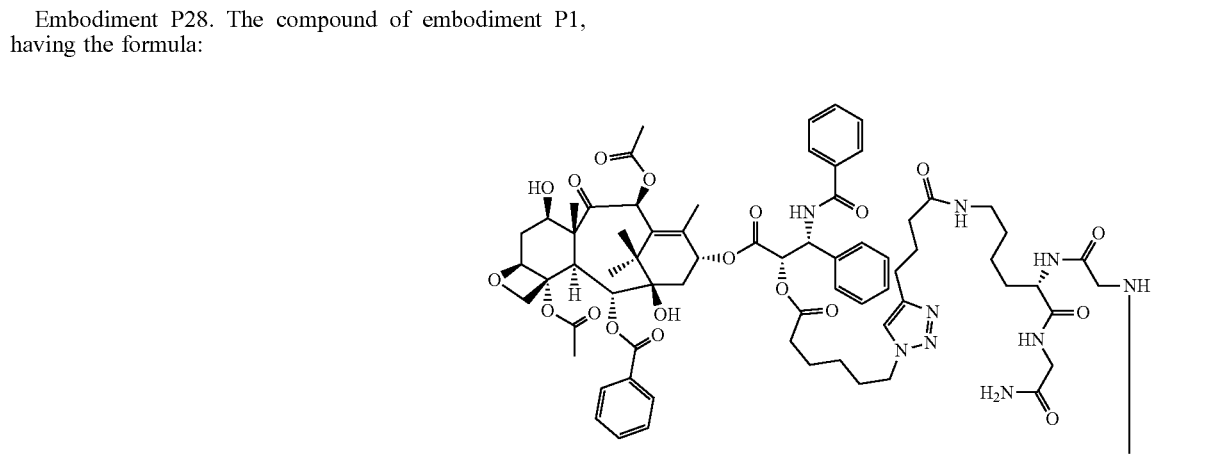

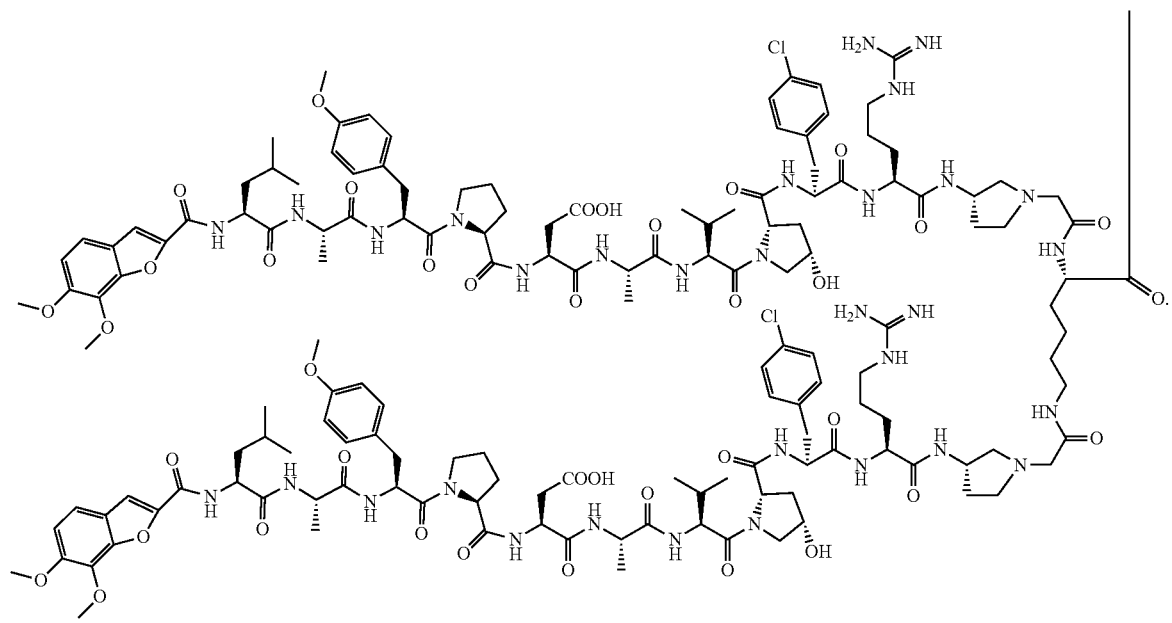

Embodiment P29. A pharmaceutical composition comprising a pharmaceutically acceptable excipient and the compound of any one of embodiments P1 to P28.

Embodiment P30. A method of treating cancer, said method comprising administering to a subject in need thereof a therapeutically effective amount of a compound of any one of embodiments P1 to P28.

Embodiment P31. A method of increasing EphA2 activity, said method comprising contacting a EphA2 protein with a compound of any one of embodiments P1 to P28.

Embodiment P32. A method of suppressing the pro-oncogenic EphA2 activity, said method comprising contacting a EphA2 protein with a compound of any one of embodiments P1 to P28.

Embodiment P33. A method of reducing levels of EphA2, said method comprising contacting a EphA2 protein with a compound of any one of embodiments P1 to P28.

Embodiment P34. A method of inhibiting cancer cell migration and invasion, said method comprising contacting a EphA2 protein with a compound of any one of embodiments P1 to P28.

Embodiment P35. A method of selectively delivering a chemotherapeutic agent to EphA2 expressing cancer cells, said method comprising contacting a EphA2 protein with a compound of any one of embodiments P1 to P28, wherein $R^{14}$ comprises a drug moiety.

VI. Additional Embodiments

Embodiment 1. A compound having the formula:

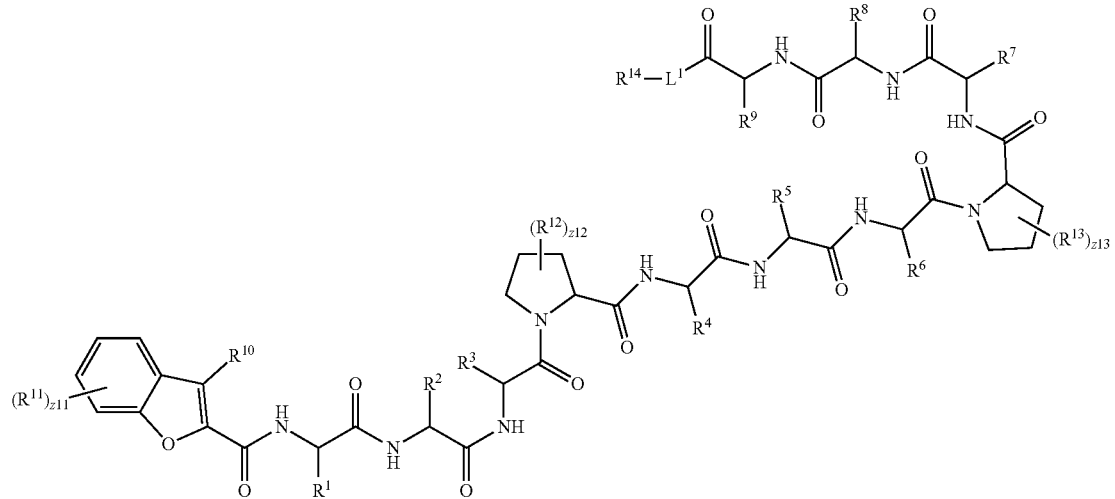

wherein, $R^1$, $R^2$, $R^3$, $R^4$, $R^5$, $R^6$, $R^7$, and $R^8$ are each independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, an amino acid side chain, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^5$ may optionally be joined to form $L^2$; $R^9$ and the nitrogen atom adjacent to the carbon to which $R^9$ is attached may optionally be joined to form a substituted or unsubstituted heterocycloalkyl;

$L^2$ is a covalent linker;

$R^9$ is an amino acid side chain, bioconjugate reactive moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ and $R^{13}$ are each independently oxo, halogen, —$CCl_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z11 is an integer from 0 to 4;
z12 is an integer from 0 to 7;
z13 is an integer from 0 to 5;
$L^1$ is a covalent linker; and
$R^{14}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, a EphA2 agonist, a drug moiety, a targeting moiety, or a detectable moiety.

Embodiment 2. The compound of embodiment 1, having the formula:
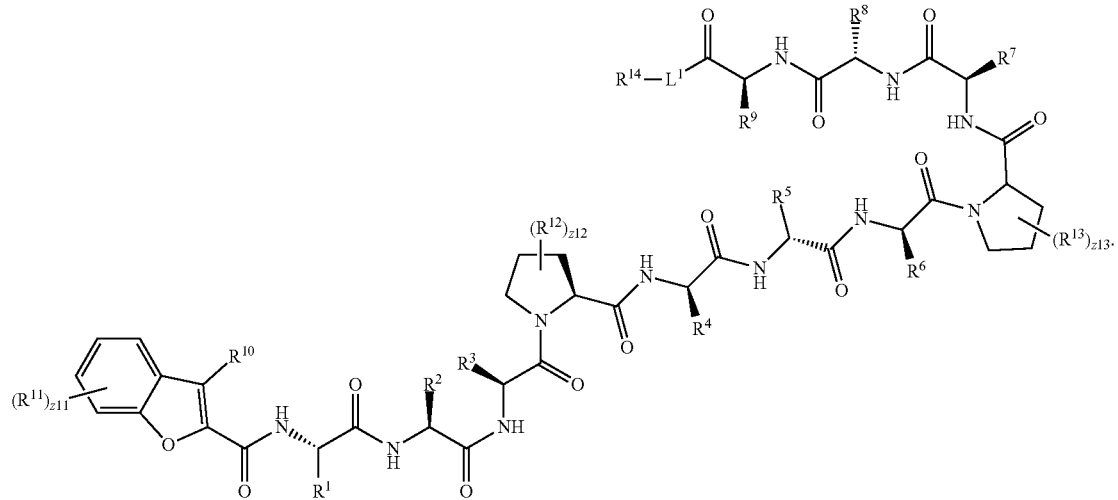
Embodiment 3. The compound of embodiment 1 or embodiment 2, wherein $R^1$ and $R^5$ are each independently the side chain of glycine, alanine, valine, leucine, isoleucine, proline, phenylalanine, methionine, or tryptophan.
Embodiment 4. The compound of embodiment 1, wherein the compound has the formula:
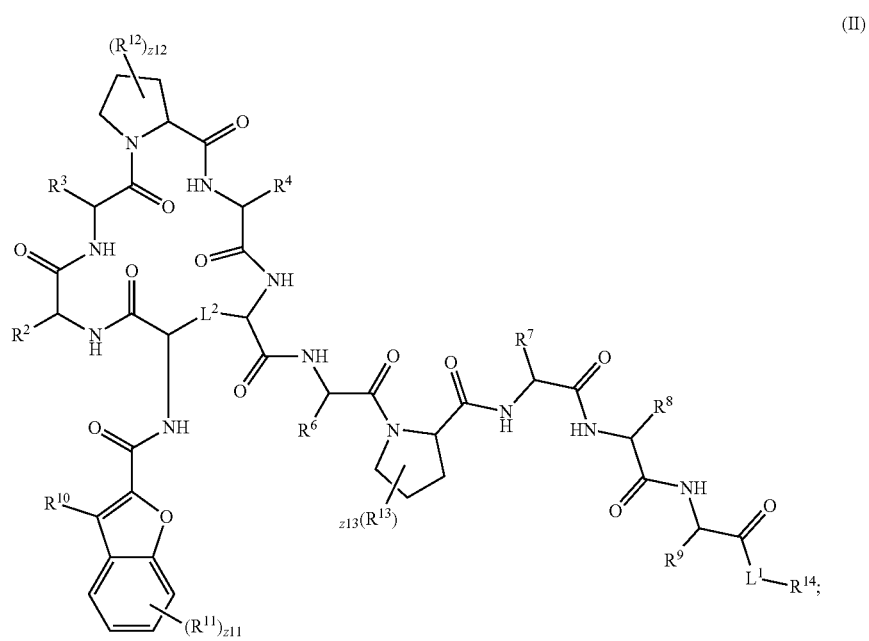
(II)

wherein,

L² is a bond, —S(O)₂—, —NH—, —O—, —S—, —S—S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 5. The compound of any one of embodiments 1 to 4, wherein R² is —CCl₃, —CBr₃, —CF₃, —CI₃, substituted or unsubstituted alkyl, substituted or unsubstituted heteroalkyl, substituted or unsubstituted cycloalkyl.

Embodiment 6. The compound of any one of embodiments 1 to 5, wherein R³ is the side chain of phenylalanine, tryptophan, tyrosine, thyroxine, 5-hydroxytryptophan, dihydroxyphenylalanine, or histidine.

Embodiment 7. The compound of any one of embodiments 1 to 5, wherein R³ is substituted or unsubstituted heterocycloalkyl, substituted or unsubstituted aryl, or substituted or unsubstituted heteroaryl.

Embodiment 8. The compound of any one of embodiments 1 to 7, wherein R⁴ is the side chain of aspartic acid, glutamic acid, 2-amino-3-(2H-1,2,3,4-tetrazol-5-yl)propanoic acid (AspTtz), or 2-amino-3-(2H-1,2,3,4-tetrazol-5-yl)butanoic acid (GluTtz).

Embodiment 9. The compound of any one of embodiments 1 to 7, wherein R⁴ is —OH, —NH₂, —COOH, —CONH₂, —SH, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted aryl, or substituted or unsubstituted heteroaryl.

Embodiment 10. The compound of any one of embodiments 1 to 9, wherein R⁶ is the side chain of an amino acid.

Embodiment 11. The compound of any one of embodiments 1 to 10, wherein R⁷ and R⁸ are each independently the side chain of an amino acid, substituted or unsubstituted aryl, or substituted or unsubstituted heteroaryl.

Embodiment 12. The compound of any one of embodiments 1 to 10, wherein R⁷ is independently

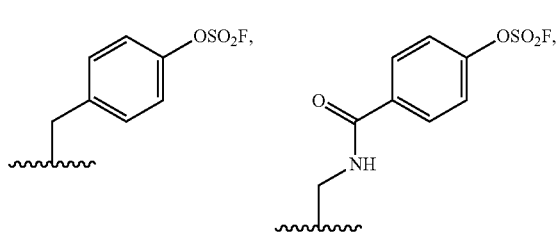

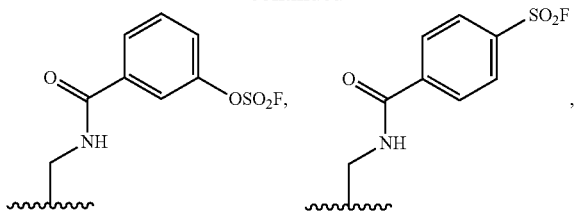

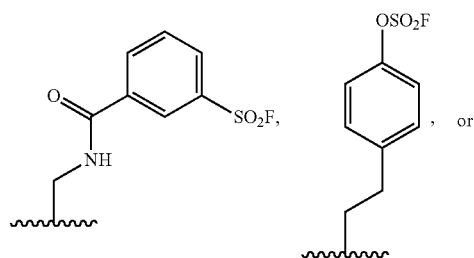

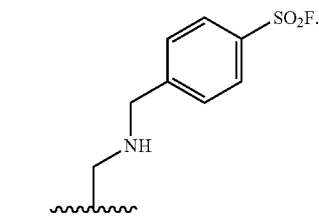

Embodiment 13. The compound of any one of embodiments 1 to 12, wherein R¹² is independently substituted or unsubstituted alkyl, substituted or unsubstituted heteroalkyl, or substituted or unsubstituted cycloalkyl.

Embodiment 14. The compound of any one of embodiments 1 to 12, wherein Rn is independently —OH, —NH₂, —COOH, —CONH₂, —SH, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted aryl, or substituted or unsubstituted heteroaryl.

Embodiment 15. The compound of any one of embodiments 1 to 14, wherein R⁹ is a bioconjugate reactive moiety.

Embodiment 16. The compound of embodiment 1, having the formula:

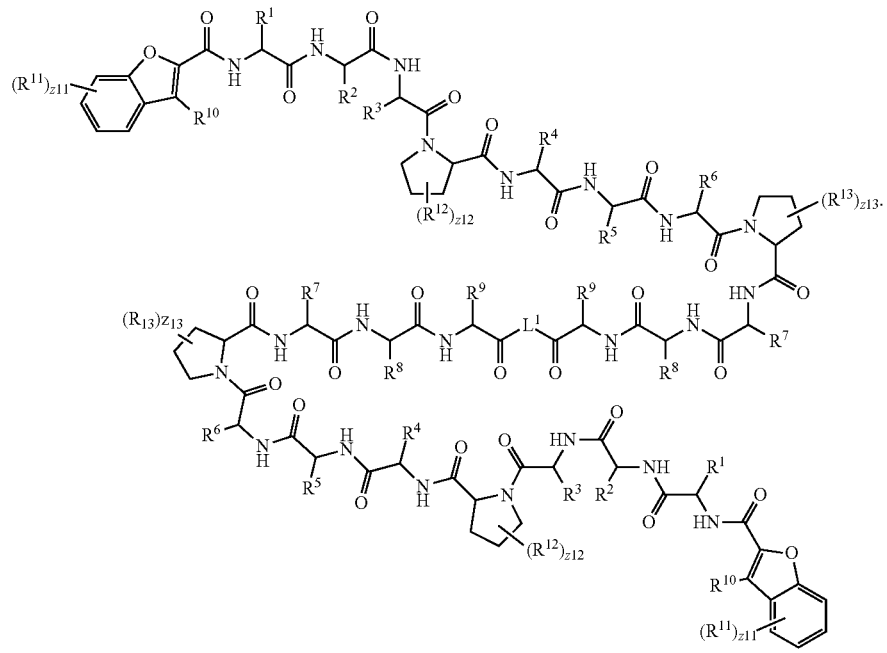

(III)

Embodiment 17. The compound of any one of embodiments 1 to 16, wherein $L^1$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 18. The compound of any one of embodiments 1 to 16, wherein -L$^1$-R$^{14}$ has the formula:

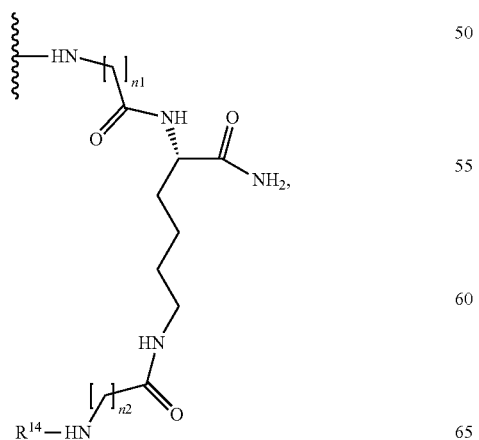

-continued

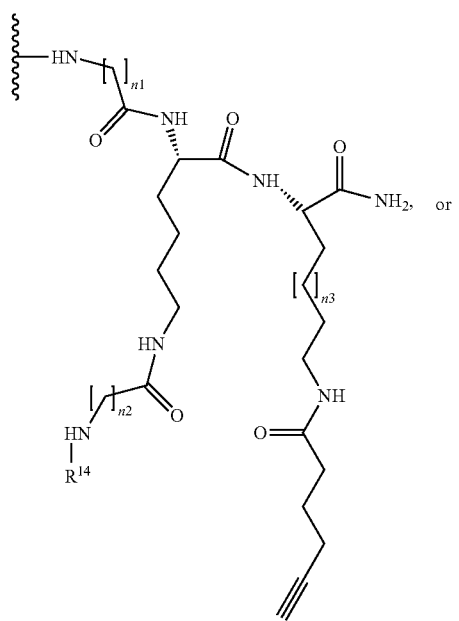

201
-continued

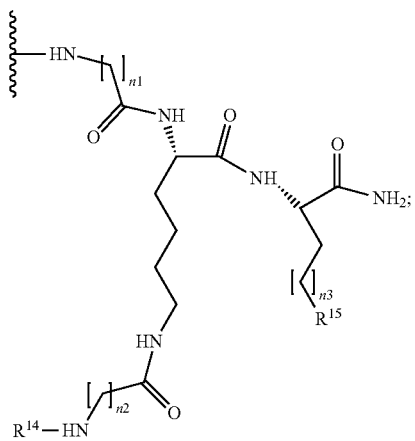

wherein, n1, n2, and n3 are each independently integers from 1 to 20;

$R^{15}$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

Embodiment 19. The compound of any one of embodiments 1 to 16, wherein $L^1$ has the formula:

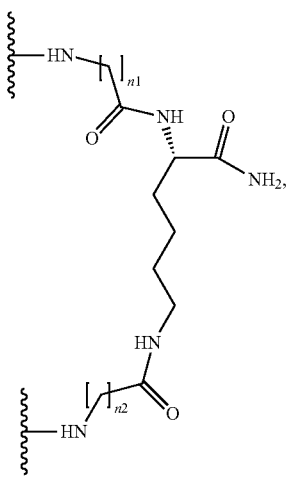

202
-continued

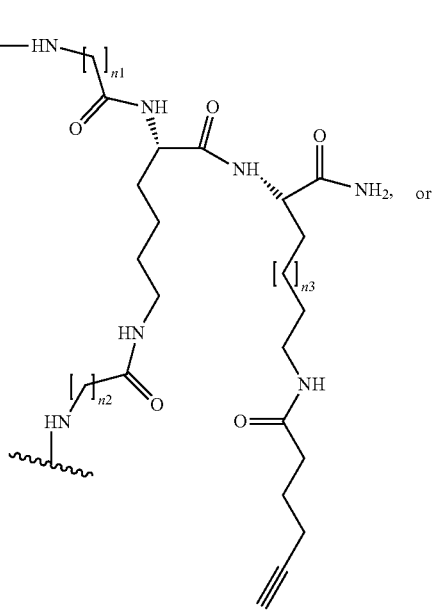

wherein, n1, n2, and n3 are each independently integers from 1 to 20;

$R^{15}$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a bioconjugate reactive moiety, a nanoparticle, a peptide, an EphA2 agonist, a drug moiety, a targeting moiety, or a detectable moiety.

Embodiment 20. The compound of any one of embodiments 1 to 19, wherein the drug moiety is a taxol moiety.

Embodiment 21. The compound of any one of embodiments 1 to 19, wherein the drug moiety is monovalent paclitaxel.

Embodiment 22. The compound of embodiment 1, having the formula:

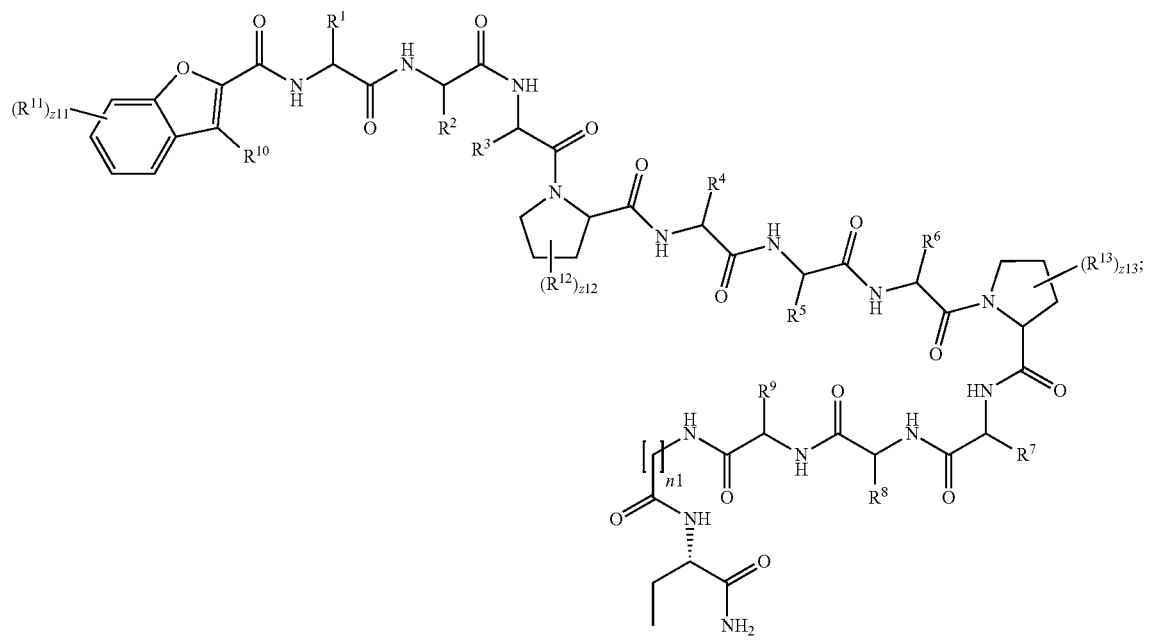
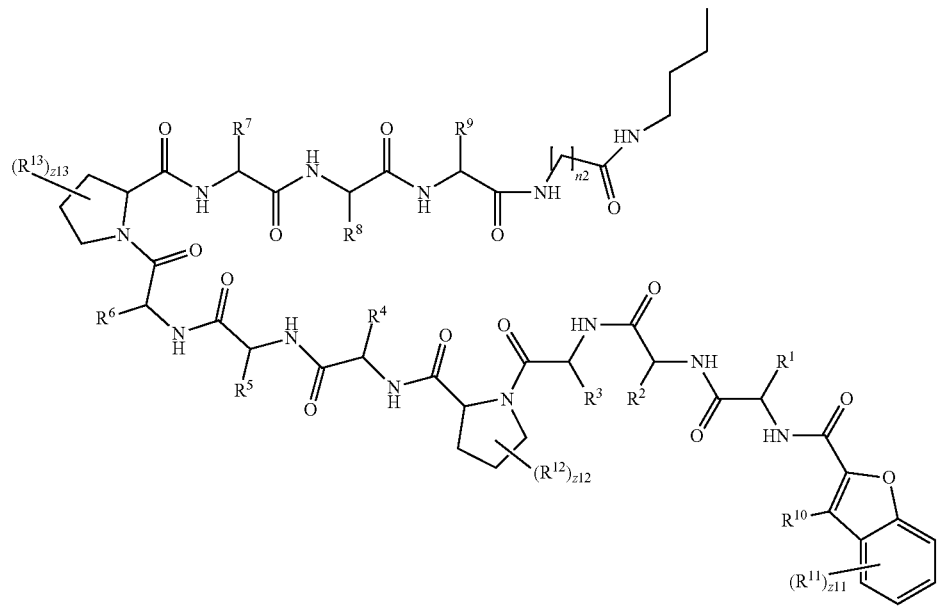
wherein,
n1 and n2 are each independently integers from 1 to 20.
Embodiment 23. The compound of embodiment 1, wherein the compound has the formula:

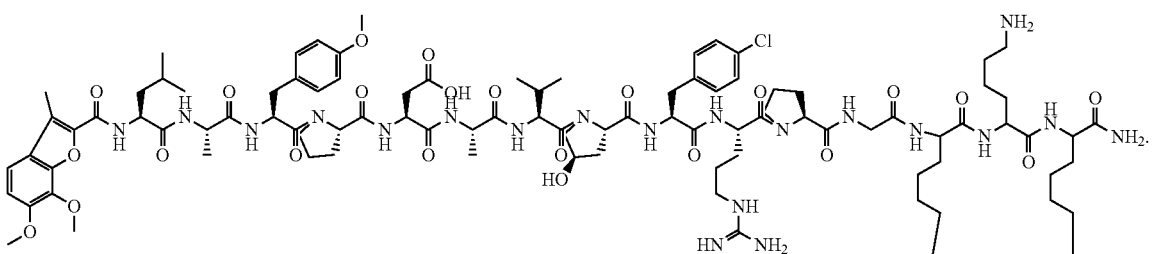
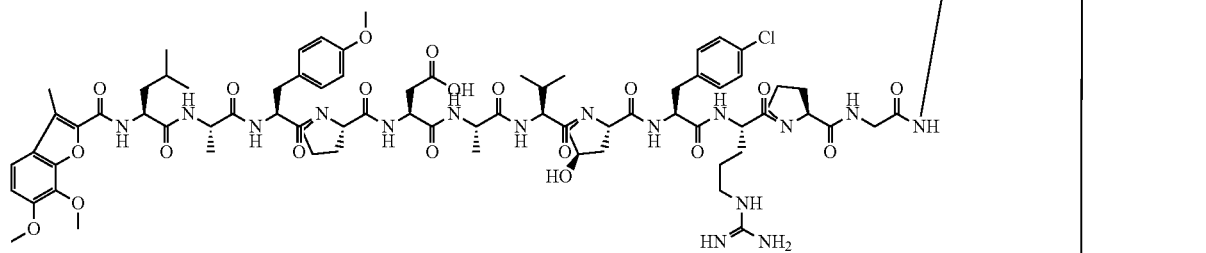
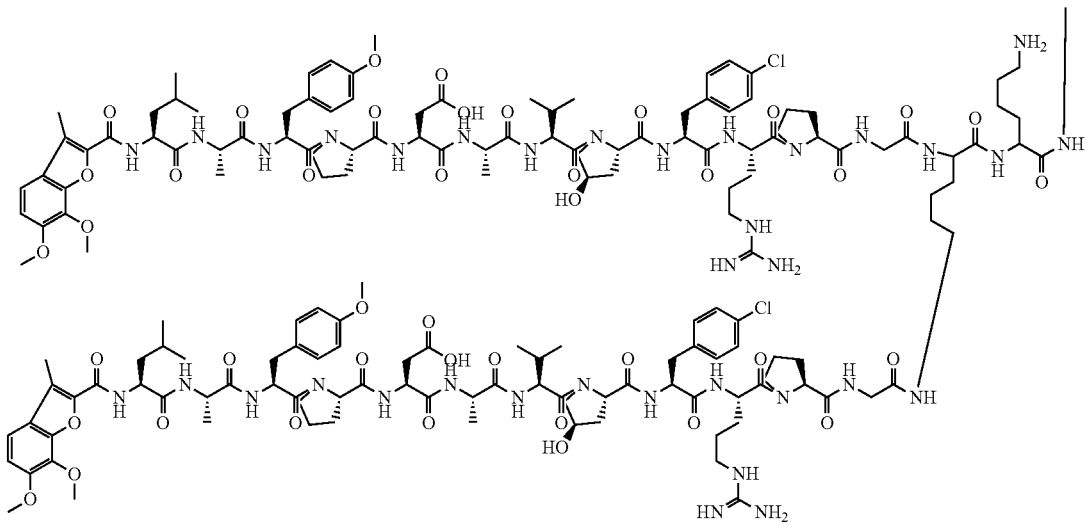
Embodiment 24. The compound of embodiment 1, wherein $R^1$, $R^2$, $R^3$, $R^4$, $R^5$, $R^6$, $R^7$, and $R^8$ are each independently an amino acid side chain.
Embodiment 25. The compound of embodiment 1, wherein $R^1$, $R^2$, $R^3$, $R^4$, $R^5$, $R^6$, $R^7$, and $R^8$ are each independently a non-natural amino acid side chain.
Embodiment 26. The compound of embodiment 1, having the formula:

(SEQ ID NO:67)
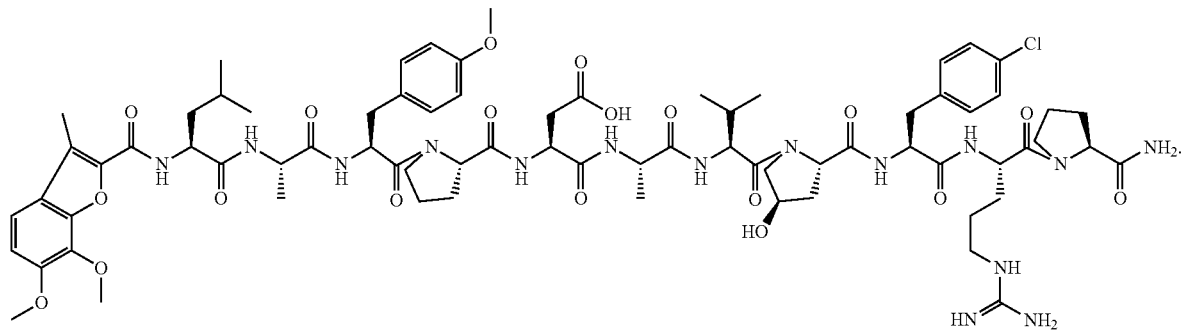
Embodiment 27. The compound of embodiment 1, having the formula:
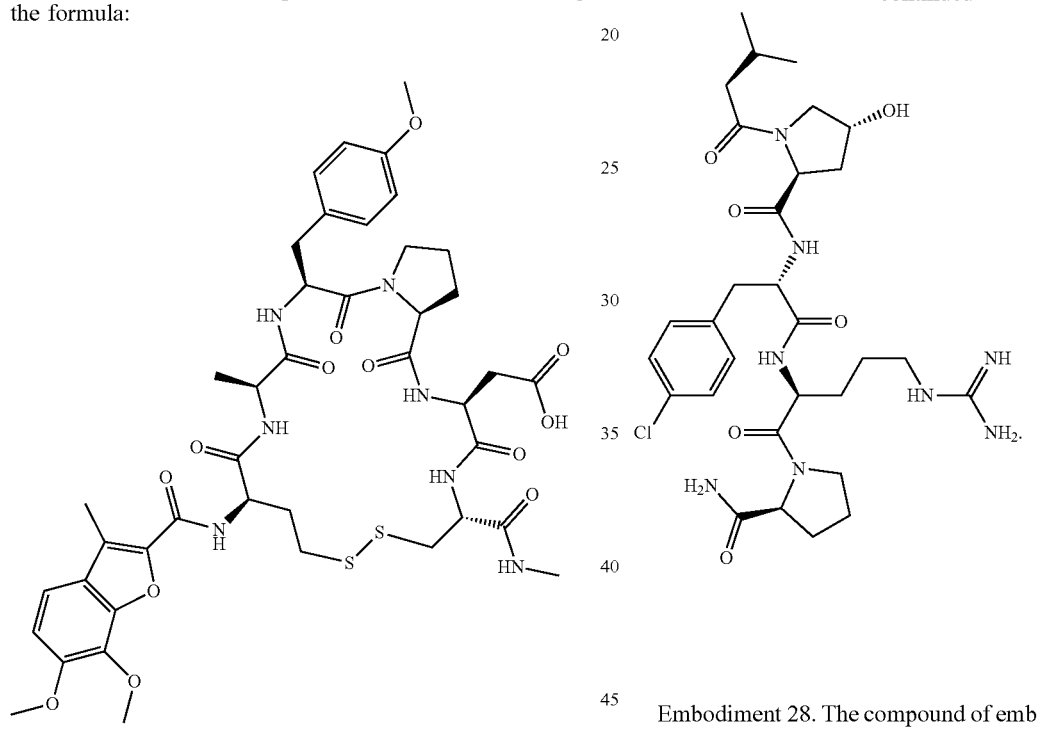
Embodiment 28. The compound of embodiment 1, having the formula:
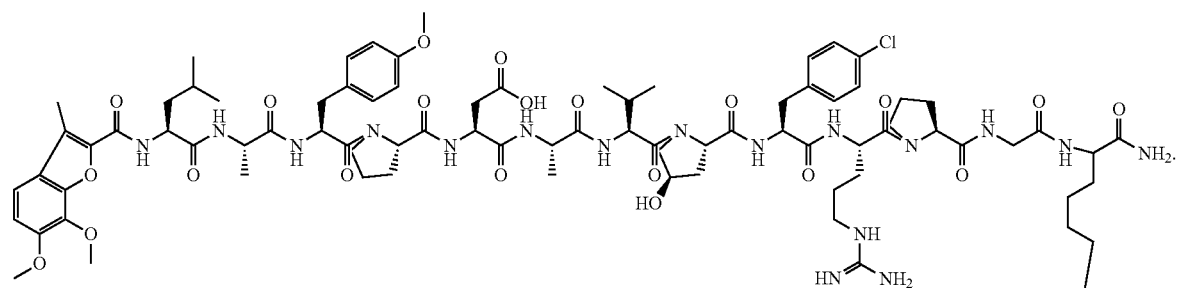

-continued
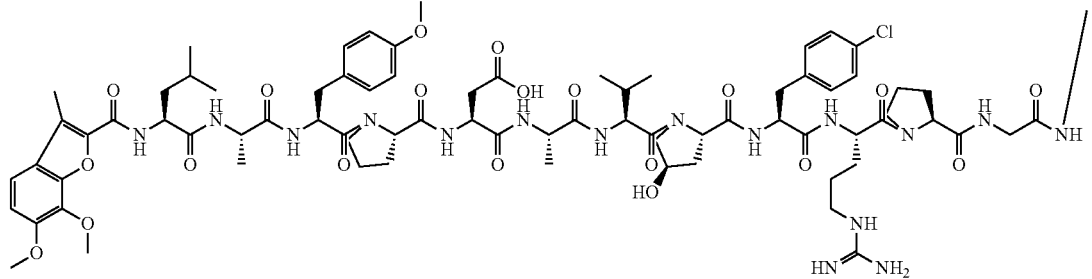
Embodiment 29. The compound of embodiment 1, having the formula:
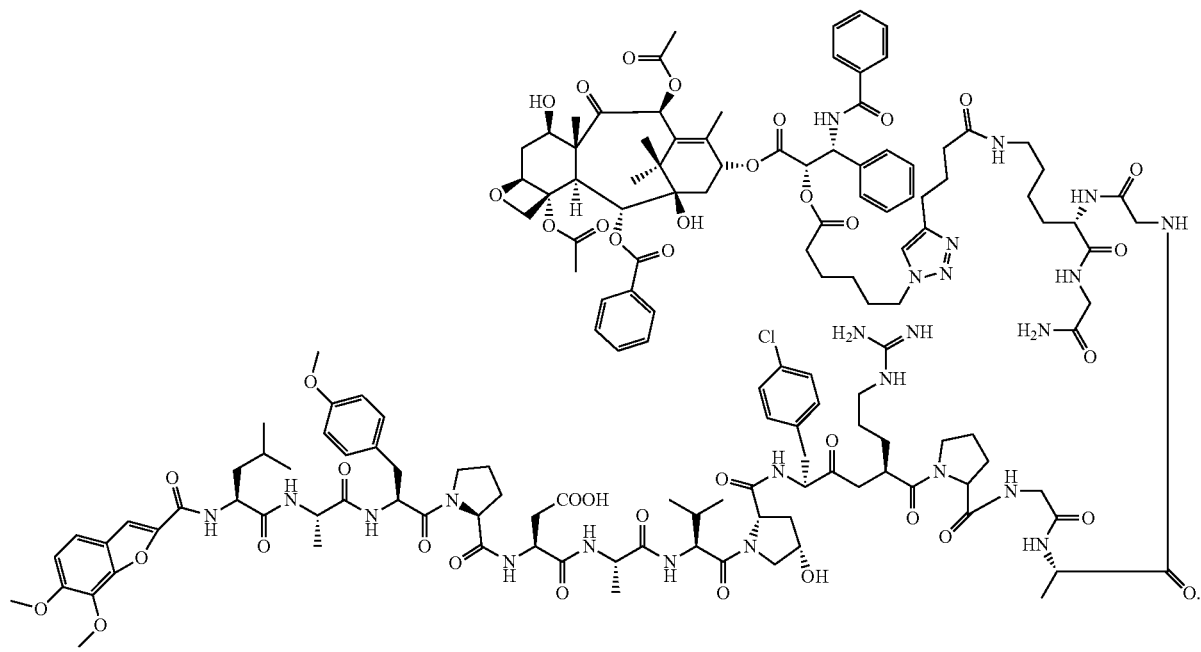
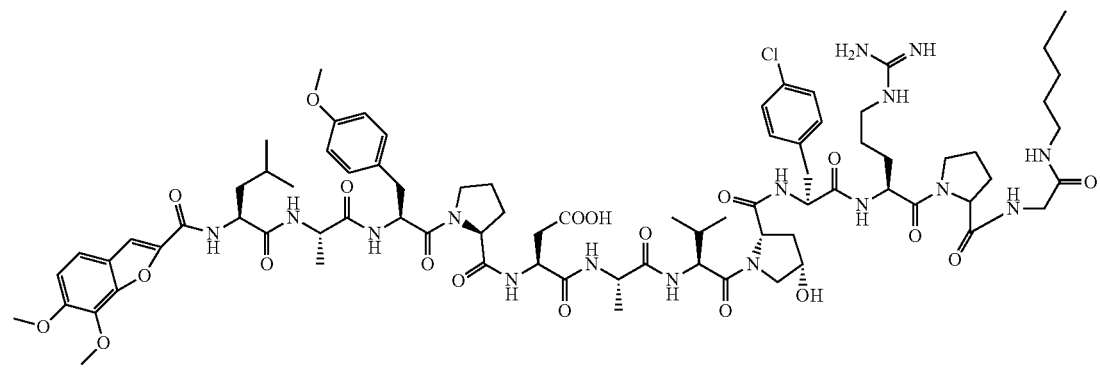

Embodiment 30. A pharmaceutical composition comprising a pharmaceutically acceptable excipient and the compound of any one of embodiments 1 to 29.

Embodiment 31. A method of treating cancer, said method comprising administering to a subject in need thereof a therapeutically effective amount of a compound of any one of embodiments 1 to 29.

Embodiment 32. A method of increasing EphA2 activity, said method comprising contacting an EphA2 protein with a compound of any one of embodiments 1 to 29.

Embodiment 33. A method of suppressing pro-oncogenic EphA2 activity, said method comprising contacting an EphA2 protein with a compound of any one of embodiments 1 to 29.

Embodiment 34. A method of reducing levels of EphA2, said method comprising contacting an EphA2 protein with a compound of any one of embodiments 1 to 29.

Embodiment 35. A method of inhibiting cancer cell migration and invasion, said method comprising contacting an EphA2 protein with a compound of any one of embodiments 1 to 29.

Embodiment 36. A method of selectively delivering a chemotherapeutic agent to EphA2 expressing cancer cells, said method comprising contacting an EphA2 protein with a compound of any one of embodiments 1 to 29, wherein $R^{14}$ comprises a drug moiety.

EXAMPLES

Example 1. Initial Optimization of 123B9 Based on Primary Sequences of Ephrin Ligands EphA2 belongs to a class of receptor tyrosine kinases that have been implicated in tumorigenesis, drug resistance, and metastatic behaviors of several solid tumors including prostate cancer (1-3), melanoma (4), urinary bladder (5), breast (6), ovarian (7), pancreatic (8-10), brain (11-13), esophagus (14), lung (15), and stomach (16) cancers, and leukemia (17-20). In cancer cells, the unbalanced overexpression of the receptor compared to its ligands (ephrin A) primes the EphA2 pro-oncogenic activity. Hence, un-ligated EphA2 receptor functions as an oncogene and its effect can be reverted by stimulation by agonistic agents, which, once engaged with the receptor, stimulate intrinsic tumor suppressive signaling pathways mediated by the EphA2 (21). Structurally, EphA2 is composed of an extracellular domain, responsible for engagement with the ephrin-A ligands. Ephrin-A ligand binding causes receptor dimerization, clustering and internalizations. The cytosolic region of the receptor contains a kinase domain, a SAM domain, and a PDZ binding motif, that trigger the cellular signaling events. Because of its possible dual role as an oncogene and a tumor suppressor, EphA2 is currently subject of fervid research for the development of possible therapeutics that target either its intracellular kinase domain (22-25), or its ligand-binding domain (26-27). Because receptor activation reverts the pro-oncogenic function of the EphA2, small molecule EphA2 agonists hold great potential for the development of novel therapeutics. Recently, antibodies directed at the ligand binding domain were shown to have the ability to suppress tumor growth in human breast cancer (MDA-MB-231) and in human gastric cancer (SNU-16) xenograft mouse models (27). More recently, we have developed novel EphA2 dimeric agonist peptides conjugated with the chemotherapeutic agent paclitaxel and demonstrated that dimerization of the peptides can trigger receptor activation at lower concentrations (compared to the monomeric peptides) and that the activated EphA2-peptide complex internalized its cargo, hence effectively working as a molecular Trojan horse for EphA2 expressing cancer cells (28). However, the carrying agonistic peptides remained of relatively weak affinity, limiting the full potential of these agents as effective EphA2 therapeutics. Indeed potent agonistic agents could be conjugated with either chemotherapy for use as peptide-drug-conjugates (PDCs), with fluorophores, metal-chelating group for PET or MRI, for use as diagnostics. In our previous studies, we used a 12-mer agonistic peptide with a relatively weak affinity for EphA2 to derive PDCs, and exploited peptide dimerization to bootstrap cellular activity from triple-digit micromolar to low micromolar. In the current study, we first deployed more extensive structure-activity relationship studies to obtain an EphA2 agonistic agent with low micromolar affinity. This allowed us to obtain a crystal structure of the complex between such agent and the EphA2 ligand binding domain. Hence, using structure-based approaches we were able to derive novel and more potent EphA2 binding agents that displayed a nanomolar affinity for the receptor as determined by isothermal titration calorimetry and in vitro displacement assays. A dimeric version of the most potent agent was extraordinarily effective in cellular assays for receptor degradation, and suppression of pro-oncogenic activity of the EphA2 in cellular models, including a remarkable inhibition of both pancreatic cancer cell migration and invasion.

Abbreviations used: EphA2-LBD ephrin type-A receptor 2 ligand-binding domain; ITC, isothermal titration calorimetry; PET, positron emission tomography; MRI, magnetic resonance imaging; Hyp, L-trans-4-hydroxyproline; Aib, α-aminoisobutyric acid; Dap, di-amino propionic acid; 4Pal, 4-pyridyl-L-alanine; Cha, 3-cyclohexyl-L-alanine; Nle, L-norleucine; hS, L-homo-serine; hC, L-homoCysteine; 3FAbu, (2S)-2-amino-4,4,4-trifluorobutanoic acid; AspTtz, 2-amino-3-(2H-1,2,3,4-tetrazol-5-yl)propanoic acid.

Figure 1B:
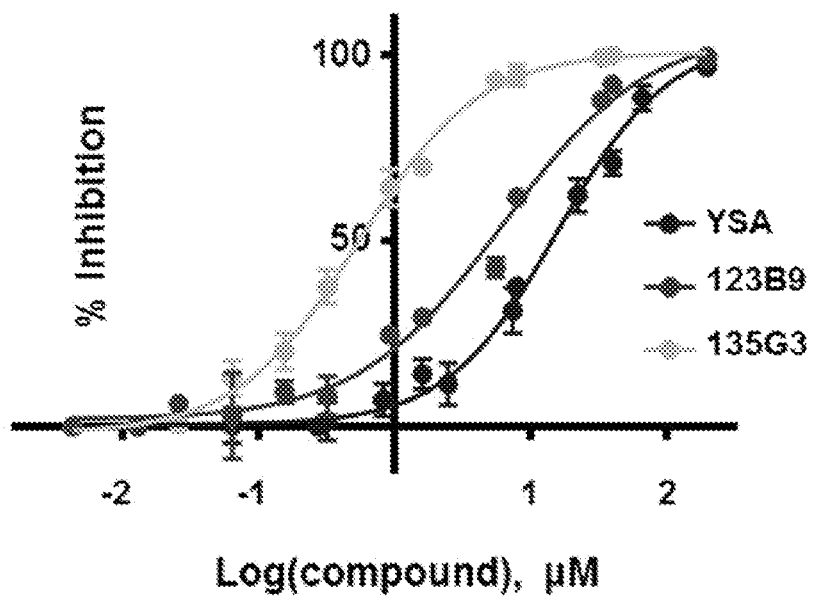

In order to more rapidly and accurately characterize the binding properties of novel 123B9 (Table 1) derived EphA2-binding agents, we first developed a DELFIA assay (FIG. 1A). Briefly, a biotinylated 123B9 peptide was prepared and used as a bait in streptavidin-coated 96-well plates (Perkin-Elmer). Subsequently, 6×His-EphA2-ligand binding domain (LBD) was added to each assay well, together with a highly fluorescent Europium-conjugated anti-6×His antibody. Hence, after incubation with a test agent and washing steps, residual fluorescence indirectly measured the ability of the given test compound to displace 123B9 from EphA2. In repeated experiments the Z' factor of this assay was 0.76 indicating that the approach was very robust as a primary assay to conduct the proposed studies. In this assay, the previously reported peptides YSA (YSAYPDSVPMMS (SEQ ID NO:2)) (29) and 123B9 (30) (Table 1) displayed $IC_{50}$ values of 16.5 μM and 6.5 μM, respectively, again in close agreement to our previous isothermal titration calorimetry studies with these agents (Table 1, FIG. 1B) (30).

TABLE 1

Tested agents and relative IC$_{50}$ values (µM) from DELFIA assay.

| ID | Sequence | IC$_{50}$ (µM) |
| --- | --- | --- |
| YSA | H$_2$N-YSAYPDSVPMMS-CONH$_2$ (SEQ ID NO: 2) | 16.2 ± 0.8, n = 14 |
| 123B9 | (4-F,3-ClPhOCH$_2$CO)SAYPDSVP(Nle)(hS)S-CONH$_2$ (SEQ ID NO: 3) | 6.6 ± 1.0, n = 4 |
| ephrins A2/A5/A4 | H$_2$N-FTPFSLGFEFRP-CONH$_2$ (SEQ ID NO: 4) | >200 |
| ephrin A3 | H$_2$N-YSAFSLGYEFHA-CONH$_2$ (SEQ ID NO: 5) | >200 |
| ephrin B2 | H$_2$N-FSPNLWGLEFQK-CONH$_2$ (SEQ ID NO: 6) | >200 |
| ephrin A1 | H$_2$N-FTPFTLGKEFKE-CONH$_2$ (SEQ ID NO: 7) | >200 |
| 135A1 (1C1) | H$_2$N-YDYVAVAGPAEY-CONH$_2$ (SEQ ID NO: 8) | >500 |
| 135A7 | H$_2$N-YSAYPLSVEFRP-CONH$_2$ (SEQ ID NO: 9) | >100 |
| 135A8 | H$_2$N-YSAYPDSVEFRP-CONH$_2$ (SEQ ID NO: 10) | 36.3 ± 6.2, |
| 135B1 | H$_2$N-YSAYPDSVEMMS-CONH$_2$ (SEQ ID NO: 11) | >100 |
| 135B12 | H$_2$N-YSAYPDSVPFRP-CONH$_2$ (SEQ ID NO: 12) | 1.9 ± 0.1, n = 22 |
| 135B2 | H$_2$N-YSAYPLSVEMMS-CONH$_2$ (SEQ ID NO: 13) | >200 |
| 135B8 | H$_2$N-FTAFPLGFEFRP-CONH$_2$ (SEQ ID NO: 14) | >100 |
| 135B9 | H$_2$N-FTAFPLGFEMMS-CONH$_2$ (SEQ ID NO: 15) | >100 |
| 135C1 | H$_2$N-YSAYPDSVPFMS-CONH$_2$ (SEQ ID NO: 16) | 7.5 ± 0.5 |
| 135C2 | H$_2$N-YSAYPDSVPF-CONH$_2$ (SEQ ID NO: 17) | 11.2 ± 1.4 |
| 135C3 | H$_2$N-YSAYPDSVPFRS-CONH$_2$ (SEQ ID NO: 18) | 4.4 ± 0.9 |
| 135C4 | H$_2$N-YSAYPDSVPFR-CONH$_2$ (SEQ ID NO: 19) | 4.9 ± 0.1 |
| 135C7 | H$_2$N-YSAYPDSVPMRS-CONH$_2$ (SEQ ID NO: 20) | 8.8 ± 0.1 |
| 135C8 | H$_2$N-YSAYPDSVPMRP-CONH$_2$ (SEQ ID NO: 21) | 8.4 ± 1.2 |
| 135C9 | H$_2$N-YSAYPDSVPMMP-CONH$_2$ (SEQ ID NO: 22) | 11.8 ± 0.4 |
| 135C10 | H$_2$N-YSAYPDSVPFMP-CONH$_2$ (SEQ ID NO: 23) | 4.6 ± 0.1 |
| 135D6 | H$_2$N-YSCYPDSVPFRP-CONH$_2$ (SEQ ID NO: 24) | >100 |
| 135D7 | H$_2$N-YSVYPDSVPFRP-CONH$_2$ (SEQ ID NO: 25) | >200 |
| 135D8 | H$_2$N-YSLYPDSVPFRP-CONH$_2$ (SEQ ID NO: 26) | >200, n = 2 |
| 135D9 | H$_2$N-YS(Aib)YPDSVPFRP-CONH$_2$ (SEQ ID NO: 27) | >200 |
| 135E2 | (4-F,3-ClPhOCH$_2$CO)SAYPDSVPFRP-CONH$_2$ (SEQ ID NO: 28) | 3.1 ± 0.4, n = 6 |
| 135E4 | H$_2$N-YSAYPDSVP(4-ClPhe)RP-CONH$_2$ (SEQ ID NO: 29) | 1.6 ± 0.2, n = 8 |
| 135E5 | H$_2$N-YSAYPDSVP(3-ClPhe)RP-CONH$_2$ (SEQ ID NO: 30) | 1.8 ± 0.1 |
| 135E6 | H$_2$N-YSAYPDSVP(4-FPhe)RP-CONH$_2$ (SEQ ID NO: 31) | 3.1 ± 0.4 |
| 135E7 | H$_2$N-YSAYPDSVP(4-CF$_3$Phe)RP-CONH$_2$ (SEQ ID NO: 32) | 1.9 ± 0.2 |
| 135E10 | H$_2$N-YSAYPDSVPF(4-Amino-Phe)P-CONH$_2$ (SEQ ID NO: 33) | 2.3 ± 0.3 |
| 135E11 | H$_2$N-YSAYPDSVPF(4-Amino-Methyl-Phe)P-CONH$_2$ (SEQ ID NO: 34) | 1.3 ± 0.2 |
| 135E12 | H$_2$N-YSAYPDSVPF(4-Guanidino-Phe)P-CONH$_2$ (SEQ ID NO: 35) | 1.0 ± 0.1 |

TABLE 1-continued

Tested agents and relative IC$_{50}$ values (µM) from DELFIA assay.

| ID | Sequence | IC$_{50}$ (µM) |
|---|---|---|
| 135F1 | H$_2$N-YSAYPDSVPFKP-CONH$_2$ (SEQ ID NO: 36) | 1.5 ± 0.1 |
| 135F2 | H$_2$N-YSAY(Hyp)DSVPFRP-CONH$_2$ (SEQ ID NO: 37) | 14.5 ± 0.8 |
| 135F3 | H$_2$N-YSAYPDSV(Hyp)FRP-CONH$_2$ (SEQ ID NO: 38) | 1.5 ± 0.1 |
| 135F4 | H$_2$N-YSAYPDSVPFR(Hyp)-CONH$_2$ (SEQ ID NO: 39) | 5.6 ± 0.5 |
| 135F5 | H$_2$N-YSA(4ClPhe)PDSVPFRP-CONH$_2$ (SEQ ID NO: 40) | 3.5 ± 0.3 |
| 135F6 | H$_2$N-YSA(3ClPhe)PDSVPFRP-CONH$_2$ (SEQ ID NO: 41) | 11.4 ± 1.3 |
| 135F8 | H$_2$N-YSAYPDSVP(4Pal)RP-CONH$_2$ (SEQ ID NO: 42) | 7.6 ± 0.1 |
| 135F10 | H$_2$N-YSAYPDSV(Hyp)(4ClPhe)RP-CONH$_2$ (SEQ ID NO: 43) | 0.94 ± 0.11, n = 6 |
| 135F12 | (4F,3ClPhOCH$_2$CO)SAYPDSVPFRP(β-Ala)K-CONH$_2$ (SEQ ID NO: 44) | 4.1 ± 0.1 |
| 135G3 | (4F,3ClPhOCH$_2$CO)SAYPDSV(Hyp)(4ClPhe)RP-CONH$_2$ (SEQ ID NO: 45) | 0.54 ± 0.03, n = 10 |
| 135C11 | (H$_2$N-YSAYPDSVPFRPG)$_2$-K-CONH | 0.60 ± 0.09, n = 6 |

SE represents duplicate measurements unless otherwise indicated.
Hyp, L-trans-4-hydroxyproline;
Aib, α-aminoisobutyric acid;
4Pal, 4-pyridyl-L-alanine;
Nle, L-norleucine;
hS, L-homo-serine.

Figure 1C:
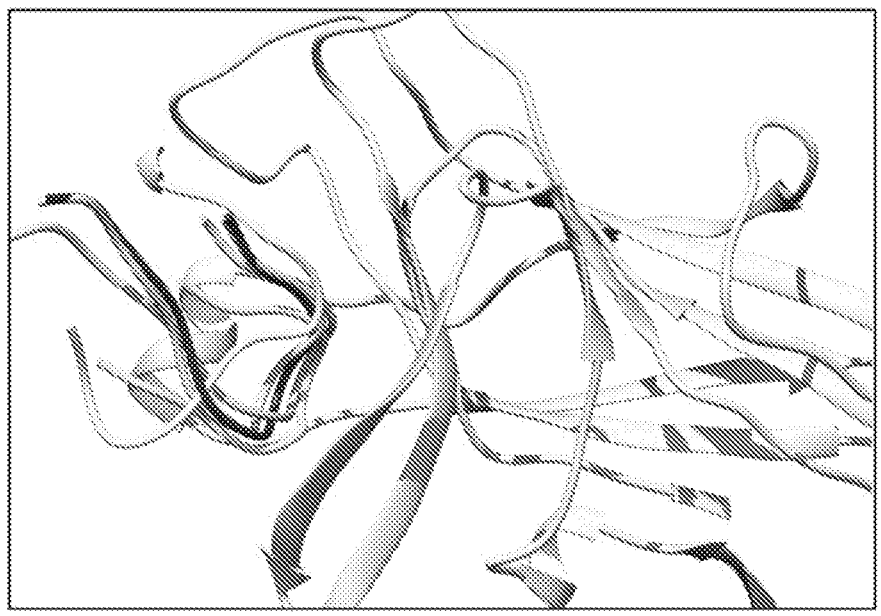
Figure 1D:
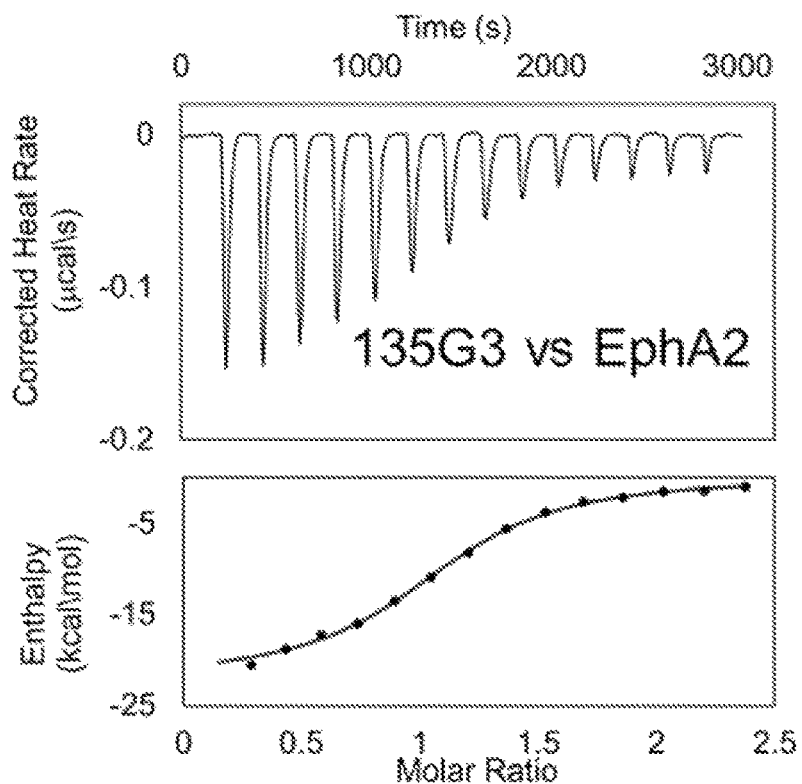
Figure 1D:
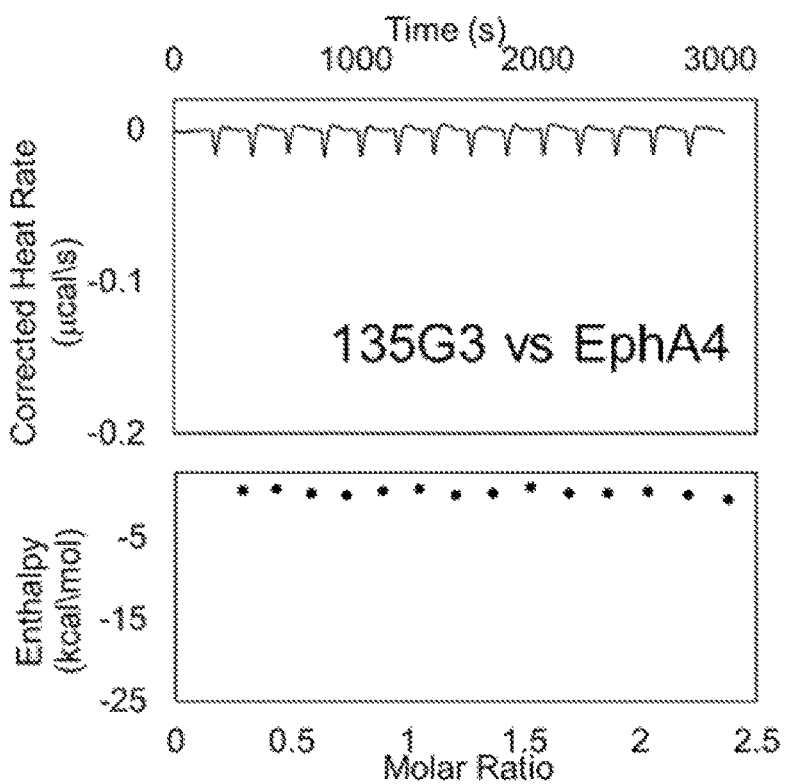

A number of putative peptide-binding regions derived from known protein binders to EphA2 (the ephrin-A ligands and an EphA2 antibody, named 1C1; (FIG. 1C) were identified, synthesized and tested, given their resemblances to 123B9 and YSA (Table 1). However, under these experimental conditions, none of these peptides displayed increased affinity for the EphA2-LBD compared to 123B9 (Table 1). Subsequently, we derived several "chimeric" peptides iteratively inserting elements of active peptides into these ephrin derived peptides. To expedite the synthesis, we first kept a Tyr at the N-terminus and subsequently we reintroduced the Tyr isostere present in 123B9 (namely, 4F,3C) phenyl acetic acid, Table 1) that we had incorporated into EphA2 targeting peptides to increase their plasma stability (30). These initial studies revealed unexpectedly that introducing the C-terminal region of the ephrin ligands (sequence FRP) into 123B9 resulted in agent 135E2 (and the corresponding N1-Tyr equivalent, 135B12) that were significantly more potent than the initial agents (Table 1). Subsequently, a second round of optimizations focused on modifications of the C-terminal peptide region and the introduction of non-natural amino acids in the attempt to further increase affinity for the receptor. These studies culminated in agent 135G3 that displayed an IC$_{50}$ value of 600 nM in the DELFIA assay (Table 1, FIG. 1B). To further validate the DELFIA displacement assay values and the selectivity of the resulting agent, we performed isothermal titration calorimetry measurements for selected agents against the ligand binding domains of EphA2 and EphA4 (FIG. 1D). These data revealed that 135G3 bound to the EphA2-LBD with a dissociation constant of 757 nM, hence comparable to the DELFIA IC$_{50}$ value. In addition, no significant binding was detected against the EphA4 confirming that the resulting agent had preserved its selectivity (FIG. 1D).

Figure 1E:
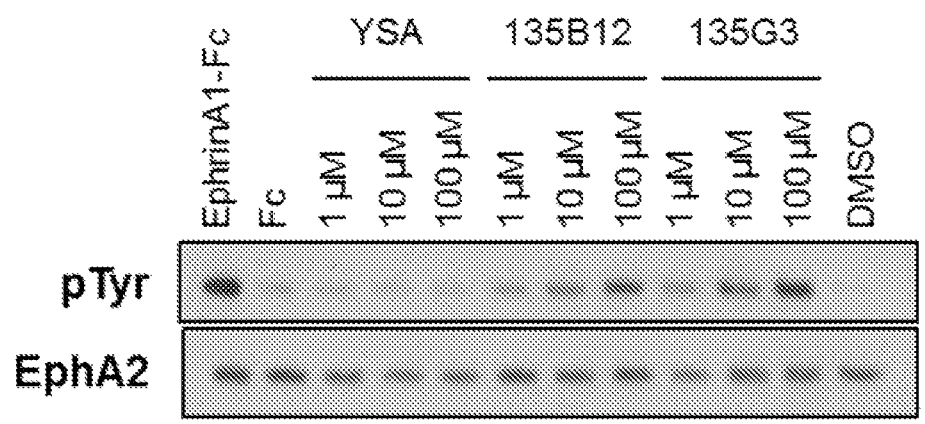

Agonistic agents, such as the ephrin ligands, cause receptor dimerization that cause phosphorylation of the kinase domain. Hence, to assess the agonistic activity of our compounds in cell, we could directly measure the phosphorylation levels of the EphA2 as illustrated in FIG. 1E. In this cellular assay, 135G3 resulted more effective in inducing receptor phosphorylation compared to both YSA and 135B12, which is in agreement with relative in vitro binding affinities of these agents to the receptor (FIG. 1E).

Example 2. The X-Ray Structure of 135E2 in Complex with the EphA2 Ligand Binding Domain Crystallization conditions were tested through sparse-matrix screening (Hampton Research Inc.) for 135E2 in complex with the ligand binding-domain of the EphA2. The crystals were subsequently reproduced by hanging-drop vapor diffusion method at 4° C., from drops mixed with 1 µl of protein complex and 1 µl of precipitant solution (1 M Tris-Cl, pH 8.0, 1.4-8M Li$_2$SO$_4$). Crystals were soaked for a few seconds in a cryoprotectant solution, composed of crystallization solution and 20% glycerol, before flash freezing in liquid nitrogen. Data were subsequently collected at the 5.0.1 beamline at the Advanced Light Source, Lawrence Berkeley National Laboratory and the diffraction data were indexed, integrated and scaled using the HKL2000 program (31). The structure was finally solved using the molecular replacement method in PHASER (32), using the PDB ID code 3C8X as a search model. The structure of the complex was refined by iterative model building using Coot (33) and PHENIX software packages (34). The statistics for data collection and structural refinement of the EphA2-peptide complex are summarized in Table 51. The structure of 135E2 in complex with the EphA2 LBD is reported in FIG. 2A together with structural superposition with the loop region from ephrinA5 bound to EphA2 (PDB ID 3MX0)

Figure 2A:
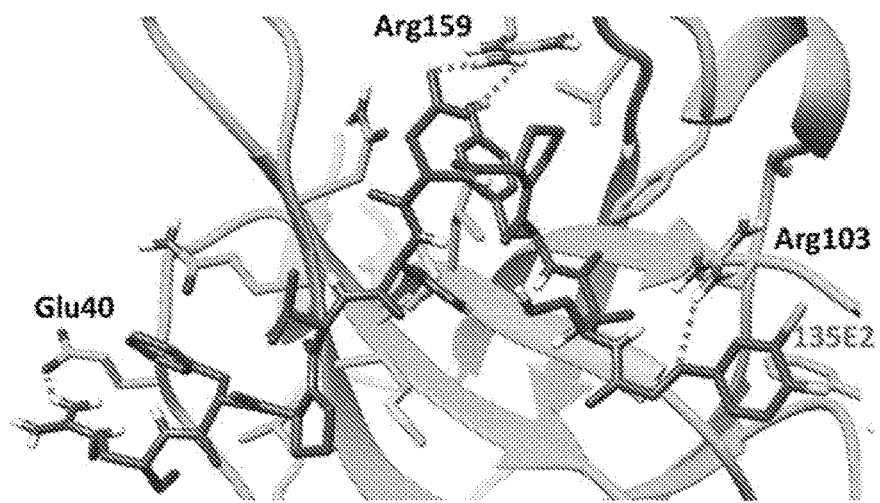
FIG. 2A-C. The X-ray structure of 135H2 in complex with the EphA2 LBD.
Figure 2B:
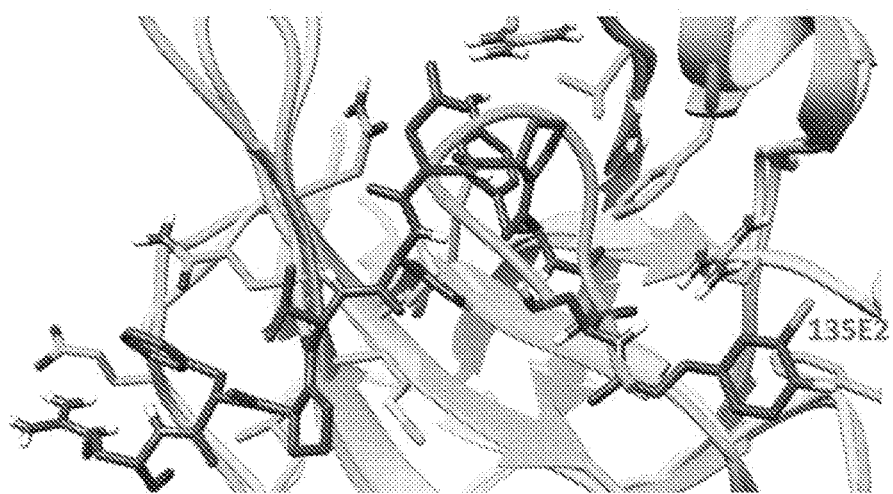
Figure 2C:
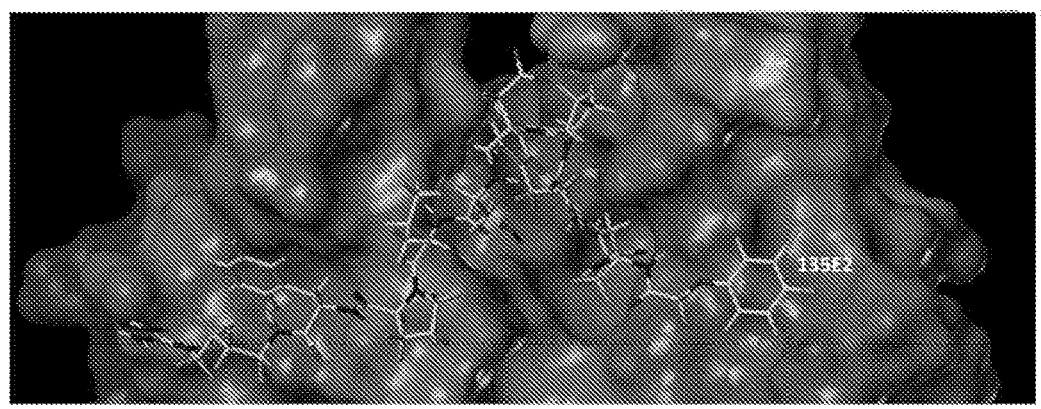

(FIG. 2B). While there is a good structural agreement in the positioning of the peptide and ephrinA5 loop region within the N-terminus region, the peptide departs for the ephrinA5 bound conformation to form a more extended structure. Hence, the gain in activity obtained by the introduction of the C-terminal FRP sequence from the ephrin ligands into 123B9 was serendipitous. In this regard, in addition to intermolecular interactions involving residue 135E2 Asp6 with EphA2 Arg159, we also observed an additional salt bridge between 135E2 Arg11 with EphA2 Glu40, that supported the observed increased activity of the agents compared to YSA and 123B9 (FIG. 2A,C). Finally, the presence of a hydrogen bond between Arg103 and the ether oxygen on the 4F,3Cl phenyl acetic acid moiety supported the observed increased activity of 123B9 versus YSA (FIG. 2A, Table 1).

TABLE S1

Data collection and refinement statistics

EphA2 - 135E2

| Data collection | |
| --- | --- |
| Space group | P212121 |
| Cell dimensions | |
| a, b, c (Å) | 89.3, 94.2, 134.5 |
| a,,Y (°) | 90, 90, 90 |
| Wavelength | 0.9774 |
| Resolution (Å) | 47.08-3.20 (3.31-3.20) [a] |
| Rsym or Rmerge | 0.24 (0.88) |
| I/σI | 3.9 (1.0) |
| $CC_{1/2}$ | 0.97 (0.555) |
| Completeness (%) | 96.0 (96.0) |
| Redundancy | 3.5 (3.3) |
| Refinement | |
| Resolution (Å) | 47.08-3.20 (.31-3.20) [a] |
| No. reflections | 18433 (1752) |
| $R_{work}/R_{free}$ | 23.5/27.4 (32.8/34.6) |
| No. atoms | |
| Protein | 5914 |
| Ligand | 48 |
| B factors | |
| Protein | 50.02 |
| ligand | 20.00 |

TABLE S1-continued

Data collection and refinement statistics

EphA2 - 135E2

| r.m.s. deviations | |
| --- | --- |
| Bond lengths (Å) | 0.006 |
| Bond angles (°) | 0.81 |
| Ramachandran favored (%) | 94.0 |
| Ramachandran allowed (%) | 6.0 |
| Ramachandran outliers (%) | 0 |

[a] Values in parentheses are for highest-resolution shell. The dataset was collected from a single crystal.

Example 3. Structure-Based Optimization of 135E2

Figure 9A:
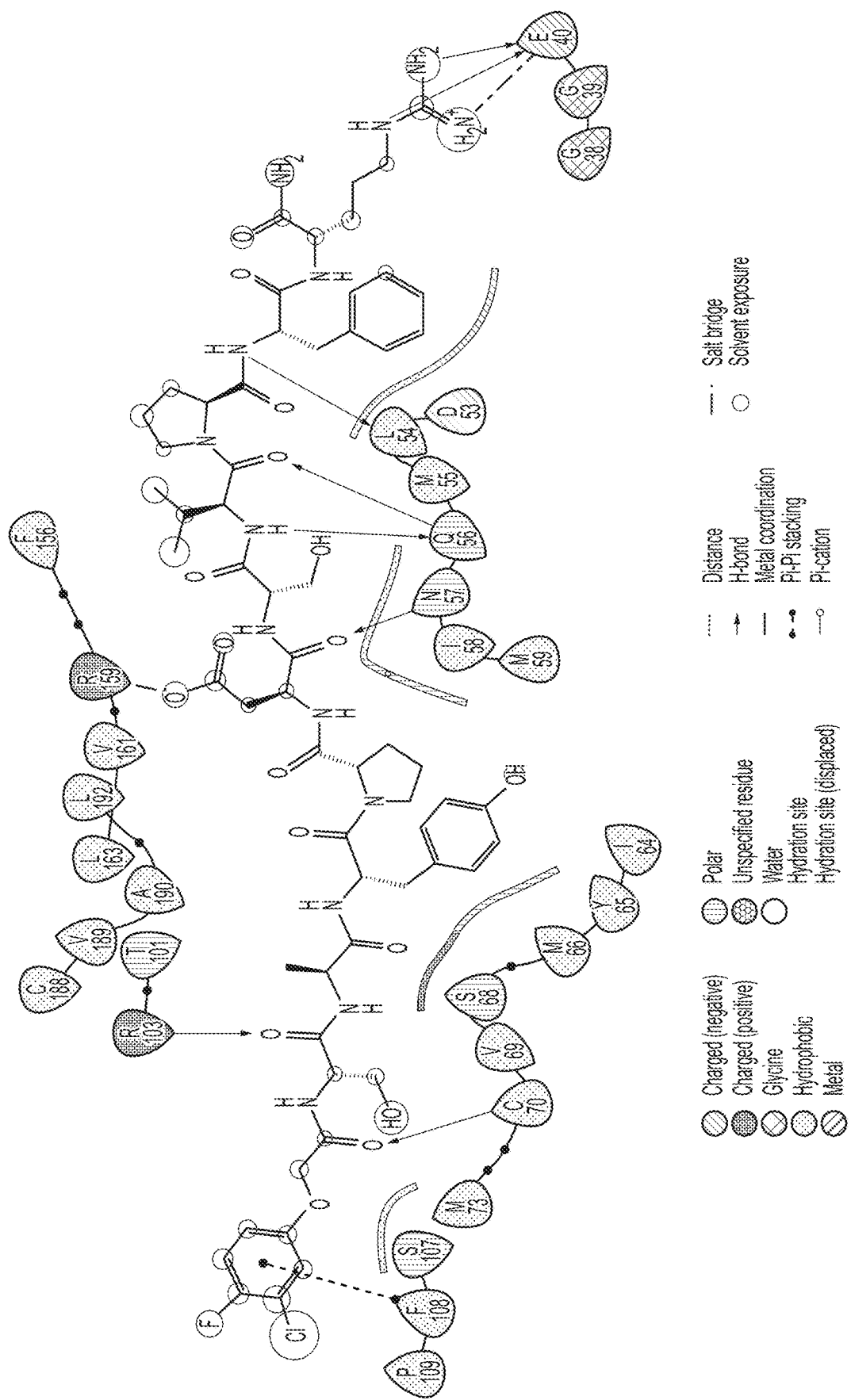
FIGS. 9A-B.

Using structure-based design strategies and the structure of the complex between 135E2 and EphA2-LBD, we have subsequently designed novel agents with improved affinity over 135G3. Given the bent bound conformation that juxtaposes the two Serine residues in 135E2 (FIG. 2A,C, FIG. 9A), we first sought to stabilize this intramolecular interaction either covalently or non-covalently (Table 2, agents 135G8, 135G9, 135F11, 135G10, 135I2, and 135I3). Cyclization of the compound using two Cys and disulfide bridge (135G8), or introducing a Glu-Dap (di-amino-propionic acid) lactam (135G9) resulted in less potent agents (Table 2). However, replacement of a disulfide bond between a Cys in position 2 and a homo-Cys in lieu of Ser 5 (but not the contrary arrangement, as in 135I2) resulted in cyclic agent 135I3 with retained affinity ($IC_{50}$~1 µM; Table 2). Introducing a possible intramolecular salt bridge, hence replacing Ser2 and Ser5 with Dap and Asp respectively, resulted in agent 135F11 that displayed a marked loss in affinity for EphA2. However, stabilizing the bound conformation with two hydrophobic residues in lieu of Ser2 and Ser5 (namely Leu2 and Ala5) resulted in an agent with a significantly increased affinity (135G10, $IC_{50}$=0.22 µM, Table 2). ITC measurements with 135G10 confirmed that the increased affinity was driven by a reduced loss in entropy upon binding compared to the parent agent 135G3 (135G3 ΔH=−21.9 kcal/mol, −TΔS=13.5 kcal/mol, FIG. 1; 135G10, ΔH=−19.4 kcal/mol, −TΔS=10.6 kcal/mol, FIG. 7), although the enthalpy/entropy compensation phenomena significantly damped the potential gain in affinity (35, 36).

TABLE 2

Novel EphA2 targeting agents and relative $IC_{50}$ values (µM).

| ID | Sequence | $IC_{50}$ (µM) |
| --- | --- | --- |
| 135G8 | $H_2$N-Y(CAYPDC)VPFRP-$CONH_2$ (SEQ ID NO: 46) | 32.9 ± 10.9 |
| 135G9 | H-Y(EAYPDDap)VPFRP-$NH_2$ (SEQ ID NO: 47) | 27.2 ± 0.3 |
| 135I2 | $H_2$N-Y(hCAYPDC)VPFRP-$CONH_2$ (SEQ ID NO: 48) | 10.1 ± 0.1 |
| 135I3 | $H_2$N-Y(CAYPDhC)VPFRP-$CONH_2$ (SEQ ID NO: 49) | 1.2 ± 0.2 |
| 135F11 | (4F,3-ClPhOCH$_2$CO)(Dap)AYPDDVPFRP-$CONH_2$ (SEQ ID NO: 50) | >200 |
| 135G10 | (4F,3ClPhOCH$_2$CO)LAYPDAV(Hyp)(4ClPhe)RP-$CONH_2$ (SEQ ID NO: 51) | 0.23 ± 0.08, n = 4 |
| 135G11 | (4F,3ClPhOCH$_2$CO)SA(4MeTyr)PDSV(Hyp)(4ClPhe)RP-$CONH_2$ (SEQ ID NO: 52) | 0.18 ± 0.05 |
| 135G12 | (4F,3ClPhOCH$_2$CO)SAYP(AspTtz)SV(Hyp)(4ClPhe)RP-$CONH_2$ (SEQ ID NO: 53) | 0.70 ± 0.09 |

TABLE 2-continued

Novel EphA2 targeting agents and relative $IC_{50}$ values (μM).

| ID | Sequence | $IC_{50}$ (μM) |
|---|---|---|
| 135H2 | (4F,3ClPhOCH$_2$CO)(Cha)AYPDAV(Hyp)(4ClPhe)RP-CONH$_2$ (SEQ ID NO: 54) | 1.7 ± 0.1 |
| 135H3 | (4F,3ClPhOCH$_2$CO)LAYPD(3FAbu)V(Hyp)(4ClPhe)RP-CONH$_2$ (SEQ ID NO: 55) | 11.2 ± 0.1 |
| 135H4 | (4F,3ClPhOCH$_2$CO)(Cha)AYPD(3FAbu)V(Hyp)(4ClPhe)RP-CONH$_2$ (SEQ ID NO: 56) | 53.2 ± 8.5 |
| 135G6 | XSAYPDSVPFRP-NH$_2$ (SEQ ID NO: 57) X = 3,6-Dimethyl-benzofuran-2-carboxylic acid | 0.66 ± 0.01 |
| 135G5 | XSAYPDSVPFRP-NH$_2$ (SEQ ID NO: 58) X = 5-Methyl-benzofuran-2-carboxylic acid | 0.50 ± 0.05 |
| 135H5 | XSAYPDSVPFRP-CONH$_2$ (SEQ ID NO: 59) X = 3-Methyl-5-Fluoro-benzofuranoic acid | 0.43 ± 0.01 |
| 135G7 | XSAYPDSVPFRP-NH$_2$ (SEQ ID NO: 60) X = 7-Methoxy-2-benzofurancarboxylic acid | 0.19 ± 0.04, n = 8 |
| 135H1 | XSAYPDSV(Hyp)(4ClPhe)RP-CONH$_2$ (SEQ ID NO: 61) X = 5-Chloro-benzodihydrofuranoic acid | 0.75 ± 0.04 |
| 135H6 | XSAYPDSVPFRP-CONH$_2$ (SEQ ID NO: 62) X = 3-Methyl-5-Chloro-benzofuranoic acid | 0.19 ± 0.01 |
| 135H7 | XSAYPDSVPFRP-CONH$_2$ (SEQ ID NO: 63) X = 3-Methyl-6,7-Diethoxy-benzofuranoic acid | 0.24 ± 0.02 |
| 135H8 | XSAYPDSVPFRP-CONH$_2$ (SEQ ID NO: 64) X = 7-Ethoxy-benzofuranoic acid | 0.17 ± 0.03 |
| 135H9 | XSAYPDSVPFRP-CONH$_2$ (SEQ ID NO: 65) X = 5-Chloro-7-Methoxy-benzofuranoic acid | 0.28 ± 0.01 |
| 135H10 | XSAYPDSVPFRP-CONH$_2$ (SEQ ID NO: 66) X = 3-Methyl-6,7-Dimethoxy-benzofuranoic acid | 0.19 ± 0.05, n = 6 |
| 135H11 | XLA(4MeTyr)PDA V(Hyp)(4ClPhe)RP-CONH$_2$ (SEQ ID NO: 67) X = 3-Methyl-6,7-Dimethoxy-benzofuranoic acid | 0.13 ± 0.02, n = 6 |
| 135I4 | X(CA(4MeTyr)PD hC)V(Hyp)(4ClPhe)RP-CONH$_2$ (SEQ ID NO: 68) X = 3-Methyl-6,7-Dimethoxy-benzofuranoic acid | 0.16 ± 0.02 |
| 135G4 | [(4F,3ClPhOCH$_2$CO)SAYPDSV(Hyp)(4ClPhe)RPG]$_2$-K-CONH$_2$ | 0.13 ± 0.01 |
| 135H12 | [XLA(4MeTyr)PDA V(Hyp)(4ClPhe)RPG]$_2$-K-CONH$_2$ X = 3-Methyl-6,7-Dimethoxy-benzofuranoic acid | 0.15 ± 0.03, n = 6 |

SE indicates duplicate measurements unless otherwise indicated.
Hyp, L-trans-4-hydroxyproline;
Aib, α-aminoisobutyric acid;
Dap, di-amino propionic acid;
4Pal, 4-pyridyl-L-alanine;
Cha, 3-cyclohexyl-L-alanine;
Nle, L-norleucine;
hS, L-homo-serine;
hC, L-homoCysteine;
3FAbu, (2S)-2-amino-4,4,4-trifluorobutanoic acid;
AspTtz, 2-amino-3-(2H-1,2,3,4-tetrazol-5-yl)propanoic acid.

Further introduction of non-natural amino acids (agents 135G11 to 135H4) at various positions resulted in agent 135G11, with slightly improved $IC_{50}$ value (Table 2).

Figure 3A:
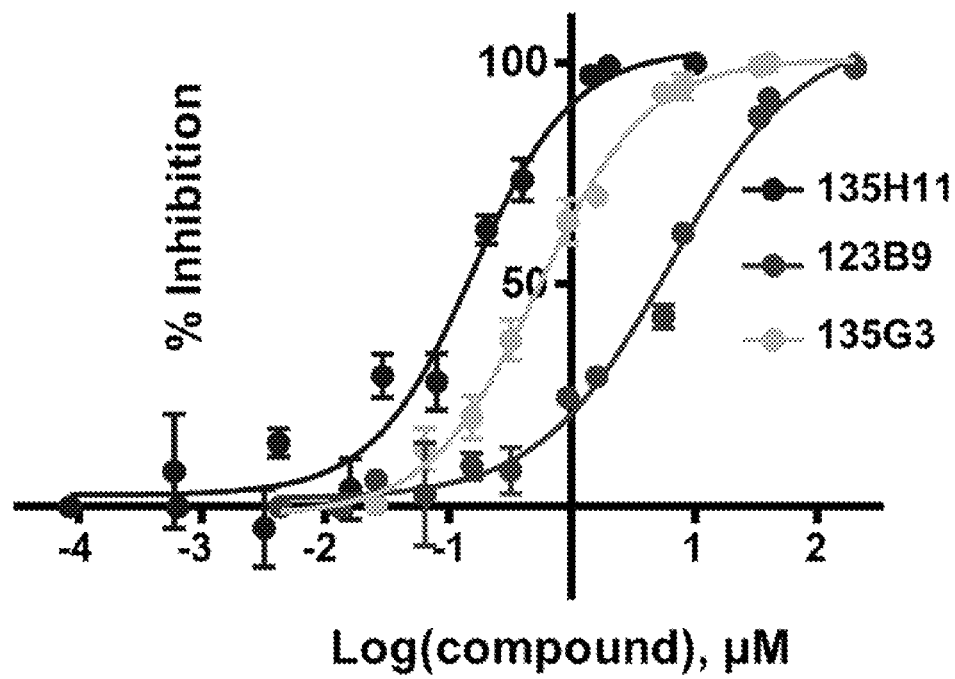
FIG. 3A-D. Design and characterization of 135H11.
Figure 3B:
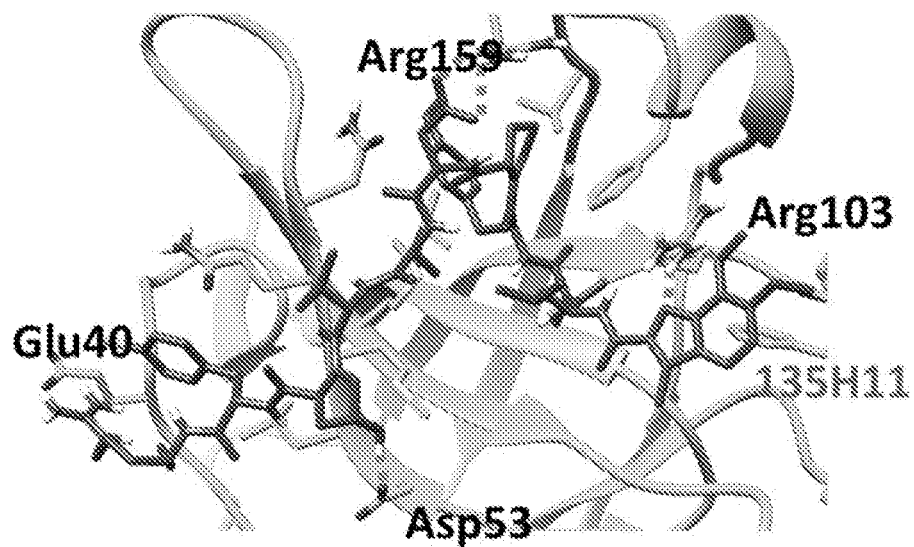
Figure 3C:
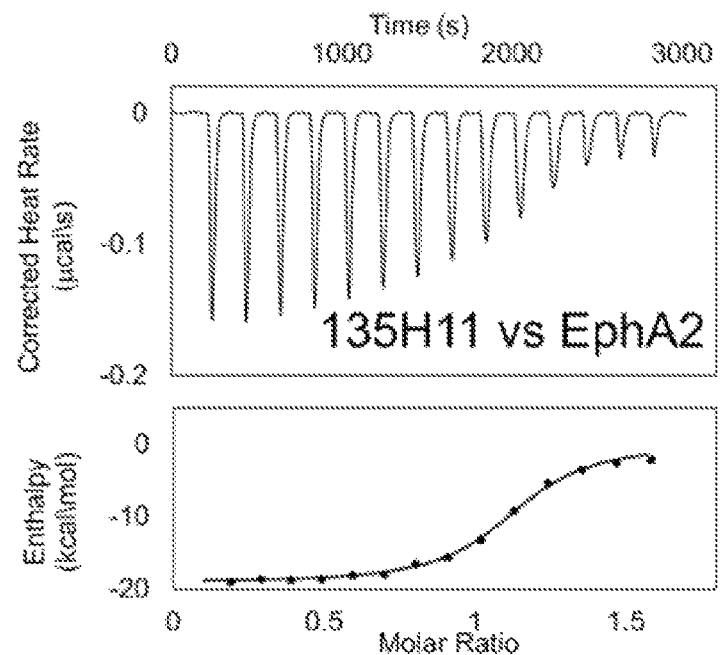
Figure 3D:
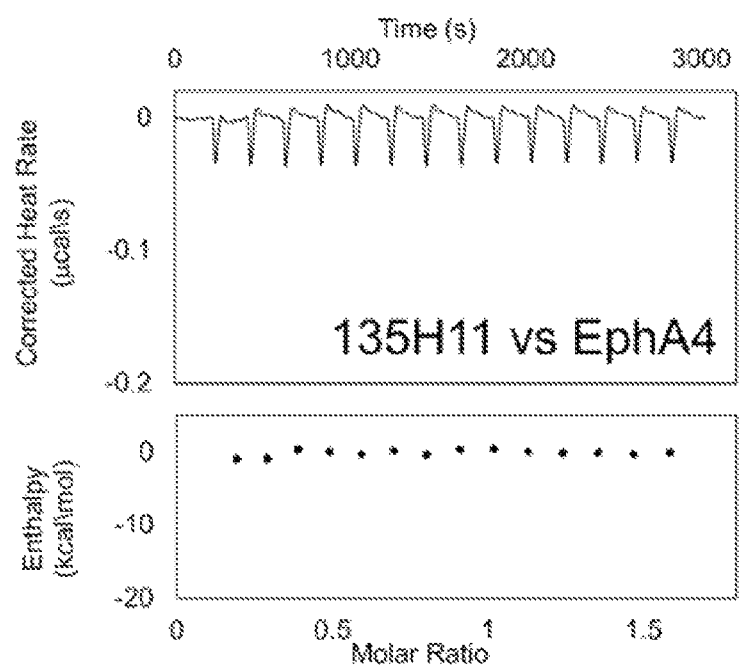
Figure 7:
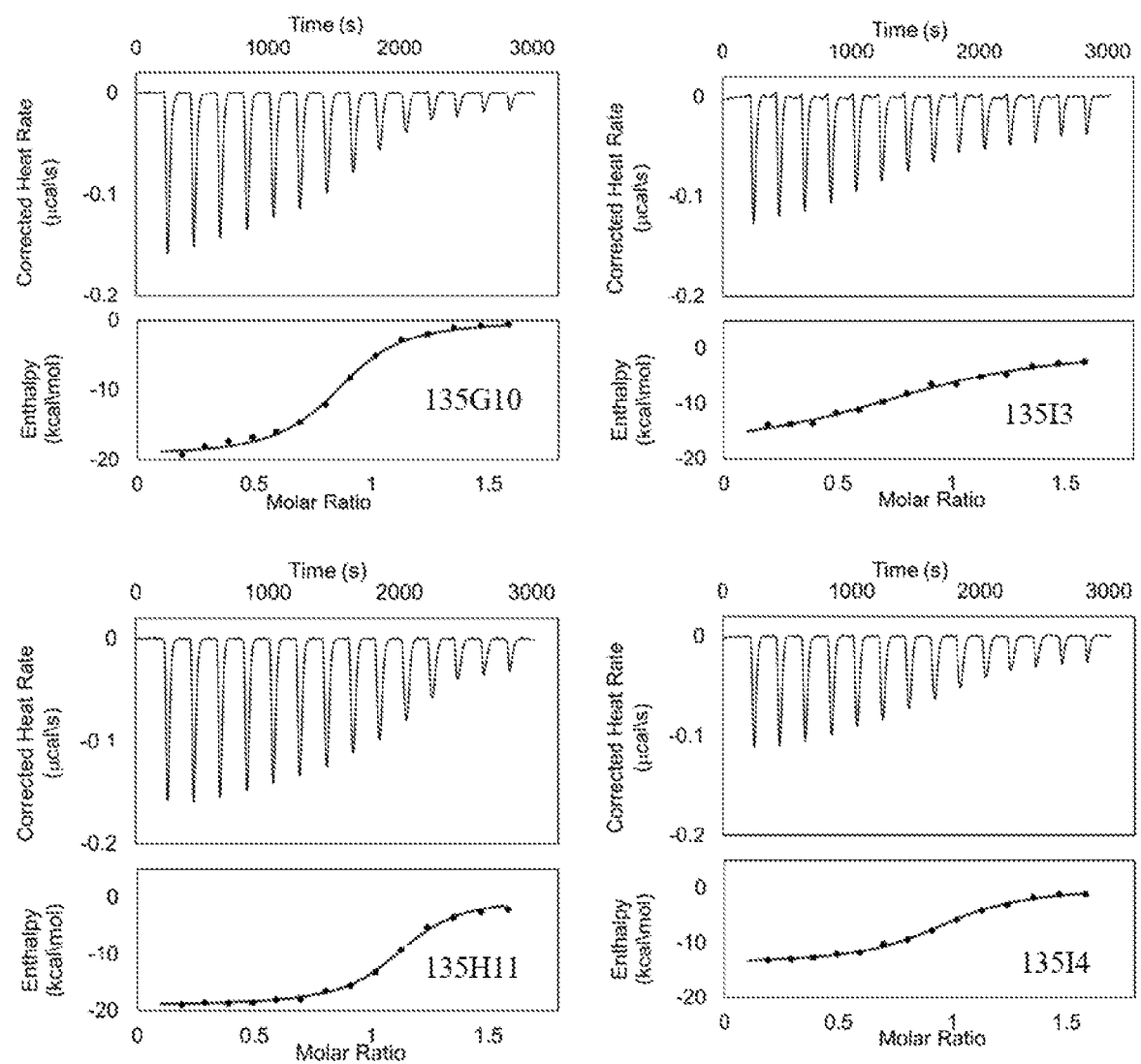
FIG. 7. Isothermal Titration calorimetry (ITC) curve for the binding between sterically constrained peptides and EphA2-LBD. ITC measurements with 135G10 (Table 1) confirmed that the increased affinity was driven by a reduced loss in entropy upon binding compared to the parent agent 135G3 (135G3 ΔH=−21.9 kcal/mol, −TΔS=13.5 kcal/mol.
Figure 9B:
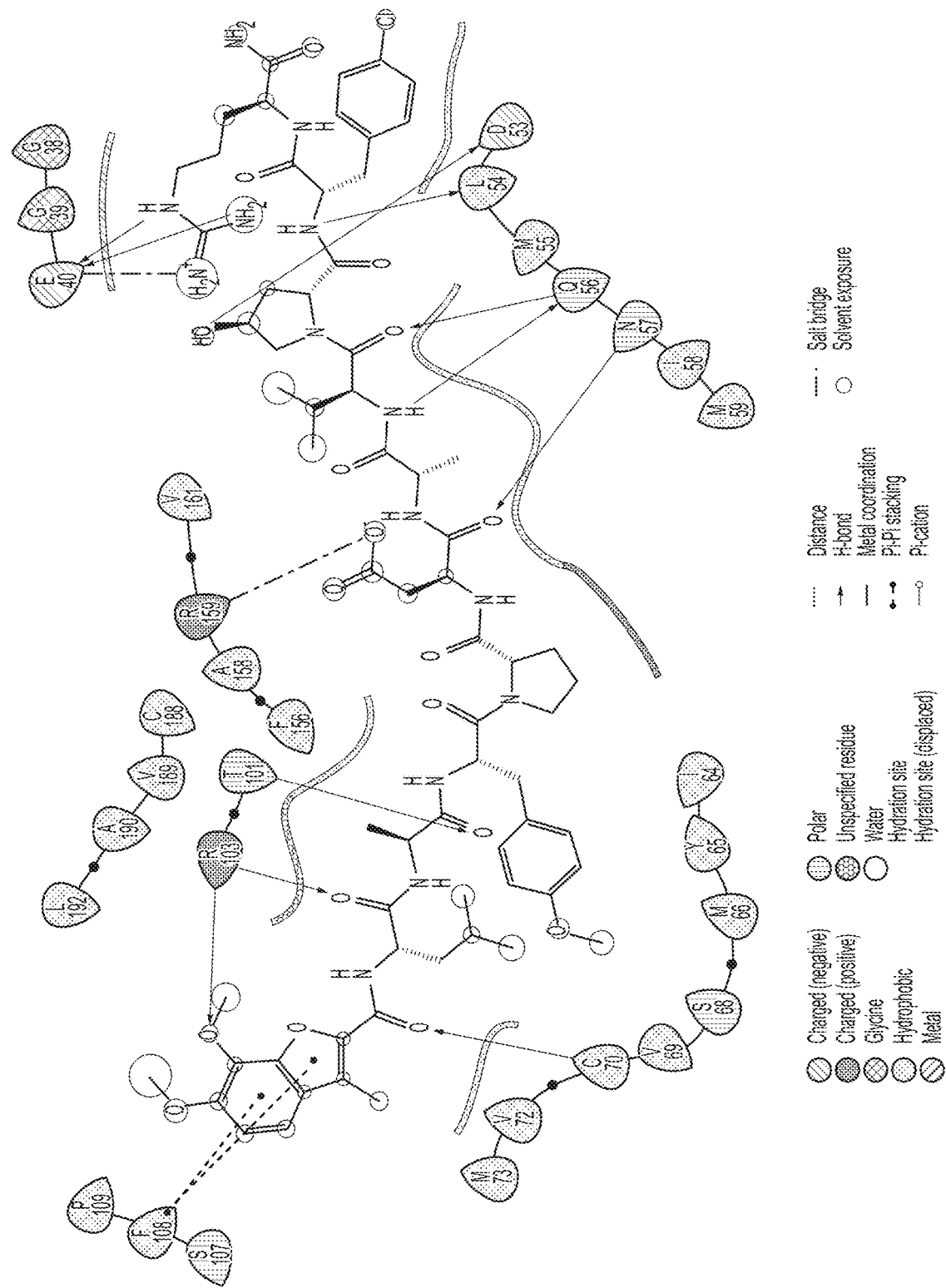

Next, we examined the binding pose for the 4F,3Cl phenyl-acetic acid moiety of 135E2 and designed novel restrained analogues. Molecular modeling studies based on the structure 135E2 in complex with EphA2 were conducted and these efforts resulted in the design and synthesis of a series of substituted benzofuranoic acids (agents 135G6 to 135H11, Table 2). These studies culminated with the selection of a 3-methyl, 6,7-dimethoxy, 2-benzofuranoic acid in 135E2 that resulted first in 135G6, and later in 135H11 (including all optimizing features), a novel agent with increased affinity for EphA2 (FIG. 3, Table 2, FIG. 9B). Modeling studies anticipated the formation of additional intermolecular hydrogen bonding between the 3-methyl, 6,7dimethoxy, 2-benzofuranoic acid moiety and Arg 103 in EphA2 (FIG. 3B). Finally, the Tyr residues in fourth position seemed engaged in a fairly hydrophobic area of the binding pocket hence it was replaced by a 4-methoxy Phe. 135H11 displayed increased affinity by ITC compared to other agents (FIG. 3C) and retained selectivity when tested against EphA4 (FIG. 3D). Its constrained cyclic equivalent (135I4, Table 2) presented a similar $IC_{50}$ value in the DELFIA assay, and its binding affinity was driven by a reduced loss in entropy upon ligand binding (FIG. 7). However, this entropic gain was entirely compensated by a dramatic loss in enthalpy of binding, suggesting a non-ideal geometry of the constrained peptide to interact with the ligand-binding domain of EphA2 (FIG. 7). These data concluded that the cyclic agent 135I4 is potentially a novel and interesting agent that could be subjected to optimization of its side chains to increase its enthalpy of binding, in addition to replacement of the disulfide bridge with more stable moieties.

Figure 10A:
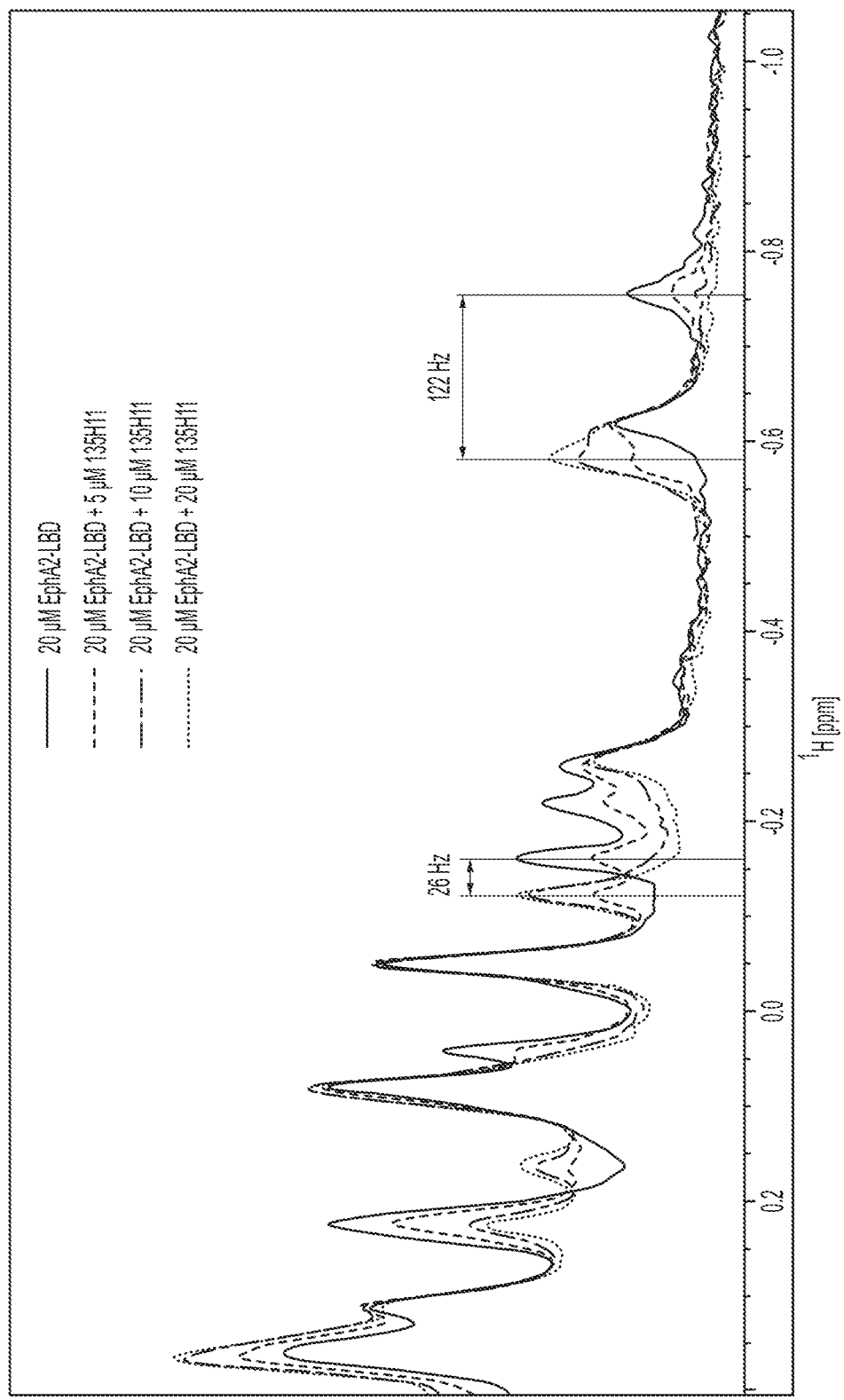
FIGS. 10A-10B. 1D 1H-aliph. and 2D [$^{15}$N, $^1$H] so-fast HSQC spectra NMR spectra of $^{15}$N-EphA2-LBD measured in absence and in presence of various concentrations of 135H11. Spectra were collected on 700 MHz Bruker NMR spectrometer equipped with a TCI cryo-probe. The spectra are of the complex upon titration appear in slow exchange in the NMR time scale.
Figure 10B:
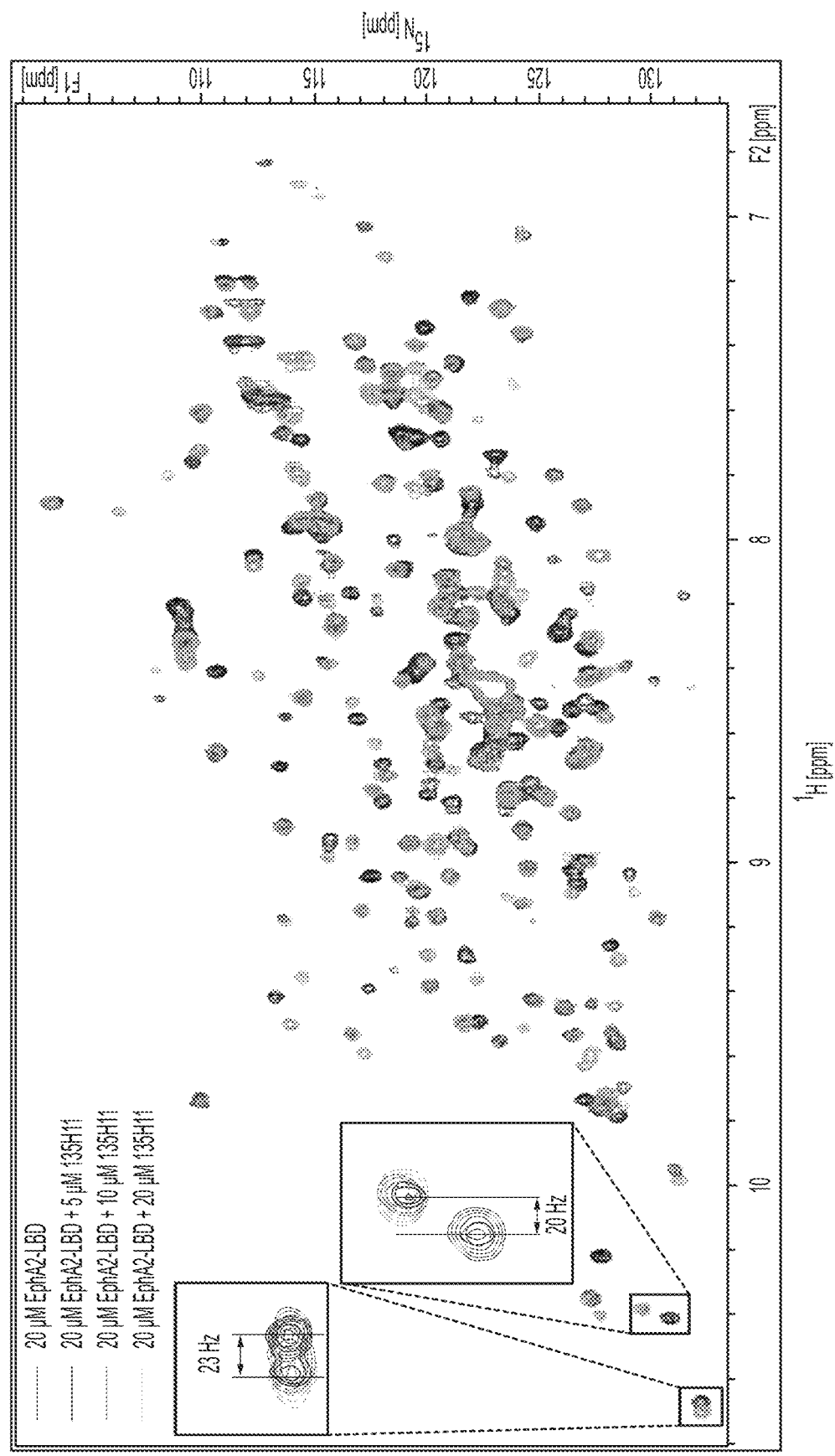

Therefore, collectively, these data suggested that linear agents 135G3 and 135H11 were the most suitable candidates for further studies at this stage of our hit-to-lead optimizations. Additional binding assays involved the use of 1D $^1H$ NMR and 2D $[^{15}N,^1H]$ correlation spectra with a $^{15}N$ labeled sample of EphA4-LBD. The spectra were collected in absence and in presence of various amounts of 135H11. The data are reported in FIGS. 10A-10B. Upon titration of 135H11, EphA4 resonances progressively disappeared, while new cross-peaks appeared, typical of binders in slow-exchange in the NMR-time scale (FIGS. 10A-10B). While it is not possible to measure the dissociation constant by NMR titration in slow exchange, measuring the chemical shifts differences of cross-peaks in the free versus bound form, we estimated that an upper limit for the off rate for the complex, $k_{off} < 120 \text{ s}^{-1}$ (FIGS. 10A-10B). Therefore, assuming a diffusion limited on rate of $10^9 M^{-1}s^{-1}$, a dissociation constant Kd<120 nM can be estimated, thus in close agreement with the DELFIA and ITC data.

Figure 6:
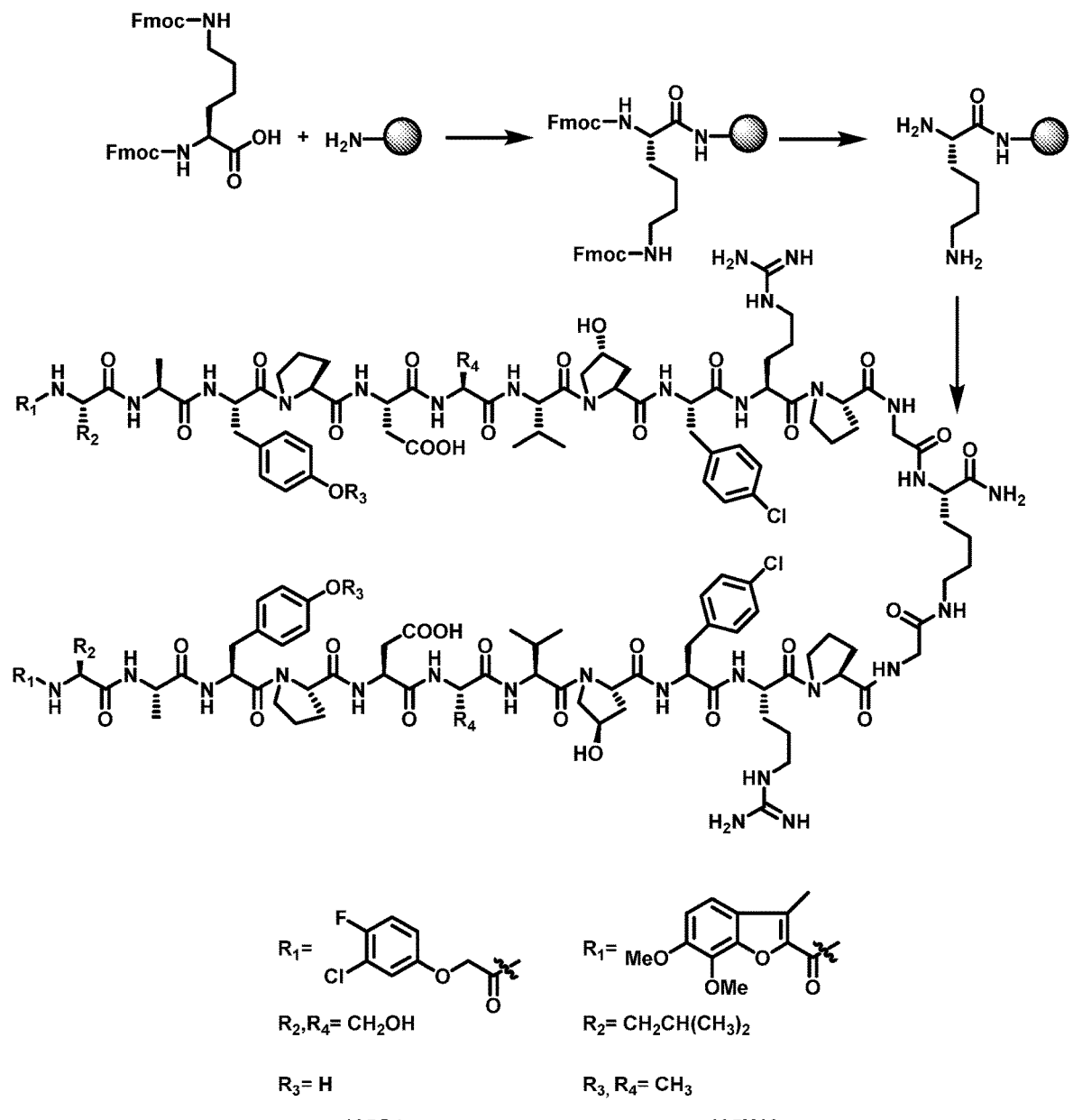
FIG. 6. Preparation of symmetrical dimers. Dimers were prepared using 0.1 mmol scale with a CEM Liberty Blue automated peptide synthesizer on Rink Amide resin, introducing a Fmoc-Lys(Fmoc)-OH as the C-terminal amino acid of the sequence. A double coupling protocol was employed to ensure the complete reaction of both elongating sequences. Standard cleavage and purification protocols were used to obtain the pure dimers.

Recently, we reported that dimerization of 123B9 resulted in an agent with dramatically increased activity in cell, presumably by facilitating receptor dimerization, and subsequent clustering and internalization.[28] Hence, we prepared a dimeric version of 135G3, namely 135G4, and a dimeric version of 135H11, namely 135H12 (Table 2, and supplementary FIG. 6). Based on previous experience with dimeric agents, we didn't expect that these agents would display increased affinity for the isolated EphA2-LBD (Table 2). However, we expected that ligand dimerization would result in increased receptor activation activity of the agent in cellular assays, presumably by facilitating receptor dimerization and subsequent clustering.

Example 4. Cellular Activity of the Novel EphA2 Agonistic Agents

Figure 4A:
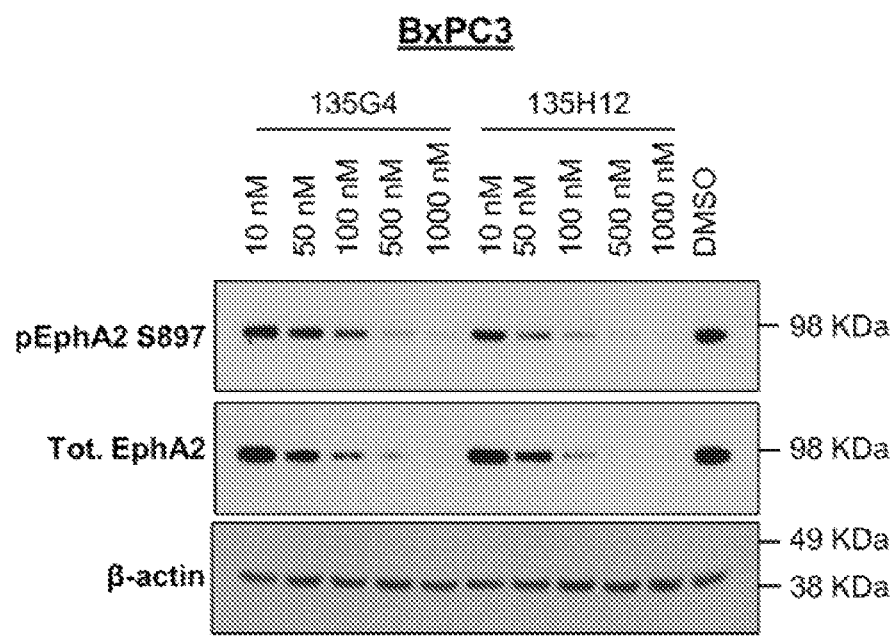
FIG. 4A-D. Dimeric EphA2 agonists degrade EphA2 receptors in cancer cells.

To assess whether optimized agents have retained their ability to function as EphA2 agonists, we first measured the ability of each agonistic agent to induce EphA2 receptor degradation. Both dimeric agents 135G4 and 135H12 were remarkably active in inducing receptor degradation and dephosphorylation of Ser897-EphA2 at sub-micromolar concentrations. However, in agreement with the relatively increased affinity of 135H11 compared to 135G3, their corresponding dimers displayed differential receptor activation, with 135H12 causing receptor degradation at nanomolar concentrations (FIG. 4A).

Figure 4B:
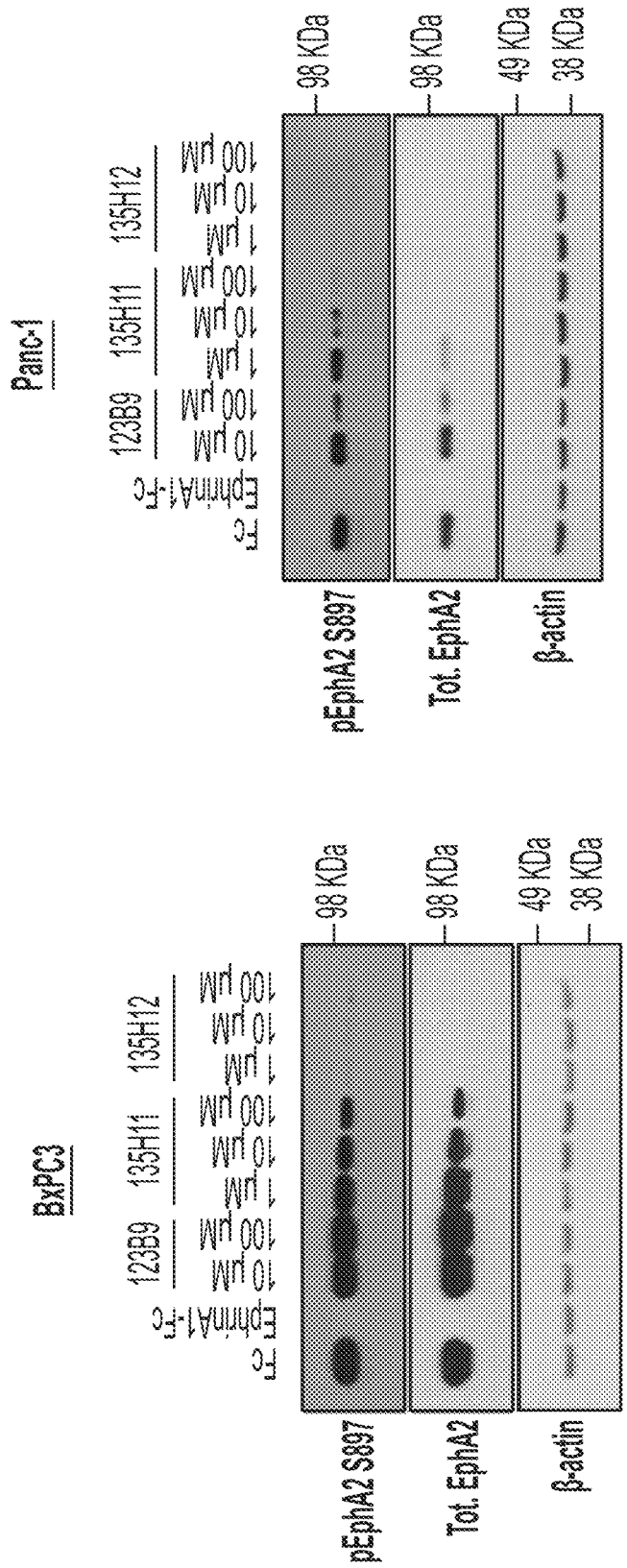
Figure 4C:
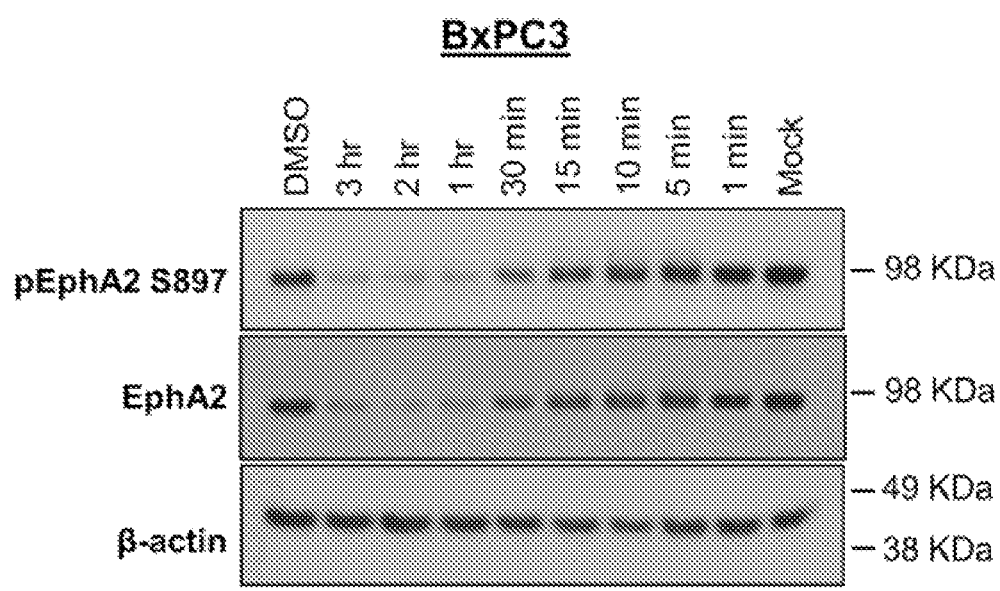
Figure 4D:
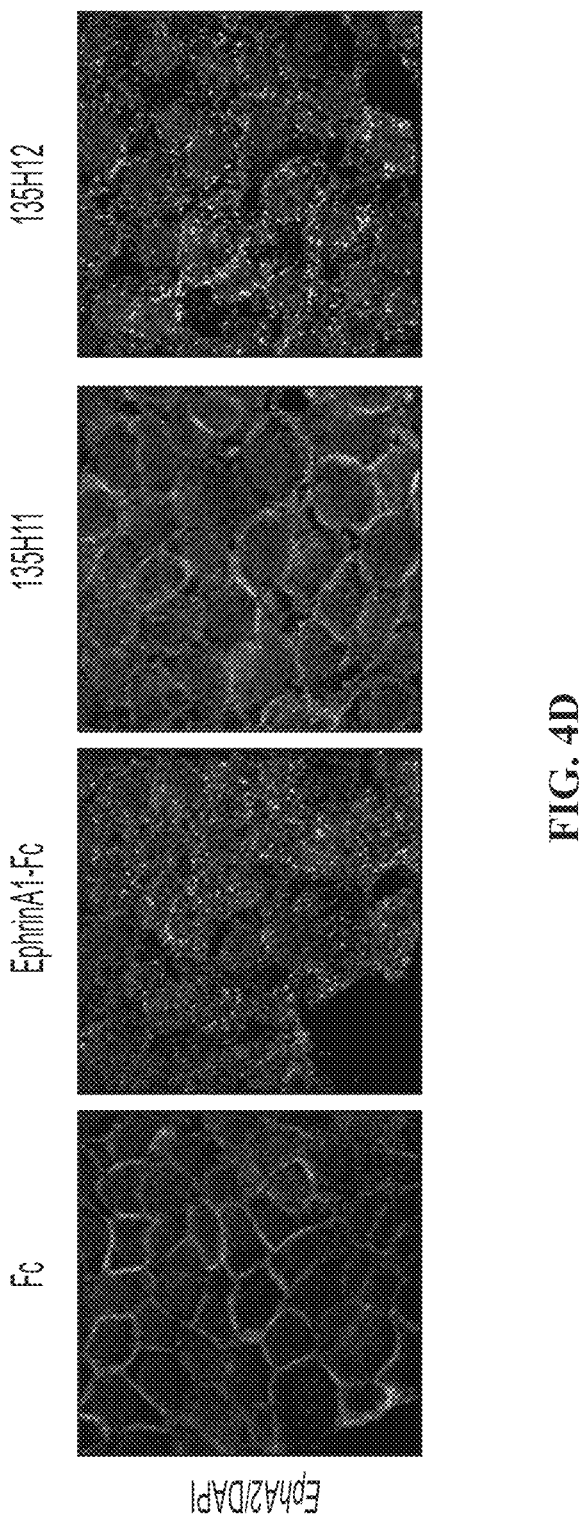
Figure 5A:
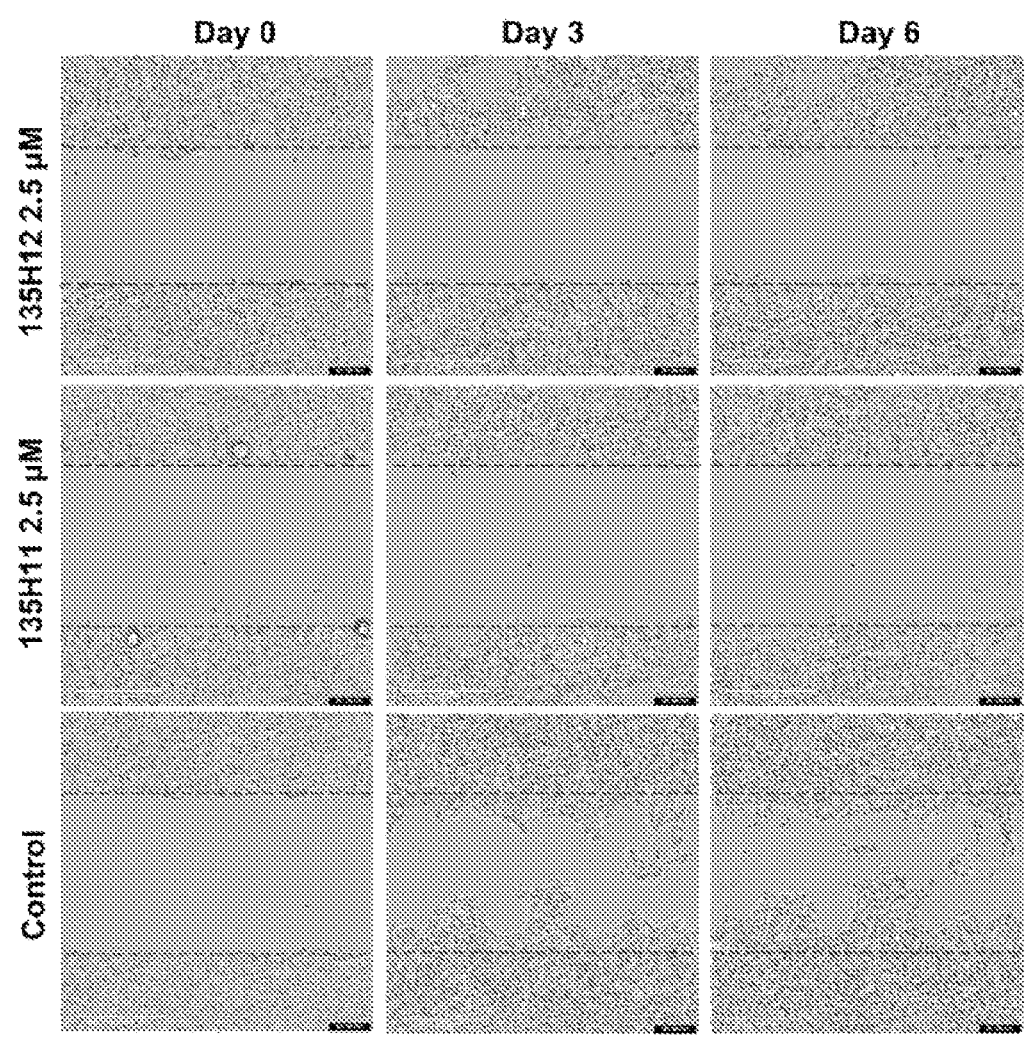
FIG. 5A-C. EphA2 agonists inhibit cell invasion and migration.
Figure 5B:
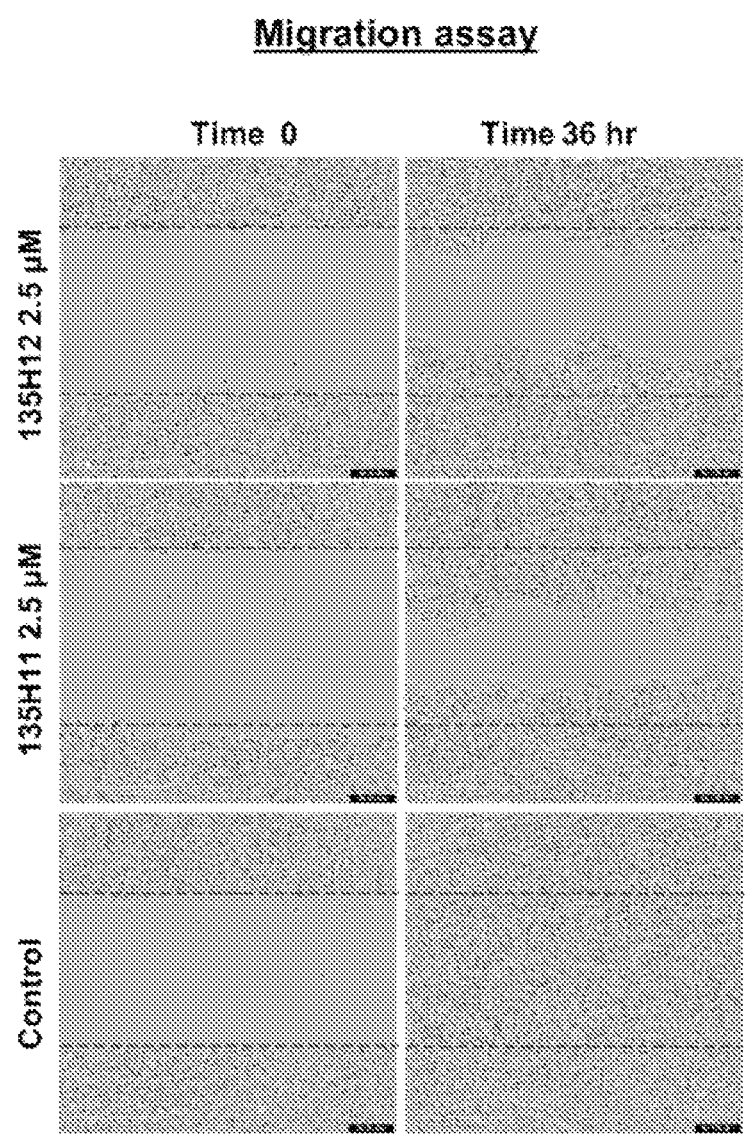
Figure 5C:
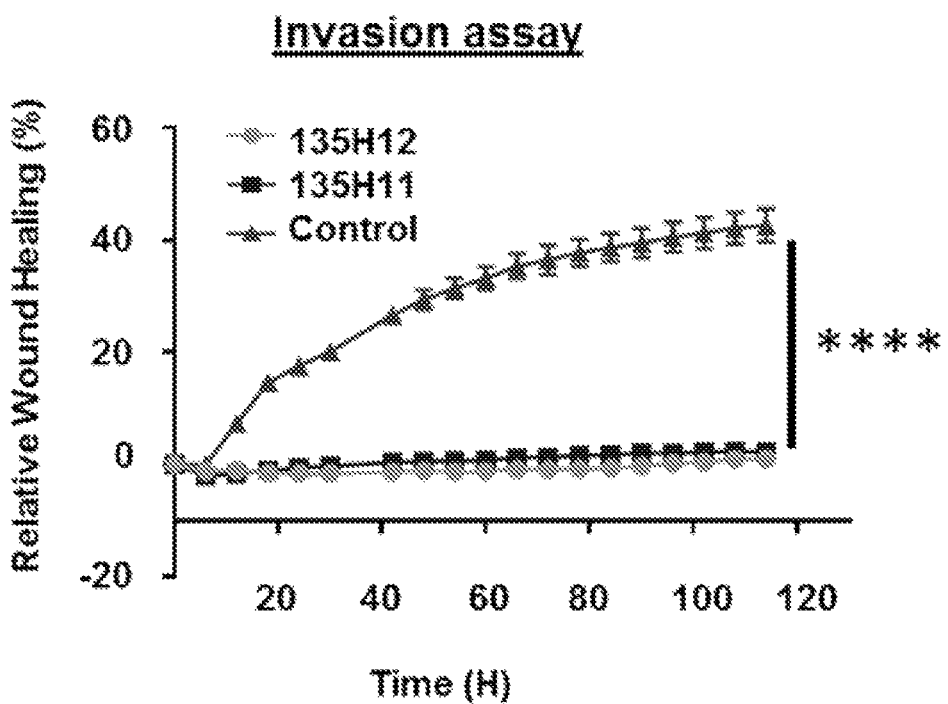
Figure 5C:
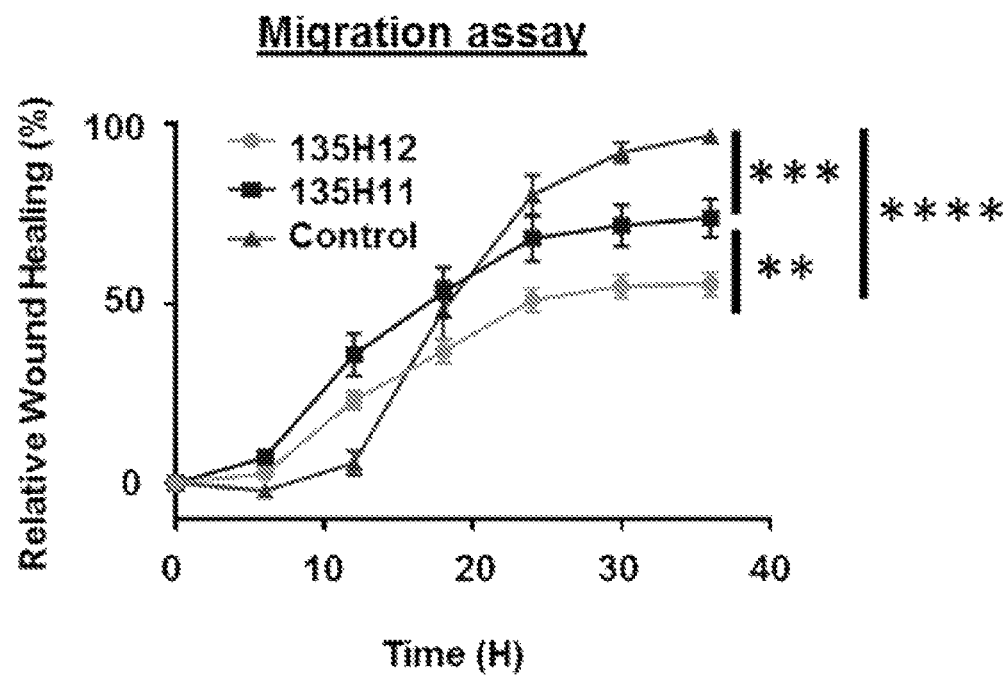

Next, we examined the ability of 135H12 to reduce pro-oncogenic pSer897-EphA2 and to degrade EphA2 in pancreatic cancer cell lines BxPC3 and PANC-1. Western blot studies showed that 135H12 was able to degrade total EphA2 more effectively than the monomer 135H11 and YSA (FIG. 4B). Moreover, to study the kinetics of EphA2 dephosphorylation and degradation upon 135H12 treatment, we treated BxPC3 cells with 1 μM 135H12 at different time points (FIG. 4C). Western blot analysis indicated that total EphA2 was reduced after 10 min and totally diminished after 1 h of 135H12 treatment. Finally, immunofluorescence data of BxPC3 cells demonstrated punctuated cytoplasmic EphA2 fluorescence in 135H12 treated cells compared to fluorescence localized at the cell membrane in 135H11 treated and untreated cells (FIG. 4D). These results confirmed the increased agonistic activity of dimeric EphA2 ligands compared to their monomeric forms.

Figure 8A:
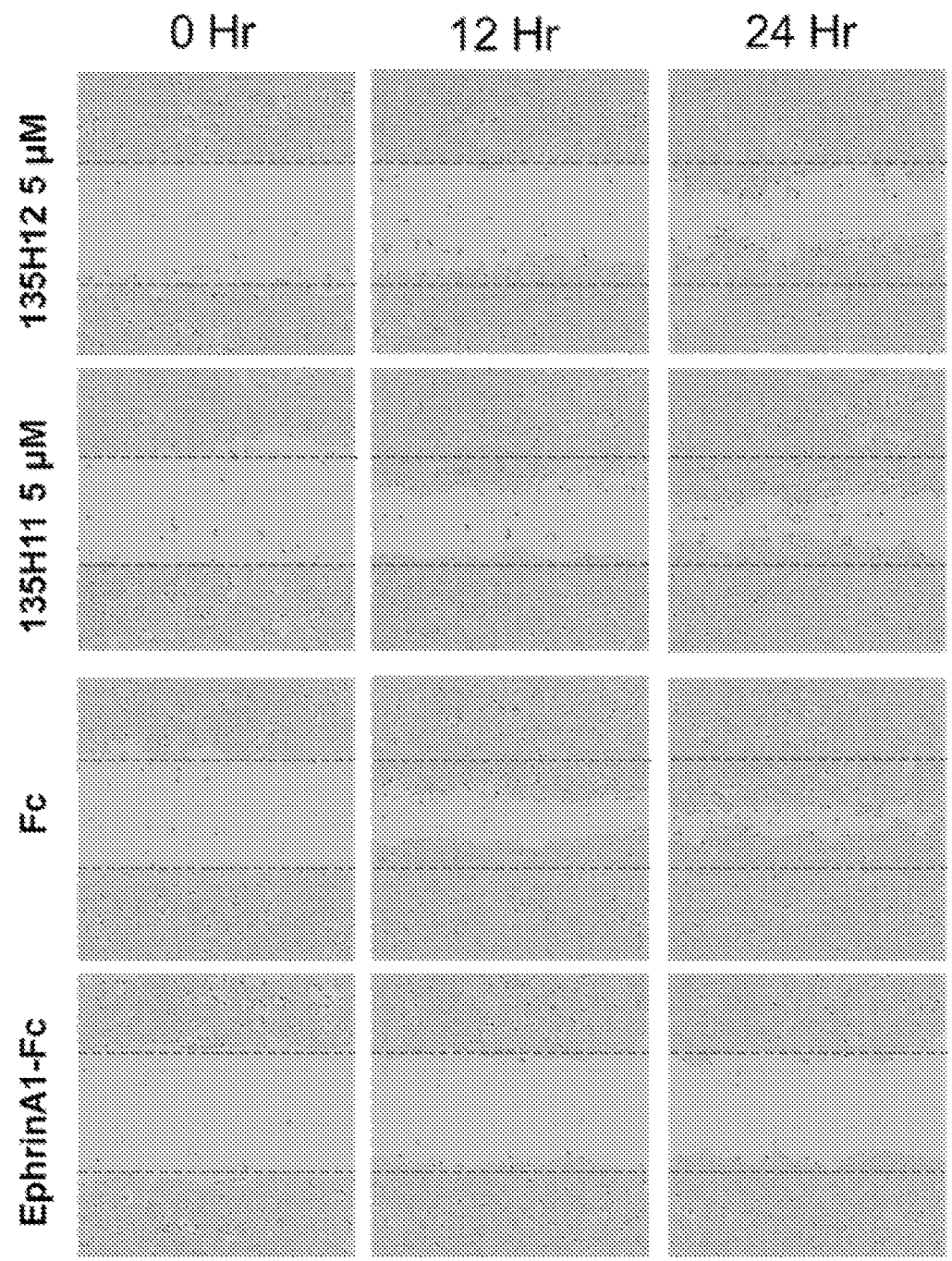
FIGS. 8A-B. Time lapse migration assay of BxPC3 cells. BxPC3 cells were scratched and treated with 135H12 at 5 µM, 135H11 at 5 µM, clustered Fc at 2 µg/mL, or clustered ephrinA1-Fc at 2 µg/mL. Wells were imaged every 4 h using IncuCyte S3 (Sartorius).
Figure 8B:
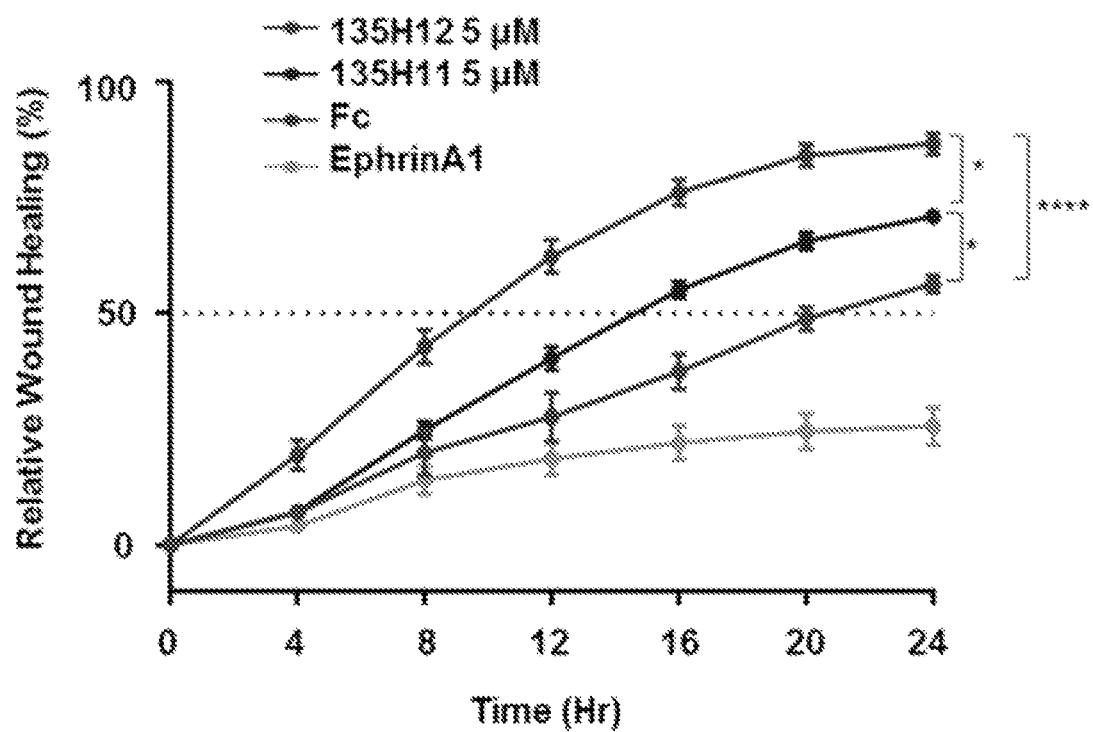

Finally, to examine whether our improved EphA2 agonistic agents prevent cell migration and invasion of cancer cells, we performed cell migration and invasion assays using the scratch wound method as detected with an IncuCyte S3 (Sartorius) and the pancreatic cancer cell line BxPC3. In this assay, a 96-pin mechanical device (WoundMaker, Sartorius) was used to create homogeneous scratch wounds per plate, and the rate of wound closure between migrating (through a surface) and invading (through a Matrigel matrix) cells are directly observed in presence and absence of test ligands. The data revealed that 135H12 at a 2.5 μM concentration is very effective in suppressing both cell migration and invasion (FIG. 5). However and notably, while the dimer is more potent in suppressing cell migration, the monomer is equally effective in suppressing cell invasion (FIG. 5 and FIGS. 8A-8B). These data conclude that 135H11 and 135H12 are potent agonistic EphA2 agents with nanomolar affinity for the receptor in vitro and low micromolar cellular activity.

Example 5. Discussion and Conclusions

EphA2 is a potential major target for novel and effective anti-cancer therapies. However, research in this field remains hampered by the lack of suitable, highly potent and selective pharmacological tools that could provide stepping stones for the development of novel therapeutics. The YSA peptide, discovered using phage display techniques, has been used in numerous applications, ranging from PDCs to incorporation in nanoparticles for delivery of diagnostics or siRNA. However, we recently reported that this peptide possessed relatively low in vitro affinity ($IC_{50}$ 15 μM, Table 1) and required a triple-digit micromolar concentration in cell-based assays to activate the receptor. In addition, we found that the YSA peptide was fairly unstable in plasma with rapid hydrolysis by amino-peptidases (30, 37). Recently, we derived the agent 123B9, replacing the first Tyr residue with a 4F, 3Cl phenylacetic acid and substituting two methionine residues in YSA with more stable residues, attaining only a modest increase in affinity ($IC_{50}$ 6.5 μM, Table 1), but greatly improving the compound resistance to plasma proteases (30). Here, by aligning the sequences of the ephrin-A ligands and the binding loop from a specific EphA2 antibody (1C1), and by systematically introducing non-natural amino acids, we attempted to derive novel and more potent agents. These data, summarized in Table 1, resulted in the identification first of agent 135E2, and subsequently of agent 135G3 with $IC_{50}$~600 nM in a displacement assay, and a dissociation constant of ~760 nM by isothermal titration calorimetry (FIG. 1). In agreement with these increased affinities in vitro, the agents were more effective in cellular assays as shown in FIG. 1E, where we observed that 135G3 displayed a remarkably increased cellular activity in inducing tyrosine receptor phosphorylation compared to YSA (FIG. 1E). Subsequently, we were able to obtain co-crystals of the complex between 135E2 and EphA2-LBD. The structure revealed several critical features that were then used to derive novel and even more potent agents. The bound conformation presented several features that were in agreement with the structure-activity relationships reported in Table 1. For example, the C-terminal Arg residue is involved in a salt bridge with EphA2 residue Glu40, while the increased activity of the 5-hydroxyproline may be due to the formation of a hydrogen bond between this residue and Asp 43 (FIG. 2A, C). Also, the peptide assumed a bent conformation that can be stabilized by introducing a covalent bridge or hydrophobic residues in lieu of residues Ser2 and Ser5 resulting in an entropy-driven increase in affinity (for example compound 135G10, Table 2, FIG. 3). Further modifications of the agent followed structure-based design strategies and resulted in the identification of a 2-benzofuranoic acid at position 1 that was predicted to introduce additional hydrogen bonding with EphA2 residue Arg103 (FIG. 3B). In agreement, compound 135H11 displayed increased affinity in the nanomolar range both by DELFIA ($IC_{50}$ 0.15 µM, Table 2) and by ITC (Kd=0.16 µM, FIG. 3D). Finally, we prepared a dimeric version of 135G3 and 135H11, namely 135G4 and 135H12, respectively, and evaluated their ability to induce receptor activation and to impair EphA2 pro-oncogenic signaling in pancreatic cancer cell lines (FIG. 4). First, and in agreement with the increased affinity of 135H11 compared to 135G3, in our in vitro displacement assay and thermodynamic measurements, its dimer, 135H12, was remarkably and significantly more potent in degrading the receptor than 135G4 in pancreatic cancer cells (FIG. 4A). In addition, both 135H11 and its dimeric version 135H12 were orders of magnitude more effective than 123B9 in causing EphA2 degradation and suppressing oncogenic pSer897-EphA2 in pancreatic cancer cell lines (FIG. 4B,C). In agreement with these properties, the agents were also remarkably effective in suppressing both cell migration and invasion in pancreatic cancer cell line (FIG. 5). Interestingly, while both 135H11 and its dimer 135H12 were equally effective in suppressing cell invasion at low micromolar concentration, the dimer was significantly more effective in suppressing also cell migration (FIG. 5, FIGS. 8A-8B). These data concluded that 135H12 represent a novel potent and effective pharmacological tool that can be further used to interrogate the role of EphA2 in tumorigenesis and cancer progression and metastasis.

The design of potent, selective, and effective agonistic small molecules or peptide mimetics targeting the ligand binding domain of the EphA2 receptor has remained a challenging task, despite several strategies that have been applied over the past decade ranging from NMR-based screening (38-40), and computational docking strategies (21, 41-43), to high-throughput (44), and phage display screening (45). More recently, studies have emerged with potential small molecule compounds (21, 41, 28), or EphA2/ephrin antagonists (42-44, 46-48) however, in our opinion, none of these agents have yet reached the level of potency and cellular efficacy that we reported here for 135H11 or 135H12. Indeed, the ability of the previously reported agents to cause receptor activation and internalization required relatively high concentrations (>50-100 µM) (45, 49-51, 28), limiting their potential translation to the clinic as effective anti-pro-oncogenic EphA2 agents.

As we demonstrated recently, small agonistic peptides can be used directly as PDCs (peptide drug conjugates) to selectively deliver a cytotoxic agent to EphA2-expressing cancer cells (28, 30, 37, 49, 51, 52). Indeed, we envision that 135H11, 135H12 and related compounds (including for example the cyclic agent 135I4, Table 1) could be used as drug delivery agents for chemotherapy, and could also be deployed to selectively introduce siRNA into cancer cells, or appropriately derivatized with imaging or other diagnostic agents (52,56). However, given the remarkable activity of 135H12 inducing EphA2 degradation in cell, and concomitant inhibition of cell migration and invasion, we anticipate that the 135H12 and related compounds could be also used directly as single agents or in combination therapy against a variety of tumors that depend on EphA2 expression to metastasize. Hence, in addition to its anticipated use in PDCs or in diagnostics as we previously reported (28, 30, 37, 49, 51, 52), we envision performing further and more detailed pharmacology studies to evaluate the in vivo pharmacokinetics, toxicity, and efficacy of 135H12 and related compounds as single agents or in combination with standard of care. In conclusion, we are confident that our present studies provide novel, potent and effective pharmacological tools targeting the EphA2 receptor and as such represent a significant advancement in the field of targeting EphA2. Our studies could open a wide range of opportunities for the development of EphA2-targeting therapeutics, ranging from more effective PDCs to the development of innovative diagnostics, or for devising more effective combination therapies targeting tumor resistance to chemotherapy and tumor metastases.

Example 6. Experimental Section: Chemistry

General. All reagents and anhydrous solvents were obtained from commercial sources, including Fmoc-protected amino acids and resins for solid phase synthesis. Some of the reported agents were synthesized by Innopep, while others were synthesized in house by standard microwave-assisted Fmoc peptide synthesis protocols on Rink amide resin using a Liberty Blue Peptide Synthesizer (CEM). For each coupling reaction, 6 eq. of Fmoc-AA, 3 eq. of DIC and 1 eq. of OximaPure in 4.5 ml of DMF were used. The coupling reaction was allowed to proceed for 5 min at 90° C. in the microwave reactor. Fmoc deprotection was performed by treating the resin-bound peptide with 20% piperidine in DMF (2×3 ml) for 3 min at 90° C.

Peptides were cleaved from the resin with a cleavage cocktail containing TFA/TIS/water/phenol (94:2:2:2) for 3 h. The cleaving solution was filtered from the resin, and the peptides precipitated in $Et_2O$, centrifuged and dried in high vacuum. The crude peptides were purified to >95% purity by preparative RP-HPLC using a Luna C18 column (Phenomenex) on a JASCO preparative HPLC system and water/acetonitrile gradient (5% to 70%) containing 0.1% TFA. Compounds were further characterized by HRMS (Table S2).

TABLE S2

Mass spectroscopy data of investigated compounds. Compounds synthesized in-house were analyzed using an Agilent LC/TOF system or a SCIEX 5800 TOF/TOF system for high MW molecules like 135H12 and 135G4. For commissioned sequences (highlighted in italics) the mass analysis was copied from the Certificate of Analysis provided by Innopep.

| Compound | Calculated Mass | Found Mass |
| --- | --- | --- |
| YSA | 1345.5684 | 1346.6443 $(M + H)^+$ |
| 123B9 | 1320.5514 | 1321.5356 $(M + H)^+$ |
| ephrins A2/A5/A4 | 1442.7347 | 1443.5896 $(M + H)^+$ |
| ephrin A3 | 1389.6354 | 1390.2656 $(M + H)^+$ |
| ephrin B2 | 1463.7561 | 1464.6654 $(M + H)^+$ |
| ephrin A1 | 1441.7606 | 1442.8432 $(M + H)^+$ |
| 135A1 (1C1) | 1315.6012 | 1315.6012 $(M - H)^-$ |

TABLE S2-continued

Mass spectroscopy data of investigated compounds. Compounds synthesized in-house were analyzed using an Agilent LC/TOF system or a SCIEX 5800 TOF/TOF system for high MW molecules like 135H12 and 135G4. For commissioned sequences (highlighted in italics) the mass analysis was copied from the Certificate of Analysis provided by Innopep.

| Compound | Calculated Mass | Found Mass |
|---|---|---|
| 135A7 | 1426.7245 | 1427.7620 (M + H)+ |
| 135A8 | 1428.6674 | 1429.7090 (M + H)+ |
| 135B1 | 1377.5654 | 1378.5579 (M + H)+ |
| 135B12 | 1396.6776 | 1419.6520 (M + Na + H)+ |
| 135B2 | 1375.6152 | 1398.7177 (M + Na + H)+ |
| 135B8 | 1426.7398 | 1427.7806 (M + H)+ |
| 135B9 | 1375.6305 | 1376.6764 (M + H)+ |
| 135C1 | 1364.5962 | 1362.6496 (M + H)+ |
| 135C2 | 1143.5310 | 1144.5133 (M + H)+ |
| 135C3 | 1386.6641 | 1387.6633 (M + H)+ |
| 135C4 | 1299.6248 | 1300.6579 (M + H)+ |
| 135C7 | 1370.6362 | 1371.6636 (M + H)+ |
| 135C8 | 1380.6496 | 1381.6849 (M + H)+ |
| 135C9 | 1355.5890 | 1356.6191 (M + H)+ |
| 135C10 | 1371.6169 | 1372.7186 (M + H)+ |
| 135D6 | 1428.6569 | 1429.6614 (M + H)+ |
| 135D7 | 1424.7000 | 1425.7000 (M + H)+ |
| 135D8 | 1438.7000 | 1439.7000 (M + H)+ |
| 135D9 | 1410.6956 | 1411.7895 (M + H)+ |
| 135E2 | 1419.6099 | 1420.6100 (M + H)+ |
| 135E4 | 1430.6386 | 1431.6785 (M + H)+ |
| 135E5 | 1430.6386 | 1431.6010 (M + H)+ |
| 135E6 | 1414.6754 | 1415.6994 (M + H)+ |
| 135E7 | 1464.6649 | 1465.6291 (M + H)+ |
| 135E10 | 1436.6241 | 1437.6154 (M + H)+ |
| 135E11 | 1450.6397 | 1451.6401 (M + H)+ |
| 135E12 | 1453.7102 | 740.8283 (M + Na + H)$^{2+}$ |
| 135F1 | 1402.6397 | 1403.6390 (M + H)+ |
| 135F2 | 1412.6725 | 1413.6695 (M + H)+ |
| 135F3 | 1412.6725 | 1413.5455 (M + H)+ |
| 135F4 | 1412.6725 | 1413.6912 (M + H)+ |
| 135F5 | 1414.6437 | 1415.6063 (M + H)+ |
| 135F6 | 1414.6437 | 1415.5974 (M + H)+ |
| 135F8 | 1397.6563 | 1398.6381 (M + H)+ |
| 135F10 | 1446.6335 | 1447.7143 (M + H)+ |
| 135F12 | 1618.7182 | 1619.7491 (M + H)+ |
| 135G3 | 1469.5585 | 1470.6225 (M + H)+ |
| 135C11 | 3019.5626 | 1510.8426 (M + H)$^{2+}$ |
| 135G8 | 1427.68 | 1427.40 (M + H)+ |
| 135G9 | 1419.84 | 1419.0 (M + H)+ |
| 135I2 | 1441.64 | 1441.0 (M + H)+ |
| 135I3 | 1441.67 | 1441.5 (M + H)+ |
| 135F11 | 1446.6208 | 1447.6485 (M + H)+ |
| 135G10 | 1479.6157 | 1481.4934 (M + H)+ |
| 135G11 | 1483.5742 | 1485.4979 (M + H)+ |
| 135G12 | 1493.5810 | 1495.4927 (M + H)+ |
| 135H2 | 1519.6470 | 1521.6168 (M + H)+ |
| 135H3 | 1547.6031 | 1549.5636 (M + H)+ |
| 135H4 | 1587.6344 | 1589.5987 (M + H)+ |
| 135G6 | 1406.33 | 1405.0 (M − H)− |
| 135G5 | 1392.33 | 1391.0 (M − H)− |
| 135H5 | 1410.32 | 1410.0 (M + H)+ |
| 135G7 | 1408.33 | 1407.0 (M − H)− |
| 135H1 | 1463.5680 | 1465.4819 (M + H)+ |
| 135H6 | 1426.97 | 1425.0 (M − H)− |
| 135H7 | 1479.7034 | 1480.6510 (M + H)+ |
| 135H8 | 1421.6616 | 1422.6306 (M + H)+ |
| 135H9 | 1441.6069 | 1442.5950 (M + H)+ |
| 135H10 | 1451.6721 | 1452.6528 (M + H)+ |
| 135H11 | 1525.7008 | 1526.6317 (M + H)+ |
| 135H12 | 3278.53 | 3279.43 (M + H)+ |
| 135G4 | 3164.23 | 3168.30 (M + H)+ |
| 135I4 | 1561.2 | 1560.0 (M − H)− |

Preparation of 135G4 and 135H12. Dimers were prepared using half the resin needed for a normal scale reaction (usually 0.1 mmol) and introducing a Fmoc-Lys(Fmoc)-OH as first amino acid of the sequence (as illustrated in FIG. 6). A double coupling protocol was employed to assure the complete reaction of both elongating sequences. Standard cleavage and purification protocol was used to obtain the pure dimers (purity>95% by HPLC).

Example 7. Experimental Section: Binding and Displacement Assays

EphA2-LBD and EphA4-LBD were expressed and purified as we previously reported (30). Isothermal Titration calorimetry (ITC) measurements were obtained with a TA Instruments micro-calorimeter. The optimized DELFIA (Dissociation-Enhanced Lanthanide Fluorescent Immunoassay) assay protocol included a 2 h incubation of 100 µL of 1 µM 123B9-biotin in 96-well streptavidin-coated plates (PerkinElmer), followed by 3 washing steps. Subsequently, after pre-incubation of test agents for 15 min with a solution 0.712 µM EphA2-LBD, 11 µL of this mixture was added to 89 µL solution containing 4.17 nM Eu-N1-labeled anti-6× His antibody (PerkinElmer) and incubated for 1 h. After washing steps, 200 µL of the DELFIA enhancement solution (PerkinElmer) was added to each well followed by a 10-min incubation, prior to fluorescence reading (VICTOR X5 microplate reader, PerkinElmer; excitation and emission wavelengths of 340 and 615 nm, respectively). Fluorescence readings were normalized to that of DMSO control and reported as percent inhibition. The $IC_{50}$ values were analyzed using GraphPad Prism Version 7 and data fitted with a nonlinear regression (least squares ordinary fit) of the log[compound] versus the observed response.

Example 8. Experimental Section: Crystallization, X-Ray Data Collection and Structure Determination The EphA2 protein sample was mixed with the peptide in a 1:2 molar ratio for complex formation. Initial crystallization conditions were identified through sparse-matrix screening (Hampton Research Inc.). The crystals were subsequently reproduced by hanging-drop vapor diffusion method at 4° C., from drops mixed from 1 µl of protein complex and 1 µl of precipitant solution (0.1M Tris-Cl, pH 8.0, 1.4-1.8M $Li_2SO_4$). Crystals were soaked for a few seconds in a cryo-protectant solution, composed of crystallization solution and 20% glycerol, before flash freezing in liquid nitrogen.

The X-ray diffraction data for the EphA2-LBD-135E2 peptide complex were collected on the BL 5.0.1 beamline at the Advanced Light Source, Lawrence Berkeley National Laboratory. The diffraction data were indexed, integrated and scaled using the HKL2000 program[31]. The structure was solved using the molecular replacement method in PHASER[32], with the structure of free EphA2 (PDB ID: 3C8X) as search model. The resulting electron density revealed that there are four EphA2-135E2 peptide complexes in each asymmetric unit, with one peptide containing AHHHHA. The structure of the complex was improved by iterative model building and refinement with Coot[33] and PHENIX software packages[34]. The same R-free test set was used throughout the refinement. The statistics for data collection and structural refinement of the complex EphA2-peptide are reported in Table S1.

Example 9. Experimental Section: Cell Lines, Cell Culture and Antibodies

BxPC-3, PANC-1 and HEK273T/17 (HEK293) cell lines were purchased from the American Type Culture Collection (ATCC). All culture media and supplements were purchased form ThermoFisher and supplemented with 10% FBS and 1% Pen Strep to make complete media. BxPC3 was cultured in complete RPMI-1640 and PANC-1 and HEK293 were cultured in complete DMEM. Anti-EphA2 antibody (1C11A12) was purchased from ThermoFisher and anti-pS897-EphA2 antibody (D9A1) was purchased from Cell Signaling Technology and both antibodies were probed at 1:1000 dilution. β-actin antibody was purchased from Santa Cruz Biotechnology and probed at 1:10,000.

Example 10. Experimental Section: EphA2 Stimulation and Immunoprecipitation

We established an EphA2-overexpressing HEK293 stable cell line as we recently reported (28). The EphA2 cell line was plated in 6-well plates. The following day, cells were starved by replacing complete media with serum-free DMEM for 2 h. Starved cells were stimulated with 0.5-1 µg/mL clustered mouse EphrinA1-Fc or Fc (R&D systems) with goat anti-human IgG Fc (Abcam, cat. no. ab97221) at various time points. During stimulation, indicated doses of compounds were added to each well. Control cells were treated with complete media containing 1% DMSO. Stimulated cells were lysed with cell lysis buffer (20 mM Tris, pH 7.4, 120 mM NaCl, 1% Triton X-100, 0.5% sodium deoxycholate, 0.1% SDS, 1% IGEPAL, 5 mM EDTA, supplemented with EDTA-free Protease Inhibitor Cocktail and PhosStop from Sigma-Aldrich) for 30 min on ice. Cell lysates were then centrifuged to clear off cell debris for 10 min at 13,000 rpm at 4° C. Protein concentration was quantified using BCA Protein Assay kit (ThermoFisher) and sample concentration was adjusted to 1 µg/µL for all samples. Pre-clear step for cell lysates was performed using Pierce Protein A/G Agarose beads (ThermoFisher) for 1 h at 4° C. Cell lysates and beads were centrifuged, and the supernatant was further incubated with 2 µg mouse antibody anti-EphA2 Receptor (ThermoFisher, cat. no. 1C11A12) at 4° C. overnight. Next day, each cell lysate-antibody complex was incubated with A/G agarose beads for 2 h at room temperature. After several washes, target protein was eluted by heating in 2×NuPAGE LDS Sample Buffer and NuPAGE Antioxidant (ThermoFisher) for 5 min at 90° C. Samples were loaded into 4-12% NuPAGE Bis-Tris Precast Gels and transferred to PVDF membrane. The membrane was blocked with 5% BSA in TBS and 0.1% Tween (TBST) for 1 h, then incubated with a 1:3000 dilution of a mouse antibody anti-Phosphotyrosine (BD Biosciences, cat. no. 610000, clone PY20) for 1 h. The antigen-antibody complex was visualized using Clarity Western ECL kit (BIO-RAD). The membrane was washed and stripped using Restore Western Blot Stripping Buffer for 1 h, and subsequently blocked with 5% non-fat milk in TBST, followed by a 1 h incubation with a primary mouse antibody anti-EphA2 receptor at a 1:2,000 dilution. The membrane was then washed with TBST and incubated with goat anti-mouse HRP.

Example 11. Experimental Section: Immunofluorescence

In chamber slides, cells were plated and allowed to adhere overnight in humidified cell culture incubators. The following day, cells were treated with the indicated ligands for 30 min. Subsequently, cells were washed with PBS and fixed with 4% Formaldehyde (Polysciences, Inc.), then blocked and permeabilized with 5% FBS and 0.3% Triton™ X-100 for 1 h. Next, wells were washed and stained with anti-EphA2 antibody, followed by three washes and further incubation with Alexafluor goat anti-mouse 488 secondary antibody (ThermoFisher). Cells were counterstained with DAPI and mounted with Prolong Diamond Antifade (ThermoFisher). Images were acquired with confocal microscope Zeiss 880 Airyscan and processed using Adobe Photoshop CC.

Example 12. Experimental Section: Time-Lapse Scratch Wound Healing Assays

Cell-migration assay: Cells were cultured in 96-well ImageLock plates (Sartorius). Next day, wells were scratched using the WoundMaker (Sartorius). Subsequently, cells were washed twice with PBS and treated with the indicated compounds in RPMI-1640 complete media. Subsequently, cells were imaged every 6 h using IncuCyte S3 (Sartorius) and relative wound areas were analyzed using the algorithm of the imager cell migration software module.

Cell invasion assay: Matrigel (Corning) was diluted in serum-free RPMI-1640 media (1:100), 50 µL of the mixture was added to ImageLock plate and incubated at 37° C. for 2 h. Next, excess media were aspirated and cells in complete media were plated and left overnight in humidified cell culture incubator. The following day, cell culture plate was aspirated, scratched with the WoundMaker, and washed twice with PBS. Subsequently, the plate was coated with a mixture of Matrigel and cold serum-free RPMI-1640 (1:1) and left in the incubator to solidify for 30 min. Finally, 100 µL of 1.5× compound-media mixture was

| ID | Sequence |
|---|---|
| 147A1 | (7-MethoxyBenzofuranoic)SAYPDSVPF(OS02F)RP-CONH$_2$ (SEQ ID NO: 69) |
| 147A2 | (7-MethoxyBenzofuranoic)SAYPDSVP-Dap(4-FSulfB)-RP-CONH$_2$ (SEQ ID NO: 70) |
| 147A3 | (7-MethoxyBenzofuranoic)SAYPDSVPF(OSO2F)-CONH$_2$ (SEQ ID NO: 71) |
| 147A4 | (7-MethoxyBenzofuranoic)LAYPDAVPF(OSO2F)-RP-CONH$_2$ (SEQ ID NO: 72) |
| 147A5 | (7-MethoxyBenzofuranoic)LAYPDAVP-Dap(4-FSB)-RP-CONH$_2$ (SEQ ID NO: 73) |
| 147A6 | (7-MethoxyBenzofuranoic)LAYPDAVP-Dap(3-FSB)-RP-CONH$_2$ (SEQ ID NO: 74) |
| 147A7 | (7-MethoxyBenzofuranoic)LAYPDAVP-Dap(4-FSulfB)-RP-CONH$_2$ (SEQ ID NO: 75) |
| 147A8 | (7-MethoxyBenzofuranoic)LAYPDAVP-Dap(3-FSulfB)-RP-CONH$_2$ (SEQ ID NO: 76) |
| 147A9 | (7-MethoxyBenzofuranoic)LAYPDAVP-hF(OSO2F)-RP-CONH$_2$ (SEQ ID NO: 77) |
| 147A10 | (7-MethoxyBenzofuranoic)LAYPDAVP-F(OSO2F)-RP-CONH$_2$ (SEQ ID NO: 78) |
| 147A11 | (7-MethoxyBenzofuranoic)LAYPDAVP-Dap(4-FSBz)-RP-CONH$_2$ (SEQ ID NO: 79) | added to the plate at various concentrations. The healing of the scratches was imaged and calculated similar to the migration assay.

Accession Codes: PDB ID 6B9L.

Example 13. Additional Data

Table 3. Examples of compounds including tyrosine reactive electrophiles, e.g., sulfonyl fluoride or fluorosulfate. Dap=L-2,3-diaminopropionic acid; hY, L-homo-phenylalanine.

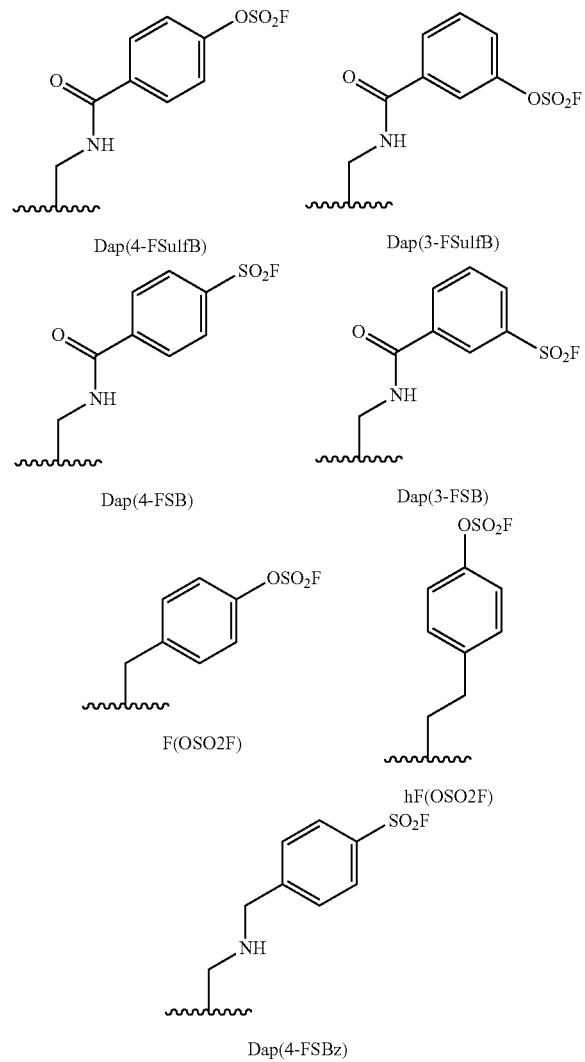

Dap(4-FSulfB)
Dap(3-FSulfB)
Dap(4-FSB)
Dap(3-FSB)
F(OSO2F)
hF(OSO2F)
Dap(4-FSBz)

Covalent adduct formation of EphA2 with 147A5 and 147A6, respectively, were confirmed by covalent gel shift. Compounds were incubated 10:1 for 2 hours at room temperature.

REFERENCES

1. Hess, A. R., Seftor, E. A., Gardner, L. M., Carles-Kinch, K., Schneider, G. B., Seftor, R. E., Kinch, M. S., and Hendrix, M. J. (2001) Molecular regulation of tumor cell vasculogenic mimicry by tyrosine phosphorylation: role of epithelial cell kinase (Eck/EphA2), Cancer Res 61, 3250-3255.
2. Walker-Daniels, J., Coffman, K., Azimi, M., Rhim, J. S., Bostwick, D. G., Snyder, P., Kerns, B. J., Waters, D. J., and Kinch, M. S. (1999) Overexpression of the EphA2 tyrosine kinase in prostate cancer, Prostate 41, 275-280.
3. Zeng, G., Hu, Z., Kinch, M. S., Pan, C. X., Flockhart, D. A., Kao, C., Gardner, T. A., Zhang, S., Li, L., Baldridge, L. A., Koch, M. O., Ulbright, T. M., Eble, J. N., and Cheng, L. (2003) High-level expression of EphA2 receptor tyrosine kinase in prostatic intraepithelial neoplasia, Am J Pathol 163, 2271-2276.
4. Margaryan, N. V., Strizzi, L., Abbott, D. E., Seftor, E. A., Rao, M. S., Hendrix, M. J., and Hess, A. R. (2009) EphA2 as a promoter of melanoma tumorigenicity, Cancer Biol Ther 8, 279-288.
5. Abraham, S., Knapp, D. W., Cheng, L., Snyder, P. W., Mittal, S. K., Bangari, D. S., Kinch, M., Wu, L., Dhariwal, J., and Mohammed, S. I. (2006) Expression of EphA2 and Ephrin A-1 in carcinoma of the urinary bladder, Clin Cancer Res 12, 353-360.
6. Ogawa, K., Pasqualini, R., Lindberg, R. A., Kain, R., Freeman, A. L., and Pasquale, E. B. (2000) The ephrinA1 ligand and its receptor, EphA2, are expressed during tumor neovascularization, Oncogene 19, 6043-6052.
7. Merritt, W. M., Thaker, P. H., Landen, C. N., Jr., Deavers, M. T., Fletcher, M. S., Lin, Y. G., Han, L. Y., Kamat, A. A., Schmandt, R., Gershenson, D. M., Kinch, M. S., and Sood, A. K. (2006) Analysis of EphA2 expression and mutant p53 in ovarian carcinoma, Cancer Biol Ther 5, 1357-1360.
8. Duxbury, M. S., Ito, H., Zinner, M. J., Ashley, S. W., and Whang, E. E. (2004) Ligation of EphA2 by Ephrin Al-Fc inhibits pancreatic adenocarcinoma cellular invasiveness, Biochem Biophys Res Commun 320, 1096-1102.
9. Duxbury, M. S., Ito, H., Zinner, M. J., Ashley, S. W., and Whang, E. E. (2004) EphA2: a determinant of malignant cellular behavior and a potential therapeutic target in pancreatic adenocarcinoma, Oncogene 23, 1448-1456.
10. Mudali, S. V., Fu, B., Lakkur, S. S., Luo, M., Embuscado, E. E., and Iacobuzio-Donahue, C. A. (2006) Patterns of EphA2 protein expression in primary and metastatic pancreatic carcinoma and correlation with genetic status, Clin Exp Metastasis 23, 357-365.
11. Wang, L. F., Fokas, E., Bieker, M., Rose, F., Rexin, P., Zhu, Y., Pagenstecher, A., Engenhart-Cabillic, R., and An, H. X. (2008) Increased expression of EphA2 correlates with adverse outcome in primary and recurrent glioblastoma multiforme patients, Oncol Rep 19, 151-156.
12. Wykosky, J., Gibo, D. M., Stanton, C., and Debinski, W. (2005) EphA2 as a novel molecular marker and target in glioblastoma multiforme, Mol Cancer Res 3, 541-551.
13. Binda, E., Visioli, A., Giani, F., Lamorte, G., Copetti, M., Fitter, K. L., Huse, J. T., Cajola, L., Zanetti, N., DiMeco, F., De Filippis, L., Mangiola, A., Maira, G., Anile, C., De Bonis, P., Reynolds, B. A., Pasquale, E. B., and Vescovi, A. L. (2012) The EphA2 receptor drives self-renewal and tumorigenicity in stem-like tumor-propagating cells from human glioblastomas, Cancer Cell 22, 765-780.
14. Miyazaki, T., Kato, H., Fukuchi, M., Nakajima, M., and Kuwano, H. (2003) EphA2 overexpression correlates with poor prognosis in esophageal squamous cell carcinoma, Int J Cancer 103, 657-663.
15. Faoro, L., Singleton, P. A., Cervantes, G. M., Lennon, F. E., Choong, N. W., Kanteti, R., Ferguson, B. D., Husain, A. N., Tretiakova, M. S., Ramnath, N., Vokes, E. E., and Salgia, R. (2010) EphA2 mutation in lung squamous cell carcinoma promotes increased cell survival, cell invasion, focal adhesions, and mammalian target of rapamycin activation, *J Biol Chem* 285, 18575-18585.
16. Yuan, W. J., Ge, J., Chen, Z. K., Wu, S. B., Shen, H., Yang, P., Hu, B., Zhang, G. W., and Chen, Z. H. (2009) Over-expression of EphA2 and EphrinA-1 in human gastric adenocarcinoma and its prognostic value for postoperative patients, *Dig Dis Sci* 54, 2410-2417.
17. Takahashi, Y., Itoh, M., Nara, N., and Tohda, S. (2014) Effect of EPH-ephrin signaling on the growth of human leukemia cells, *Anticancer research* 34, 2913-2918.
18. Trinidad, E. M., Zapata, A. G., and Alonso-Colmenar, L. M. (2010) Eph-ephrin bidirectional signaling comes into the context of lymphocyte transendothelial migration, *Cell adhesion & migration* 4, 363-367.
19. Alonso, C. L., Trinidad, E. M., de Garcillan, B., Ballesteros, M., Castellanos, M., Cotillo, I., Munoz, J. J., and Zapata, A. G. (2009) Expression profile of Eph receptors and ephrin ligands in healthy human B lymphocytes and chronic lymphocytic leukemia B-cells, *Leukemia research* 33, 395-406.
20. Guan, M., Liu, L., Zhao, X., Wu, Q., Yu, B., Shao, Y., Yang, H., Fu, X., Wan, J., and Zhang, W. (2011) Copy number variations of EphA3 are associated with multiple types of hematologic malignancies, *Clinical lymphoma, myeloma & leukemia* 11, 50-53.
21. Petty, A., Myshkin, E., Qin, H., Guo, H., Miao, H., Tochtrop, G. P., Hsieh, J. T., Page, P., Liu, L., Lindner, D. J., Acharya, C., MacKerell, A. D., Jr., Ficker, E., Song, J., and Wang, B. (2012) A small molecule agonist of EphA2 receptor tyrosine kinase inhibits tumor cell migration in vitro and prostate cancer metastasis in vivo, *PLoS One* 7, e42120.
22. Amato, K. R., Wang, S., Hastings, A. K., Youngblood, V. M., Santapuram, P. R., Chen, H., Cates, J. M., Colvin, D. C., Ye, F., Brantley-Sieders, D. M., Cook, R. S., Tan, L., Gray, N. S., and Chen, J. (2014) Genetic and pharmacologic inhibition of EPHA2 promotes apoptosis in NSCLC, *J Clin Invest* 124, 2037-2049.
23. Amato, K. R., Wang, S., Tan, L., Hastings, A. K., Song, W., Lovly, C. M., Meador, C. B., Ye, F., Lu, P., Balko, J. M., Colvin, D. C., Cates, J. M., Pao, W., Gray, N. S., and Chen, J. (2016) EPHA2 Blockade Overcomes Acquired Resistance to EGFR Kinase Inhibitors in Lung Cancer, *Cancer Res* 76, 305-318.
24. Miao, B., Ji, Z., Tan, L., Taylor, M., Zhang, J., Choi, H. G., Frederick, D. T., Kumar, R., Wargo, J. A., Flaherty, K. T., Gray, N. S., and Tsao, H. (2015) EPHA2 is a mediator of vemurafenib resistance and a novel therapeutic target in melanoma, *Cancer Discov* 5, 274-287.
25. Heinzlmeir, S., Kudlinzki, D., Sreeramulu, S., Klaeger, S., Gande, S. L., Linhard, V., Wilhelm, M., Qiao, H., Helm, D., Ruprecht, B., Saxena, K., Medard, G., Schwalbe, H., and Kuster, B. (2016) Chemical Proteomics and Structural Biology Define EPHA2 Inhibition by Clinical Kinase Drugs, *ACS Chem Biol* 11, 3400-3411.
26. Petty, A., Idippily, N., Bobba, V., Geldenhuys, W. J., Zhong, B., Su, B., and Wang, B. (2018) Design and synthesis of small molecule agonists of EphA2 receptor, *Eur J Med Chem* 143, 1261-1276.
27. Hasegawa, J., Sue, M., Yamato, M., Ichikawa, J., Ishida, S., Shibutani, T., Kitamura, M., Wada, T., and Agatsuma, T. (2016) Novel anti-EPHA2 antibody, DS-8895a for cancer treatment, *Cancer Biol Ther* 17, 1158-1167.
28. Salem, A. F., Wang, S., Billet, S., Chen, J. F., Udompholkul, P., Gambini, L., Baggio, C., Tseng, H. R., Posadas, E. M., Bhowmick, N. A., and Pellecchia, M. (2018) Reduction of Circulating Cancer Cells and Metastases in Breast-Cancer Models by a Potent EphA2-Agonistic Peptide-Drug Conjugate, *J Med Chem* 61, 2052-2061.
29. Koolpe, M., Dail, M., and Pasquale, E. B. (2002) An ephrin mimetic peptide that selectively targets the EphA2 receptor, *J Biol Chem* 277, 46974-46979.
30. Wu, B., Wang, S., De, S. K., Bartle, E., Quinn, B. A., Zharkikh, I., Purves, A., Stebbins, J. L., Oshima, R. G., Fisher, P. B., and Pellecchia, M. (2015) Design and Characterization of Novel EphA2 Agonists for Targeted Delivery of Chemotherapy to Cancer Cells, *Chem Biol* 22, 876-887.
31. Otwinowski, Z., and Minor, W. (1997) Processing of X-ray diffraction data collected in oscillation mode, *Macromolecular Crystallography, Pt A* 276, 307-326.
32. McCoy, A. J., Grosse-Kunstleve, R. W., Adams, P. D., Winn, M. D., Storoni, L. C., and Read, R. J. (2007) Phaser crystallographic software, *J Appl Crystallogr* 40, 658-674.
33. Emsley, P., and Cowtan, K. (2004) Coot: model-building tools for molecular graphics, *Acta Crystallogr D Biol Crystallogr* 60, 2126-2132.
34. Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002) PHENIX: building new software for automated crystallographic structure determination, *Acta Crystallogr D Biol Crystallogr* 58, 1948-1954.
35. Khrapunov, S. (2018) The enthalpy-entropy compensation phenomenon. Limitations for the use of some basic thermodynamic equations, *Curr Protein Pept Sci*.
36. Fox, J. M., Zhao, M., Fink, M. J., Kang, K., and Whitesides, G. M. (2018) The Molecular Origin of Enthalpy/Entropy Compensation in Biomolecular Recognition, *Annu Rev Biophys*.
37. Barile, E., Wang, S., Das, S. K., Noberini, R., Dahl, R., Stebbins, J. L., Pasquale, E. B., Fisher, P. B., and Pellecchia, M. (2014) Design, synthesis and bioevaluation of an EphA2 receptor-based targeted delivery system, *ChemMedChem* 9, 1403-1412.
38. Wu, B., De, S. K., Kulinich, A., Salem, A. F., Koeppen, J., Wang, R., Barile, E., Wang, S., Zhang, D., Ethell, I., and Pellecchia, M. (2017) Potent and Selective EphA4 Agonists for the Treatment of ALS, *Cell Chem Biol* 24, 293-305.
39. Wu, B., Barile, E., De, S. K., Wei, J., Purves, A., and Pellecchia, M. (2015) High-Throughput Screening by Nuclear Magnetic Resonance (HTS by NMR) for the Identification of PPIs Antagonists, *Curr Top Med Chem* 15, 2032-2042.
40. Wu, B., Zhang, Z., Noberini, R., Barile, E., Giulianotti, M., Pinilla, C., Houghten, R. A., Pasquale, E. B., and Pellecchia, M. (2013) HTS by NMR of combinatorial libraries: a fragment-based approach to ligand discovery, *Chem Biol* 20, 19-33.
1. Hess, A. R., Seftor, E. A., Gardner, L. M., Carles-Kinch, K., Schneider, G. B., Seftor, R. E., Kinch, M. S., and Hendrix, M. J. (2001) Molecular regulation of tumor cell vasculogenic mimicry by tyrosine phosphorylation: role of epithelial cell kinase (Eck/EphA2), *Cancer Res* 61, 3250-3255.
2. Walker-Daniels, J., Coffman, K., Azimi, M., Rhim, J. S., Bostwick, D. G., Snyder, P., Kerns, B. J., Waters, D. J., and Kinch, M. S. (1999) Overexpression of the EphA2 tyrosine kinase in prostate cancer, *Prostate* 41, 275-280.
3. Zeng, G., Hu, Z., Kinch, M. S., Pan, C. X., Flockhart, D. A., Kao, C., Gardner, T. A., Zhang, S., Li, L., Baldridge, L. A., Koch, M. O., Ulbright, T. M., Eble, J. N., and Cheng, L. (2003) High-level expression of EphA2 receptor tyrosine kinase in prostatic intraepithelial neoplasia, *Am J Pathol* 163, 2271-2276.
4. Margaryan, N. V., Strizzi, L., Abbott, D. E., Seftor, E. A., Rao, M. S., Hendrix, M. J., and Hess, A. R. (2009) EphA2 as a promoter of melanoma tumorigenicity, *Cancer Biol Ther* 8, 279-288.
5. Abraham, S., Knapp, D. W., Cheng, L., Snyder, P. W., Mittal, S. K., Bangari, D. S., Kinch, M., Wu, L., Dhariwal, J., and Mohammed, S. I. (2006) Expression of EphA2 and Ephrin A-1 in carcinoma of the urinary bladder, *Clin Cancer Res* 12, 353-360.
6. Ogawa, K., Pasqualini, R., Lindberg, R. A., Kain, R., Freeman, A. L., and Pasquale, E. B. (2000) The ephrinA1 ligand and its receptor, EphA2, are expressed during tumor neovascularization, *Oncogene* 19, 6043-6052.
7. Merritt, W. M., Thaker, P. H., Landen, C. N., Jr., Deavers, M. T., Fletcher, M. S., Lin, Y. G., Han, L. Y., Kamat, A. A., Schmandt, R., Gershenson, D. M., Kinch, M. S., and Sood, A. K. (2006) Analysis of EphA2 expression and mutant p53 in ovarian carcinoma, *Cancer Biol Ther* 5, 1357-1360.
8. Duxbury, M. S., Ito, H., Zinner, M. J., Ashley, S. W., and Whang, E. E. (2004) Ligation of EphA2 by Ephrin Al-Fc inhibits pancreatic adenocarcinoma cellular invasiveness, *Biochem Biophys Res Commun* 320, 1096-1102.
9. Duxbury, M. S., Ito, H., Zinner, M. J., Ashley, S. W., and Whang, E. E. (2004) EphA2: a determinant of malignant cellular behavior and a potential therapeutic target in pancreatic adenocarcinoma, *Oncogene* 23, 1448-1456.
10. Mudali, S. V., Fu, B., Lakkur, S. S., Luo, M., Embuscado, E. E., and Iacobuzio-Donahue, C. A. (2006) Patterns of EphA2 protein expression in primary and metastatic pancreatic carcinoma and correlation with genetic status, *Clin Exp Metastasis* 23, 357-365.
11. Wang, L. F., Fokas, E., Bieker, M., Rose, F., Rexin, P., Zhu, Y., Pagenstecher, A., Engenhart-Cabillic, R., and An, H. X. (2008) Increased expression of EphA2 correlates with adverse outcome in primary and recurrent glioblastoma multiforme patients, *Oncol Rep* 19, 151-156.
12. Wykosky, J., Gibo, D. M., Stanton, C., and Debinski, W. (2005) EphA2 as a novel molecular marker and target in glioblastoma multiforme, *Mol Cancer Res* 3, 541-551.
13. Binda, E., Visioli, A., Giani, F., Lamorte, G., Copetti, M., Fitter, K. L., Huse, J. T., Cajola, L., Zanetti, N., DiMeco, F., De Filippis, L., Mangiola, A., Maira, G., Anile, C., De Bonis, P., Reynolds, B. A., Pasquale, E. B., and Vescovi, A. L. (2012) The EphA2 receptor drives self-renewal and tumorigenicity in stem-like tumor-propagating cells from human glioblastomas, *Cancer Cell* 22, 765-780.
14. Miyazaki, T., Kato, H., Fukuchi, M., Nakajima, M., and Kuwano, H. (2003) EphA2 overexpression correlates with poor prognosis in esophageal squamous cell carcinoma, *Int J Cancer* 103, 657-663.
15. Faoro, L., Singleton, P. A., Cervantes, G. M., Lennon, F. E., Choong, N. W., Kanteti, R., Ferguson, B. D., Husain, A. N., Tretiakova, M. S., Ramnath, N., Vokes, E. E., and Salgia, R. (2010) EphA2 mutation in lung squamous cell carcinoma promotes increased cell survival, cell invasion, focal adhesions, and mammalian target of rapamycin activation, *J Biol Chem* 285, 18575-18585.
16. Yuan, W. J., Ge, J., Chen, Z. K., Wu, S. B., Shen, H., Yang, P., Hu, B., Zhang, G. W., and Chen, Z. H. (2009) Over-expression of EphA2 and EphrinA-1 in human gastric adenocarcinoma and its prognostic value for postoperative patients, *Dig Dis Sci* 54, 2410-2417.
17. Takahashi, Y., Itoh, M., Nara, N., and Tohda, S. (2014) Effect of EPH-ephrin signaling on the growth of human leukemia cells, *Anticancer research* 34, 2913-2918.
18. Trinidad, E. M., Zapata, A. G., and Alonso-Colmenar, L. M. (2010) Eph-ephrin bidirectional signaling comes into the context of lymphocyte transendothelial migration, *Cell adhesion & migration* 4, 363-367.
19. Alonso, C. L., Trinidad, E. M., de Garcillan, B., Ballesteros, M., Castellanos, M., Cotillo, I., Munoz, J. J., and Zapata, A. G. (2009) Expression profile of Eph receptors and ephrin ligands in healthy human B lymphocytes and chronic lymphocytic leukemia B-cells, *Leukemia research* 33, 395-406.
20. Guan, M., Liu, L., Zhao, X., Wu, Q., Yu, B., Shao, Y., Yang, H., Fu, X., Wan, J., and Zhang, W. (2011) Copy number variations of EphA3 are associated with multiple types of hematologic malignancies, *Clinical lymphoma, myeloma & leukemia* 11, 50-53.
21. Petty, A., Myshkin, E., Qin, H., Guo, H., Miao, H., Tochtrop, G. P., Hsieh, J. T., Page, P., Liu, L., Lindner, D. J., Acharya, C., MacKerell, A. D., Jr., Ficker, E., Song, J., and Wang, B. (2012) A small molecule agonist of EphA2 receptor tyrosine kinase inhibits tumor cell migration in vitro and prostate cancer metastasis in vivo, *PLoS One* 7, e42120.
22. Amato, K. R., Wang, S., Hastings, A. K., Youngblood, V. M., Santapuram, P. R., Chen, H., Cates, J. M., Colvin, D. C., Ye, F., Brantley-Sieders, D. M., Cook, R. S., Tan, L., Gray, N. S., and Chen, J. (2014) Genetic and pharmacologic inhibition of EPHA2 promotes apoptosis in NSCLC, *J Clin Invest* 124, 2037-2049.
23. Amato, K. R., Wang, S., Tan, L., Hastings, A. K., Song, W., Lovly, C. M., Meador, C. B., Ye, F., Lu, P., Balko, J. M., Colvin, D. C., Cates, J. M., Pao, W., Gray, N. S., and Chen, J. (2016) EPHA2 Blockade Overcomes Acquired Resistance to EGFR Kinase Inhibitors in Lung Cancer, *Cancer Res* 76, 305-318.
24. Miao, B., Ji, Z., Tan, L., Taylor, M., Zhang, J., Choi, H. G., Frederick, D. T., Kumar, R., Wargo, J. A., Flaherty, K. T., Gray, N. S., and Tsao, H. (2015) EPHA2 is a mediator of vemurafenib resistance and a novel therapeutic target in melanoma, *Cancer Discov* 5, 274-287.
25. Heinzlmeir, S., Kudlinzki, D., Sreeramulu, S., Klaeger, S., Gande, S. L., Linhard, V., Wilhelm, M., Qiao, H., Helm, D., Ruprecht, B., Saxena, K., Medard, G., Schwalbe, H., and Kuster, B. (2016) Chemical Proteomics and Structural Biology Define EPHA2 Inhibition by Clinical Kinase Drugs, *ACS Chem Biol* 11, 3400-3411.
26. Petty, A., Idippily, N., Bobba, V., Geldenhuys, W. J., Zhong, B., Su, B., and Wang, B. (2018) Design and synthesis of small molecule agonists of EphA2 receptor, *Eur J Med Chem* 143, 1261-1276.
27. Hasegawa, J., Sue, M., Yamato, M., Ichikawa, J., Ishida, S., Shibutani, T., Kitamura, M., Wada, T., and Agatsuma, T. (2016) Novel anti-EPHA2 antibody, DS-8895a for cancer treatment, *Cancer Biol Ther* 17, 1158-1167.
28. Salem, A. F., Wang, S., Billet, S., Chen, J. F., Udompholkul, P., Gambini, L., Baggio, C., Tseng, H. R., Posadas, E. M., Bhowmick, N. A., and Pellecchia, M. (2018) Reduction of Circulating Cancer Cells and Metastases in Breast-Cancer Models by a Potent EphA2-Agonistic Peptide-Drug Conjugate, *J Med Chem* 61, 2052-2061.
29. Koolpe, M., Dail, M., and Pasquale, E. B. (2002) An ephrin mimetic peptide that selectively targets the EphA2 receptor, *J Biol Chem* 277, 46974-46979.
30. Wu, B., Wang, S., De, S. K., Barile, E., Quinn, B. A., Zharkikh, I., Purves, A., Stebbins, J. L., Oshima, R. G., Fisher, P. B., and Pellecchia, M. (2015) Design and Characterization of Novel EphA2 Agonists for Targeted Delivery of Chemotherapy to Cancer Cells, *Chem Biol* 22, 876-887.

31. Otwinowski, Z., and Minor, W. (1997) Processing of X-ray diffraction data collected in oscillation mode, *Macromolecular Crystallography, Pt A* 276, 307-326.

32. McCoy, A. J., Grosse-Kunstleve, R. W., Adams, P. D., Winn, M. D., Storoni, L. C., and Read, R. J. (2007) Phaser crystallographic software, *J Appl Crystallogr* 40, 658-674.

33. Emsley, P., and Cowtan, K. (2004) Coot: model-building tools for molecular graphics, *Acta Crystallogr D Biol Crystallogr* 60, 2126-2132.

34. Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002) PHENIX: building new software for automated crystallographic structure determination, *Acta Crystallogr D Biol Crystallogr* 58, 1948-1954.

35. Khrapunov, S. (2018) The enthalpy-entropy compensation phenomenon. Limitations for the use of some basic thermodynamic equations, *Curr Protein Pept Sci*.

36. Fox, J. M., Zhao, M., Fink, M. J., Kang, K., and Whitesides, G. M. (2018) The Molecular Origin of Enthalpy/Entropy Compensation in Biomolecular Recognition, *Annu Rev Biophys*.

37. Barile, E., Wang, S., Das, S. K., Noberini, R., Dahl, R., Stebbins, J. L., Pasquale, E. B., Fisher, P. B., and Pellecchia, M. (2014) Design, synthesis and bioevaluation of an EphA2 receptor-based targeted delivery system, *ChemMedChem* 9, 1403-1412.

38. Wu, B., De, S. K., Kulinich, A., Salem, A. F., Koeppen, J., Wang, R., Barile, E., Wang, S., Zhang, D., Ethell, I., and Pellecchia, M. (2017) Potent and Selective EphA4 Agonists for the Treatment of ALS, *Cell Chem Biol* 24, 293-305.

39. Wu, B., Barile, E., De, S. K., Wei, J., Purves, A., and Pellecchia, M. (2015) High-Throughput Screening by Nuclear Magnetic Resonance (HTS by NMR) for the Identification of PPIs Antagonists, *Curr Top Med Chem* 15, 2032-2042.

40. Wu, B., Zhang, Z., Noberini, R., Barile, E., Giulianotti, M., Pinilla, C., Houghten, R. A., Pasquale, E. B., and Pellecchia, M. (2013) HTS by NMR of combinatorial libraries: a fragment-based approach to ligand discovery, *Chem Biol* 20, 19-33.

41. Petty, A., Idippily, N., Bobba, V., Geldenhuys, W. J., Zhong, B., Su, B., and Wang, B. (2017) Design and synthesis of small molecule agonists of EphA2 receptor, *Eur J Med Chem*.

42. Hassan-Mohamed, I., Giorgio, C., Incerti, M., Russo, S., Pala, D., Pasquale, E. B., Zanotti, I., Vicini, P., Barocelli, E., Rivara, S., Mor, M., Lodola, A., and Tognolini, M. (2014) UniPR129 is a competitive small molecule Eph-ephrin antagonist blocking in vitro angiogenesis at low micromolar concentrations, *Br J Pharmacol* 171, 5195-5208.

43. Tognolini, M., Incerti, M., Pala, D., Russo, S., Castelli, R., Hassan-Mohamed, I., Giorgio, C., and Lodola, A. (2014) Target hopping as a useful tool for the identification of novel EphA2 protein-protein antagonists, *ChemMedChem* 9, 67-72.

44. Giorgio, C., Incerti, M., Corrado, M., Rusnati, M., Chiodelli, P., Russo, S., Callegari, D., Ferlenghi, F., Ballabeni, V., Barocelli, E., Lodola, A., and Tognolini, M. (2017) Pharmacological evaluation of new bioavailable small molecules targeting Eph/ephrin interaction, *Biochem Pharmacol*.

45. Mitra, S., Duggineni, S., Koolpe, M., Zhu, X., Huang, Z., and Pasquale, E. B. (2010) Structure-activity relationship analysis of peptides targeting the EphA2 receptor, *Biochemistry* 49, 6687-6695.

46. Incerti, M., Tognolini, M., Russo, S., Pala, D., Giorgio, C., Hassan-Mohamed, I., Noberini, R., Pasquale, E. B., Vicini, P., Piersanti, S., Rivara, S., Barocelli, E., Mor, M., and Lodola, A. (2013) Amino acid conjugates of lithocholic acid as antagonists of the EphA2 receptor, *J Med Chem* 56, 2936-2947.

47. Castelli, R., Tognolini, M., Vacondio, F., Incerti, M., Pala, D., Callegari, D., Bertoni, S., Giorgio, C., Hassan-Mohamed, I., Zanotti, I., Bugatti, A., Rusnati, M., Festuccia, C., Rivara, S., Barocelli, E., Mor, M., and Lodola, A. (2015) Delta(5)-Cholenoyl-amino acids as selective and orally available antagonists of the Eph-ephrin system, *Eur J Med Chem* 103, 312-324.

48. Tandon, M., Vemula, S. V., and Mittal, S. K. (2011) Emerging strategies for EphA2 receptor targeting for cancer therapeutics, *Expert Opin Ther Targets* 15, 31-51.

49. Wang, S., Placzek, W. J., Stebbins, J. L., Mitra, S., Noberini, R., Koolpe, M., Zhang, Z., Dahl, R., Pasquale, E. B., and Pellecchia, M. (2012) Novel targeted system to deliver chemotherapeutic drugs to EphA2-expressing cancer cells, *J Med Chem* 55, 2427-2436.

50. Duggineni, S., Mitra, S., Lamberto, I., Han, X., Xu, Y., An, J., Pasquale, E. B., and Huang, Z. (2013) Design and Synthesis of Potent Bivalent Peptide Agonists Targeting the EphA2 Receptor, *ACS Med Chem Lett* 4.

51. Wang, S., Noberini, R., Stebbins, J. L., Das, S., Zhang, Z., Wu, B., Mitra, S., Billet, S., Fernandez, A., Bhowmick, N. A., Kitada, S., Pasquale, E. B., Fisher, P. B., and Pellecchia, M. (2013) Targeted delivery of paclitaxel to EphA2-expressing cancer cells, *Clin Cancer Res* 19, 128-137.

52. Quinn, B. A., Wang, S., Bartle, E., Das, S. K., Emdad, L., Sarkar, D., De, S. K., Morvaridi, S. K., Stebbins, J. L., Pandol, S. J., Fisher, P. B., and Pellecchia, M. (2016) Therapy of pancreatic cancer via an EphA2 receptor-targeted delivery of gemcitabine, *Oncotarget* 7, 17103-17110.

53. Patel, A. R., Chougule, M., and Singh, M. (2014) EphA2 targeting pegylated nanocarrier drug delivery system for treatment of lung cancer, *Pharm Res* 31, 2796-2809.

54. Xie, X., Yang, Y., Lin, W., Liu, H., Liu, H., Yang, Y., Chen, Y., Fu, X., and Deng, J. (2015) Cell-penetrating peptide-siRNA conjugate loaded YSA-modified nanobubbles for ultrasound triggered siRNA delivery, *Colloids Surf B Biointerfaces* 136, 641-650.

55. Cai, W., Ebrahimnejad, A., Chen, K., Cao, Q., Li, Z. B., Tice, D. A., and Chen, X. (2007) Quantitative radioimmuno PET imaging of EphA2 in tumor-bearing mice, *Eur J Nucl Med Mol Imaging* 34, 2024-2036.

56. Liu, Y., Lan, X., Wu, T., Lang, J., Jin, X., Sun, X., Wen, Q., and An, R. (2014) (99m)Tc-labeled SWL specific peptide for targeting EphA2 receptor, *Nucl Med Biol* 41, 450-456.

What is claimed is:
1. A compound having the following formula:

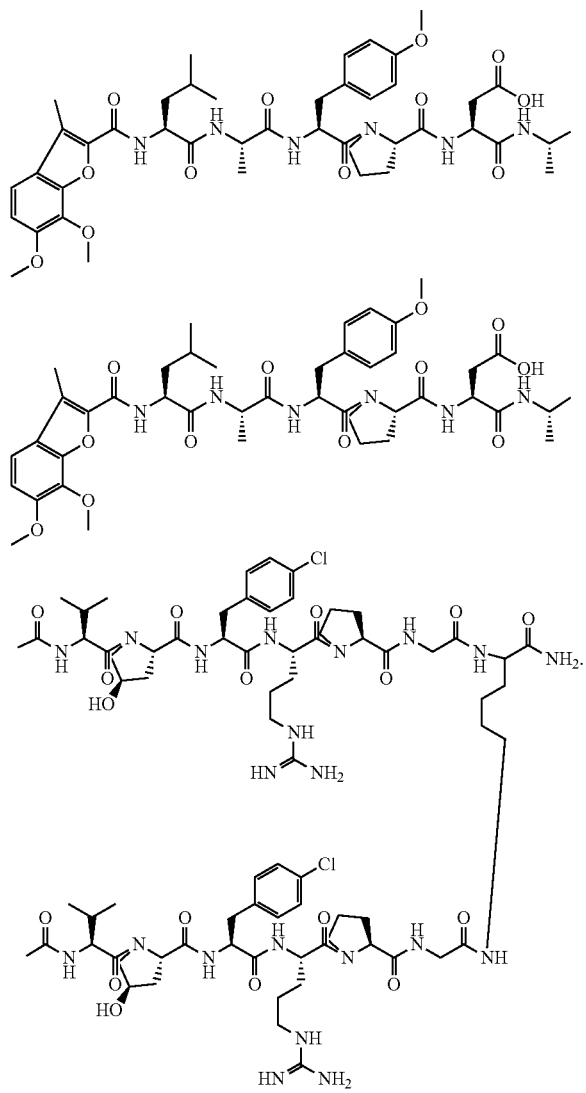

2. A pharmaceutical composition comprising a pharmaceutically acceptable excipient and the compound of claim 1.

3. A method of treating cancer, said method comprising administering to a subject in need thereof a therapeutically effective amount of a compound of claim 1.

4. A method of suppressing pro-oncogenic EphA2 activity, said method comprising contacting an EphA2 protein with a compound of claim 1.

5. A method of inhibiting cancer cell migration and invasion, said method comprising contacting an EphA2 protein with a compound of claim 1.

* * * * *

SEQUENCE LISTING

<160> NUMBER OF SEQ ID NOS: 85

<210> SEQ ID NO 1
<211> LENGTH: 976
<212> TYPE: PRT
<213> ORGANISM: Artificial Sequence
<220> FEATURE:
<223> OTHER INFORMATION: Synthetic polypeptide

<400> SEQUENCE: 1

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
                20                  25                  30

Asp Phe Ala Ala Ala Gly Gly Glu Leu Gly Trp Leu Thr His Pro Tyr
            35                  40                  45

Gly Lys Gly Trp Asp Leu Met Gln Asn Ile Met Asn Asp Met Pro Ile
50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln

```
            355                 360                 365
Cys Trp Pro Glu Ser Gly Glu Cys Gly Pro Cys Glu Ala Ser Val Arg
370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
                420                 425                 430

Ser Ile Asn Gln Thr Glu Pro Pro Lys Val Arg Leu Glu Gly Arg Ser
            435                 440                 445

Thr Thr Ser Leu Ser Val Ser Trp Ser Ile Pro Pro Pro Gln Gln Ser
            450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
                500                 505                 510

Glu Gly Gln Gly Ala Gly Ser Lys Val His Glu Phe Gln Thr Leu Ser
            515                 520                 525

Pro Glu Gly Ser Gly Asn Leu Ala Val Ile Gly Val Ala Val Gly
            530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
                580                 585                 590

Thr Tyr Glu Asp Pro Asn Gln Ala Val Leu Lys Phe Thr Thr Glu Ile
            595                 600                 605

His Pro Ser Cys Val Thr Arg Gln Lys Val Ile Gly Ala Gly Glu Phe
            610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
                660                 665                 670

His Asn Ile Ile Arg Leu Glu Gly Val Ile Ser Lys Tyr Lys Pro Met
            675                 680                 685

Met Ile Ile Thr Glu Tyr Met Glu Asn Gly Ala Leu Asp Lys Phe Leu
            690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
                740                 745                 750

Cys Lys Val Ser Asp Phe Gly Leu Ser Arg Val Leu Glu Asp Asp Pro
            755                 760                 765

Glu Ala Thr Tyr Thr Thr Ser Gly Gly Lys Ile Pro Ile Arg Trp Thr
770                 775                 780
```

-continued

```
Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
            805                 810                 815

Pro Tyr Trp Glu Leu Ser Asn His Glu Val Met Lys Ala Ile Asn Asp
        820                 825                 830

Gly Phe Arg Leu Pro Thr Pro Met Asp Cys Pro Ser Ala Ile Tyr Gln
    835                 840                 845

Leu Met Met Gln Cys Trp Gln Gln Glu Arg Ala Arg Arg Pro Lys Phe
850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
            885                 890                 895

Ser Thr Ser Gly Ser Glu Gly Val Pro Phe Arg Thr Val Ser Glu Trp
        900                 905                 910

Leu Glu Ser Ile Lys Met Gln Gln Tyr Thr Glu His Phe Met Ala Ala
    915                 920                 925

Gly Tyr Thr Ala Ile Glu Lys Val Val Gln Met Thr Asn Asp Asp Ile
930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
            965                 970                 975

<210> SEQ ID NO 2
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 2

Tyr Ser Ala Tyr Pro Asp Ser Val Pro Met Met Ser
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MOD_RES
<222> LOCATION: (9)..(9)
<223> OTHER INFORMATION: Nle
<220> FEATURE:
<221> NAME/KEY: MISC_FEATURE
<222> LOCATION: (10)..(10)
<223> OTHER INFORMATION: (S)-2-amino-4-hydroxybutanoic acid

<400> SEQUENCE: 3

Ser Ala Tyr Pro Asp Ser Val Pro Leu Ser Ser
1               5                   10

<210> SEQ ID NO 4
<211> LENGTH: 12
```

```
<212> TYPE: PRT
<213> ORGANISM: Artificial Sequence
<220> FEATURE:
<223> OTHER INFORMATION: Synthetic polypeptide

<400> SEQUENCE: 4

Phe Thr Pro Phe Ser Leu Gly Phe Glu Phe Arg Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 5

Tyr Ser Ala Phe Ser Leu Gly Tyr Glu Phe His Ala
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 6

Phe Ser Pro Asn Leu Trp Gly Leu Glu Phe Gln Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 7

Phe Thr Pro Phe Thr Leu Gly Lys Glu Phe Lys Glu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 8

Tyr Asp Tyr Val Ala Val Ala Gly Pro Ala Glu Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 9

Tyr Ser Ala Tyr Pro Leu Ser Val Glu Phe Arg Pro
1               5                   10

<210> SEQ ID NO 10
<211> LENGTH: 12
<212> TYPE: PRT
```

```
<213> ORGANISM: Artificial Sequence
<220> FEATURE:
<223> OTHER INFORMATION: Synthetic polypeptide

<400> SEQUENCE: 10

Tyr Ser Ala Tyr Pro Asp Ser Val Glu Phe Arg Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 11

Tyr Ser Ala Tyr Pro Asp Ser Val Glu Met Met Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 12

Tyr Ser Ala Tyr Pro Asp Ser Val Pro Phe Arg Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 13

Tyr Ser Ala Tyr Pro Leu Ser Val Glu Met Met Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 14

Phe Thr Ala Phe Pro Leu Gly Phe Glu Phe Arg Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 15

Phe Thr Ala Phe Pro Leu Gly Phe Glu Met Met Ser
1               5                   10

<210> SEQ ID NO 16
<211> LENGTH: 12
<212> TYPE: PRT
<213> ORGANISM: Artificial Sequence
```

```
<220> FEATURE:
<223> OTHER INFORMATION: Synthetic polypeptide

<400> SEQUENCE: 16

Tyr Ser Ala Tyr Pro Asp Ser Val Pro Phe Met Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 17

Tyr Ser Ala Tyr Pro Asp Ser Val Pro Phe
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 18

Tyr Ser Ala Tyr Pro Asp Ser Val Pro Phe Arg Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 19

Tyr Ser Ala Tyr Pro Asp Ser Val Pro Phe Arg
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 20

Tyr Ser Ala Tyr Pro Asp Ser Val Pro Met Arg Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 21

Tyr Ser Ala Tyr Pro Asp Ser Val Pro Met Arg Pro
1               5                   10

<210> SEQ ID NO 22
<211> LENGTH: 12
<212> TYPE: PRT
<213> ORGANISM: Artificial Sequence
<220> FEATURE:
```

<223> OTHER INFORMATION: Synthetic polypeptide

<400> SEQUENCE: 22

Tyr Ser Ala Tyr Pro Asp Ser Val Pro Met Met Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 23

Tyr Ser Ala Tyr Pro Asp Ser Val Pro Phe Met Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 24

Tyr Ser Cys Tyr Pro Asp Ser Val Pro Phe Arg Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 25

Tyr Ser Val Tyr Pro Asp Ser Val Pro Phe Arg Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 26

Tyr Ser Leu Tyr Pro Asp Ser Val Pro Phe Arg Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (3)..(3)
<223> OTHER INFORMATION: Aib

<400> SEQUENCE: 27

Tyr Ser Ala Tyr Pro Asp Ser Val Pro Phe Arg Pro
1               5                   10

<210> SEQ ID NO 28
<211> LENGTH: 11

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one

<400> SEQUENCE: 28

Ser Ala Tyr Pro Asp Ser Val Pro Phe Arg Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: 4-chloro-L-phenylalanine

<400> SEQUENCE: 29

Tyr Ser Ala Tyr Pro Asp Ser Val Pro Phe Arg Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: 3-chloro-L-phenylalanine

<400> SEQUENCE: 30

Tyr Ser Ala Tyr Pro Asp Ser Val Pro Phe Arg Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: 4-fluoro-L-phenylalanine

<400> SEQUENCE: 31

Tyr Ser Ala Tyr Pro Asp Ser Val Pro Phe Arg Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: 4-trifluoromethyl-L-phenylalanine

<400> SEQUENCE: 32
```

```
Tyr Ser Ala Tyr Pro Asp Ser Val Pro Phe Arg Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (11)..(11)
<223> OTHER INFORMATION: 4-amino-L-phenylalanine

<400> SEQUENCE: 33

Tyr Ser Ala Tyr Pro Asp Ser Val Pro Phe Phe Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (11)..(11)
<223> OTHER INFORMATION: 4-(methylamino)-L-phenylalanine

<400> SEQUENCE: 34

Tyr Ser Ala Tyr Pro Asp Ser Val Pro Phe Phe Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (11)..(11)
<223> OTHER INFORMATION: 4-guanidino-L-phenylalanine

<400> SEQUENCE: 35

Tyr Ser Ala Tyr Pro Asp Ser Val Pro Phe Phe Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 36

Tyr Ser Ala Tyr Pro Asp Ser Val Pro Phe Lys Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (5)..(5)
<223> OTHER INFORMATION: 4Hyp
```

```
<400> SEQUENCE: 37

Tyr Ser Ala Tyr Pro Asp Ser Val Pro Phe Arg Pro
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (9)..(9)
<223> OTHER INFORMATION: 4Hyp

<400> SEQUENCE: 38

Tyr Ser Ala Tyr Pro Asp Ser Val Pro Phe Arg Pro
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (12)..(12)
<223> OTHER INFORMATION: 4Hyp

<400> SEQUENCE: 39

Tyr Ser Ala Tyr Pro Asp Ser Val Pro Phe Arg Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: 4-chloro-L-phenylalanine

<400> SEQUENCE: 40

Tyr Ser Ala Phe Pro Asp Ser Val Pro Phe Arg Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: 3-chloro-L-phenylalanine

<400> SEQUENCE: 41

Tyr Ser Ala Phe Pro Asp Ser Val Pro Phe Arg Pro
1               5                   10

<210> SEQ ID NO 42
<211> LENGTH: 12
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: 4-pyridyl-L-alanine

<400> SEQUENCE: 42

Tyr Ser Ala Tyr Pro Asp Ser Val Pro Ala Arg Pro
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
<222> LOCATION: (10)..(10)
<223> OTHER INFORMATION: 4-chloro-L-phenylalanine

<400> SEQUENCE: 43

Tyr Ser Ala Tyr Pro Asp Ser Val Pro Phe Arg Pro
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MOD_RES
<222> LOCATION: (12)..(12)
<223> OTHER INFORMATION: bAla

<400> SEQUENCE: 44

Ser Ala Tyr Pro Asp Ser Val Pro Phe Arg Pro Ala Lys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MOD_RES
<222> LOCATION: (8)..(8)
<223> OTHER INFORMATION: 4Hyp
<220> FEATURE:
<221> NAME/KEY: MISC_FEATURE
<222> LOCATION: (9)..(9)
<223> OTHER INFORMATION: 4-chloro-L-phenylalanine

<400> SEQUENCE: 45

Ser Ala Tyr Pro Asp Ser Val Pro Phe Arg Pro
```

```
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(7)
<223> OTHER INFORMATION: Cyclized to form a disulfide bond

<400> SEQUENCE: 46

Tyr Cys Ala Tyr Pro Asp Cys Val Pro Phe Arg Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(7)
<223> OTHER INFORMATION: Cyclized to form an amide bond
<220> FEATURE:
<221> NAME/KEY: MOD_RES
<222> LOCATION: (7)..(7)
<223> OTHER INFORMATION: Dpr

<400> SEQUENCE: 47

Tyr Glu Ala Tyr Pro Asp Ala Val Pro Phe Arg Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: 2-amino-4-sulfanylbutanoic acid
<220> FEATURE:
<221> NAME/KEY: MISC_FEATURE
<222> LOCATION: (2)..(7)
<223> OTHER INFORMATION: Cyclized to form a disulfide bond

<400> SEQUENCE: 48

Tyr Cys Ala Tyr Pro Asp Cys Val Pro Phe Arg Pro
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(7)
<223> OTHER INFORMATION: Cyclized to form a disulfide bond
<220> FEATURE:
<221> NAME/KEY: MISC_FEATURE
<222> LOCATION: (7)..(7)
<223> OTHER INFORMATION: 2-amino-4-sulfanylbutanoic acid

<400> SEQUENCE: 49
```

Tyr Cys Ala Tyr Pro Asp Cys Val Pro Phe Arg Pro
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MOD_RES
<222> LOCATION: (1)..(1)
<223> OTHER INFORMATION: Dpr

<400> SEQUENCE: 50

Ala Ala Tyr Pro Asp Asp Val Pro Phe Arg Pro
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MOD_RES
<222> LOCATION: (8)..(8)
<223> OTHER INFORMATION: 4Hyp
<220> FEATURE:
<221> NAME/KEY: MISC_FEATURE
<222> LOCATION: (9)..(9)
<223> OTHER INFORMATION: 4-chloro-L-phenylalanine

<400> SEQUENCE: 51

Leu Ala Tyr Pro Asp Ala Val Pro Phe Arg Pro
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MISC_FEATURE
<222> LOCATION: (3)..(3)
<223> OTHER INFORMATION: O-methyl-L-tyrosine
<220> FEATURE:
<221> NAME/KEY: MOD_RES
<222> LOCATION: (8)..(8)
<223> OTHER INFORMATION: 4Hyp
<220> FEATURE:
<221> NAME/KEY: MISC_FEATURE
<222> LOCATION: (9)..(9)
<223> OTHER INFORMATION: 4-chloro-L-phenylalanine

<400> SEQUENCE: 52

Ser Ala Tyr Pro Asp Ser Val Pro Phe Arg Pro

```
1               5                   10
```

<210> SEQ ID NO 53
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MISC_FEATURE
<222> LOCATION: (5)..(5)
<223> OTHER INFORMATION: 2-amino-3-(2H-1,2,3,4-tetrazol-5-yl)propanoic
      acid
<220> FEATURE:
<221> NAME/KEY: MOD_RES
<222> LOCATION: (8)..(8)
<223> OTHER INFORMATION: 4Hyp
<220> FEATURE:
<221> NAME/KEY: MISC_FEATURE
<222> LOCATION: (9)..(9)
<223> OTHER INFORMATION: 4-chloro-L-phenylalanine

<400> SEQUENCE: 53

Ser Ala Tyr Pro Ala Ser Val Pro Phe Arg Pro
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MISC_FEATURE
<222> LOCATION: (1)..(1)
<223> OTHER INFORMATION: 3-cyclohexyl-L-alanine
<220> FEATURE:
<221> NAME/KEY: MOD_RES
<222> LOCATION: (8)..(8)
<223> OTHER INFORMATION: 4Hyp
<220> FEATURE:
<221> NAME/KEY: MISC_FEATURE
<222> LOCATION: (9)..(9)
<223> OTHER INFORMATION: 4-chloro-L-phenylalanine

<400> SEQUENCE: 54

Ala Ala Tyr Pro Asp Ala Val Pro Phe Arg Pro
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MISC_FEATURE
<222> LOCATION: (6)..(6)
<223> OTHER INFORMATION: (2S)-2-amino-4,4,4-trifluorobutanoic acid

```
<220> FEATURE:
<221> NAME/KEY: MOD_RES
<222> LOCATION: (8)..(8)
<223> OTHER INFORMATION: 4Hyp
<220> FEATURE:
<221> NAME/KEY: MISC_FEATURE
<222> LOCATION: (9)..(9)
<223> OTHER INFORMATION: 4-chloro-L-phenylalanine

<400> SEQUENCE: 55

Leu Ala Tyr Pro Asp Ala Val Pro Phe Arg Pro
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by 2-(3-chloro-4-
      fluorophenoxy)-ethan-1-one
<220> FEATURE:
<221> NAME/KEY: MISC_FEATURE
<222> LOCATION: (1)..(1)
<223> OTHER INFORMATION: 3-cyclohexyl-L-alanine
<220> FEATURE:
<221> NAME/KEY: MISC_FEATURE
<222> LOCATION: (6)..(6)
<223> OTHER INFORMATION: (2S)-2-amino-4,4,4-trifluorobutanoic acid
<220> FEATURE:
<221> NAME/KEY: MOD_RES
<222> LOCATION: (8)..(8)
<223> OTHER INFORMATION: 4Hyp
<220> FEATURE:
<221> NAME/KEY: MISC_FEATURE
<222> LOCATION: (9)..(9)
<223> OTHER INFORMATION: 4-chloro-L-phenylalanine

<400> SEQUENCE: 56

Ala Ala Tyr Pro Asp Ala Val Pro Phe Arg Pro
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3,6-dimethyl-benzofuran-2-carboxylic acid

<400> SEQUENCE: 57

Xaa Ser Ala Tyr Pro Asp Ser Val Pro Phe Arg Pro
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 5-methyl-benzofuran-2-carboxylic acid

<400> SEQUENCE: 58
```

```
Xaa Ser Ala Tyr Pro Asp Ser Val Pro Phe Arg Pro
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-5-fluorobenzofuranoic acid

<400> SEQUENCE: 59

Xaa Ser Ala Tyr Pro Asp Ser Val Pro Phe Arg Pro
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 7-methoxy-2-benzofurancarboxylic acid

<400> SEQUENCE: 60

Xaa Ser Ala Tyr Pro Asp Ser Val Pro Phe Arg Pro
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 5-chloro-benzodihydrofuranoic acid
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
<222> LOCATION: (10)..(10)
<223> OTHER INFORMATION: 4-chloro-L-phenylalanine

<400> SEQUENCE: 61

Xaa Ser Ala Tyr Pro Asp Ser Val Pro Phe Arg Pro
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-5-chlorobenzofuranoic acid

<400> SEQUENCE: 62

Xaa Ser Ala Tyr Pro Asp Ser Val Pro Phe Arg Pro
1               5                   10
```

```
<210> SEQ ID NO 63
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-6,7-diethoxybenzofuranoic acid

<400> SEQUENCE: 63

Xaa Ser Ala Tyr Pro Asp Ser Val Pro Phe Arg Pro
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 7-ethoxybenzofuranoic acid

<400> SEQUENCE: 64

Xaa Ser Ala Tyr Pro Asp Ser Val Pro Phe Arg Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 5-chloro-7-methoxybenzofuranoic acid

<400> SEQUENCE: 65

Xaa Ser Ala Tyr Pro Asp Ser Val Pro Phe Arg Pro
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-6,7-dimethoxybenzofuranoic acid

<400> SEQUENCE: 66

Xaa Ser Ala Tyr Pro Asp Ser Val Pro Phe Arg Pro
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-6,7-dimethoxybenzofuranoic acid
```

```
<220> FEATURE:
<221> NAME/KEY: MISC_FEATURE
<222> LOCATION: (4)..(4)
<223> OTHER INFORMATION: O-methyl-L-tyrosine
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
<222> LOCATION: (10)..(10)
<223> OTHER INFORMATION: 4-chloro-L-phenylalanine

<400> SEQUENCE: 67

Xaa Leu Ala Tyr Pro Asp Ala Val Pro Phe Arg Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-6,7-dimethoxybenzofuranoic acid
<220> FEATURE:
<221> NAME/KEY: MISC_FEATURE
<222> LOCATION: (2)..(7)
<223> OTHER INFORMATION: Cyclized to form disulfide bond
<220> FEATURE:
<221> NAME/KEY: MISC_FEATURE
<222> LOCATION: (4)..(4)
<223> OTHER INFORMATION: O-methyl-L-tyrosine
<220> FEATURE:
<221> NAME/KEY: MISC_FEATURE
<222> LOCATION: (7)..(7)
<223> OTHER INFORMATION: 2-amino-4-sulfanylbutanoic acid
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
<222> LOCATION: (10)..(10)
<223> OTHER INFORMATION: 4-chloro-L-phenylalanine

<400> SEQUENCE: 68

Xaa Cys Ala Tyr Pro Asp Cys Val Pro Phe Arg Pro
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(4-
      ((fluorosulfonyl)oxy)phenyl)propanoic acid

<400> SEQUENCE: 69

Ser Ala Tyr Pro Asp Ser Val Pro Phe Arg Pro
1               5                   10
```

```
<210> SEQ ID NO 70
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(4-
      ((fluorosulfonyl)oxy)benzamido)propanoic acid

<400> SEQUENCE: 70

Ser Ala Tyr Pro Asp Ser Val Pro Ala Arg Pro
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(4-
      ((fluorosulfonyl)oxy)phenyl)propanoic acid

<400> SEQUENCE: 71

Ser Ala Tyr Pro Asp Ser Val Pro Phe
1               5

<210> SEQ ID NO 72
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(4-
      ((fluorosulfonyl)oxy)phenyl)propanoic acid

<400> SEQUENCE: 72

Leu Ala Tyr Pro Asp Ala Val Pro Phe Arg Pro
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
```

```
      yl)-methanone
<220> FEATURE:
<221> NAME/KEY: MISC_FEATURE
<222> LOCATION: (9)..(9)
<223> OTHER INFORMATION: (S)-2-amino-3-(4-
      (fluorosulfonyl)benzamido)propanoic acid

<400> SEQUENCE: 73

Leu Ala Tyr Pro Asp Ala Val Pro Ala Arg Pro
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(3-
      (fluorosulfonyl)benzamido)propanoic acid

<400> SEQUENCE: 74

Leu Ala Tyr Pro Asp Ala Val Pro Ala Arg Pro
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(4-
      ((fluorosulfonyl)oxy)benzamido)propanoic acid

<400> SEQUENCE: 75

Leu Ala Tyr Pro Asp Ala Val Pro Ala Arg Pro
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(3-
      ((fluorosulfonyl)oxy)benzamido)propanoic acid

<400> SEQUENCE: 76

Leu Ala Tyr Pro Asp Ala Val Pro Ala Arg Pro
```

```
1               5                   10
```

<210> SEQ ID NO 77
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-4-(4-
      ((fluorosulfonyl)oxy)phenyl)butanoic acid

<400> SEQUENCE: 77

```
Leu Ala Tyr Pro Asp Ala Val Pro Phe Arg Pro
1               5                   10
```

<210> SEQ ID NO 78
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-(4-
      ((fluorosulfonyl)oxy)phenyl)propanoic acid

<400> SEQUENCE: 78

```
Leu Ala Tyr Pro Asp Ala Val Pro Phe Arg Pro
1               5                   10
```

<210> SEQ ID NO 79
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminus modified by (7-methoxybenzofuran-2-
      yl)-methanone
<220> FEATURE:
<221> NAME/KEY: MISC_FEATURE
<222> LOCATION: (9)..(9)
<223> OTHER INFORMATION: (S)-2-amino-3-((4-
      (fluorosulfonyl)benzyl)amino)propanoic acid

<400> SEQUENCE: 79

```
Leu Ala Tyr Pro Asp Ala Val Pro Ala Arg Pro
1               5                   10
```

<210> SEQ ID NO 80
<211> LENGTH: 7
<212> TYPE: PRT
<213> ORGANISM: Artificial Sequence
<220> FEATURE:
<223> OTHER INFORMATION: Synthetic polypeptide

```
<400> SEQUENCE: 80

Asp Leu Met Gln Asn Ile Met
1               5

<210> SEQ ID NO 81
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-6,7-dimethoxybenzofuranoic acid
<220> FEATURE:
<221> NAME/KEY: MISC_FEATURE
<222> LOCATION: (4)..(4)
<223> OTHER INFORMATION: O-methyl-L-tyrosine
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
<222> LOCATION: (10)..(10)
<223> OTHER INFORMATION: 4-chloro-L-phenylalanine
<220> FEATURE:
<221> NAME/KEY: MISC_FEATURE
<222> LOCATION: (13)..(13)
<223> OTHER INFORMATION: Modified by a chemical linker

<400> SEQUENCE: 81

Xaa Leu Ala Tyr Pro Asp Ala Val Pro Phe Arg Pro Gly
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-6,7-dimethoxybenzofuranoic acid
<220> FEATURE:
<221> NAME/KEY: MISC_FEATURE
<222> LOCATION: (4)..(4)
<223> OTHER INFORMATION: O-methyl-L-tyrosine
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
```

```
<222> LOCATION: (10)..(10)
<223> OTHER INFORMATION: 4-fluorosulfonyl-L-phenylalanine

<400> SEQUENCE: 82

Xaa Leu Ala Tyr Pro Asp Ala Val Pro Phe Arg Pro
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X is 3-methyl-6,7-dimethoxybenzofuranoic acid
<220> FEATURE:
<221> NAME/KEY: MISC_FEATURE
<222> LOCATION: (4)..(4)
<223> OTHER INFORMATION: O-methyl-L-tyrosine
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
<222> LOCATION: (10)..(10)
<223> OTHER INFORMATION: 4-(fluorosulfonyl)oxy-L-phenylalanine

<400> SEQUENCE: 83

Xaa Leu Ala Tyr Pro Asp Ala Val Pro Phe Arg Pro
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 84

Ala Tyr Pro Asp Ala Val Pro
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 85

Ala Tyr Pro Asp Ser Val Pro
1               5
```